United States Patent
Brafman et al.

(10) Patent No.: US 12,405,265 B2
(45) Date of Patent: Sep. 2, 2025

(54) TRANSIENT REPORTERS AND METHODS FOR BASE EDITING ENRICHMENT

(71) Applicant: ARIZONA BOARD OF REGENTS ON BEHALF OF ARIZONA STATE UNIVERSITY, Scottsdale, AZ (US)

(72) Inventors: David Brafman, Phoenix, AZ (US); Xiao Wang, Chandler, AZ (US); Nicholas Brookhouser, Tempe, AZ (US); Stefan Tekel, Tempe, AZ (US); Kylie Standage-Beier, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 212 days.

(21) Appl. No.: 17/347,360

(22) Filed: Jun. 14, 2021

(65) Prior Publication Data
US 2021/0389303 A1    Dec. 16, 2021

Related U.S. Application Data

(60) Provisional application No. 63/038,220, filed on Jun. 12, 2020.

(51) Int. Cl.
| | | |
|---|---|---|
| *G01N 33/50* | (2006.01) | |
| *C07K 14/435* | (2006.01) | |
| *C12N 9/22* | (2006.01) | |
| *C12N 15/11* | (2006.01) | |
| *C12N 15/90* | (2006.01) | |

(52) U.S. Cl.
CPC ... *G01N 33/5073* (2013.01); *C07K 14/43595* (2013.01); *C12N 9/22* (2013.01); *C12N 15/11* (2013.01); *C12N 15/907* (2013.01); *C12N 2310/20* (2017.05); *C12N 2800/80* (2013.01)

(58) Field of Classification Search
CPC .......... G01N 33/5073; C07K 14/43595; C12N 9/22; C12N 15/11; C12N 15/907; C12N 2310/20; C12N 2800/80; C12N 15/90
See application file for complete search history.

(56) References Cited

U.S. PATENT DOCUMENTS 8,987,257 B2 * 3/2015 Radetich .................. A61P 25/28
   544/118
2020/0032251 A1 * 1/2020 McLaughlin ........ C12N 15/907

OTHER PUBLICATIONS

Gauthier, Nicholas P., et al. "Cell-selective labeling using amino acid precursors for proteomic studies of multicellular environments." nAture methods 10.8 (2013): 768-773. (Year: 2013).*
Synthetic construct mCherry-P2A-wild type lysine racemase (mCherry-P2A-wild-type-lyr) gene, complete cds GenBank: KC962563.1 (Year: 2013).*
Standage-Beier, Kylie, et al. "A transient reporter for editing enrichment (TREE) in human cells." Nucleic acids research 47.19 (2019): e120-e120. (Year: 2019).*
Anzalone et al., Search-and-replace genome editing without double-strand breaks or donor DNA, Nature, 2019, 576:149-157.
Billon et al., CRISPR-mediated base editing enables efficient disruption of eukaryotic genes through induction of STOP codons, Molecular Cell, 2017, 67:1068-1079.
Boettcher et al., Choosing the Right Tool for the Job: RNAi, TALEN, or CRISPR, Molecular Cell, 2015, 58:575-585.
Brookhouser et al., BIG-TREE: Base-Edited Isogenic hPSC Line Generation Using a Transient Reporter for Editing Enrichment, Stem Cell Reports, 2020, 14:184-191.
Brookhouser et al., May I Cut in? Gene Editing Approaches in Human Induced Pluripotent Stem Cells, Cells, 2017, vol. 6, pp. 1-21.
Carlson-Stevermer et al., Genome editing in human pluripotent stem cells, Methods Mol. Biol., 2017, 1590:165-174.
Chapman et al., Playing the end game: DNA double-strand break repair pathway choice, Molecular Cell, 2012, 47:497-510.
Chen et al., Enhanced proofreading governs CRISPR-Cas9 targeting accuracy, Nature, 2017, 550:407-410.
Cheng et al., Expanding C-T base editing toolkit with diversified cytidine deaminases, Nature Communications, 2019, 10:3612, pp. 1-10.
Coelho et al., BE-FLARE: a fluorescent reporter of base editing activity reveals editing characteristics of APOBEC3A and APOBEC3B, BMC Biol., 2018, 16:150, pp. 1-11.
Dai et al., The genes associated with early-onset Alzheimer's disease, Oncotarget, 2018, 9:15132-15143.
Eggenschwiler et al., Improved bi-allelic modification of a transcriptionally silent locus in patient-derived iPSC by Cas9 nickase, Sci Rep, 2016, 6:38198, pp. 1-14.
Gaudelli et al., Programmable base editing of A,T to G,C in genomic DNA without DNA cleavage, Nature, 2017, 551:464-471.
Gaudelli et al., Directed evolution of adenine base editors with increased activity and therapeutic application, Nature Biotechnology, 2020, 38(7):892-900.
Glaser et al., GFP to BFP Conversion: A Versatile Assay for the Quantification of CRISPR/Cas9-mediated Genome Editing, Molecular Therapy—Nucleic Acids, 2016, 5:e334, 4 pages.
Grunewald et al., A dual-deaminase CRISPR base editor enables concurrent adenine and cytosine editing, Nature Biotechnology, 2020, 38(7):861-864.
Gurumurthy et al., Creation of CRISPR-based germline-genome-engineered mice without ex vivo handling of zygotes by i-GONAD, Nature Protocols, 2019, 14(8):2452-2482.

(Continued)

*Primary Examiner* — Kara D Johnson
*Assistant Examiner* — Constantina E Stavrou
(74) *Attorney, Agent, or Firm* — Quarles & Brady, LLP

(57) ABSTRACT

Provided herein are compositions and methods for real-time identification and isolation of base-edited cell populations. Also provided herein are methods for producing enriched isogenic lines of genetically modified cells, including base-edited human pluripotent stem cells. In particular, provided herein are methods utilizing transient expression of reporter proteins, the detectable signal of which is altered following base editing. Using the transient reporter with a base editor permits enrichment of isogenic populations of base-edited cells.

1 Claim, 57 Drawing Sheets

Specification includes a Sequence Listing.

(56) References Cited

OTHER PUBLICATIONS

Haapaniemi et al., CRISPR-Cas9 genome editing induces a p53-mediated DNA damage response. Nat. Med., 2018, 24:927-930.

Hauser et al., Impact of apolipoprotein E on Alzheimer's disease, Curr. Alzheimer Res., 2013, 10:809-817.

He et al., Knock-in of large reporter genes in human cells via CRISPR/Cas9-induced homology-dependent and independent DNA repair, Nucleic Acids Res., 2016, 44:e85, 14 pages.

Hockemeyer et al., Induced Pluripotent Stem Cells Meet Genome Editing, Cell Stem Cell, 2016, 18:573-586.

Hsu et al., Development and applications of CRISPR-Cas9 for genome engineering, Cell, 2014, 157:1262-1278.

Hu et al., Evolved Cas9 variants with broad PAM compatibility and high DNA specificity, Nature, 2018, 556:57-63.

Huang et al., Developing ABEmax-NG with Precise Targeting and Expanded Editing Scope to Model Pathogenic Splice Site Mutations In Vivo, iScience, 2019, 15:640-648.

Huang et al., Circularly permuted and PAM-modified Cas9 variants broaden the targeting scope of base editors, Nat. Biotechnol., 2019, 37:626-631.

Ihry et al., Genome-scale CRISPR screens identify human pluripotency-specific genes, Cell Rep., 2019, 27:616-630.

Ihry et al., p53 inhibits CRISPR-Cas9 engineering in human pluripotent stem cells, Nat. Med., 2018, 24:939-946.

Katti et al., GO: a functional reporter system to identify and enrich base editing activity, Nucleic Acids Res., 2020, 48:2841-2852.

Khera et al., Genome-wide polygenic scores for common diseases identify individuals with risk equivalent to monogenic mutations, Nat. Genet., 2018, 50:1219-1224.

Kim et al., Genome-wide target specificity of CRISPR RNA-guided adenine base editors, Nature Biotechnology, 2019, 37:430-435.

Kim et al., CRISPR/Cpf1-mediated DNA-free plant genome editing, Nature Communications, 2017, 8:14406, pp. 1-7.

Kim et al., Highly efficient RNA-guided base editing in mouse embryos, Nature Biotechnology, 2017, 35:435-437.

Kim et al., Increasing the genome-targeting scope and precision of base editing with engineered Cas9-cytidine deaminase fusions, Nature Biotechnology, 2017, 35:371-376.

Kluesner et al., EditR: A Method to Quantify Base Editing from Sanger Sequencing, CRISPR Journal, 2018, 1:239-250.

Kobayashi et al., Pathogenic variant burden in the ExAC database: an empirical approach to evaluating population data for clinical variant interpretation, Genome Med., 2017, 9:13, pp. 1-14.

Koblan et al., Improving cytidine and adenine base editors by expression optimization and ancestral reconstruction, Nat. Biotechnol., 2018, 36:843-846.

Komor et al., Editing the genome without double-stranded DNA breaks, ACS Chem. Biol., 2018, 13:383-388.

Komor et al., Programmable editing of a target base in genomic DNA without double-stranded DNA cleavage, Nature, 2016, 533:420-424.

Komor et al., Improved base excision repair inhibition and bacteriophage Mu Gam protein yields C:G-to-T:A base editors with higher efficiency and product purity, Science Advances, 2017, 3:eaao4774, pp. 1-9.

Kosicki et al., Repair of double-strand breaks induced by CRISPR-Cas9 leads to large deletions and complex rearrangements, Nat. Biotechnol., 2018, 36:765-771.

Kwart et al., Precise and efficient scarless genome editing in stem cells using CORRECT, Nat Protoc, 2017, 12:329-354.

Landrum et al., ClinVar: improving access to variant interpretations and supporting evidence, Nucleic Acids Res., 2018, 46:D1062-D1067.

Lee et al., CRISPR-pass: Gene rescue of nonsense mutations using adenine base editors, Molecular Therapy, 2019, 27(8):1364-1371.

Lee et al., Simultaneous targeting of linked loci in mouse embryos using base editing, Scientific Reports, 2019, 9:1662, pp. 1-8.

Levy et al., Cytosine and adenine base editing of the brain, liver, retina, heart and skeletal muscle of mice via adeno-associated viruses, Nature Biomedical Engineering, 2020, 4(1):97-110.

Li et al., CRISPR-Cas9-mediated base-editing screening in mice identifies DND1 amino acids that are critical for primordial germ cell development, Nature Cell Biology, 2018, 20(11):1315-1325.

Li et al., Base editing with a Cpf1-cytidine deaminase fusion, Nature Biotechnology, 2018, 36(4):324-327.

Lin et al., Prime genome editing in rice and wheat, Nature Biotechnology, 2020, 38(5):582-585.

Lino et al., Delivering CRISPR: a review of the challenges and approaches, Drug Deliv, 2018, 25:1234-1257.

Liu et al., Delivery strategies of the CRISPR-Cas9 geneediting system for therapeutic applications, J Control Release, 2017, 266:17-26.

Liu et al., Efficient generation of mouse models of human diseases via ABE- and BE-mediated base editing, Nat Commun, 2018, 9:2338, pp. 1-8.

Liu et al., Highly efficient base editing with expanded targeting scope using SpCas9-NG in rabbits, FASEB J., 2020, 34:588-596.

Logue et al., Two rare AKAP9 variants are associated with Alzheimer's disease in African Americans, Alzheimers Dement, 2014, 10:609-618.

Ma et al., Targeted AID-mediated mutagenesis (TAM) enables efficient genomic diversification in mammalian cells, Nature Methods, 2016, 13(12):1029-1035.

Martin et al., A panel of eGFP reporters for single base editing by APOBEC-Cas9 editosome complexes, Sci Rep, 2019, 9:497, pp. 1-8.

Moon et al., Recent advances in the CRISPR genome editing tool set, Exp. Mol. Med., 2019, 51:130, pp. 1-11.

Nishida et al., Targeted nucleotide editing using hybrid prokaryotic and vertebrate adaptive immune systems, Science, 2016, 353(6305):1248, aaf8729-1 thru aaf8729-8.

Ortmann et al., Variability of human pluripotent stem cell lines, Curr. Opin. Genet. Dev., 2017, 46:179-185.

Panyam et al., Biodegradable nanoparticles for drug and gene delivery to cells and tissue, Advanced Drug Delivery Reviews, 2012, 64:61-71.

Paquet et al., Efficient introduction of specific homozygous and heterozygous mutations using CRISPR/Cas9, Nature, 2016, 533:125-129.

Park et al., Disease-specific induced pluripotent stem cells, Cell, 2008, 134:877-886.

Pau, A table of senile forms of cataract. Clinical picture, prognosis, biochemistry and etiology, Klin Monbl Augenheilkd, 1988, 193:550-553.

Rees et al., Base editing: precision chemistry on the genome and transcriptome of living cells, Nat Rev Genet, 2018, 19:770-788.

Rees et al., Development of hRad51-Cas9 nickase fusions that mediate HDR without double-stranded breaks, Nat Commun, 2019, 10:2212, pp. 1-12.

Rees et al., Improving the DNA specificity and applicability of base editing through protein engineering and protein delivery, Nature Communications, 2017, 8:15790, pp. 1-10.

Ryu et al., Adenine base editing in mouse embryos and an adult mouse model of Duchenne muscular dystrophy, Nature Biotechnology, 2018, 36(6):536-539.

Sakata et al., Base editors for simultaneous introduction of C-to-T and A-to-G mutations, Nature Biotechnology, 2020, 38(7):865-869.

Shimatani et al., Targeted base editing in rice and tomato using a CRISPR-Cas9 cytidine deaminase fusion, Nature Biotechnology, 2017, 35(5):441-443.

Si et al., Impact of single nucleotide polymorphisms on P450 oxidoreductase and peroxisome proliferator-activated receptor alpha on tacrolimus pharmacokinetics in renal transplant recipients, Pharmacogenomics Journal, 2019, 19:42-52.

Slaymaker et al., Rationally engineered Cas9 nucleases with improved specificity, Science, 2016, 351:84-88.

Sod-Moriah et al., Long term effects of dibromochloropropane (DBCP) on male rats' reproductive system, Andrologia, 1988, 20:60-66.

(56) References Cited

OTHER PUBLICATIONS

St Martin et al., A fluorescent reporter for quantification and enrichment of DNA editing by APOBEC-Cas9 or cleavage by Cas9 in living cells, Nucleic Acids Res., 2018, 46:e84, 10 pages.

Standage-Beier et al., A transient reporter for editing enrichment (TREE) in human cells, Nucleic Acids Res., 2019, 47:e120, pp. 1-13.

Stemmer et al., CCTop: An Intuitive, Flexible and Reliable CRISPR/Cas9 Target Prediction Tool, PLoS ONE, 2015, 10:e0124633, 11 pages.

Takayama et al., Highly efficient biallelic genome editing of human ES/IPS cells using a CRISPR/Cas9 or TALEN system, Nucleic Acids Res., 2017, 45:5198-5207.

Tan et al., Engineering of high-precision base editors for site-specific single nucleotide replacement, Nat. Commun., 2019, 10:439, pp. 1-10.

Thuronyi et al., Continuous evolution of base editors with expanded target compatibility and improved activity, Nat. Biotechnol., 2019, 37:1070-1079.

Tong et al., Highly efficient DSB-free base editing for streptomycetes with CRISPR-BEST, Proceedings of the National Academy of Sciences, 2019, 116(41):20366-20375.

Traxler et al., A genome-editing strategy to treat B-hemoglobinopathies that recapitulates a mutation associated with a benign genetic condition, Nat. Med., 2016, 22:987-990.

Van Rheenen et al., Genetic correlations of polygenic disease traits: from theory to practice, Nat. Rev. Genet., 2019, 20:567-581.

Wang et al., BEON: A Functional Fluorescence Reporter for Quantification and Enrichment of Adenine Base-Editing Activity, Mol. Ther., 2020, 28(7):1696-1705.

Wang et al., Efficient Gene Silencing by Adenine Base Editor-Mediated Start Codon Mutation, Mol. Ther., 2020, 28:431-440.

Wang et al., Expanding targeting scope, editing window, and base transition capability of base editing in Corynebacterium glutamicum, Biotechnology and Bioengineering, 2019, 116(11):3016-3029.

Xie et al., Efficient base editing for multiple genes and loci in pigs using base editors, Nature Communications, 2019, 10:2852, pp. 1-13.

Yang et al., Methods and applications of CRISPR/Cas system for genome editing in stem cells, Cell Regen, 2019, 8:33-41.

Yang et al., Engineering and optimising deaminase fusions for genome editing, Nature Communications, 2016, 7:13330, pp. 1-11.

Yu et al., Small Molecules Enhance CRISPR Genome Editing in Pluripotent Stem Cells, Cell Stem Cell, 2015, 16:142-147.

Zafra et al., Optimized base editors enable efficient editing in cells, organoids and mice, Nature Biotechnology, 2018, 36(9):888-893.

Zhang et al., Simultaneous zygotic inactivation of multiple genes in mouse through CRISPR/Cas9-mediated base editing, Development, 2018, 145, pp. 1-11.

Zhang et al., Dual base editor catalyzes both cytosine and adenine base conversions in human cells, Nature Biotechnology, 2020, 38(7):856-860.

Zheng et al., Highly efficient base editing in bacteria using a Cas9-cytidine deaminase fusion, Commun Biol, 2018, 1:32, pp. 1-6.

Zong et al., Precise base editing in rice, wheat and maize with a Cas9-cytidine deaminase fusion, Nature Biotechnology, 2017, 35(5):438-440.

\* cited by examiner

FIG. 9

U6 Promoter
sg(BG) guide
sgRNA hairpin
U6 Promoter
sg(NT) guide
sgRNA hairpin

SEQ ID NO: 262

>pDT-sgRNA, sg(BG):sg(NT) 3492 bp
TCGCGCGTTTCGGTGATGACGGTGAAAACCTCTGACACATGCAGCTCCCGGAGACGGTCACAGCTTGTCTGTAA
GCGGATGCCGGGAGCAGACAAGCCCGTCAGGGCGCGTCAGCGGGTGTTGGCGGGTGTCGGGGCTGGCTTAA
CTATGCGGCATCAGAGCAGATTGTACTGAGAGTGCACCATATGCGGTGTGAAATACCGCACAGATGCGTAAGGA
GAAAATACCGCATCAGGCGCCATTCGCCATTCAGGCTGCGCAACTGTTGGGAAGGGCGATCGGTGCGGGCCTC
TTCGCTATTACGCCAGCTGGCGAAAGGGGGATGTGCTGCAAGGCGATTAAGTTGGGTAACGCCAGGGTTTTCC
CAGTCACGACGTTGTAAAACGACGGCCAGTGAATTCGAGGGCCTATTTCCCATGATTCCTTCATATTTGCATATA
CGATACAAGGCTGTTAGAGAGATAATTGGAATTAATTTGACTGTAAACACAAAGATATTAGTACAAAATACGTGAC
GTAGAAAGTAATAATTTCTTGGGTAGTTTGCAGTTTTAAAATTATGTTTTAAAATGGACTATCATATGCTTACCGTA
ACTTGAAAGTATTTCGATTTCTTGGCTTTATATATCTTGTGGAAAGGACGAAACACCGACCCACGGCGTGCAGTG
GTGCTTTTTTGTTTTAGAGCTAGAAATAGCAAGTTAAAATAAGGCTAGTCCGTTATCAACTTGAAAAAGTGGCACCGAGTCG
GTGCTTTTTGTTTTAGAGCTAGAAATAGCAAGTTAAAATAAGGCTAGTCCGTTATCAACTTGAAAAAGTGGCACCGAGTCG
GTGCTTTTTTGTTTTAGAGCTAGAAATAGCAAGTTAAAATAAGGCTAGTCCGTTATCAACTTGAAAAAGTGGCACCGAGTCG
CAGACAGAGAGGGCCTATTTCCCATGATTCCTTCATATTTGCATATACGATACAAGGCTGTTAGAGAGATAATTG
GAATTAATTTGACTGTAAACACAAAGATATTAGTACAAAATACGTGACGTAGAAAGTAATAATTTCTTGGGTAGTTT
GCAGTTTTAAAATTATGTTTTAAAATGGACTATCATATGCTTACCGTAACTTGAAAGTATTTCGATTTCTTGGCTTT
ATATATCTTGTGGAAAGGACGAAACACCGGGTCTTCGAGAAGACCTGTTTTAGAGCTAGAAATAGCAAGTTAAAA
TAAGGCTAGTCCGTTATCAACTTGAAAAAGTGGCACCGAGTCGGTGCTTTTTTGTTTTAGAGCTAGAAATAGCAA
GTTAAAATAAGGCTAGTCCGTTTTTAGCGCGTGCGCCAATTCTGCAGACAAAAAGCTTGGCGTAATCATGGTCAT
AGCTGTTTCCTGTGTGAAATTGTTATCCGCTCACAATTCCACACAACATACGAGCCGGAAGCATAAAGTGTAAAG
CCTGGGGTGCCTAATGAGTGAGCTAACTCACATTAATTGCGTTGCGCTCACTGCCCGCTTTCCAGTCGGGAAAC
CTGTCGTGCCAGCTGCATTAATGAATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTACAGAGTTCTTGAAGT
GGTGGCCTAACTACGGCTACACTAGAAGAACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGCAGCA
GATTACGCGCAGAAAAAAGGATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAACGATCAAGGCGAGTTACATGATCCC
CCATGTTGTGCAAAAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCCGGCGTCAATACGGGATA
ATACCGCGCCACATAGCAGAACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGT
TGAATACTCATACTCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCACCTGACGTCTAAGA
AACCATTATTATCATGACATTAACCTATAAAAATAGGCGTATCACGAGGCCCTTTCGTC

FIG. 23

FIG. 27 a) Untransfected Site-1

| SEQ ID NO | Indel | Editing window / PAM | % of Reads |
|---|---|---|---|
| SEQ ID NO: 263 | WT | GGCCCAGACTGAGCACGTGATGG | 99.7 |
| SEQ ID NO: 264 | 18 | GGTCCAGACTGAGCACGTGATGG | 0.1 |
| SEQ ID NO: 265 | 17 | GGCTCAGACTGAGCACGTGATGG | 0.1 |
| SEQ ID NO: 266 | 16 | GGCTCAGACTGAGCACGTGATGG | 0.1 |
| SEQ ID NO: 267 | 12 | GGCCCAGATTGAGCACGTGATGG | 0.0 |
| SEQ ID NO: 268 | 18,17 | GGTTCAGACTGAGCACGTGATGG | 0.0 |
| SEQ ID NO: 269 | 18,16 | GGTCTAGACTGAGCACGTGATGG | 0.0 |
| SEQ ID NO: 270 | 18,12 | GGTCCAGATTGAGCACGTGATGG | 0.0 |
| SEQ ID NO: 271 | 17,16 | GGCTTAGACTGAGCACGTGATGG | 0.0 |
| SEQ ID NO: 272 | 17,12 | GGCTCAGATTGAGCACGTGATGG | 0.0 |
| SEQ ID NO: 273 | 16,12 | GGCTTAGACTGAGCACGTGATGG | 0.0 |
| SEQ ID NO: 274 | 18,17,16 | GGCTTAGACTGAGCACGTGATGG | 0.0 |
| SEQ ID NO: 275 | 17,16,12 | GGCTTAGATTGAGCACGTGATGG | 0.0 |
| SEQ ID NO: 276 | 18,16,12 | GGTCTAGATTGAGCACGTGATGG | 0.0 |
| SEQ ID NO: 277 | 18,17,12 | GGTTCAGATTGAGCACGTGATGG | 0.0 |
| SEQ ID NO: 278 | 18,17,16,12 | GGTTTAGATTGAGCACGTGATGG | 0.0 |

TREE:Site-1

| Editing window / PAM | % of Reads | SEQ ID NO |
|---|---|---|
| GGCCCAGACTGAGCACGTGATGG | 5.2 | SEQ ID NO: 279 |
| GGTCCAGACTGAGCACGTGATGG | 0.0 | SEQ ID NO: 280 |
| GGCTCAGACTGAGCACGTGATGG | 0.1 | SEQ ID NO: 281 |
| GGCTCAGACTGAGCACGTGATGG | 0.3 | SEQ ID NO: 282 |
| GGCCCAGATTGAGCACGTGATGG | 0.0 | SEQ ID NO: 283 |
| GGTTCAGACTGAGCACGTGATGG | 0.0 | SEQ ID NO: 284 |
| GGTCTAGACTGAGCACGTGATGG | 0.0 | SEQ ID NO: 285 |
| GGTCCAGATTGAGCACGTGATGG | 0.0 | SEQ ID NO: 286 |
| GGCTTAGACTGAGCACGTGATGG | 85.2 | SEQ ID NO: 287 |
| GGCTCAGATTGAGCACGTGATGG | 0.1 | SEQ ID NO: 288 |
| GGCCTAGACTGAGCACGTGATGG | 0.2 | SEQ ID NO: 289 |
| GGCTTAGACTGAGCACGTGATGG | 6.2 | SEQ ID NO: 290 |
| GGCTTAGATTGAGCACGTGATGG | 2.4 | SEQ ID NO: 291 |
| GGTCTAGATTGAGCACGTGATGG | 0.0 | SEQ ID NO: 292 |
| GGTTCAGATTGAGCACGTGATGG | 0.0 | SEQ ID NO: 293 |
| GGTTTAGATTGAGCACGTGATGG | 0.1 | SEQ ID NO: 294 | b) Untransfected APOE

| SEQ ID NO | Indel | Editing window / PAM | % of Reads |
|---|---|---|---|
| SEQ ID NO: 295 | WT | GAAGCGCCTGGCAGTGTACCAGG | 99.4 |
| SEQ ID NO: 296 | 16 | GAAGTGCCTGGCAGTGTACCAGG | 2.5 |
| SEQ ID NO: 297 | 14 | GAAGCGTCTGGCAGTGTACCAGG | 0.1 |
| SEQ ID NO: 298 | 13 | GAAGCGCTTGGCAGTGTACCAGG | 0.1 |
| SEQ ID NO: 299 | 16,14 | GAAGTGTCTGGCAGTGTACCAGG | 1.1 |
| SEQ ID NO: 300 | 16,13 | GAAGTGCTTGGCAGTGTACCAGG | 0.4 |
| SEQ ID NO: 301 | 14,13 | GAAGCGTTTGGCAGTGTACCAGG | 0.5 |
| SEQ ID NO: 302 | 16,14,13 | GAAGTGTTTGGCAGTGTACCAGG | 1.9 |

TREE:APOE

| Editing window / PAM | % of Reads | SEQ ID NO |
|---|---|---|
| GAAGCGCCTGGCAGTGTACCAGG | 64.2 | SEQ ID NO: 303 |
| GAAGTGCCTGGCAGTGTACCAGG | 5.2 | SEQ ID NO: 304 |
| GAAGCGTCTGGCAGTGTACCAGG | 1.1 | SEQ ID NO: 305 |
| GAAGCGCTTGGCAGTGTACCAGG | 1.0 | SEQ ID NO: 306 |
| GAAGTGTCTGGCAGTGTACCAGG | 1.2 | SEQ ID NO: 307 |
| GAAGTGCTTGGCAGTGTACCAGG | 1.0 | SEQ ID NO: 308 |
| GAAGCGTTTGGCAGTGTACCAGG | 7.0 | SEQ ID NO: 309 |
| GAAGTGTTTGGCAGTGTACCAGG | 19.2 | SEQ ID NO: 310 |

SEQ ID NO: 238
SEQ ID NO: 239
SEQ ID NO: 240
SEQ ID NO: 241

FIG. 39 (CONTINUED)

>pQT-sgRNA-1xStop SEQ ID NO: 187
TCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGGCGCCATT
CGCCATTCAGGCTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGCCAGGGTTTTCC
CAGTCACGACGTTGTAAAACGACGGCCAGTGAATTC................................
...................................................................
...................................................................
...................................................................
...................................... pUC19 Backbone GCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATT
AATTGCGTTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTTCCTCGC
TCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCCAG
TGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTA
CTCAACCAAGTCATTCTGAGAATAGTGTATGCGGCGACCGAGTTGCTCTTGCCCGGCGTCA
ATACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTC
GTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCAC
CTGACGTCTAAGAAACCATTATTATCATGACATTAACCTATAAAAATAGGCGTATCACGAGGC
CCTTTCGTC

FIG. 40 (CONTINUED)

>pDT-sgRNA-2xStep SEQ ID NO: 188
TCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGGCGCCATT
CGCCATTCAGGCTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGCCAGGGTTTTCC
CAGTCACGACGTTGTAAAACGACGGCCAGTGAATTC................................................
......................................................................................
......................................................................................
......................................................................................

AGACAGAA................................................................
......................................................................................
......................................................................................
...............GTGACCTGCAGGCATGCAAGCTTG
GCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATT
AATTGCGTTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTTCCTCGC
TCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCGG
TAAGACAGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGG
GCAGAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCCAG
TGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTA
CTCAACCAAGTCATTCTGAGAATAGTGTATGCGGCGACCGAGTTGCTCTTGCCCGGCGTCA
ATACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTC
GTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCAC
CTGACGTCTAAGAAACCATTATTATCATGACATTAACCTATAAAAATAGGCGTATCACGAGGC
CCTTTCGTC

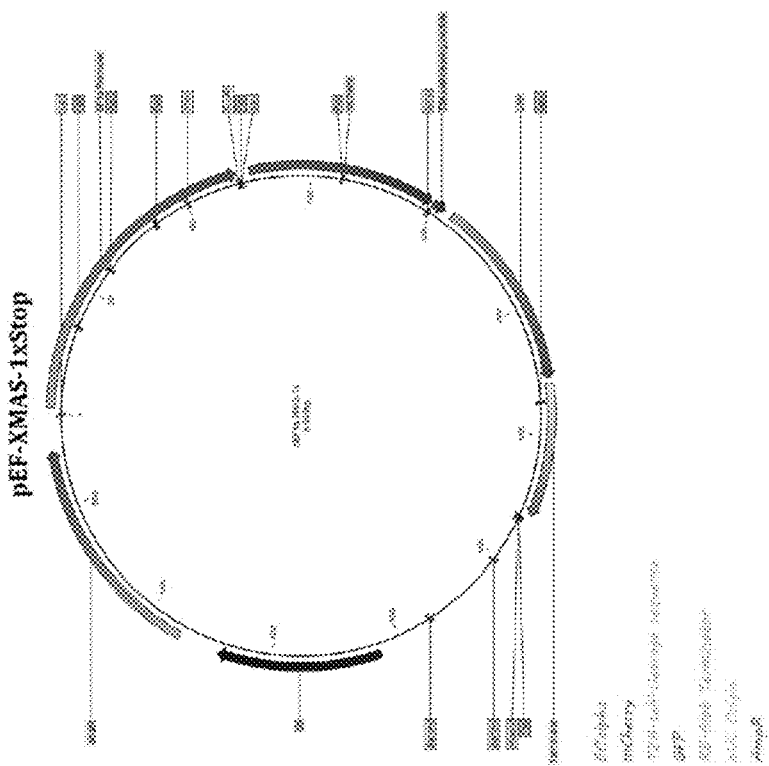

BFP coding sequence
Protospacer
Histidine 66 "CAC" Codon
PAM "CGG"

SEQ ID NO: 258

>BFP reporter coding sequence
ATGGTGAGCAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCGTGACCACCCTGACCCAC
GGCGTGCAGTGCTTCGCCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCCGAGG
TGAAGTTCGAGGGCGACACCCTGGTGAACCGCATCGAGCTGAAGGGCATCGACTTCAAGGAGGACGG
CAACATCCTGGGGCACAAGCTGGAGTACAACTACAACAGCCACAACGTCTATATCATGGCCGACAAG
CAGAAGAACGGCATCAAGGTGAACTTCAAGATCCGCCACAACATCGAGGACGGCAGCGTGCAGCTCG
CCGACCACTACCAGCAGAACACCCCCATCGGCGACGGCCCCGTGCTGCTGCCCGACAACCACTACCTG
AGCACCCAGTCCGCCCTGAGCAAAGACCCCAACGAGAAGCGCGATCACATGGTCCTGCTGGAGTTCGT
GACCGCCGCCGGGATCACTCTCGGCATGGACGAGCTGTACAAGTAA

FIG. 45 (Continued)

SEQ ID NO: 259

>XMAS 1xStop Reporter Coding Sequence
ATGGTGAGCAAGGGCGAGGAGGATAACATGGCCATCATCAAGGAGTTCATGCGCTTCAAGGTGCACA
TGGAGGGCTCCGTGAACGGCCACGAGTTCGAGATCGAGGGCGAGGGCGAGGGCCGCCCCTACGAGGG
CACCCAGACCGCCAAGCTGAAGGTGACCAAGGGTGGCCCCCTGCCCTTCGCCTGGGACATCCTGTCC
CCTCAGTTCATGTACGGCTCCAAGGCCTACGTGAAGCACCCCGCCGACATCCCCGACTACTTGAAGCTG
TCCTTCCCCGAGGGCTTCAAGTGGGAGCGCGTGATGAACTTCGAGGACGGCGGCGTGGTGACCGTGAC
CCAGGACTCCTCCCTGCAGGACGGCGAGTTCATCTACAAGGTGAAGCTGCGCGGCACCAACTTCCCCT
CCGACGGCCCCGTAATGCAGAAGAAGACCATGGGCTGGGAGGCCTCCTCCGAGCGGATGTACCCGGA
GGACGGCGCCCTGAAGGGCGAGATCAAGCAGAGGCTGAAGCTGAAGGACGGCGGCCACTACGACGCT
GAGGTCAAGACCACTTACAAGGCCAAGAAGCCCGTGCAGCTGCCCGGCGCCTACAACGTCAACATCA
AGTTGGACATCACTTCCCACAATGAGGACTACACCATCGTGGAACAGTACGAACGAGCCCGAGGGCCG
CCACTCCACCGGCGGCATGGACGAGCTGTACAAGCCCCGGACTAGTTTAA<u>TGTCGCTCAAGCCA</u>AGTGCGGGGGCGCATGCCGTGACCA
AGGCGGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTCATCT
GCACCACCGGCAAGCTGCCCGTGCCCTGGCCCACCCTCGTGACCACCCTGACCTACGGCGTGCAGTGC
TTCAGCCGCTACCCCGACCACATGAAGCAGCACGACTTCTTCAAGTCCGCCATGCCCGAAGGCTACGT
CCAGGAGCGCACCATCTTTTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCAACATCCTGG
GGCACAAGCTGGAGTACAACTACAACAGCCACAACGTCTATATCATGGCCGACAAGCAGAAGAACGG
CATCAAGGTGAACTTCAAGATCCGGCACAACATCGAGGACGGCAGCGTGCAGCTCGCCGACCACTACC
AGCAGAACACCCCCATCGGCGACGGCCCCGTGCTGCTGCCCGACAACCACTACCTGAGCACCCAGTCC
GCCCTGAGCAAAGACCCCAACGAGAAGCGCGATCACATGGTCCTGCTGGAGTTCGTGACCGCCGCCGG
GGATCACTCCTCCGGCATGGACGAGCTGTACAAGTAA >XMAS 1xStop Reporter Protospacer and PAM sequence
<u>GTGACGGGGTTCAGGAGCA</u>GGG    SEQ ID NO: 315

FIG. 45 (Continued)

>XMAS 1xStop Reporter Coding Sequence   SEQ ID NO: 260

ATGTGAGCAAGGGCGAGGAGGATAACATGGCCATCATCAAGGAGTTCATGCGTTCAAGGTGCACA
TGGAGGGCTCCGTGAACGGCCACGAGTTCGAGATCGAGGGCGAGGGCGAGGGCCGCCCCTACGAGGG
CACCCAGACCGCCAAGCTGAAGGTGACCAAGGGTGGCCCCCTGCCCTTCGCCTGGGACATCCTGTCC
CCTCAGTTCATGTACGGCTCCAAGGCCTACGTGAAGCACCCCGCCGACATCCCCGACTACTTGAAGCTG
TCCTTCCCCGAGGGCTTCAAGTGGGAACGCGTGATGAACTTCGAGGACGGCGGCGTGGTGACCGTGAC
CCAGGACTCCTCCCTGCAGGACGGCGAGTTCATCTACAAGGTGAAGCTGCGCGGCACCAACTTCCCCT
CCGACGGCCCCGTAATGCAGAAGAAGACCATGGGCTGGGAGGCCTCCTCCGAGCGTATGTACCCCGA
GGACGGCGCCCTGAAGGGCGAGATCAAGCAGAGGCTGAAGCTGAAGGACGGCGGCCACTACGACGCT
GAGGTCAAGACCACCTACAAGGCCAAGAAGCCCGTGCAGCTGCCCGGCGCCTACAACGTCAACATCA
AGTTGGACATCACCTCCCACAACGAGGACTACACCATCGTGGAACAGTACGAGCGCGCCGAGGGCCG
CCACTCCACCGGCGGCATGGACGAGCTGTACAAGCTGTACAAGCCCCG<u>ACTAGT</u>GATGAGTGGTTCAGGAGGGCATGCCGTGAGCA
AGGGCGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTCATCT
GCACCACCGGCAAGCTGCCCGTGCCCTGGCCCACCCTCGTGACCACCCTGACCTACGGCGTGCAGTGC
TTCAGCCGCTACCCCGACCATATGAAGCAGCACGACTTCTTCAAGTCCGCCATGCCCGAAGGCTACGT
CCAGGAGCGCACCATCTTCTTCAAGGACGACGGCAACTACAAGACGCGTGCCGAGGTGAAGTTCGAG
GGCGACACCCTGGTGAACCGCATCGAGCTGAAGGCCATCGACTTCAAGGAGGACGGCAACATCCTGG
GGCACAAGCTGGAGTACAACTACAACAGCCACAACGTCTATATCATGGCCGACAAGCAGAAGAACGG
CATCAAGGTGAACTTCAAGACCCGCCACAACATCGAGGACGGCAGCGTGCAGCTCGCCGACCACTAC
CAGCAGAACACCCCCATCGGCGACGGCCCCGTGCTGCTGCCCGACAACCACTACCTGAGCACCCAGTCC
GCCCTGAGCAAAGACCCCAACGAGAAGCGCGATCACATGGTCCTGCTGGAGTTCGTGACCGCCGCCGG
GGATCACTCTCGGCAATGGACGAGCTGTACAAGTAA

>XMAS 2xStop Reporter Protospacer and PAM sequence   SEQ ID NO: 261

<u>GTTCAATGAGGTGGTTCAGGAGG</u>

FIG. 46

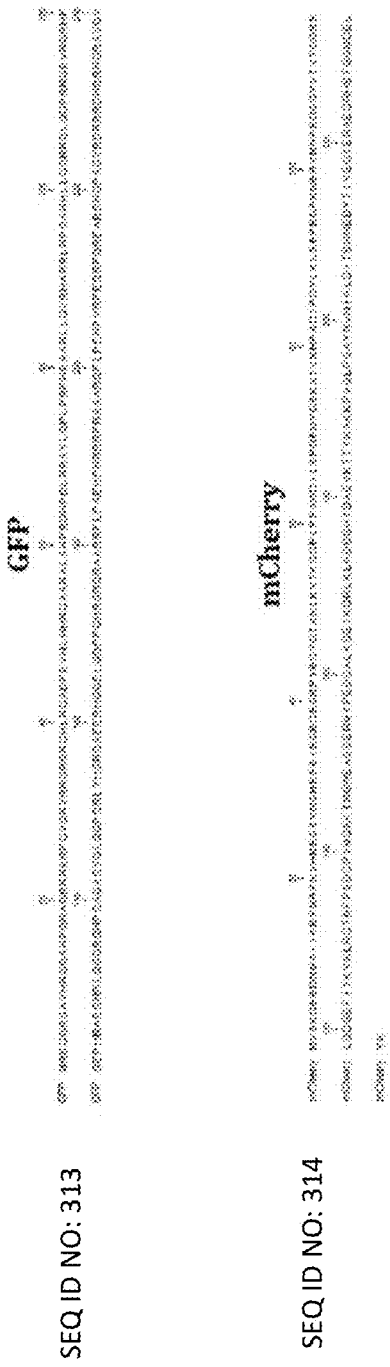

SEQ ID NO: 313 — GFP

SEQ ID NO: 314 — mCherry

XMAS 1x stop Translation prior to editing: SEQ ID NO: 316
MVSKGEEDNMAIIKEFMRFKVHMEGSVNGHEFEIEGEGEGRPYEGTQTAKLKVTKGGPLPFAWDILSPQFMYGSKAYVKHPADIPDYLKLSFPEG
FKWERVMNFEDGGVVTVTQDSSLQDGEFIYKVKLRGTNFPSDGPVMQKKTMGWEASSERMYPEDGALKGEIKQRLKLKDGGHYDAEVKTTYKA
KKPVQLPGAYNVNIKLDITSHNEDYTIVEQYERAEGRHSTGGMDELYKPREGRGSLLTCGDVEENPGPTS-
WGGSGGACVSKGEELFTGVVPILVELDGDVNGHKFSVSGEGEGDATYGKLTLKFICTTGKLPVPWPTLVTTLTYGVQCFSRYPDHMKQHDFFKSA
MPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQ
QNTPIGDGPVLLPDNHYLSTQSALSKDPNEKRDHMVLLEFVTAAGITLGMDELYK- XMAS1x stop Translation after editing: SEQ ID NO: 317
MVSKGEEDNMAIIKEFMRFKVHMEGSVNGHEFEIEGEGEGRPYEGTQTAKLKVTKGGPLPFAWDILSPQFMYGSKAYVKHPADIPDYLKLSFPEG
FKWERVMNFEDGGVVTVTQDSSLQDGEFIYKVKLRGTNFPSDGPVMQKKTMGWEASSERMYPEDGALKGEIKQRLKLKDGGHYDAEVKTTYKA
KKPVQLPGAYNVNIKLDITSHNEDYTIVEQYERAEGRHSTGGMDELYKPREGRGSLLTCGDVEENPGPTSWWGGSGGACVSKGEELFTGVVPILV
ELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAE
VKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALS
KDPNEKRDHMVLLEFVTAAGITLGMDELYK- Figure 46 (continued)

XMAS 2x stop Translation no editing ; SEQ ID NO: 318
MVSKGEEDNMAIIKEFMRFKVHMEGSVNGHEFEIEGEGEGRPYEGTQTAKLKVTKGGPLPFAWDILSPQFMYGSKAYVKHPADIPDYLKL
SFPEGFKWERVMNFEDGGVVTVTQDSSLQDGEFIYKVKLRGTNFPSDGPVMQKKTMGWEASSERMYPEDGALKGEIKQRLKLKDGGHY
DAEVKTTYKAKKPVQLPGAYNVNIKLDITSHNEDYTIVEQYERAEGRHSTGGMDELYKPREGRGSLLTCGDVEENPGPTS--
GSSGGACVSKGEELFTGVVPILVELDGDVNGHKFSVSGEGEGDATYGKLTLKFICTTGKLPVPWPTLVTTLTYGVQCFSRYPDHMKQHDFF
KSAMPEGYVQERTIFFKDDGNYKTRAEVKFEGDTLVNRIELKGIDFKEDGNILGHKLEYNYNSHNVYIMADKQKNGIKVNFKIRHNIEDGSV
QLADHYQQQNTPIGDGPVLLPDNHYLSTQSALSKDPNEKRDHMVLLEFVTAAGITLGMDELYK- XMAS 2x stop After editing SEQ ID NO: 319
MVSKGEEDNMAIIKEFMRFKVHMEGSVNGHEFEIEGEGEGRPYEGTQTAKLKVTKGGPLPFAWDILSPQFMYGSKAYVKHPADIPDYLKL
SFPEGFKWERVMNFEDGGVVTVTQDSSLQDGEFIYKVKLRGTNFPSDGPVMQKKTMGWEASSERMYPEDGALKGEIKQRLKLKDGGHY
DAEVKTTYKAKKPVQLPGAYNVNIKLDITSHNEDYTIVEQYERAEGRHSTGGMDELYKPREGRGPTSWWGGSGGAC
VSKGEELFTGVVPILVELDGDVNGHKFSVSGEGEGDATYGKLTLKFICTTGKLPVPWPTLVTTLTYGVQCFSRYPDHMKQHDFFKSAMPEG
YVQERTIFFKDDGNYKTRAEVKFEGDTLVNRIELKGIDFKEDGNILGHKLEYNYNSHNVYIMADKQKNGIKVNFKIRHNIEDGSVQLADHYQ
QNTPIGDGPVLLPDNHYLSTQSALSKDPNEKRDHMVLLEFVTAAGITLGMDELYK-

SEQUENCE LISTING

<160> NUMBER OF SEQ ID NOS: 327

<210> SEQ ID NO 1
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

```
Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 2
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr His Gly Val Gln Cys Phe Gly Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 3
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gacccacggc gtgcagtgct tgttttagag ctagaaatag caagttaaaa taaggctagt    60
ccgttatcaa cttgaaaaag tggcaccgag tcggtgcttt tttgtttt                108

<210> SEQ ID NO 4
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gggtcttcga agacctgt tttagagcta gaaatagcaa gttaaaataa ggctagtccg      60
ttatcaactt gaaaaagtgg caccgagtcg gtgcttttt gtttt                    105

<210> SEQ ID NO 5
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ggcccagact gagcacgtga gttttagagc tagaaatagc aagttaaaat aaggctagtc    60
cgttatcaac ttgaaaaagt ggcaccgagt cggtgctttt tgttttt                 107

<210> SEQ ID NO 6
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaacacaaag catagactgc gttttagagc tagaaatagc aagttaaaat aaggctagtc    60
cgttatcaac ttgaaaaagt ggcaccgagt cggtgctttt tgttttt                 107

<210> SEQ ID NO 7
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggcactgcgg ctggaggtgg gttttagagc tagaaatagc aagttaaaat aaggctagtc    60
cgttatcaac ttgaaaaagt ggcaccgagt cggtgctttt tgttttt                 107

<210> SEQ ID NO 8
<211> LENGTH: 107
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 8
gaagcgcctg gcagtgtacc gttttagagc tagaaatagc aagttaaaat aaggctagtc    60
cgttatcaac ttgaaaaagt ggcaccgagt cggtgctttt ttgtttt                 107

<210> SEQ ID NO 9
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtgctgttag caccctggaa agttttagag ctagaaatag caagttaaaa taaggctagt    60
ccgttatcaa cttgaaaaag tggcaccgag tcggtgcttt tttgtttt                108

<210> SEQ ID NO 10
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gtggcagagc ggccagcgct gttttagagc tagaaatagc aagttaaaat aaggctagtc    60
cgttatcaac ttgaaaaagt ggcaccgagt cggtgctttt ttgtttt                 107

<210> SEQ ID NO 11
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gcacccagac cgccaagctg agttttagag ctagaaatag caagttaaaa taaggctagt    60
ccgttatcaa cttgaaaaag tggcaccgag tcggtgcttt tttgtttt                108

<210> SEQ ID NO 12
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacccaggac tcctccctgc gttttagagc tagaaatagc aagttaaaat aaggctagtc    60
cgttatcaac ttgaaaaagt ggcaccgagt cggtgctttt ttgtttt                 107

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 13
gcaagcagag gctgaagctg agttttagag ctagaaatag caagttaaaa taaggctagt        60
ccgttatcaa cttgaaaaag tggcaccgag tcggtgcttt tttgtttt                    108

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggcccagact gagcacgtga                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaacacaaag catagactgc                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcactgcgg ctggaggtgg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaagcgcctg gcagtgtacc                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gacccacggc gtgcagtgct t                                                  21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
gtgctgttag caccctggaa a                                          21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgtgggctg cctagaaagg                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccagccaaa cttgtcaacc                                            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccagccccat ctgtcaaact                                            20

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgaatggatt ccttggaaac aatga                                      25

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggtcttctt tcccctcccc tgccctcc                                   28

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
ggcctggagg cgggggctca gaga                                          24

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggacgagacc atgaaggagt tgaaggc                                       27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccacctgctc cttcacctcg tccag                                         25

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggcccagact gagcacgtga                                               20

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggcctgggtc aa                                                       12

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcctttcct ctg                                                      13

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
```

```
tcacgtgctc agtctgggcc                                               20
```

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
gaggaaagga agccctgct                                                19
```

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

```
caggccaggg ctgga                                                    15
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
gaacacaaag catagactgc                                               20
```

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
cccgctggcc ctgt                                                     14
```

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
tcaggctggc ccgc                                                     14
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
gcagtctatg ctttgtgttc                                              20
```

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
ccagcccgct ggccctgta                                               19
```

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
agctattcag gct                                                     13
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
gtggcactgc ggctggaggt                                              20
```

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gatgacaggc aggggca                                                 17
```

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
cagcaccaga                                                         10
```

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
acctccagcc gcagtgcc                                                18
```

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgcggtgcc cctgcct                                                    17

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aagcggagac tctggtgc                                                   18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gaagcgcctg gcagtgtacc                                                 20

<210> SEQ ID NO 47
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctgcgcaagc tgcg                                                       14

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcggcgccct cgcg                                                       14

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggtacactgc caggcgcttc                                                 20

```
<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggatggcgct ga                                                             12

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcctcgcctc ccacc                                                          15

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatgcgcttc cggaagacc                                                      19

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcttcttgag cttctcagcg                                                     20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggtagcatgt tcaggcacca g                                                   21

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
catccctagt accgaatccc atatagc                                             27
```

```
<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
catcctccca cctaagcctt tcaa                                            24

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttgagttaat agcattataa caatttccac a                                    31

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
actccttaca accggaaggc aaac                                            24

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggacgtggt gaagcccgtg gtg                                             23

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
taggtctcta gggggcctct g                                               21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggctgccca acagccccac t                                               21

<210> SEQ ID NO 62
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
tcccctgttg acctggagaa                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cactgtactt gccctgacca                                               20

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tgagatgtgg gcagaaggg                                                19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ttggtgttga cagggagcaa                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gtccaaaggc ccaagaacct                                               20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
tgagagggaa cagaagggct                                               20

<210> SEQ ID NO 68
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gctcatctta atctgctcag cc                                              22

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tcctagcact ttggaaggtc g                                               21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaaggagcag ctcttcctgg                                                 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtctgcacca tctcccacaa                                                 20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgtggagag tgagtaagcc a                                               21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acggtaggat gatttcaggc a                                               21

<210> SEQ ID NO 74
<211> LENGTH: 26
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 74 tttttttggta ctcgagtgtt attcag                                          26

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cacaaagcag tgtagctcag g                                                21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggcatggctt ctgagactca                                                  20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccccttgcac tccctgtctt t                                                21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gaagaggctg cccatgagag                                                  20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tttggcaatg gaggcattgg                                                  20

<210> SEQ ID NO 80
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 80
ggtctgaggc tcgaatcctg                                                   20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgtggcctc catatccctg                                                   20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tttccaccag aactcagccc                                                   20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cctcggttcc tccacaacac                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gcaggggagg gataaagcag                                                   20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cacgggaagg acaggagaag                                                   20

<210> SEQ ID NO 86
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 86
atgtgggctg cctagaaagg                                            20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cccagccaaa cttgtcaacc                                            20

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggacgagacc atgaaggagt tgaaggc                                    27

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccacctgctc cttcacctcg tccag                                      25

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gacccacggc gtgcagtgct t                                          21

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggcccagact gagcacgtga                                            20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
gaacacaaag catagactgc                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggcactgcgg ctggaggtgg                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaagcgcctg gcagtgtacc                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gtggcagagc ggccagcgct                                              20

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gcacccagac cgccaagctg a                                            21

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gacccaggac tcctccctgc                                              20

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 98
gcaagcagag gctgaagctg a                                              21

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gggtcttcga gaagacct                                                  18

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
atgtgggctg cctagaaagg                                                20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cccagccaaa cttgtcaacc                                                20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ccagccccat ctgtcaaact                                                20

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tgaatggatt ccttggaaac aatga                                          25

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 104
tggtcttctt tccctcccc tgccctcc                                          28

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggcctggagg cggggctca gaga                                              24

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggacgagacc atgaaggagt tgaaggc                                          27

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ccacctgctc cttcacctcg tccag                                            25

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tcagaaggac cctgacccac ct                                               22

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atgaaacctg gacctgggga ggtata                                           26

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
```
agctgtgacc ggcgcctacg                                           20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggattctcc tccacgtcac                                           20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gatgcgcttc cggaagacc                                            19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gcttcttgag cttctcagcg                                           20

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggtagcatgt tcaggcacca g                                         21

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
catccctagt accgaatccc atatagc                                   27

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
catcctccca cctaagcctt tcaa                                              24

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ttgagttaat agcattataa caatttccac a                                      31

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gatacaccat aaagggttt gactg                                              25

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
accatttccc cccaattcta ctc                                               23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
catctgcatt ggcttgaaac atc                                               23

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ttacaaaagt gctaaatgat gcacat                                            26

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
actcagtaaa gctcctcttc aac                                               23

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ttttgcttag gtccactggg c                                          21

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gttgatgggg tggttcagga                                            20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gttgatgagg tggttcagga                                            20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gaacacaaag catagactgc                                            20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gagtatgagg catagactgc                                            20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gatgagataa tgatgagtca                                            20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggattgaccc aggccagggc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gtagaaaaag tatagactgc                                              20

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcttgaccaa tagccttgac a                                            21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gatatttgca ttgagatagt g                                            21

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gaaaatagtt gaagaaaaag                                              20

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcacagaaga taccgagact g                                            21

-continued

```
<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gggtcttcga gaagacct                                                       18

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tccttggaaa caatgataac aagac                                               25

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ccagccccat ctgtcaaact                                                     20

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gcttatattc tagggagaca gacat                                               25

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acctgaggtc agaagtttga ga                                                  22

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gtctgaggtc acacagtggg                                                     20

<210> SEQ ID NO 141
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
agagcaggga ccacatctac                                                   20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gccaaacttg tcaaccagta                                                   20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
atgtgggctg cctagaaagg                                                   20

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tccatttata tgaaatgttc agaaaaggca aat                                    33

<210> SEQ ID NO 145
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gtaactatat gctctctgat tctcctatta gc                                     32

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cctaccttcc cagggttt                                                     18

<210> SEQ ID NO 147
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
aagaagtcct ggtatcttct atg                                                23

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tcagacgttc cagaagcgag                                                    20

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gacaagaagg tgaaaaacgg ctg                                                23

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gattcaaagc ataccagaga atagt                                              25

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tcaaactagt atgcatttca acaac                                              25

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gagtgtagct gttttctca ggtt                                                24

<210> SEQ ID NO 153
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 153
gaatacccaa ccataagaag aacag                                         25

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gaacacaaag catagactgc                                               20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gagtatgagg catagactgc                                               20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gatgagataa tgatgagtca                                               20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggattgaccc aggccagggc                                               20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gcagtctata cttttttctac                                              20

<210> SEQ ID NO 159
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 159
cttgaccaat agccttgaca                                                    20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
atatttgcat tgagatagtg                                                    20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 gaaatagtt gaagaaaaag                                                     20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cacagaagat accgagactg                                                    20

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cagcattatc catttgctgc ca                                                 22

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
tggagacagc gagtctacag c                                                  21

<210> SEQ ID NO 165
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 165
taacaccatt atagctgaag tgggg                                          25

<210> SEQ ID NO 166
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tgagttacac acaagccagt taaattc                                        27

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
agggagtgga catgaggcga                                                20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
cccaagagga agtcccaagg                                                20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ccttgggaag agaagggggtc                                               20

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gagataccgg aagctttgat gtaaga                                         26

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 171
cttggggaga aaggtccagg                                           20

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
caagcttttc ctcctgggat gtaaaa                                    26

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ctggcaagct gttctcacat g                                         21

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gaggctgagg caggagtatg                                           20

<210> SEQ ID NO 175
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gttttcagta gaagagtata taatacataa t                              31

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
atattctcag cctaggcctg                                           20

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tgttggacat gggtgcctta tt                                            22

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ttcaccctct ctggatggcg                                               20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gcaggaggag gcagtgaaag                                               20

<210> SEQ ID NO 180
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cagagaaata acactctggc agctg                                         25

<210> SEQ ID NO 181
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cagcatttat cacgcagtat tgttattg                                      28

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tcatttcgtg ttgtgcttta tcacttaaaa                                    30

<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gtgagcagta aacttaattg ttgatacaat aaatc                                    35

<210> SEQ ID NO 184
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cttttagaat gaaagtgtgc atcttagtaa agaaa                                    35

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gttcctcact gattctcagc agg                                                 23

<210> SEQ ID NO 186
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cacaaaaggg ataaatgctc tatccattt                                           29

<210> SEQ ID NO 187
<211> LENGTH: 3439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
tcgcgcgttt cggtgatgac ggtgaaaacc tctgacacat gcagctcccg gagacggtca         60
cagcttgtct gtaagcggat gccgggagca gacaagcccg tcaggcgcg tcagcgggtg        120 ttggcgggtg tcgggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta acgccagggt        360
tttcccagtc acgacgttgt aaaacgacgg ccagtgaatt cgagggccta tttcccatga        420
ttccttcata tttgcatata cgatacaagg ctgttagaga gataattgga attaatttga        480
ctgtaaacac aaagatatta gtacaaaata cgtgacgtag aaagtaataa tttcttgggt        540
agtttgcagt tttaaaatta tgttttaaaa tggactatca tatgcttacc gtaacttgaa        600
agtatttcga tttcttggct ttatatatct tgtggaaagg acgaaacacc gttgatgggg        660
tggttcagga gttttagagc tagaaatagc aagttaaaat aaggctagtc cgttatcaac        720
ttgaaaaagt ggcaccgagt cggtgctttt ttgttttaga gctagaaata gcaagttaaa        780

```
ataaggctag tccgttttta gcgcgtgcgc caattctgca gacagagagg gcctatttcc    840
catgattcct tcatatttgc atatacgata caaggctgtt agagagataa ttggaattaa    900
tttgactgta aacacaaaga tattagtaca aaatacgtga cgtagaaagt aataatttct    960
tgggtagttt gcagttttaa aattatgttt taaaatggac tatcatatgc ttaccgtaac   1020
ttgaaagtat ttcgatttct tggctttata tatcttgtgg aaaggacgaa acaccgggtc   1080
ttcgagaaga cctgttttag agctagaaat agcaagttaa ataaggcta gtccgttatc    1140
aacttgaaaa agtggcaccg agtcggtgct ttttttctag agtcgacctg caggcatgca   1200
agcttggcgt aatcatggtc atagctgttt cctgtgtgaa attgttatcc gctcacaatt   1260
ccacacaaca tacgagccgg aagcataaag tgtaaagcct ggggtgccta atgagtgagc   1320
taactcacat taattgcgtt gcgctcactg cccgctttcc agtcgggaaa cctgtcgtgc   1380
cagctgcatt aatgaatcgg ccaacgcgcg gggagaggcg gtttgcgtat tgggcgctct   1440
tccgcttcct cgctcactga ctcgctgcgc tcggtcgttc ggctgcggcg agcggtatca   1500
gctcactcaa aggcggtaat acggttatcc acagaatcag gggataacgc aggaaagaac   1560
atgtgagcaa aaggccagca aaaggccagg aaccgtaaaa aggccgcgtt gctggcgttt   1620
ttccataggc tccgccccc tgacgagcat cacaaaaatc gacgctcaag tcagaggtgg   1680
cgaaacccga caggactata agataccag gcgtttcccc ctggaagctc cctcgtgcgc   1740
tctcctgttc cgaccctgcc gcttaccgga tacctgtccg cctttctccc ttcgggaagc   1800
gtggcgcttt ctcatagctc acgctgtagg tatctcagtt cggtgtaggt cgttcgctcc   1860
aagctgggct gtgtgcacga accccccgtt cagcccgacc gctgcgcctt atccggtaac   1920
tatcgtcttg agtccaaccc ggtaagacac gacttatcgc cactggcagc agccactggt   1980
aacaggatta gcagagcgag gtatgtaggc ggtgctacag agttcttgaa gtggtggcct   2040
aactacggct acactagaag aacagtattt ggtatctgcg ctctgctgaa gccagttacc   2100
ttcggaaaaa gagttggtag ctcttgatcc ggcaaacaaa ccaccgctgg tagcggtggt   2160
tttttgttt gcaagcagca gattacgcgc agaaaaaaag gatctcaaga agatcctttg   2220
atcttttcta cggggtctga cgctcagtgg aacgaaaact cacgttaagg gattttggtc   2280
atgagattat caaaaaggat cttcacctag atccttttaa attaaaaatg aagttttaaa   2340
tcaatctaaa gtatatatga gtaaacttgg tctgacagtt accaatgctt aatcagtgag   2400
gcacctatct cagcgatctg tctatttcgt tcatccatag ttgcctgact ccccgtcgtg   2460
tagataacta cgatacggga gggcttacca tctggcccca gtgctgcaat gataccgcga   2520
gacccacgct caccggctcc agatttatca gcaataaacc agccagccgg aagggccgag   2580
cgcagaagtg gtcctgcaac tttatccgcc tccatccagt ctattaattg ttgccgggaa   2640
gctagagtaa gtagttcgcc agttaatagt ttgcgcaacg ttgttgccat tgctacaggc   2700
atcgtggtgt cacgctcgtc gtttggtatg gcttcattca gctccggttc caacgatca   2760
aggcgagtta catgatcccc catgttgtgc aaaaaagcgg ttagctcctt cggtcctccg   2820
atcgttgtca gaagtaagtt ggccgcagtg ttatcactca tggttatggc agcactgcat   2880
aattctctta ctgtcatgcc atccgtaaga tgcttttctg tgactggtga gtactcaacc   2940
aagtcattct gagaatagtg tatgcggcga ccgagttgct cttgcccggc gtcaatacgg   3000
gataataccg cgccacatag cagaacttta aaagtgctca tcattggaaa acgttcttcg   3060
gggcgaaaac tctcaaggat cttaccgctg ttgagatcca gttcgatgta acccactcgt   3120
```

```
gcacccaact gatcttcagc atcttttact ttcaccagcg tttctgggtg agcaaaaaca    3180
ggaaggcaaa atgccgcaaa aagggaata agggcgacac ggaaatgttg aatactcata    3240
ctcttccttt ttcaatatta ttgaagcatt tatcagggtt attgtctcat gagcggatac    3300
atatttgaat gtatttagaa aaataaacaa ataggggttc cgcgcacatt tccccgaaaa    3360
gtgccacctg acgtctaaga aaccattatt atcatgacat taacctataa aaataggcgt    3420
atcacgaggc cctttcgtc                                                 3439

<210> SEQ ID NO 188
<211> LENGTH: 3439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagggccta tttcccatga     420
ttccttcata tttgcatata cgatacaagg ctgttagaga gataattgga attaatttga     480
ctgtaaacac aaagatatta gtacaaaata cgtgacgtag aaagtaataa tttcttgggt     540
agtttgcagt tttaaaatta tgttttaaaa tggactatca tatgcttacc gtaacttgaa     600
agtatttcga tttcttggct ttatatatct tgtggaaagg acgaaacacc gttgatgagg     660
tggttcagga gttttagagc tagaaatagc aagttaaaat aaggctagtc cgttatcaac     720
ttgaaaaagt ggcaccgagt cggtgctttt tgttttaga gctagaaata gcaagttaaa     780
ataaggctag tccgttttta gcgcgtgcgc caattctgca gacagagagg gcctatttcc     840
catgattcct tcatatttgc atatacgata caaggctgtt agagagataa ttggaattaa     900
tttgactgta aacacaaaga tattagtaca aaatacgtga cgtagaaagt aataatttct     960
tgggtagttt gcagttttaa aattatgttt taaaatggac tatcatatgc ttaccgtaac    1020
ttgaaagtat ttcgatttct tggctttata tatcttgtgg aaaggacgaa acaccgggtc    1080
ttcgagaaga cctgttttag agctagaaat agcaagttaa aataaggcta gtccgttatc    1140
aacttgaaaa agtggcaccg agtcggtgct ttttttctag agtcgacctg caggcatgca    1200
agcttggcgt aatcatggtc atagctgttt cctgtgtgaa attgttatcc gctcacaatt    1260
ccacacaaca tacgagccgg aagcataaag tgtaaagcct ggggtgccta atgagtgagc    1320
taactcacat taattgcgtt gcgctcactg cccgctttcc agtcgggaaa cctgtcgtgc    1380
cagctgcatt aatgaatcgg ccaacgcgcg gggagaggcg gtttgcgtat tgggcgctct    1440
tccgcttcct cgctcactga ctcgctgcgc tcggtcgttc ggctgcggcg agcggtatca    1500
gctcactcaa aggcggtaat acggttatcc acagaatcag gggataacgc aggaaagaac    1560
atgtgagcaa aaggccagca aaaggccagg aaccgtaaaa aggccgcgtt gctggcgttt    1620
ttccataggc tccgcccccc tgacgagcat cacaaaaatc gacgctcaag tcagaggtgg    1680
```

```
cgaaacccga caggactata aagataccag gcgtttcccc ctggaagctc cctcgtgcgc    1740
tctcctgttc cgaccctgcc gcttaccgga tacctgtccg cctttctccc ttcgggaagc    1800
gtggcgcttt ctcatagctc acgctgtagg tatctcagtt cggtgtaggt cgttcgctcc    1860
aagctgggct gtgtgcacga accccccgtt cagcccgacc gctgcgcctt atccggtaac    1920
tatcgtcttg agtccaaccc ggtaagacac gacttatcgc cactggcagc agccactggt    1980
aacaggatta gcagagcgag gtatgtaggc ggtgctacag agttcttgaa gtggtggcct    2040
aactacggct acactagaag aacagtattt ggtatctgcg ctctgctgaa gccagttacc    2100
ttcggaaaaa gagttggtag ctcttgatcc ggcaaacaaa ccaccgctgg tagcggtggt    2160 tttttttgttt gcaagcagca gattacgcgc agaaaaaaag gatctcaaga agatcctttg    2220
atcttttcta cggggtctga cgctcagtgg aacgaaaact cacgttaagg gattttggtc    2280
atgagattat caaaaaggat cttcacctag atccttttaa attaaaaatg aagttttaaa    2340
tcaatctaaa gtatatatga gtaaacttgg tctgacagtt accaatgctt aatcagtgag    2400
gcacctatct cagcgatctg tctatttcgt tcatccatag ttgcctgact ccccgtcgtg    2460
tagataacta cgatacggga gggcttacca tctggcccca gtgctgcaat gataccgcga    2520
gacccacgct caccggctcc agatttatca gcaataaacc agccagccgg aagggccgag    2580
cgcagaagtg gtcctgcaac tttatccgcc tccatccagt ctattaattg ttgccgggaa    2640
gctagagtaa gtagttcgcc agttaatagt ttgcgcaacg ttgttgccat tgctacaggc    2700
atcgtggtgt cacgctcgtc gtttggtatg gcttcattca gctccggttc ccaacgatca    2760
aggcgagtta catgatcccc catgttgtgc aaaaaagcgg ttagctcctt cggtcctccg    2820
atcgttgtca gaagtaagtt ggccgcagtg ttatcactca tggttatggc agcactgcat    2880
aattctctta ctgtcatgcc atccgtaaga tgcttttctg tgactggtga gtactcaacc    2940
aagtcattct gagaatagtg tatgcggcga ccgagttgct cttgcccggc gtcaatacgg    3000
gataataccg cgccacatag cagaacttta aaagtgctca tcattggaaa acgttcttcg    3060
gggcgaaaac tctcaaggat cttaccgctg ttgagatcca gttcgatgta acccactcgt    3120
gcacccaact gatcttcagc atcttttact ttcaccagcg tttctgggtg agcaaaaaca    3180
ggaaggcaaa atgccgcaaa aaagggaata agggcgacac ggaaatgttg aatactcata    3240
ctcttccttt ttcaatatta ttgaagcatt tatcagggtt attgtctcat gagcggatac    3300
atatttgaat gtatttagaa aaataaacaa ataggggttc cgcgcacatt tccccgaaaa    3360
gtgccacctg acgtctaaga aaccattatt atcatgacat taacctataa aaataggcgt    3420
atcacgaggc cctttcgtc                                                 3439
```

<210> SEQ ID NO 189
<211> LENGTH: 5849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189

```
gtcgacattg attattgact agatcatcgc gtgaggctcc ggtgcccgtc agtgggcaga      60
gcgcacatcg cccacagtcc ccgagaagtt ggggggaggg gtcggcaatt gaaccggtgc     120
ctagagaagg tggcgcgggg taaactggga aagtgatgtc gtgtactggc tccgcctttt     180
tcccgagggt gggggagaac cgtatataag tgcagtagtc gccgtgaacg ttcttttttcg     240
```

```
caacgggttt gccgccagaa cacaggtaag tgccgtgtgt ggttcccgcg ggcctggcct    300
ctttacgggt tatggccctt gcgtgccttg aattacttcc acgccctgg ctgcagtacg     360 tgattcttga tcccgagctt cgggttggaa gtgggtggga gagttcgagg ccttgcgctt    420
aaggagcccc ttcgcctcgt gcttgagttg aggcctggcc tgggcgctgg ggccgccgcg    480
tgcgaatctg gtggcacctt cgcgcctgtc tcgctgcttt cgataagtct ctagccattt    540 aaaattttg atgacctgct gcgacgcttt ttttctggca agatagtctt gtaaatgcgg      600
gccaagatct gcacactggt atttcggttt ttggggccgc gggcggcgac ggggcccgtg    660
cgtcccagcg cacatgttcg gcgaggcggg gcctgcgagc gcggccaccg agaatcggac    720 ggggggtagtc tcaagctggc cggcctgctc tggtgcctgg cctcgcgccg ccgtgtatcg    780
ccccgccctg ggcggcaagg ctggcccggt cggcaccagt tgcgtgagcg gaaagatggc    840
cgcttcccgg ccctgctgca gggagctcaa aatggaggac gcggcgctcg ggagagcggg    900
cgggtgagtc acccacacaa aggaaaaggg cctttccgtc ctcagccgtc gcttcatgtg    960
actccacgga gtaccgggcg ccgtccaggc acctcgatta gttctcgagc tttttggagta  1020 cgtcgtcttt aggttggggg gagggttttt atgcgatgga gtttccccac actgagtggg  1080
tggagactga agttaggcca gcttggcact tgatgtaatt ctccttggaa tttgcccttt   1140
ttgagtttgg atcttggttc attctcaagc ctcagacagt ggttcaaagt ttttttcttc   1200
catttcaggt gtcgtgagga attctgcagt cgacggtacc gcctacgcta gcgctaccgg    1260
tcgccaccat ggtgagcaag ggcgaggagg ataacatggc catcatcaag gagttcatgc   1320
gcttcaaggt gcatgggag ggctccgtga acggccacga gttcgagatc gagggcgagg    1380
gcgagggccg ccctacgag ggcacccaga ccgccaagct gaaggtgacc aagggtggcc     1440
ccctgccctt cgcctgggac atcctgtccc ctcagttcat gtacggctcc aaggcctacg   1500
tgaagcaccc cgccgacatc cccgactact gaagctgtc cttccccgag ggcttcaagt    1560
gggagcgcgt gatgaacttc gaggacggcg gcgtggtgac cgtgacccag gactcctccc   1620
tgcaggacgg cgagttcatc tacaaggtga agctgcgcgg caccaacttc ccctccgacg   1680
gccccgtaat gcagaagaag accatgggct gggaggcctc ctccgagcgg atgtaccccg   1740
aggacggcgc cctgaagggc gagatcaagc agaggctgaa gctgaaggac ggcggccact   1800
acgacgctga ggtcaagacc acctacaagg ccaagaagcc cgtgcagctg cccggcgcct   1860
acaacgtcaa catcaagttg gacatcacct cccacaacga ggactacacc atcgtggaac   1920
agtacgaacg cgccgagggc cgccactcca ccggcggcat ggacgagctg tacaagcccc   1980
gggagggcag aggaagtctt ctaacatgcg gtgacgtgga ggagaatccc ggccctacta   2040
gttgatgggg tggttcagga ggggcatgcg tgagcaaggg cgaggagctg ttcaccgggg   2100
tggtgcccat cctggtcgag ctggacggcg acgtaaacgg ccacaagttc agcgtgtccg   2160
gcgagggcga gggcgatgcc acctacggca agctgaccct gaagttcatc tgcaccaccg   2220
gcaagctgcc cgtgccctgg cccacccctcg tgaccaccct gacctacggc gtgcagtgct   2280
tcagccgcta ccccgaccac atgaagcagc acgacttctt caagtccgcc atgcccgaag   2340
gctacgtcca ggagcgcacc atcttcttca aggacgacgg caactacaag acccgcgccg   2400
aggtgaagtt cgagggcgac accctggtga accgcatcga gctgaagggc atcgacttca   2460
aggaggacgg caaatccctg ggcacaagc tggagtacaa ctacaacagc cacaacgtct   2520
atatcatggc cgacaagcag aagaacggca tcaaggtgaa cttcaagatc cgccacaaca   2580
tcgaggacgg cagcgtgcag ctcgccgacc actaccagca gaacacccc atcggcgacg    2640
```

```
gccccgtgct gctgcccgac aaccactacc tgagcaccca gtccgccctg agcaagacc      2700 ccaacgagaa gcgcgatcac atggtcctgc tggagttcgt gaccgccgcc gggatcactc      2760
tcggcatgga cgagctgtac aagtaaagcg gccgcactcc tcaggtgcag gctgcctatc      2820
agaaggtggt ggctggtgtg gccaatgccc tggctcacaa ataccactga gatctttttc      2880
cctctgccaa aaattatggg gacatcatga agccccttga gcatctgact tctggctaat      2940
aaaggaaatt tattttcatt gcaatagtgt gttggaattt tttgtgtctc tcactcggaa      3000
ggacatatgg gagggcaaat catttaaaac atcagaatga gtatttggtt tagagtttgg      3060
caacatatgc catatgctgg ctgccatgaa caaaggtggc tataaagagg tcatcagtat      3120
atgaaacagc ccctgctgt ccattcctta ttccatagaa aagccttgac ttgaggttag      3180 attttttta tattttgttt tgtgttattt ttttctttaa catccctaaa attttcctta      3240
catgttttac tagccagatt tttcctcctc tcctgactac tcccagtcat agctgtccct      3300
cttctcttat gaagatccct cgacctgcag cccaagcttg gcgtaatcat ggtcatagct      3360
gtttcctgtg tgaaattgtt atccgctcac aattccacac aacatacgag ccggaagcat      3420
aaagtgtaaa gcctggggtg cctaatgagt gagctaactc acattaattg cgttgcgctc      3480
actgcccgct ttccagtcgg gaaacctgtc gtgccagcgg atccgcatct caattagtca      3540
gcaaccatag tcccgcccct aactccgccc atccgcccc taactccgcc cagttccgcc      3600
cattctccgc cccatggctg actaattttt tttatttatg cagaggccga ggccgcctcg      3660
gcctctgagc tattccagaa gtagtgagga ggcttttttg gaggcctagg cttttgcaaa      3720
aagctaactt gtttattgca gcttataatg gttacaaata aagcaatagc atcacaaatt      3780
tcacaaataa agcatttttt tcactgcatt ctagttgtgg tttgtccaaa ctcatcaatg      3840
tatcttatca tgtctggatc cgctgcatta atgaatcggc caacgcgcgg ggagaggcgg      3900
tttgcgtatt gggcgctctt ccgcttcctc gctcactgac tcgctgcgct cggtcgttcg      3960
gctgcggcga gcggtatcag ctcactcaaa ggcggtaata cggttatcca cagaatcagg      4020
ggataacgca ggaaagaaca tgtgagcaaa aggccagcaa aaggccagga accgtaaaaa      4080
ggccgcgttg ctggcgtttt tccataggct ccgcccccct gacgagcatc acaaaaatcg      4140
acgctcaagt cagaggtggc gaaacccgac aggactataa agataccagg cgtttccccc      4200
tggaagctcc ctcgtgcgct ctcctgttcc gaccctgccg cttaccggat acctgtccgc      4260
ctttctccct tcgggaagcg tggcgctttc tcaatgctca cgctgtaggt atctcagttc      4320
ggtgtaggtc gttcgctcca agctgggctg tgtgcacgaa ccccccgttc agcccgaccg      4380
ctgcgcctta tccggtaact atcgtcttga gtccaacccg gtaagacacg acttatcgcc      4440
actggcagca gccactggta acaggattag cagagcgagg tatgtaggcg gtgctacaga      4500
gttcttgaag tggtggccta actacggcta cactagaagg acagtatttg gtatctgcgc      4560
tctgctgaag ccagttacct tcggaaaaag agttggtagc tcttgatccg gcaaacaaac      4620
caccgctggt agcggtggtt tttttgtttg caagcagcag attacgcgca gaaaaaaagg      4680
atctcaagaa gatcctttga tcttttctac ggggtctgac gctcagtgga acgaaaactc      4740
acgttaaggg attttggtca tgagattatc aaaaaggatc ttcacctaga tccttttaaa      4800
ttaaaaatga agttttaaat caatctaaag tatatatgag taaacttggt ctgacagtta      4860
ccaatgctta atcagtgagg cacctatctc agcgatctgt ctatttcgtt catccatagt      4920
tgcctgactc cccgtcgtgt agataactac gatacgggag ggcttaccat ctggccccag      4980
```

| | |
|---|---|
| tgctgcaatg ataccgcgag acccacgctc accggctcca gatttatcag caataaacca | 5040 |
| gccagccgga agggccgagc gcagaagtgg tcctgcaact ttatccgcct ccatccagtc | 5100 |
| tattaattgt tgccgggaag ctagagtaag tagttcgcca gttaatagtt tgcgcaacgt | 5160 |
| tgttgccatt gctacaggca tcgtggtgtc acgctcgtcg tttggtatgg cttcattcag | 5220 |
| ctccggttcc caacgatcaa ggcgagttac atgatccccc atgttgtgca aaaaagcggt | 5280 |
| tagctccttc ggtcctccga tcgttgtcag aagtaagttg gccgcagtgt tatcactcat | 5340 |
| ggttatggca gcactgcata attctcttac tgtcatgcca tccgtaagat gcttttctgt | 5400 |
| gactggtgag tactcaacca agtcattctg agaatagtgt atgcggcgac cgagttgctc | 5460 |
| ttgcccggcg tcaatacggg ataataccgc gccacatagc agaactttaa aagtgctcat | 5520 |
| cattggaaaa cgttcttcgg ggcgaaaact ctcaaggatc ttaccgctgt tgagatccag | 5580 |
| ttcgatgtaa cccactcgtg cacccaactg atcttcagca tcttttactt tcaccagcgt | 5640 |
| ttctgggtga gcaaaaacag gaaggcaaaa tgccgcaaaa aagggaataa gggcgacacg | 5700 |
| gaaatgttga atactcatac tcttcctttt tcaatattat tgaagcattt atcagggtta | 5760 |
| ttgtctcatg agcggataca tatttgaatg tatttagaaa aataaacaaa taggggttcc | 5820 |
| gcgcacattt ccccgaaaag tgccacctg | 5849 |

<210> SEQ ID NO 190
<211> LENGTH: 5849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190

| | |
|---|---|
| gtcgacattg attattgact agatcatcgc gtgaggctcc ggtgcccgtc agtgggcaga | 60 |
| gcgcacatcg cccacagtcc ccgagaagtt ggggggaggg tcggcaatt gaaccggtgc | 120 |
| ctagagaagg tggcgcgggg taaactggga aagtgatgtc gtgtactggc tccgcctttt | 180 |
| tcccgagggt gggggagaac cgtatataag tgcagtagtc gccgtgaacg ttctttttcg | 240 |
| caacgggttt gccgccagaa cacaggtaag tgccgtgtgt ggttcccgcg ggcctggcct | 300 |
| ctttacgggt tatggccctt gcgtgccttg aattacttcc acgccctgg ctgcagtacg | 360 |
| tgattcttga tcccgagctt cgggttggaa gtgggtggga gagttcgagg ccttgcgctt | 420 |
| aaggagcccc ttcgcctcgt gcttgagttg aggcctggcc tgggcgctgg ggccgccgcg | 480 |
| tgcgaatctg gtggcacctt cgcgcctgtc tcgctgcttt cgataagtct ctagccattt | 540 |
| aaaattttg atgacctgct gcgacgcttt ttttctggca agatagtctt gtaaatgcgg | 600 |
| gccaagatct gcacactggt atttcggttt tggggccgc gggcggcgac ggggcccgtg | 660 |
| cgtcccagcg cacatgttcg gcgaggcggg gcctgcgagc gcggccaccg agaatcggac | 720 |
| gggggtagtc tcaagctggc cggcctgctc tggtgcctgg cctcgcgccg ccgtgtatcg | 780 |
| ccccgccctg ggcggcaagg ctggcccggt cggcaccagt tgccgtgagc gaaagatggc | 840 |
| cgcttccggg ccctgctgca gggagctcaa aatggaggac gcggcgctcg ggagagcggg | 900 |
| cgggtgagtc acccacacaa aggaaaaggg cctttccgtc ctcagccgtc gcttcatgtg | 960 |
| actccacgga gtaccgggcg ccgtccaggc acctcgatta gttctcgagc ttttggagta | 1020 |
| cgtcgtcttt aggttggggg gaggggtttt atgcgatgga gtttccccac actgagtggg | 1080 |
| tggagactga agttaggcca gcttggcact tgatgtaatt ctccttggaa tttgcccttt | 1140 |

```
ttgagtttgg atcttggttc attctcaagc ctcagacagt ggttcaaagt ttttttcttc    1200
catttcaggt gtcgtgagga attctgcagt cgacggtacc gcctacgcta gcgctaccgg    1260
tcgccaccat ggtgagcaag ggcgaggagg ataacatggc catcatcaag gagttcatgc    1320
gcttcaaggt gcacatggag ggctccgtga acggccacga gttcgagatc gagggcgagg    1380
gcgagggccg cccctacgag ggcacccaga ccgccaagct gaaggtgacc aagggtggcc    1440
ccctgccctt cgcctgggac atcctgtccc ctcagttcat gtacggctcc aaggcctacg    1500
tgaagcaccc cgccgacatc cccgactact gaagctgtc cttccccgag ggcttcaagt    1560
gggagcgcgt gatgaacttc gaggacggcg gcgtggtgac cgtgacccag gactcctccc    1620
tgcaggacgg cgagttcatc tacaaggtga agctgcgcgg caccaacttc ccctccgacg    1680
gccccgtaat gcagaagaag accatggcc gggaggcctc ctccgagcgg atgtaccccg    1740
aggacggcgc cctgaagggc gagatcaagc agaggctgaa gctgaaggac ggcggccact    1800
acgacgctga ggtcaagacc acctacaagg ccaagaagcc cgtgcagctg cccggcgcct    1860
acaacgtcaa catcaagttg gacatcacct cccacaacga ggactacacc atcgtggaac    1920
agtacgaacg cgccgagggc cgccactcca ccggcggcat ggacgagctg tacaagcccc    1980
gggagggcag aggaagtctt ctaacatgcg gtgacgtgga ggagaatccc ggccctacta    2040
gttgatgagg tggttcagga ggggcatgcg tgagcaaggg cgaggagctg ttcaccgggg    2100
tggtgcccat cctggtcgag ctggacgcg acgtaaacgg ccacaagttc agcgtgtccg    2160
gcgagggcga gggcgatgcc acctacggca agctgaccct gaagttcatc tgcaccaccg    2220
gcaagctgcc cgtgccctgg cccaccctcg tgaccaccct gacctacggc gtgcagtgct    2280
tcagccgcta ccccgaccac atgaagcagc acgacttctt caagtccgcc atgcccgaag    2340
gctacgtcca ggagcgcacc atcttcttca aggacgacgg caactacaag acccgcgccg    2400
aggtgaagtt cgagggcgac accctggtga accgcatcga gctgaagggc atcgacttca    2460
aggaggacgg caacatcctg gggcacaagc tggagtacaa ctacaacagc cacaacgtct    2520
atatcatggc cgacaagcag aagaacggca tcaaggtgaa cttcaagatc cgccacaaca    2580
tcgaggacgg cagcgtgcag ctcgccgacc actaccagca gaacacccc atcggcgacg    2640 gccccgtgct gctgcccgac aaccactacc tgagcaccca gtccgccctg agcaaagacc    2700
ccaacgagaa gcgcgatcac atggtcctgc tggagttcgt gaccgccgcc gggatcactc    2760
tcggcatgga cgagctgtac aagtaaagcg gccgcactcc tcaggtgcag gctgcctatc    2820
agaaggtggt ggctggtgtg gccaatgccc tggctcacaa ataccactga gatctttttc    2880
cctctgccaa aaattatggg gacatcatga agccccttga gcatctgact tctggctaat    2940
aaaggaaatt tattttcatt gcaatagtgt gttggaattt tttgtgtctc tcactcggaa    3000
ggacatatgg gagggcaaat catttaaaac atcagaatga gtatttggtt tagagtttgg    3060
caacatatgc catatgctgg ctgccatgaa caaaggtggc tataaagagg tcatcagtat    3120
atgaaacagc cccctgctgt ccattcctta ttccatagaa aagccttgac ttgaggttag    3180
atttttttta tattttgttt tgtgttattt ttttctttaa catccctaaa attttcctta    3240
catgttttac tagccagatt tttcctcctc tcctgactac tcccagtcat agctgtccct    3300
cttctcttat gaagatccct cgacctgcag cccaagcttg gcgtaatcat ggtcatagct    3360
gtttcctgtg tgaaattgtt atccgctcac aattccacac aacatacgag ccggaagcat    3420
aaagtgtaaa gcctggggtg cctaatgagt gagctaactc acattaattg cgttgcgctc    3480
actgcccgct ttccagtcgg gaaacctgtc gtgccagcgg atccgcatct caattagtca    3540
```

```
gcaaccatag tcccgcccct aactccgccc atcccgcccc taactccgcc cagttccgcc    3600
cattctccgc cccatggctg actaattttt tttatttatg cagaggccga ggccgcctcg    3660
gcctctgagc tattccagaa gtagtgagga ggcttttttg gaggcctagg cttttgcaaa    3720
aagctaactt gtttattgca gcttataatg gttacaaata aagcaatagc atcacaaatt    3780
tcacaaataa agcattttt tcactgcatt ctagttgtgg tttgtccaaa ctcatcaatg    3840
tatcttatca tgtctggatc cgctgcatta atgaatcggc caacgcgcgg ggagaggcgg    3900
tttgcgtatt gggcgctctt ccgcttcctc gctcactgac tcgctgcgct cggtcgttcg    3960
gctgcggcga gcggtatcag ctcactcaaa ggcggtaata cggttatcca cagaatcagg    4020
ggataacgca ggaaagaaca tgtgagcaaa aggccagcaa aaggccagga accgtaaaaa    4080
ggccgcgttg ctggcgtttt tccataggct ccgcccccct gacgagcatc acaaaaatcg    4140
acgctcaagt cagaggtggc gaaacccgac aggactataa agataccagg cgtttccccc    4200
tggaagctcc ctcgtgcgct ctcctgttcc gaccctgccg cttaccggat acctgtccgc    4260 cttctccct tcgggaagcg tggcgcttc tcaatgctca cgctgtaggt atctcagttc    4320
ggtgtaggtc gttcgctcca agctgggctg tgtgcacgaa ccccccgttc agcccgaccg    4380
ctgcgcctta tccggtaact atcgtcttga gtccaacccg gtaagacacg acttatcgcc    4440
actggcagca gccactggta acaggattag cagagcgagg tatgtaggcg gtgctacaga    4500
gttcttgaag tggtggccta actacggcta cactagaagg acagtatttg gtatctgcgc    4560
tctgctgaag ccagttacct tcggaaaaag agttggtagc tcttgatccg gcaaacaaac    4620
caccgctggt agcggtggtt ttttgtttg caagcagcag attacgcgca gaaaaaaagg    4680
atctcaagaa gatcctttga tcttttctac ggggtctgac gctcagtgga acgaaaactc    4740
acgttaaggg attttggtca tgagattatc aaaaaggatc ttcacctaga tccttttaaa    4800
ttaaaaatga agttttaaat caatctaaag tatatatgag taaacttggt ctgacagtta    4860
ccaatgctta atcagtgagg cacctatctc agcgatctgt ctatttcgtt catccatagt    4920
tgcctgactc cccgtcgtgt agataactac gatacgggag ggcttaccat ctggccccag    4980
tgctgcaatg ataccgcgag acccacgctc accggctcca gatttatcag caataaacca    5040
gccagccgga agggccgagc gcagaagtgg tcctgcaact ttatccgcct ccatccagtc    5100
tattaattgt tgccgggaag ctagagtaag tagttcgcca gttaatagtt tgcgcaacgt    5160
tgttgccatt gctacaggca tcgtggtgtc acgctcgtcg tttggtatgg cttcattcag    5220
ctccggttcc caacgatcaa ggcgagttac atgatccccc atgttgtgca aaaaagcggt    5280
tagctccttc ggtcctccga tcgttgtcag aagtaagttg gccgcagtgt tatcactcat    5340
ggttatggca gcactgcata attctcttac tgtcatgcca tccgtaagat gcttttctgt    5400
gactggtgag tactcaacca agtcattctg agaatagtgt atgcggcgac cgagttgctc    5460
ttgcccggcg tcaatacggg ataataccgc gccacatagc agaactttaa aagtgctcat    5520
cattggaaaa cgttcttcgg ggcgaaaact ctcaaggatc ttaccgctgt tgagatccag    5580
ttcgatgtaa cccactcgtg cacccaactg atcttcagca tcttttactt tcaccagcgt    5640
ttctgggtga gcaaaaacag gaaggcaaaa tgccgcaaaa aagggaataa gggcgacacg    5700
gaaatgttga atactcatac tcttcctttt tcaatattat tgaagcattt atcagggtta    5760
ttgtctcatg agcggataca tatttgaatg tatttagaaa aataaacaaa taggggttcc    5820
gcgcacattt ccccgaaaag tgccacctg                                      5849
```

<210> SEQ ID NO 191
<211> LENGTH: 9319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 191

```
gctgcttcgc gatgtacggg ccagatatac gcgttgacat tgattattga ctagtcgtga      60
ggctccggtg cccgtcagtg ggcagagcgc acatcgccca cagtccccga gaagttgggg     120
ggaggggtcg gcaattgaac cggtgcctag agaaggtggc gcggggtaaa ctgggaaagt     180
gatgtcgtgt actggctccg cctttttccc gagggtgggg gagaaccgta tataagtgca     240
gtagtcgccg tgaacgttct ttttcgcaac gggtttgccg ccagaacaca ggtaagtgcc     300
gtgtgtggtt cccgcgggcc tggcctcttt acgggttatg gcccttgcgt gccttgaatt     360
acttccacgc ccctgctgc agtacgtgat tcttgatccc gagcttcggg ttggaagtgg      420
gtgggagagt tcgaggcctt gcgcttaagg agccccttcg cctcgtgctt gagttgaggc     480
ctggcctggg cgctggggcc gccgcgtgcg aatctggtgg caccttcgcg cctgtctcgc     540
tgctttcgat aagtctctag ccatttaaaa tttttgatga cctgctgcga cgcttttttt     600
ctggcaagat agtcttgtaa atgcgggcca agatctgcac actggtattt cggttttttgg    660
ggccgcgggc ggcgacgggg cccgtgcgtc ccagcgcaca tgttcggcga ggcggggcct     720
gcgagcgcgg ccaccgagaa tcggacgggg gtagtctcaa gctggccggc ctgctctggt     780
gcctggcctc gcgccgccgt gtatcgcccc gccctgggcg gcaaggctgg cccggtcggc     840
accagttgcg tgagcggaaa gatgccgct tcccggccct gctgcaggga gctcaaaatg      900
gaggacgcgg cgctcgggag agcgggcggg tgagtcaccc acacaaagga aaagggcctt     960
tccgtcctca gccgtcgctt catgtgactc cacggagtac cggcgcgcgt ccaggcacct    1020
cgattagttc tcgagctttt ggagtacgtc gtctttaggt tgggggggagg ggttttatgc    1080
gatggagttt ccccacactg agtgggtgga gactgaagtt aggccagctt ggcacttgat    1140
gtaattctcc ttggaatttg ccctttttga gtttggatct tggttcattc tcaagcctca    1200
gacagtggtt caaagttttt ttcttccatt tcaggtgtcg tgaggcggcc gctaatacga    1260
ctcactatag ggagagccgc caccatgtcc gaagtcgagt tttcccatga gtactggatg    1320
agacacgcat tgactctcgc aaagagggct tgggatgaac gcgaggtgcc cgtgggggca    1380
gtactcgtgc ataacaatcg cgtaatcggc gaaggttgga ataggccgat cggacgccac    1440
gaccccactg cacatgcgga aatcatggcc cttcgacagg gagggcttgt gatgcagaat    1500
tatcgactta tcgatgcgac gctgtacgtc acgcttgaac cttgcgtaat gtgcgcggga    1560
gctatgattc actcccgcat tggacgagtt gtattcggtg cccgcgacgc caagacgggt    1620
gccgcaggtt cactgatgga cgtgctgcat cacccaggca tgaaccaccg ggtagaaatc    1680
acagaaggca tattggcgga cgaatgtgcg gcgctgttgt ccgacttttt tcgcatgcgg    1740
aggcaggaga tcaaggccca gaaaaaagca caatcctcta ctgactctgg tggttcttct    1800
ggtggttcta gcggcagcga gactcccggg acctcagagt ccgccacacc cgaaagttct    1860
ggtggttctt ctggtggttc ttccgaagtc gagtttttccc atgagtactg gatgagacac    1920
gcattgactc tcgcaaagag ggctcgagat gaacgcgagg tgcccgtggg gcagtactc    1980
gtgctcaaca atcgcgtaat cggcgaaggt tggaataggg caatcggact ccacgacccc    2040
```

```
actgcacatg cggaaatcat ggcccttcga cagggagggc ttgtgatgca gaattatcga    2100
cttatcgatg cgacgctgta cgtcacgttt gaaccttgcg taatgtgcgc gggagctatg    2160
attcactccc gcattggacg agttgtattc ggtgttcgca acgccaagac gggtgccgca    2220
ggttcactga tggacgtgct gcattaccca ggcatgaacc accgggtaga aatcacagaa    2280
ggcatattgg cggacgaatg tgcggcgctg ttgtgttact ttttcgcat gcccaggcag     2340 gtctttaacg cccagaaaaa agcacaatcc tctactgact ctggtggttc ttctggtggt    2400
tctagcggca gcgagactcc cgggacctca gagtccgcca cacccgaaag ttctggtggt    2460
tcttctggtg gttctgataa aaagtattct attggtttag ccatcggcac taattccgtt    2520
ggatgggctg tcataaccga tgaatacaaa gtaccttcaa agaaatttaa ggtgttgggg    2580
aacacagacc gtcattcgat taaaaagaat cttatcggtg ccctcctatt cgatagtggc    2640
gaaacggcag aggcgactcg cctgaaacga accgctcgga aaggtatac acgtcgcaag    2700 aaccgaatat gttacttaca agaaattttt agcaatgaga tggccaaagt tgacgattct    2760
ttctttcacc gtttggaaga gtccttcctt gtcgaagagg acaagaaaca tgaacggcac    2820
cccatctttg gaaacatagt agatgaggtg gcatatcatg aaaagtaccc aacgatttat    2880
cacctcagaa aaaagctagt tgactcaact gataaagcgg acctgaggtt aatctacttg    2940
gctcttgccc atatgataaa gttccgtggg cactttctca ttgagggtga tctaaatccg    3000
gacaactcgg atgtcgacaa actgttcatc cagttagtac aaacctataa tcagttgttt    3060
gaagagaacc ctataaatgc aagtggcgtg gatgcgaagg ctattcttag cgcccgcctc    3120
tctaaatccc gacggctaga aaacctgatc gcacaattac ccggagagaa gaaaaatggg    3180
ttgttcggta accttatagc gctctcacta ggcctgacac caaattttaa gtcgaacttc    3240
gacttagctg aagatgccaa attgcagctt agtaaggaca cgtacgatga cgatctcgac    3300
aatctactgg cacaaattgg agatcagtat gcggacttat ttttggctgc caaaaacctt    3360
agcgatgcaa tcctcctatc tgacatactg agagttaata ctgagattac caaggcgccg    3420
ttatccgctt caatgatcaa aaggtacgat gaacatcacc aagacttgac acttctcaag    3480
gccctagtcc gtcagcaact gcctgagaaa tataaggaaa tattctttga tcagtcgaaa    3540
aacgggtacg caggttatat tgacggcgga gcgagtcaag aggaattcta caagtttatc    3600
aaacccatat tagagaagat ggatgggacg gaagagttgc ttgtaaaact caatcgcgaa    3660
gatctactgc gaaagcagcg gactttcgac aacggtagca ttccacatca aatccactta    3720
ggcgaattgc atgctatact agaaggcag gaggattttt atccgttcct caaagacaat    3780
cgtgaaaaga ttgagaaaat cctaaccttt cgcataccct actatgtggg acccctggcc    3840
cgagggaact ctcggttcgc atggatgaca agaaagtccg aagaaacgat tactccatgg    3900
aattttgagg aagttgtcga taaaggtgcg tcagctcaat cgttcatcga gaggatgacc    3960
aactttgaca agaatttacc gaacgaaaaa gtattgccta agcacagttt actttacgag    4020
tatttcacag tgtacaatga actcacgaaa gttaagtatg tcactgaggg catgcgtaaa    4080
cccgcctttc taagcggaga acagaagaaa gcaatagtag atctgttatt caagaccaac    4140
cgcaaagtga cagttaagca attgaaagag gactacttta gaaaattga atgcttcgat    4200 tctgtcgaga tctccggggt agaagatcga tttaatgcgt cacttggtac gtatcatgac    4260
ctcctaaaga taattaaaga taaggacttc ctggataacg aagagaatga agatatctta    4320
gaagatatag tgttgactct taccctcttt gaagatcggg aaatgattga ggaaagacta    4380
aaaacatacg ctcacctgtt cgacgataag gttatgaaac agttaaagag gcgtcgctat    4440
```

```
acgggctggg gacgattgtc gcggaaactt atcaacggga taagagacaa gcaaagtggt   4500
aaaactattc tcgattttct aaagagcgac ggcttcgcca ataggaactt tatgcagctg   4560
atccatgatg actctttaac cttcaaagag gatatacaaa aggcacaggt ttccggacaa   4620
ggggactcat tgcacgaaca tattgcgaat cttgctggtt cgccagccat caaaaagggc   4680
atactccaga cagtcaaagt agtggatgag ctagttaagg tcatgggacg tcacaaaccg   4740
gaaaacattg taatcgagat ggcacgcgaa aatcaaacga ctcagaaggg gcaaaaaaac   4800
agtcgagagc ggatgaagag aatagaagag ggtattaaag aactgggcag ccagatctta   4860
aaggagcatc ctgtgaaaaa tacccaattg cagaacgaga aactttacct ctattaccta   4920
caaaatggaa gggacatgta tgttgatcag gaactggaca taaaccgttt atctgattac   4980
gacgtcgatc acattgtacc ccaatccttt ttgaaggacg attcaatcga caataaagtg   5040
cttacacgct cggataagaa ccgagggaaa agtgacaatg ttccaagcga ggaagtcgta   5100
aagaaaatga gaactattg gcggcagctc ctaaatgcga aactgataac gcaaagaaag   5160
ttcgataact taactaaagc tgagaggggt ggcttgtctg aacttgacaa ggccggattt   5220
attaaacgtc agctcgtgga aacccgccaa atcacaaagc atgttgcaca gatactagat   5280
tcccgaatga atacgaaata cgacgagaac gataagctga ttcgggaagt caaagtaatc   5340
actttaaagt caaaattggt gtcggacttc agaaaggatt ttcaattcta taagttagg   5400 gagataaata actaccacca tgcgcacgac gcttatctta atgccgtcgt agggaccgca   5460
ctcattaaga aatacccgaa gctagaaagt gagtttgtgt atggtgatta caagtttat    5520 gacgtccgta agatgatcgc gaaaagcgaa caggagatag gcaaggctac agccaaatac   5580
ttcttttatt ctaacattat gaatttcttt aagacgaaaa tcactctggc aaacggagag   5640
atacgcaaac gaccttaat tgaaaccaat ggggagacag gtgaaatcgt atgggataag    5700
ggccgggact tcgcgacggt gagaaaagtt ttgtccatgc cccaagtcaa catagtaaag   5760
aaaactgagg tgcagaccgg agggttttca aaggaatcga ttcttccaaa aaggaatagt   5820
gataagctca tcgctcgtaa aaaggactgg gacccgaaaa agtacggtgg cttcgatagc   5880
cctacagttg cctattctgt cctagtagtg gcaaagttg agaagggaaa atccaagaaa    5940
ctgaagtcag tcaaagaatt attggggata cgattatgg agcgctcgtc ttttgaaaag    6000
aaccccatcg acttccttga ggcgaaaggt tacaaggaag taaaaaagga tctcataatt   6060
aaactaccaa agtatagtct gtttgagtta gaaaatggcc gaaaacggat gttggctagc   6120 gccgagagc ttcaaaaggg gaacgaactc gcactaccgt ctaaatacgt gaatttcctg    6180
tatttagcgt cccattacga gaagttgaaa ggttcacctg aagataacga acagaagcaa   6240 cttttttgttg agcagcacaa acattatctc gacgaaatca tagagcaaat ttcggaattc   6300
agtaagagag tcatcctagc tgatgccaat ctggacaaag tattaagcgc atacaacaag   6360
cacagggata aacccatacg tgagcaggcg gaaaatatta tccatttgtt tactcttacc   6420
aacctcggcg ctccagccgc attcaagtat tttgacacaa cgatagatcg caaacgatac   6480
acttctacca aggaggtgct agacgcgaca ctgattcacc aatccatcac gggattatat   6540
gaaactcgga tagatttgtc acagcttggg ggtgactctg tggttctcc caagaagaag    6600 aggaaagtct aaccggtcat catcaccatc accattgagt ttaaacccgc tgatcagcct   6660
cgactgtgcc ttctagttgc cagccatctg ttgtttgccc ctcccccgtg ccttccttga   6720
ccctggaagg tgccactccc actgtccttt cctaataaaa tgaggaaatt gcatcgcatt   6780
```

```
gtctgagtag gtgtcattct attctggggg gtggggtggg gcaggacagc aaggggg agg    6840
attgggaaga caatagcagg catgctgggg atgcggtggg ctctatggct tctgaggcgg    6900
aaagaaccag ctggggctcg ataccgtcga cctctagcta gagcttggcg taatcatggt    6960
catagctgtt tcctgtgtga aattgttatc cgctcacaat tccacacaac atacgagccg    7020
gaagcataaa gtgtaaagcc tagggtgcct aatgagtgag ctaactcaca ttaattgcgt    7080
tgcgctcact gcccgctttc cagtcgggaa acctgtcgtg ccagctgcat taatgaatcg    7140
gccaacgcgc ggggagaggc ggtttgcgta ttgggcgctc ttccgcttcc tcgctcactg    7200
actcgctgcg ctcggtcgtt cggctgcggc gagcggtatc agctcactca aaggcggtaa    7260
tacggttatc cacagaatca ggggataacg caggaaagaa catgtgagca aaaggccagc    7320
aaaaggccag gaaccgtaaa aaggccgcgt tgctggcgtt tttccatagg ctccgccccc    7380
ctgacgagca tcacaaaaat cgacgctcaa gtcagaggtg gcgaaacccg acaggactat    7440
aaagatacca ggcgtttccc cctggaagct ccctcgtgcg ctctcctgtt ccgaccctgc    7500
cgcttaccgg atacctgtcc gcctttctcc cttcgggaag cgtggcgctt tctcatagct    7560
cacgctgtag gtatctcagt tcggtgtagg tcgttcgctc caagctgggc tgtgtgcacg    7620
aaccccccgt tcagcccgac cgctgcgcct tatccggtaa ctatcgtctt gagtccaacc    7680
cggtaagaca cgacttatcg ccactggcag cagccactgg taacaggatt agcagagcga    7740
ggtatgtagg cggtgctaca gagttcttga agtggtggcc taactacggc tacactagaa    7800
gaacagtatt tggtatctgc gctctgctga agccagttac cttcggaaaa agagttggta    7860
gctcttgatc cggcaaacaa accaccgctg gtagcggtgg tttttttgtt tgcaagcagc    7920
agattacgcg cagaaaaaaa ggatctcaag aagatccttt gatcttttct acggggtctg    7980
acgctcagtg gaacgaaaac tcacgttaag ggattttggt catgagatta tcaaaaagga    8040
tcttcaccta gatcctttta aattaaaaat gaagttttaa atcaatctaa agtatatatg    8100
agtaaacttg gtctgacagt taccaatgct taatcagtga ggcacctatc tcagcgatct    8160
gtctatttcg ttcatccata gttgcctgac tccccgtcgt gtagataact acgatacggg    8220
agggcttacc atctggcccc agtgctgcaa tgataccgcg agacccacgc tcaccggctc    8280
cagatttatc agcaataaac cagccagccg gaagggccga gcgcagaagt ggtcctgcaa    8340
ctttatccgc ctccatccag tctattaatt gttgccggga agctagagta agtagttcgc    8400
cagttaatag tttgcgcaac gttgttgcca ttgctacagg catcgtggtg tcacgctcgt    8460
cgtttggtat ggcttcattc agctccggtt cccaacgatc aaggcgagtt acatgatccc    8520
ccatgttgtg caaaaaagcg gttagctcct tcggtcctcc gatcgttgtc agaagtaagt    8580
tggccgcagt gttatcactc atggttatgg cagcactgca taattctctt actgtcatgc    8640
catccgtaag atgcttttct gtgactggtg agtactcaac caagtcattc tgagaatagt    8700
gtatgcggcg accgagttgc tcttgcccgg cgtcaatacg ggataatacc gcgccacata    8760
gcagaacttt aaaagtgctc atcattggaa aacgttcttc ggggcgaaaa ctctcaagga    8820
tcttaccgct gttgagatcc agttcgatgt aacccactcg tgcacccaac tgatcttcag    8880
catcttttac tttcaccagc gtttctgggt gagcaaaaac aggaaggcaa aatgccgcaa    8940
aaaagggaat aagggcgaca cggaaatgtt gaatactcat actcttcctt tttcaatatt    9000
attgaagcat ttatcagggt tattgtctca tgagcggata catatttgaa tgtatttaga    9060
aaaataaaca aataggggtt ccgcgcacat ttccccgaaa agtgccacct gacgtcgacg    9120
gatcgggaga tcgatctccc gatcccctag ggtcgactct cagtacaatc tgctctgatg    9180
```

```
ccgcatagtt aagccagtat ctgctccctg cttgtgtgtt ggaggtcgct gagtagtgcg    9240
cgagcaaaat ttaagctaca acaaggcaag gcttgaccga caattgcatg aagaatctgc    9300
ttagggttag gcgttttgc                                                 9319
```

<210> SEQ ID NO 192
<211> LENGTH: 9403
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
gctgcttcgc gatgtacggg ccagatatac gcgttgacat tgattattga ctagtcgtga      60
ggctccggtg cccgtcagtg ggcagagcgc acatcgccca cagtccccga gaagttgggg     120
ggaggggtcg gcaattgaac cggtgcctag agaaggtggc gcggggtaaa ctgggaaagt     180
gatgtcgtgt actggctccg cctttttccc gagggtgggg gagaaccgta tataagtgca     240
gtagtcgccg tgaacgttct ttttcgcaac gggtttgccg ccagaacaca ggtaagtgcc     300
gtgtgtggtt cccgcgggcc tggcctcttt acgggttatg gcccttgcgt gccttgaatt     360
acttccacgc ccctggctgc agtacgtgat tcttgatccc gagcttcggg ttggaagtgg     420
gtgggagagt tcgaggcctt gcgcttaagg agccccttcg cctcgtgctt gagttgaggc     480
ctggcctggg cgctggggcc gccgcgtgcg aatctggtgg caccttcgcg cctgtctcgc     540
tgctttcgat aagtctctag ccatttaaaa tttttgatga cctgctgcga cgcttttttt     600
ctggcaagat agtcttgtaa atgcgggcca agatctgcac actggtattt cggttttttgg    660 ggccgcgggc ggcgacgggg cccgtgcgtc ccagcgcaca tgttcggcga ggcggggcct     720
gcgagcgcgg ccaccgagaa tcggacgggg gtagtctcaa gctggccggc ctgctctggt     780
gcctggcctc gcgccgccgt gtatcgcccc gccctgggcg gcaaggctgg cccggtcggc     840
accagttgcg tgagcggaaa gatggccgct tcccggccct gctgcaggga gctcaaaatg     900
gaggacgcgg cgctcgggag agcgggcggg tgagtcaccc acacaaagga aaagggcctt     960
tccgtcctca gccgtcgctt catgtgactc cacggagtac cgggcgccgt ccaggcacct    1020
cgattagttc tcgagctttt ggagtacgtc gtctttaggt tggggggagg ggttttatgc    1080
gatggagttt ccccacactg agtgggtgga gactgaagtt aggccagctt ggcacttgat    1140
gtaattctcc ttggaatttg ccctttttga gtttggatct tggttcattc tcaagcctca    1200
gacagtggtt caaagttttt ttcttccatt tcaggtgtcg tgaggcggcc gctaatacga    1260
ctcactatag ggagagccgc caccatgaaa cggacagccg acggaagcga gttcgagtca    1320
ccaaagaaga agcggaaagt ctctgaagtc gagtttagcc acgagtattg gatgaggcac    1380
gcactgaccc tggcaaagcg agcatgggat gaaagagaag tccccgtggg cgccgtgctg    1440
gtgcacaaca atagagtgat cggagaggga tggaacaggc caatcggccg ccacgaccct    1500
accgcacacg cagagatcat ggcactgagg cagggaggcc tggtcatgca gaattaccgc    1560
ctgatcgatg ccaccctgta tgtgacactg gagccatgcg tgatgtgcgc aggagcaatg    1620
atccacagca ggatcggaag agtggtgttc ggagcacggg acgccaagac cggcgcagca    1680 ggctcccctga tggatgtgct gcaccacccc ggcatgaacc accgggtgga gatcacagag    1740
ggaatcctgg cagacgagtg cgccgccctg ctgagcgatt tctttagaat gcggagcag     1800 gagatcaagg cccagaagaa ggcacagagc tccaccgact ctggaggatc tagcggagga    1860
```

```
tcctctggaa gcgagacacc aggcacaagc gagtccgcca caccagagag ctccggcggc    1920
tcctccggag gatcctctga ggtggagttt tcccacgagt actggatgag acatgccctg    1980
accctggcca gagggcacg cgatgagagg gaggtgcctg tgggagccgt gctggtgctg     2040
aacaatagag tgatcggcga gggctggaac agagccatcg gcctgcacga cccaacagcc    2100
catgccgaaa ttatggccct gagacagggc ggcctggtca tgcagaacta cagactgatt    2160
gacgccaccc tgtacgtgac attcgagcct tgcgtgatgt gcgccggcgc catgatccac    2220
tctaggatcg gccgcgtggt gtttggcgtg aggaacgcaa aaaccggcgc cgcaggctcc    2280
ctgatggacg tgctgcacta ccccggcatg aatcaccgcg tcgaaattac cgagggaatc    2340
ctggcagatg aatgtgccgc cctgctgtgc tatttctttc ggatgcctag acaggtgttc    2400
aatgctcaga gaaggcccca gagctccacc gactccggag gatctagcgg aggctcctct    2460
ggctctgaga cacctggcac aagcgagagc gcaacacctg aaagcagcgg gggcagcagc    2520 gggggtcag acaagaagta cagcatcggc ctggccatcg gcaccaactc tgtgggctgg    2580
gccgtgatca ccgacgagta caaggtgccc agcaagaaat tcaaggtgct gggcaacacc    2640
gaccggcaca gcatcaagaa gaacctgatc ggagccctgc tgttcgacag cggcgaaaca    2700
gccgaggcca cccggctgaa gagaaccgcc agaagaagat acaccagacg gaagaaccgg    2760
atctgctatc tgcaagagat cttcagcaac gagatggcca aggtggacga cagcttcttc    2820
cacagactgg aagagtcctt cctggtggaa gaggataaga gcacgagcg gcaccccatc    2880 ttcggcaaca tcgtggacga ggtggcctac acgagaagt accccaccat ctaccacctg    2940
agaaagaaac tggtggacag caccgacaag gccgacctgc ggctgatcta tctggccctg    3000
gcccacatga tcaagttccg gggccacttc ctgatcgagg gcgacctgaa ccccgacaac    3060
agcgacgtgg acaagctgtt catccagctg gtgcagacct acaaccagct gttcgaggaa    3120
aaccccatca cgccagcgg cgtggacgcc aaggccatcc tgtctgccag actgagcaag    3180
agcagacggc tggaaaatct gatcgcccag ctgcccggcg agaagaagaa tggcctgttc    3240
ggaaacctga ttgccctgag cctgggcctg accccccaact tcaagagcaa cttcgacctg    3300
gccgaggatg ccaaactgca gctgagcaag gacacctacg acgacgacct ggacaacctg    3360
ctggcccaga tcggcgacca gtacgccgac ctgtttctgg ccgccaagaa cctgtccgac    3420
gccatcctgc tgagcgacat cctgagagtg aacaccgaga tcaccaaggc ccccctgagc    3480
gcctctatga tcaagagata cgacgagcac caccaggacc tgaccctgct gaaagctctc    3540
gtgcggcagc agctgcctga aagtacaaa gagattttct tcgaccagag caagaacggc    3600
tacgccggct acattgacgg cggagccagc caggaagagt tctacaagtt catcaagccc    3660
atcctggaaa agatggacgg caccgaggaa ctgctcgtga agctgaacag agaggacctg    3720
ctgcggaagc agcggacctt cgacaacggc agcatccccc accagatcca cctgggagag    3780
ctgcacgcca ttctgcggcg gcaggaagat ttttacccat tcctgaagga caaccggaa    3840 aagatcgaga agatcctgac cttccgcatc ccctactacg tgggccctct ggccagggga    3900
aacagcagat tcgcctggat gaccagaaag agcgaggaaa ccatcacccc ctggaacttc    3960
gaggaagtgg tggacaaggg cgcttccgcc cagagcttca tcgagcggat gaccaacttc    4020
gataagaacc tgcccaacga aaaggtgctg cccaagcaca gcctgctgta cgagtacttc    4080
accgtgtata acgagctgac caaagtgaaa tacgtgaccg agggaatgag aaagcccgcc    4140
ttcctgagcg gcgagcagaa aaaggccatc gtggacctgc tgttcaagac caaccggaaa    4200
```

```
gtgaccgtga agcagctgaa agaggactac ttcaagaaaa tcgagtgctt cgactccgtg    4260
gaaatctccg gcgtggaaga tcggttcaac gcctccctgg cacatacca cgatctgctg    4320 aaaattatca aggacaagga cttcctggac aatgaggaaa acgaggacat tctggaagat    4380
atcgtgctga ccctgacact gtttgaggac agagagatga tcgaggaacg gctgaaaacc    4440
tatgcccacc tgttcgacga caaagtgatg aagcagctga agcggcggag atacaccggc    4500
tggggcaggc tgagccggaa gctgatcaac ggcatccggg acaagcagtc cggcaagaca    4560
atcctggatt tcctgaagtc cgacggcttc gccaacagaa acttcatgca gctgatccac    4620
gacgacagcc tgacctttaa agaggacatc cagaaagccc aggtgtccgg ccagggcgat    4680
agcctgcacg agcacattgc caatctggcc ggcagccccg ccattaagaa gggcatcctg    4740
cagacagtga aggtggtgga cgagctcgtg aaagtgatgg gccggcacaa gcccgagaac    4800
atcgtgatcg aaatggccag agagaaccag accacccaga agggacagaa gaacagccgc    4860
gagagaatga agcggatcga agagggcatc aaagagctgg gcagccagat cctgaaagaa    4920
caccccgtgg aaaacaccca gctgcagaac gagaagctgt acctgtacta cctgcagaat    4980
gggcgggata tgtacgtgga ccaggaactg gacatcaacc ggctgtccga ctacgatgtg    5040
gaccatatcg tgcctcagag ctttctgaag gacgactcca tcgacaacaa ggtgctgacc    5100
agaagcgaca agaaccgggg caagagcgac aacgtgccct ccgaagaggt cgtgaagaag    5160
atgaagaact actggcggca gctgctgaac gccaagctga ttacccagag aaagttcgac    5220
aatctgacca aggccgagag aggcggcctg agcgaactgg ataaggccgg cttcatcaag    5280
agacagctgg tggaaacccg gcagatcaca aagcacgtgg cacagatcct ggactcccgg    5340
atgaacacta gtacgacga aatgacaag ctgatccggg aagtgaaagt gatcaccctg    5400
aagtccaagc tggtgtccga tttccggaag gatttccagt tttacaaagt gcgcgagatc    5460
aacaactacc accacgccca cgacgcctac ctgaacgccg tcgtgggaac cgccctgatc    5520
aaaaagtacc ctaagctgga aagcgagttc gtgtacggcg actacaaggt gtacgacgtg    5580
cggaagatga tcgccaagag cgagcaggaa atcggcaagg ctaccgccaa gtacttcttc    5640
tacagcaaca tcatgaactt tttcaagacc gagattaccc tggccaacgg cgagatccgg    5700
aagcggcctc tgatcgagac aaacggcgaa accggggaga tcgtgtggga taagggccgg    5760 gatttttgcca ccgtgcggaa agtgctgagc atgccccaag tgaatatcgt gaaaaagacc    5820
gaggtgcaga caggcggctt cagcaaagag tctatcctgc ccaagaggaa cagcgataag    5880
ctgatcgcca gaaagaagga ctgggaccct aagaagtacg gcggcttcga cagcccacc    5940 gtggcctatt ctgtgctggt ggtggccaaa gtggaaaagg gcaagtccaa gaaactgaag    6000
agtgtgaaag agctgctggg gatcaccatc atggaaagaa gcagcttcga gaagaatccc    6060
atcgactttc tggaagccaa gggctacaaa gaagtgaaaa aggacctgat catcaagctg    6120
cctaagtact ccctgttcga gctggaaaac ggccggaaga atgctggc ctctgccggc    6180 gaactgcaga agggaaacga actggccctg ccctccaaat atgtgaactt cctgtacctg    6240
gccagccact atgagaagct gaagggctcc ccgaggata tgagcagaa acagctgttt    6300 gtggaacagc acaagcacta cctggacgag atcatcgagc agatcagcga gttctccaag    6360
agagtgatcc tggccgacgc taatctggac aaagtgctgt ccgcctacaa caagcaccgg    6420
gataagccca tcagagagca ggccgagaat atcatccacc tgtttaccct gaccaatctg    6480
ggagcccctg ccgccttcaa gtactttgac accaccatcg accggaagag gtacaccagc    6540
accaaagagg tgctggacgc caccctgatc caccagagca tcaccggcct gtacgagaca    6600
```

```
cggatcgacc tgtctcagct gggaggtgac tctggcggct caaaaagaac cgccgacggc    6660
agcgaattcg agcccaagaa gaagaggaaa gtctaaccgg tcatcatcac catcaccatt    6720
gagtttaaac ccgctgatca gcctcgactg tgccttctag ttgccagcca tctgttgttt    6780
gcccctcccc cgtgccttcc ttgaccctgg aaggtgccac tcccactgtc ctttcctaat    6840
aaaatgagga aattgcatcg cattgtctga gtaggtgtca ttctattctg ggggtgggg     6900 tggggcagga cagcaagggg gaggattggg aagacaatag caggcatgct ggggatgcgg    6960
tgggctctat ggcttctgag gcggaaagaa ccagctgggg ctcgataccg tcgacctcta    7020
gctagagctt ggcgtaatca tggtcatagc tgtttcctgt gtgaaattgt tatccgctca    7080
caattccaca acatacga gccggaagca taaagtgtaa agcctagggt gcctaatgag      7140
tgagctaact cacattaatt gcgttgcgct cactgcccgc tttccagtcg ggaaacctgt    7200
cgtgccagct gcattaatga atcggccaac gcgcgggag aggcggtttg cgtattggc     7260 gctcttccgc ttcctcgctc actgactcgc tgcgctcggt cgttcggctg cggcgagcgg    7320
tatcagctca ctcaaaggcg gtaatacggt tatccacaga atcaggggat aacgcaggaa    7380
agaacatgtg agcaaaaggc cagcaaaagg ccaggaaccg taaaaaggcc gcgttgctgg    7440
cgttttccca taggctccgc ccccctgacg agcatcacaa aaatcgacgc tcaagtcaga    7500
ggtggcgaaa cccgacagga ctataaagat accaggcgtt tccccctgga agctccctcg    7560
tgcgctctcc tgttccgacc ctgccgctta ccggatacct gtccgccttt ctcccttcgg    7620
gaagcgtggc gctttctcat agctcacgct gtaggtatct cagttcggtg taggtcgttc    7680
gctccaagct gggctgtgtg cacgaacccc ccgttcagcc cgaccgctgc gccttatccg    7740
gtaactatcg tcttgagtcc aacccggtaa gacacgactt atcgccactg gcagcagcca    7800
ctggtaacag gattagcaga gcgaggtatg taggcggtgc tacagagttc ttgaagtggt    7860
ggcctaacta cggctacact agaagaacag tatttggtat ctgcgctctg ctgaagccag    7920
ttaccttcgg aaaaagagtt ggtagctctt gatccggcaa acaaaccacc gctggtagcg    7980
gtggtttttt tgtttgcaag cagcagatta cgcgcagaaa aaaaggatct caagaagatc    8040
ctttgatctt ttctacgggg tctgacgctc agtggaacga aaactcacgt taagggattt    8100
tggtcatgag attatcaaaa aggatcttca cctagatcct tttaaattaa aaatgaagtt    8160
ttaaatcaat ctaaagtata tatgagtaaa cttggtctga cagttaccaa tgcttaatca    8220
gtgaggcacc tatctcagcg atctgtctat ttcgttcatc catagttgcc tgactccccg    8280
tcgtgtagat aactacgata cgggagggct taccatctgg ccccagtgct gcaatgatac    8340
cgcgagaccc acgctcaccg gctccagatt tatcagcaat aaaccagcca gccggaaggg    8400
ccgagcgcag aagtggtcct gcaactttat ccgcctccat ccagtctatt aattgttgcc    8460
gggaagctag agtaagtagt tcgccagtta atagtttgcg caacgttgtt gccattgcta    8520
caggcatcgt ggtgtcacgc tcgtcgtttg gtatggcttc attcagctcc ggttcccaac    8580
gatcaaggcg agttacatga tcccccatgt tgtgcaaaaa agcggttagc tccttcggtc    8640
ctccgatcgt tgtcagaagt aagttggccg cagtgttatc actcatggtt atggcagcac    8700
tgcataattc tcttactgtc atgccatccg taagatgctt ttctgtgact ggtgagtact    8760
caaccaagtc attctgagaa tagtgtatgc ggcgaccgag ttgctcttgc ccggcgtcaa    8820
tacgggataa taccgcgcca catagcagaa ctttaaaagt gctcatcatt ggaaaacgtt    8880
cttcggggcg aaaactctca aggatcttac cgctgttgag atccagttcg atgtaaccca    8940
```

```
ctcgtgcacc caactgatct tcagcatctt ttactttcac cagcgtttct gggtgagcaa    9000
aaacaggaag gcaaaatgcc gcaaaaaagg gaataagggc gacacggaaa tgttgaatac    9060
tcatactctt cctttttcaa tattattgaa gcatttatca gggttattgt ctcatgagcg    9120
gatacatatt tgaatgtatt tagaaaaata aacaaatagg ggttccgcgc acatttcccc    9180
gaaaagtgcc acctgacgtc gacggatcgg gagatcgatc tcccgatccc ctagggtcga    9240
ctctcagtac aatctgctct gatgccgcat agttaagcca gtatctgctc cctgcttgtg    9300
tgttggaggt cgctgagtag tgcgcgagca aaatttaagc tacaacaagg caaggcttga    9360
ccgacaattg catgaagaat ctgcttaggg ttaggcgttt tgc                      9403
```

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Leu Thr His Gly Val Gln Cys Phe Gly Arg
1               5                   10

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ctgacccacg gcgtgcagtg cttcggccgc                                       30

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Leu Thr Tyr Gly Val Gln Cys Phe Gly Arg
1               5                   10

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ctgacctacg gcgtgcagtg cttcggccgc                                       30

<210> SEQ ID NO 197
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cctgacccac ggcgtgcagt gcttcggcc                               29

<210> SEQ ID NO 198
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cgaaacaccg ggtcttcgag aagacctgtt ttagag                       36

<210> SEQ ID NO 199
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ctctaaaaca ggtcttctcg aagacccggt gtttcg                       36

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agttgatggg gtggttcagg agggg                                   25

<210> SEQ ID NO 201
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
agttgatgag gtggttcagg agggg                                   25

<210> SEQ ID NO 202
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
agttggtggg gtggttcagg agggg                                   25

<210> SEQ ID NO 203
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203

```
agttggtggg gtggttcagg agggg                                    25
```

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204

```
ggcccagact gagcacgtga                                          20
```

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205

```
ggcccagact gagcacgtga                                          20
```

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

```
gaacacaaag catagactgc                                          20
```

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

```
gaacacaaag catagactgc                                          20
```

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208

```
ggcactgcgg ctggaggtgg                                          20
```

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209

```
ggcactgcgg ctggaggtgg                                          20
```

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210

```
gaagcgcctg gcagtgtacc                                          20
```

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

```
gaagcgcctg gcagtgtacc                                          20
```

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212

```
ggcccagact gagcacgtga                                          20
```

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213

```
ggcccagact gagcacgtga                                          20
```

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214

```
gaacacaaag catagactgc                                          20
```

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215

```
gaacacaaag catagactgc                                          20
```

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ggcactgcgg ctggaggtgg                                              20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ggcactgcgg ctggaggtgg                                              20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ccctacatcg tgcagtgctt                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ccccaagtag tgcagtgctt                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
aaccaagatg tgcagtgctt                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
aaccagcgcc tgcagtgctt                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ccccatggct tgctgtgctt                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cacccagact gagcacgtgc                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gacacagacc gggcacgtga                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
agctcagact gagcaagtga                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
agaccagact gagcaagaga                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gagccagaat gagcacgtga                                              20

```
<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gaacacaatg catagattgc                                                      20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gcagtctatg ctttatgttt                                                      20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tgcactgcgg ccggaggagg                                                      20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggctctgcgg ctggagggg                                                       20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ggcacgacgg ctggaggtgg                                                      20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggcatcacgg ctggaggtgg                                                      20

<210> SEQ ID NO 234
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ggcgctgcgg cgggaggtgg                                              20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ggcccagact gagcacgtga                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ggcccagact gagcacgtga                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gaagcgcctg gcagtgtacc                                              20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gaagcgcctg gcagtgtacc                                              20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ggcccagact gagcacgtga                                              20

<210> SEQ ID NO 240
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gaacacaaag catagactgc                                               20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggcactgcgg ctggaggtgg                                               20

<210> SEQ ID NO 242
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gtgatcatca tcacc                                                    15

<210> SEQ ID NO 243
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tggactgagt ggctc                                                    15

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gtagaggagg tggttcagga                                               20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ttagagcagg tggttcagga                                               20

<210> SEQ ID NO 246
<211> LENGTH: 20
<212> TYPE: DNA
```

<213> ORGANISM: Artificial Sequence
<220> FEATURE:
<223> OTHER INFORMATION: Description of Artificial Sequence: Synthetic
    oligonucleotide

<400> SEQUENCE: 246
caatacaaag gatagactgc                                            20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 247
ggagagagag catagactgc                                            20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 248
taagacacaa tgatgagtca                                            20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 249
ctggagatat tgatgagtca                                            20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 250
aggttggccc aggccagggc                                            20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 251
cagtggaccc aggccagggc                                            20

<210> SEQ ID NO 252
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 252
tttgatgagg aggttcagga                                                   20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ccaaacaaaa catagactgc                                                   20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggtgagagaa agatgagtca                                                   20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ttgtggaccc aggccagggc                                                   20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gatgagataa tgatgagtca                                                   20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
cacagaagat accgagactg                                                   20

<210> SEQ ID NO 258
<211> LENGTH: 720
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 258

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccctgaccca | cggcgtgcag | tgcttcggcc | gctacccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagca | cccagtccgc | cctgagcaaa | gaccccaacg | agaagcgcga | tcacatggtc | 660 |
| ctgctggagt | tcgtgaccgc | cgccgggatc | actctcggca | tggacgagct | gtacaagtaa | 720 |

<210> SEQ ID NO 259
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

| | | | | | |
|---|---|---|---|---|---|
| atggtgagca | agggcgagga | ggataacatg | gccatcatca | aggagttcat | gcgcttcaag | 60 |
| gtgcacatgg | agggctccgt | gaacggccac | gagttcgaga | tcgagggcga | gggcgagggc | 120 |
| cgcccctacg | agggcaccca | gaccgccaag | ctgaaggtga | ccaagggtgg | ccccctgccc | 180 |
| ttcgcctggg | acatcctgtc | ccctcagttc | atgtacggct | ccaaggccta | cgtgaagcac | 240 |
| cccgccgaca | tccccgacta | cttgaagctg | tccttccccg | agggcttcaa | gtgggagcgc | 300 |
| gtgatgaact | tcgaggacgg | cggcgtggtg | accgtgaccc | aggactcctc | cctgcaggac | 360 |
| ggcgagttca | tctacaaggt | gaagctgcgc | ggcaccaact | tcccctccga | cggccccgta | 420 |
| atgcagaaga | agaccatggg | ctgggaggcc | tcctccgagc | ggatgtaccc | cgaggacggc | 480 |
| gccctgaagg | gcgagatcaa | gcagaggctg | aagctgaagg | acggcggcca | ctacgacgct | 540 |
| gaggtcaaga | ccacctacaa | ggccaagaag | cccgtgcagc | tgcccggcgc | ctacaacgtc | 600 |
| aacatcaagt | tggacatcac | ctcccacaac | gaggactaca | ccatcgtgga | acagtacgaa | 660 |
| cgcgccgagg | gccgccactc | caccggcggc | atggacgagc | tgtacaagcc | cggagggc | 720 |
| agaggaagtc | ttctaacatg | cggtgacgtg | gaggagaatc | ccggccctac | tagttgatgg | 780 |
| ggtggttcag | gagggcatg | cgtgagcaag | ggcgaggagc | tgttcaccgg | ggtggtgccc | 840 |
| atcctggtcg | agctggacgg | cgacgtaaac | ggccacaagt | tcagcgtgtc | cggcgagggc | 900 |
| gagggcgatg | ccacctacgg | caagctgacc | ctgaagttca | tctgcaccac | cggcaagctg | 960 |
| cccgtgccct | ggcccaccct | cgtgaccacc | ctgacctacg | gcgtgcagtg | cttcagccgc | 1020 |
| taccccgacc | acatgaagca | gcacgacttc | ttcaagtccg | ccatgcccga | aggctacgtc | 1080 |
| caggagcgca | ccatcttctt | caaggacgac | ggcaactaca | agacccgcgc | cgaggtgaag | 1140 |
| ttcgagggcg | acaccctggt | gaaccgcatc | gagctgaagg | gcatcgactt | caaggaggac | 1200 |

| | |
|---|---|
| ggcaacatcc tggggcacaa gctggagtac aactacaaca gccacaacgt ctatatcatg | 1260 |
| gccgacaagc agaagaacgg catcaaggtg aacttcaaga tccgccacaa catcgaggac | 1320 |
| ggcagcgtgc agctcgccga ccactaccag cagaacaccc ccatcggcga cggccccgtg | 1380 |
| ctgctgcccg acaaccacta cctgagcacc cagtccgccc tgagcaaaga ccccaacgag | 1440 |
| aagcgcgatc acatggtcct gctggagttc gtgaccgccg ccgggatcac tctcggcatg | 1500 |
| gacgagctgt acaagtaa | 1518 |

<210> SEQ ID NO 260
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 260

| | |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttccccg agggcttcaa gtgggagcgc | 300 |
| gtgatgaact tcgaggacgg cggcgtggtg accgtgaccc aggactcctc cctgcaggac | 360 |
| ggcgagttca tctacaaggt gaagctgcgc ggcaccaact cccctccga cggccccgta | 420 |
| atgcagaaga gaccatggg ctgggaggcc tcctccgagc ggatgtaccc cgaggacggc | 480 |
| gccctgaagg gcgagatcaa gcagaggctg aagctgaagg acggcggcca ctacgacgct | 540 |
| gaggtcaaga ccacctacaa ggccaagaag cccgtgcagc tgcccggcgc ctacaacgtc | 600 |
| aacatcaagt tggacatcac ctcccacaac gaggactaca ccatcgtgga acagtacgaa | 660 |
| cgcgccgagg gccgccactc caccggcggc atggacgagc tgtacaagcc ccgggagggc | 720 |
| agaggaagtc ttctaacatg cggtgacgtg gaggagaatc ccggccctac tagttgatga | 780 |
| ggtggttcag gagggcatg cgtgagcaag ggcgaggagc tgttcaccgg ggtggtgccc | 840 |
| atcctggtcg agctggacgg cgacgtaaac ggccacaagt tcagcgtgtc cggcgagggc | 900 |
| gagggcgatg ccacctacgg caagctgacc ctgaagttca tctgcaccac cggcaagctg | 960 |
| cccgtgccct ggcccaccct cgtgaccacc ctgacctacg gcgtgcagtg cttcagccgc | 1020 |
| taccccgacc acatgaagca gcacgacttc ttcaagtccg ccatgcccga aggctacgtc | 1080 |
| caggagcgca ccatcttctt caaggacgac ggcaactaca agacccgcgc cgaggtgaag | 1140 |
| ttcgagggcg acaccctggt gaaccgcatc gagctgaagg gcatcgactt caaggaggac | 1200 |
| ggcaacatcc tggggcacaa gctggagtac aactacaaca gccacaacgt ctatatcatg | 1260 |
| gccgacaagc agaagaacgg catcaaggtg aacttcaaga tccgccacaa catcgaggac | 1320 |
| ggcagcgtgc agctcgccga ccactaccag cagaacaccc ccatcggcga cggccccgtg | 1380 |
| ctgctgcccg acaaccacta cctgagcacc cagtccgccc tgagcaaaga ccccaacgag | 1440 |
| aagcgcgatc acatggtcct gctggagttc gtgaccgccg ccgggatcac tctcggcatg | 1500 |
| gacgagctgt acaagtaa | 1518 |

<210> SEQ ID NO 261
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gttgatgagg tggttcagga ggg                                            23

<210> SEQ ID NO 262
<211> LENGTH: 3490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagggccta tttcccatga    420
ttccttcata tttgcatata cgatacaagg ctgttagaga gataattgga attaatttga    480
ctgtaaacac aaagatatta gtacaaaata cgtgacgtag aaagtaataa tttcttgggt    540
agtttgcagt tttaaaatta tgttttaaaa tggactatca tatgcttacc gtaacttgaa    600
agtatttcga tttcttggct ttatatatct tgtggaaagg acgaaacacc gacccacggc    660
gtgcagtgct tgttttagag ctagaaatag caagttaaaa taaggctagt ccgttatcaa    720
cttgaaaaag tggcaccgag tcggtgcttt tttgttttag agctagaaat agcaagttaa    780 ataaggcta gtccgttttt agcgcgtgcg ccaattctgc agacagagag gcctatttc    840 ccatgattcc ttcatatttg catatacgat acaaggctgt tagagagata attggaatta    900
atttgactgt aaacacaaag atattagtac aaaatacgtg acgtagaaag taataatttc    960
ttgggtagtt tgcagtttta aaattatgtt ttaaatgga ctatcatatg cttaccgtaa    1020
cttgaaagta tttcgatttc ttggctttat atatcttgtg gaaaggacga acaccgggt    1080 cttcgagaag acctgtttta gagctagaaa tagcaagtta aaataaggct agtccgttat    1140
caacttgaaa aagtggcacc gagtcggtgc ttttttgttt tagagctaga aatagcaagt    1200
taaaataagg ctagtccgtt tttagcgcgt gcgccaattc tgcagacaaa agcttggcg    1260 taatcatggt catagctgtt tcctgtgtga aattgttatc cgctcacaat tccacacaac    1320
atacgagccg gaagcataaa gtgtaaagcc tggggtgcct aatgagtgag ctaactcaca    1380
ttaattgcgt tgcgctcact gcccgctttc cagtcgggaa acctgtcgtg ccagctgcat    1440
taatgaatcg gccaacgcgc ggggagaggc ggtttgcgta ttgggcgctc ttccgcttcc    1500
tcgctcactg actcgctgcg ctcggtcgtt cggctgcggc gagcggtatc agctcactca    1560
aaggcggtaa tacggttatc cacagaatca ggggataacg caggaaagaa catgtgagca    1620
aaaggccagc aaaaggccag gaaccgtaaa aaggccgcgt tgctggcgtt ttttccatag    1680
gctccgcccc ctgacgagca tcacaaaaat cgacgctcaa gtcagaggtg gcgaaacccg    1740
```

| | |
|---|---:|
| acaggactat aaagatacca ggcgtttccc cctggaagct ccctcgtgcg ctctcctgtt | 1800 |
| ccgaccctgc cgcttaccgg atacctgtcc gcctttctcc cttcgggaag cgtggcgctt | 1860 |
| tctcatagct cacgctgtag gtatctcagt tcggtgtagg tcgttcgctc caagctgggc | 1920 |
| tgtgtgcacg aacccccgt tcagcccgac cgctgcgcct tatccggtaa ctatcgtctt | 1980 |
| gagtccaacc cggtaagaca cgacttatcg ccactggcag cagccactgg taacaggatt | 2040 |
| agcagagcga ggtatgtagg cggtgctaca gagttcttga agtggtggcc taactacggc | 2100 |
| tacactagaa gaacagtatt tggtatctgc gctctgctga agccagttac cttcggaaaa | 2160 |
| agagttggta gctcttgatc cggcaaacaa accaccgctg gtagcggtgg ttttttttgtt | 2220 |
| tgcaagcagc agattacgcg cagaaaaaaa ggatctcaag aagatccttt gatcttttct | 2280 |
| acggggtctg acgctcagtg gaacgaaaac tcacgttaag ggattttggt catgagatta | 2340 |
| tcaaaaagga tcttcaccta gatccttta aattaaaaat gaagttttaa atcaatctaa | 2400 |
| agtatatatg agtaaacttg gtctgacagt taccaatgct taatcagtga ggcacctatc | 2460 |
| tcagcgatct gtctatttcg ttcatccata gttgcctgac tccccgtcgt gtagataact | 2520 |
| acgatacggg agggcttacc atctggcccc agtgctgcaa tgataccgcg agacccacgc | 2580 |
| tcaccggctc cagatttatc agcaataaac cagccagccg aagggccga gcgcagaagt | 2640 |
| ggtcctgcaa ctttatccgc ctccatccag tctattaatt gttgccggga agctagagta | 2700 |
| agtagttcgc cagttaatag tttgcgcaac gttgttgcca ttgctacagg catcgtggtg | 2760 |
| tcacgctcgt cgtttggtat ggcttcattc agctccggtt cccaacgatc aaggcgagtt | 2820 |
| acatgatccc ccatgttgtg caaaaaagcg gttagctcct tcggtcctcc gatcgttgtc | 2880 |
| agaagtaagt tggccgcagt gttatcactc atggttatgg cagcactgca taattctctt | 2940 |
| actgtcatgc catccgtaag atgcttttct gtgactggtg agtactcaac caagtcattc | 3000 |
| tgagaatagt gtatgcggcg accgagttgc tcttgcccgg cgtcaatacg ggataatacc | 3060 |
| gcgccacata gcagaacttt aaaagtgctc atcattggaa aacgttcttc ggggcgaaaa | 3120 |
| ctctcaagga tcttaccgct gttgagatcc agttcgatgt aacccactcg tgcacccaac | 3180 |
| tgatcttcag catcttttac tttcaccagc gtttctgggt gagcaaaaac aggaaggcaa | 3240 |
| aatgccgcaa aaaagggaat aagggcgaca cggaaatgtt gaatactcat actcttcctt | 3300 |
| tttcaatatt attgaagcat ttatcagggt tattgtctca tgagcggata catatttgaa | 3360 |
| tgtatttaga aaaataaaca ataggggtt ccgcgcacat ttccccgaaa agtgccacct | 3420 |
| gacgtctaag aaaccattat tatcatgaca ttaacctata aaaataggcg tatcacgagg | 3480 |
| ccctttcgtc | 3490 |

```
<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
```

| | |
|---|---:|
| ggcccagact gagcacgtga tgg | 23 |

```
<210> SEQ ID NO 264
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 264
ggtccagact gagcacgtga tgg                                          23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggctcagact gagcacgtga tgg                                          23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ggcctagact gagcacgtga tgg                                          23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggcccagatt gagcacgtga tgg                                          23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ggttcagact gagcacgtga tgg                                          23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ggtctagact gagcacgtga tgg                                          23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 270
ggtccagatt gagcacgtga tgg                                              23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ggcttagact gagcacgtga tgg                                              23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ggctcagatt gagcacgtga tgg                                              23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ggcctagatt gagcacgtga tgg                                              23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggtttagact gagcacgtga tgg                                              23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ggcttagatt gagcacgtga tgg                                              23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 276
ggtctagatt gagcacgtga tgg					23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ggttcagatt gagcacgtga tgg					23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ggtttagatt gagcacgtga tgg					23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ggcccagact gagcacgtga tgg					23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ggtccagact gagcacgtga tgg					23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ggctcagact gagcacgtga tgg					23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 282
ggcctagact gagcacgtga tgg                                              23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggcccagatt gagcacgtga tgg                                              23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ggttcagact gagcacgtga tgg                                              23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ggtctagact gagcacgtga tgg                                              23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggtccagatt gagcacgtga tgg                                              23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggcttagact gagcacgtga tgg                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
```
ggctcagatt gagcacgtga tgg 23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggcctagatt gagcacgtga tgg 23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ggtttagact gagcacgtga tgg 23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ggcttagatt gagcacgtga tgg 23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ggtctagatt gagcacgtga tgg 23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ggttcagatt gagcacgtga tgg 23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ggtttagatt gagcacgtga tgg                                              23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gaagcgcctg gcagtgtacc agg                                              23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gaagtgcctg gcagtgtacc agg                                              23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gaagcgtctg gcagtgtacc agg                                              23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gaagcgcttg gcagtgtacc agg                                              23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gaagtgtctg gcagtgtacc agg                                              23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gaagtgcttg gcagtgtacc agg                                              23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gaagcgtttg gcagtgtacc agg                                              23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gaagtgtttg gcagtgtacc agg                                              23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gaagcgcctg gcagtgtacc agg                                              23

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gaagtgcctg gcagtgtacc agg                                              23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gaagcgtctg gcagtgtacc agg                                              23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gaagcgcttg gcagtgtacc agg                                              23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 307
gaagtgtctg gcagtgtacc agg                                           23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 308
gaagtgcttg gcagtgtacc agg                                           23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 309
gaagcgtttg gcagtgtacc agg                                           23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 310
gaagtgtttg gcagtgtacc agg                                           23

<210> SEQ ID NO 311
<211> LENGTH: 257
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 311

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe

```
                    85                  90                  95
Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Lys Lys Thr
                130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
                180                 185                 190

Leu Pro Gly Ala Tyr Asn Val Asn Ile Lys Leu Asp Ile Thr Ser His
                195                 200                 205

Asn Glu Asp Tyr Thr Ile Val Glu Gln Tyr Glu Arg Ala Glu Gly Arg
                210                 215                 220

His Ser Thr Gly Gly Met Asp Glu Leu Tyr Lys Pro Arg Glu Gly Arg
225                 230                 235                 240

Gly Ser Leu Leu Thr Cys Gly Asp Val Glu Glu Asn Pro Gly Pro Thr
                245                 250                 255

Ser

<210> SEQ ID NO 312
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
                35                  40                  45

Ala Lys Leu Lys Val Thr Lys Gly Gly Pro Leu Pro Phe Ala Trp Asp
                50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Lys Lys Thr
                130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
```

180                 185                 190
Leu Pro Gly Ala Tyr Asn Val Asn Ile Lys Leu Asp Ile Thr Ser His
            195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys Pro Arg Glu Gly Arg
225                 230                 235                 240

Gly Ser Leu Leu Thr Cys Gly Asp Val Glu Glu Asn Pro Gly Pro Thr
            245                 250                 255

Ser

<210> SEQ ID NO 313
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Met Arg Glu Gln Gly Arg Gly Ala Val His Arg Gly Gly Ala His Pro
1               5                   10                  15

Gly Arg Ala Gly Arg Arg Lys Arg Pro Gln Val Gln Arg Val Arg
            20                  25                  30

Arg Gly Arg Gly Arg Cys His Leu Arg Gln Ala Asp Pro Glu Val His
            35                  40                  45

Leu His His Arg Gln Ala Ala Arg Ala Leu Ala His Pro Arg Asp His
    50                  55                  60

Pro Asp Leu Arg Arg Ala Val Leu Gln Pro Leu Pro Arg Pro His Glu
65                  70                  75                  80

Ala Ala Arg Leu Leu Gln Val Arg His Ala Arg Arg Leu Arg Pro Gly
                85                  90                  95

Ala His His Leu Leu Gln Gly Arg Gln Leu Gln Asp Pro Arg Arg
                100                 105                 110

Gly Glu Val Arg Gly Arg His Pro Gly Glu Pro His Arg Ala Glu Gly
            115                 120                 125

His Arg Leu Gln Gly Gly Arg Gln His Pro Gly Ala Gln Ala Gly Val
    130                 135                 140

Gln Leu Gln Gln Pro Gln Arg Leu Tyr His Gly Arg Gln Ala Glu Glu
145                 150                 155                 160

Arg His Gln Gly Glu Leu Gln Asp Pro Pro Gln His Arg Gly Arg Gln
                165                 170                 175

Arg Ala Ala Arg Arg Pro Leu Pro Ala Glu His Pro His Arg Arg Arg
            180                 185                 190

Pro Arg Ala Ala Ala Arg Gln Pro Leu Pro Glu His Pro Val Arg Pro
        195                 200                 205

Glu Gln Arg Pro Gln Arg Glu Ala Arg Ser His Gly Pro Ala Gly Val
    210                 215                 220

Arg Asp Arg Arg Arg Asp His Ser Arg His Gly Arg Ala Val Gln Val
225                 230                 235                 240

<210> SEQ ID NO 314
<211> LENGTH: 236
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 314

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Gly Gln Tyr Glu Arg Ala Glu Gly
    210                 215                 220

Arg His Ser Thr Gly Gly Met Asp Glu Leu Tyr Lys
225                 230                 235

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gttgatgggg tggttcagga ggg                                         23

<210> SEQ ID NO 316
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

-continued

Glu Ile Glu Gly Glu Gly Gly Arg Pro Tyr Glu Gly Thr Gln Thr
       35                  40                  45

Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
65                   70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
             115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
             180                 185                 190

Gln Leu Pro Gly Ala Tyr Asn Val Asn Ile Lys Leu Asp Ile Thr Ser
         195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Pro Arg Glu Gly
225                 230                 235                 240

Arg Gly Ser Leu Leu Thr Cys Gly Asp Val Glu Glu Asn Pro Gly Pro
                245                 250                 255

Thr Ser Trp Gly Gly Ser Gly Gly Ala Cys Val Ser Lys Gly Glu Glu
             260                 265                 270

Leu Phe Thr Gly Val Val Pro Ile Leu Val Glu Leu Asp Gly Asp Val
         275                 280                 285

Asn Gly His Lys Phe Ser Val Ser Gly Glu Gly Glu Gly Asp Ala Thr
290                 295                 300

Tyr Gly Lys Leu Thr Leu Lys Phe Ile Cys Thr Thr Gly Lys Leu Pro
305                 310                 315                 320

Val Pro Trp Pro Thr Leu Val Thr Thr Leu Thr Tyr Gly Val Gln Cys
                325                 330                 335

Phe Ser Arg Tyr Pro Asp His Met Lys Gln His Asp Phe Phe Lys Ser
             340                 345                 350

Ala Met Pro Glu Gly Tyr Val Gln Glu Arg Thr Ile Phe Phe Lys Asp
         355                 360                 365

Asp Gly Asn Tyr Lys Thr Arg Ala Glu Val Lys Phe Glu Gly Asp Thr
370                 375                 380

Leu Val Asn Arg Ile Glu Leu Lys Gly Ile Asp Phe Lys Glu Asp Gly
385                 390                 395                 400

Asn Ile Leu Gly His Lys Leu Glu Tyr Asn Tyr Asn Ser His Asn Val
                405                 410                 415

Tyr Ile Met Ala Asp Lys Gln Lys Asn Gly Ile Lys Val Asn Phe Lys
             420                 425                 430

Ile Arg His Asn Ile Glu Asp Gly Ser Val Gln Leu Ala Asp His Tyr
         435                 440                 445

Gln Gln Asn Thr Pro Ile Gly Asp Gly Pro Val Leu Leu Pro Asp Asn

```
                    450                 455                 460
His Tyr Leu Ser Thr Gln Ser Ala Leu Ser Lys Asp Pro Asn Glu Lys
465                 470                 475                 480

Arg Asp His Met Val Leu Leu Glu Phe Val Thr Ala Ala Gly Ile Thr
                    485                 490                 495

Leu Gly Met Asp Glu Leu Tyr Lys
            500

<210> SEQ ID NO 317
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Pro Arg Glu Gly
225                 230                 235                 240

Arg Gly Ser Leu Leu Thr Cys Gly Asp Val Glu Glu Asn Pro Gly Pro
                245                 250                 255

Thr Ser Trp Trp Gly Gly Ser Gly Gly Ala Cys Val Ser Lys Gly Glu
            260                 265                 270

Glu Leu Phe Thr Gly Val Val Pro Ile Leu Val Glu Leu Asp Gly Asp
        275                 280                 285

Val Asn Gly His Lys Phe Ser Val Ser Gly Glu Gly Glu Gly Asp Ala
290                 295                 300
```

```
Thr Tyr Gly Lys Leu Thr Leu Lys Phe Ile Cys Thr Thr Gly Lys Leu
305                 310                 315                 320

Pro Val Pro Trp Pro Thr Leu Val Thr Thr Leu Thr Tyr Gly Val Gln
                325                 330                 335

Cys Phe Ser Arg Tyr Pro Asp His Met Lys Gln His Asp Phe Phe Lys
            340                 345                 350

Ser Ala Met Pro Glu Gly Tyr Val Gln Glu Arg Thr Ile Phe Phe Lys
        355                 360                 365

Asp Asp Gly Asn Tyr Lys Thr Arg Ala Glu Val Lys Phe Glu Gly Asp
    370                 375                 380

Thr Leu Val Asn Arg Ile Glu Leu Lys Gly Ile Asp Phe Lys Glu Asp
385                 390                 395                 400

Gly Asn Ile Leu Gly His Lys Leu Glu Tyr Asn Tyr Asn Ser His Asn
                405                 410                 415

Val Tyr Ile Met Ala Asp Lys Gln Lys Asn Gly Ile Lys Val Asn Phe
                420                 425                 430

Lys Ile Arg His Asn Ile Glu Asp Gly Ser Val Gln Leu Ala Asp His
            435                 440                 445

Tyr Gln Gln Asn Thr Pro Ile Gly Asp Gly Pro Val Leu Leu Pro Asp
450                 455                 460

Asn His Tyr Leu Ser Thr Gln Ser Ala Leu Ser Lys Asp Pro Asn Glu
465                 470                 475                 480

Lys Arg Asp His Met Val Leu Leu Glu Phe Val Thr Ala Ala Gly Ile
                485                 490                 495

Thr Leu Gly Met Asp Glu Leu Tyr Lys
            500                 505

<210> SEQ ID NO 318
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160
```

Ala Leu Lys Gly Glu Ile Lys Gln Arg Leu Lys Leu Lys Asp Gly Gly
              165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Pro Arg Glu Gly
225                 230                 235                 240

Arg Gly Ser Leu Leu Thr Cys Gly Asp Val Glu Glu Asn Pro Gly Pro
                245                 250                 255

Thr Ser Gly Gly Ser Gly Gly Ala Cys Val Ser Lys Gly Glu Glu Leu
            260                 265                 270

Phe Thr Gly Val Val Pro Ile Leu Val Glu Leu Asp Gly Asp Val Asn
        275                 280                 285

Gly His Lys Phe Ser Val Ser Gly Glu Gly Glu Gly Asp Ala Thr Tyr
    290                 295                 300

Gly Lys Leu Thr Leu Lys Phe Ile Cys Thr Thr Gly Lys Leu Pro Val
305                 310                 315                 320

Pro Trp Pro Thr Leu Val Thr Thr Leu Thr Tyr Gly Val Gln Cys Phe
                325                 330                 335

Ser Arg Tyr Pro Asp His Met Lys Gln His Asp Phe Phe Lys Ser Ala
            340                 345                 350

Met Pro Glu Gly Tyr Val Gln Glu Arg Thr Ile Phe Phe Lys Asp Asp
        355                 360                 365

Gly Asn Tyr Lys Thr Arg Ala Glu Val Lys Phe Glu Gly Asp Thr Leu
    370                 375                 380

Val Asn Arg Ile Glu Leu Lys Gly Ile Asp Phe Lys Glu Asp Gly Asn
385                 390                 395                 400

Ile Leu Gly His Lys Leu Glu Tyr Asn Tyr Asn Ser His Asn Val Tyr
                405                 410                 415

Ile Met Ala Asp Lys Gln Lys Asn Gly Ile Lys Val Asn Phe Lys Ile
            420                 425                 430

Arg His Asn Ile Glu Asp Gly Ser Val Gln Leu Ala Asp His Tyr Gln
        435                 440                 445

Gln Asn Thr Pro Ile Gly Asp Gly Pro Val Leu Leu Pro Asp Asn His
    450                 455                 460

Tyr Leu Ser Thr Gln Ser Ala Leu Ser Lys Asp Pro Asn Glu Lys Arg
465                 470                 475                 480

Asp His Met Val Leu Leu Glu Phe Val Thr Ala Ala Gly Ile Thr Leu
                485                 490                 495

Gly Met Asp Glu Leu Tyr Lys
            500

<210> SEQ ID NO 319
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Val Ser Lys Gly Glu Glu Asp Asn Met Ala Ile Ile Lys Glu Phe

```
  1               5                    10                   15
Met Arg Phe Lys Val His Met Glu Gly Ser Val Asn Gly His Glu Phe
             20                  25                  30
Glu Ile Glu Gly Glu Gly Gly Arg Pro Tyr Glu Gly Thr Gln Thr
             35                  40                  45
Ala Lys Leu Lys Val Thr Lys Gly Gly Pro Leu Pro Phe Ala Trp Asp
 50                  55                  60
Ile Leu Ser Pro Gln Phe Met Tyr Gly Ser Lys Ala Tyr Val Lys His
 65                  70                  75                  80
Pro Ala Asp Ile Pro Asp Tyr Leu Lys Leu Ser Phe Pro Glu Gly Phe
                 85                  90                  95
Lys Trp Glu Arg Val Met Asn Phe Glu Asp Gly Gly Val Val Thr Val
                 100                 105                 110
Thr Gln Asp Ser Ser Leu Gln Asp Gly Glu Phe Ile Tyr Lys Val Lys
                 115                 120                 125
Leu Arg Gly Thr Asn Phe Pro Ser Asp Gly Pro Val Met Gln Lys Lys
                 130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                 165                 170                 175
His Tyr Asp Ala Glu Val Lys Thr Thr Tyr Lys Ala Lys Lys Pro Val
                 180                 185                 190
Gln Leu Pro Gly Ala Tyr Asn Val Asn Ile Lys Leu Asp Ile Thr Ser
                 195                 200                 205
His Asn Glu Asp Tyr Thr Ile Val Glu Gln Tyr Glu Arg Ala Glu Gly
                 210                 215                 220
Arg His Ser Thr Gly Gly Met Asp Glu Leu Tyr Lys Pro Arg Glu Gly
225                 230                 235                 240
Arg Gly Ser Leu Leu Thr Cys Gly Asp Val Glu Glu Asn Pro Gly Pro
                 245                 250                 255
Thr Ser Trp Trp Gly Ser Gly Gly Ala Cys Val Ser Lys Gly Glu
                 260                 265                 270
Glu Leu Phe Thr Gly Val Val Pro Ile Leu Val Glu Leu Asp Gly Asp
                 275                 280                 285
Val Asn Gly His Lys Phe Ser Val Ser Gly Glu Gly Glu Gly Asp Ala
                 290                 295                 300
Thr Tyr Gly Lys Leu Thr Leu Lys Phe Ile Cys Thr Thr Gly Lys Leu
305                 310                 315                 320
Pro Val Pro Trp Pro Thr Leu Val Thr Thr Leu Thr Tyr Gly Val Gln
                 325                 330                 335
Cys Phe Ser Arg Tyr Pro Asp His Met Lys Gln His Asp Phe Phe Lys
                 340                 345                 350
Ser Ala Met Pro Glu Gly Tyr Val Gln Glu Arg Thr Ile Phe Phe Lys
                 355                 360                 365
Asp Asp Gly Asn Tyr Lys Thr Arg Ala Glu Val Lys Phe Glu Gly Asp
                 370                 375                 380
Thr Leu Val Asn Arg Ile Glu Leu Lys Gly Ile Asp Phe Lys Glu Asp
385                 390                 395                 400
Gly Asn Ile Leu Gly His Lys Leu Glu Tyr Asn Tyr Asn Ser His Asn
                 405                 410                 415
Val Tyr Ile Met Ala Asp Lys Gln Lys Asn Gly Ile Lys Val Asn Phe
                 420                 425                 430
```

Lys Ile Arg His Asn Ile Glu Asp Gly Ser Val Gln Leu Ala Asp His
            435                 440                 445

Tyr Gln Gln Asn Thr Pro Ile Gly Asp Gly Pro Val Leu Leu Pro Asp
        450                 455                 460

Asn His Tyr Leu Ser Thr Gln Ser Ala Leu Ser Lys Asp Pro Asn Glu
465                 470                 475                 480

Lys Arg Asp His Met Val Leu Leu Glu Phe Val Thr Ala Ala Gly Ile
                485                 490                 495

Thr Leu Gly Met Asp Glu Leu Tyr Lys
            500                 505

<210> SEQ ID NO 320
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Trp Gly Gly Ser Gly Gly Ala Cys Val Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Ser Gly Glu Gly Glu Gly Asp Ala Thr Tyr Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Gln His Asp Phe Phe Lys Ser Ala Met
                85                  90                  95

Pro Glu Gly Tyr Tyr Gln Glu Arg Thr Ile Phe Phe Lys Asp Asp Gly
            100                 105                 110

Asn Tyr Lys Thr Arg Ala Glu Val Lys Phe Glu Gly Asp Thr Leu Val
        115                 120                 125

Asn Arg Ile Glu Leu Lys Gly Ile Asp Phe Lys Glu Asp Gly Asn Ile
    130                 135                 140

Leu Gly His Lys Leu Glu Tyr Asn Tyr Asn Ser His Asn Val Tyr Ile
145                 150                 155                 160

Met Ala Asp Lys Gln Lys Asn Gly Ile Lys Val Asn Phe Lys Ile Arg
                165                 170                 175

His Asn Ile Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr Leu Gly
225                 230                 235                 240

Met Asp Glu Leu Tyr Lys
                245

<210> SEQ ID NO 321
<211> LENGTH: 245
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 321

```
Gly Gly Ser Gly Gly Ala Cys Val Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Ser Gly Glu Gly Glu Gly Asp Ala Thr Tyr Gly Lys
        35                  40                  45

Leu Thr Leu Lys Phe Ile Cys Thr Thr Gly Lys Leu Pro Val Pro Trp
50                  55                  60

Pro Thr Leu Val Thr Thr Leu Thr Tyr Gly Val Gln Cys Phe Ser Arg
65                  70                  75                  80

Tyr Pro Asp His Met Lys Gln His Asp Phe Phe Lys Ser Ala Met Pro
                85                  90                  95

Glu Gly Tyr Tyr Gln Glu Arg Thr Ile Phe Phe Lys Asp Asp Gly Asn
            100                 105                 110

Tyr Lys Thr Arg Ala Glu Val Lys Phe Glu Gly Asp Thr Leu Val Asn
        115                 120                 125

Arg Ile Glu Leu Lys Gly Ile Asp Phe Lys Glu Asp Gly Asn Ile Leu
130                 135                 140

Gly His Lys Leu Glu Tyr Asn Tyr Asn Ser His Asn Val Tyr Ile Met
145                 150                 155                 160

Ala Asp Lys Gln Lys Asn Gly Ile Lys Val Asn Phe Lys Ile Arg His
                165                 170                 175

Asn Ile Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser Thr Gln Ser Ala Leu Ser Lys Asp Pro Asn Glu Lys Arg Asp His
210                 215                 220

Met Val Leu Leu Glu Phe Val Thr Ala Ala Gly Ile Thr Leu Gly Met
225                 230                 235                 240

Asp Glu Leu Tyr Lys
                245
```

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

```
Trp Gly Gly Ser Gly Gly
1               5
```

<210> SEQ ID NO 323
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Gly Gly Ser Gly Gly
1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ser Trp Trp Gly Gly Ser Gly Gly
1               5

<210> SEQ ID NO 325
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Lys Arg Leu Ala Val Tyr
1               5

<210> SEQ ID NO 326
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Trp Gly Gly Ser Gly Gly Ala Cys Val Ser Lys Gly Glu Glu Leu Phe
1               5                   10                  15

Thr Gly Val Val Pro Ile Leu Val Glu Leu Asp Gly Asp Val Asn Gly
                20                  25                  30

His Lys Phe Ser Val Ser Gly Glu Gly Glu Gly Asp Ala Thr Tyr Gly
            35                  40                  45

Lys Leu Thr Leu Lys Phe Ile Cys Thr Thr Gly Lys Leu Pro Val Pro
        50                  55                  60

Trp Pro Thr Leu Val Thr Thr Leu Thr Tyr Gly Val Gln Cys Phe Ser
65                  70                  75                  80

Arg Tyr Pro Asp His Met Lys Gln His Asp Phe Phe Lys Ser Ala Met
                85                  90                  95

Pro Glu Gly Tyr Val Gln Glu Arg Thr Ile Phe Phe Lys Asp Asp Gly
            100                 105                 110

Asn Tyr Lys Thr Arg Ala Glu Val Lys Phe Glu Gly Asp Thr Leu Val
        115                 120                 125

Asn Arg Ile Glu Leu Lys Gly Ile Asp Phe Lys Glu Asp Gly Asn Ile
    130                 135                 140

Leu Gly His Lys Leu Glu Tyr Asn Tyr Asn Ser His Asn Val Tyr Ile
145                 150                 155                 160

Met Ala Asp Lys Gln Lys Asn Gly Ile Lys Val Asn Phe Lys Ile Arg
                165                 170                 175

```
His Asn Ile Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
            195                 200                 205

Leu Ser Thr Gln Ser Ala Leu Ser Lys Asp Pro Asn Glu Lys Arg Asp
            210                 215                 220

His Met Val Leu Leu Glu Phe Val Thr Ala Ala Gly Ile Thr Leu Gly
225                 230                 235                 240

Met Asp Glu Leu Tyr Lys
                245

<210> SEQ ID NO 327
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Gly Gly Ser Gly Gly Ala Cys Val Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Ser Gly Glu Gly Glu Gly Asp Ala Thr Tyr Gly Lys
            35                  40                  45

Leu Thr Leu Lys Phe Ile Cys Thr Thr Gly Lys Leu Pro Val Pro Trp
50                  55                  60

Pro Thr Leu Val Thr Thr Leu Thr Tyr Gly Val Gln Cys Phe Ser Arg
65                  70                  75                  80

Tyr Pro Asp His Met Lys Gln His Asp Phe Phe Lys Ser Ala Met Pro
                85                  90                  95

Glu Gly Tyr Val Gln Glu Arg Thr Ile Phe Phe Lys Asp Asp Gly Asn
            100                 105                 110

Tyr Lys Thr Arg Ala Glu Val Lys Phe Glu Gly Asp Thr Leu Val Asn
            115                 120                 125

Arg Ile Glu Leu Lys Gly Ile Asp Phe Lys Glu Asp Gly Asn Ile Leu
            130                 135                 140

Gly His Lys Leu Glu Tyr Asn Tyr Asn Ser His Asn Val Tyr Ile Met
145                 150                 155                 160

Ala Asp Lys Gln Lys Asn Gly Ile Lys Val Asn Phe Lys Ile Arg His
                165                 170                 175

Asn Ile Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
            195                 200                 205

Ser Thr Gln Ser Ala Leu Ser Lys Asp Pro Asn Glu Lys Arg Asp His
            210                 215                 220

Met Val Leu Leu Glu Phe Val Thr Ala Ala Gly Ile Thr Leu Gly Met
225                 230                 235                 240

Asp Glu Leu Tyr Lys
                245
```

TRANSIENT REPORTERS AND METHODS FOR BASE EDITING ENRICHMENT

CROSS-REFERENCE TO RELATED PATENT APPLICATIONS

The present application claims the benefit of priority under 35 U.S.C. § 119(e) to U.S. Provisional Application No. 63/038,220, filed on Jun. 12, 2020, the content of which is incorporated herein by reference in its entirety.

STATEMENT REGARDING FEDERALLY SPONSORED RESEARCH

This invention was made with government support under R01 GM106081, R01 GM121698, R01 GM131405 and R21 AG056706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 8, 2024, is named 112624_01257_M20-204L_SL.txt and is 171,515 bytes in size.

BACKGROUND

The rapid advancement of CRISPR/Cas-based technologies has allowed for the modification (i.e., deletion, mutation and insertion) of human cells at precise genomic locations. For applications in which precise editing of a single nucleotide is desired, the CRISPR/Cas machinery can be used to introduce site-specific double-stranded breaks (DSB) followed by homology-directed repair (HDR) using an exogenous DNA template. However, HDR is inefficient in mammalian cells, especially in recalcitrant cells such as human pluripotent stem cells (hPSCs), and repair of DSB is predominantly achieved through non-homologous end joining (NHEJ). In addition, NHEJ results in insertion or deletion of nucleotides (indels), resulting in undesired disruption (e.g. frameshift mutations, premature stop codons, deletion) of the targeted genes.

As an alternative to standard gene editing approaches that require a DSB, several groups have reported the development of deaminase base editors that do not rely on HDR to introduce single nucleotide genomic changes. Broadly speaking, these base editors consist of a fusion of three components—a DOA nickase Cas endonuclease, cytidine deaminase (APOBEC1), and a DNA uracil glycosylase inhibitor (UGI). This complex is capable of converting cytosine to thymine (or adenine to guanine on the complementary strand) without the need for a DSB and homology repair template. Overall, genome modification through the use of base editors has been shown to result in formation of fewer indels when compared to HDR-based methods.

Despite the advantages that deaminase base editors offer, identification and isolation of cell populations that have been successfully edited remains challenging. Specifically, there is no readily detectable phenotype to distinguish edited from unedited cells. In turn, isolation of edited cell populations requires single cell isolation followed by downstream sequencing verification. Some progress has been made to help enrich for edited cells, such as co-transfecting plasmids with a fluorescent reporter and using flow cytometry to isolate reporter-positive cells. Similarly, base editors fused to fluorescent proteins have been used to enrich for edited cell populations. However, these techniques are only reporters of transfection (RoT) and do not report on base editing activity within a cell population. Accordingly, there remains a need in the art for materials and efficient methods for selecting and enriching for base-edited human cells. There also remains a need in the art for efficient methods for producing isogenic populations of base edited human cells, particularly human pluripotent stem cell populations having targeted genetic modifications.

BRIEF SUMMARY OF THE DISCLOSURE

In a first aspect, a polynucleotide encoding one or more reporter polypeptides, the polynucleotide including a PAM site adjacent to a base that when the base is edited a change in a function or characteristic of the one or more reporter polypeptides occurs. The polynucleotide may encode at least one reporter polypeptide with at least 90% sequence identity to SEQ ID NO: 2, wherein the polynucleotide encodes histidine at amino acid at position number 66 relative to SEQ ID NO: 1, and encodes glycine at amino acid position number 72 relative to SEQ ID NO: 1. Alternatively, the polynucleotide may encode a reporter polypeptide with at least 90% sequence identity to one of SEQ ID NO: 316 or 318. In one alternative, the polynucleotide comprises a polynucleotide selected from the group consisting of SEQ ID NO: 258, 259 and 260.

In a second aspect, provided herein is a kit. The kit can comprise or consist essentially of a first nucleic acid sequence encoding one or more reporter proteins, wherein the first nucleic acid includes a PAM site adjacent to a base that when edited causes a change in a function or characteristic of the one or more reporter proteins; a second nucleic acid sequence encoding a first sgRNA adjacent to a protospacer adjacent motif (PAM), wherein the first sgRNA comprises a protospacer sequence and is complementary to a portion of the nucleic acid sequence encoding one or more reporter proteins; a third nucleic acid sequence encoding a second sgRNA adjacent to a protospacer adjacent motif (PAM), wherein the sgRNA comprises a protospacer sequence and is complementary to a portion of a gene of interest to be base edited or comprises a cloning site to allow insertion of a complementary portion of a gene of interest to be base edited; and a fourth nucleic acid sequence encoding a base editor. The base editor can be selected from a cytidine deaminase base editor, an adenine base editor, Cas9-mediated adenosine base editor, and a prime editor. One or more of the first, second, third, or fourth nucleic acids can be provided in one or more vectors. The vector can be an episomal vector. The reporter protein can be a fluorescent protein or a variant thereof, luciferase or a variant thereof, β-galactosidase (lacZ), chloramphenyl acetyltransferase (CAT), β-glucuronidase (GUS), secretory alkaline phosphatase (SEAP), a survival selection protein, or a reporter protein that directly or indirectly produces or catalyzes a colorimetric reaction. The fluorescent protein can be a green fluorescent protein (GFP), a blue fluorescent protein (BFP), red fluorescent protein (RFP), luciferase, or mCherry, or a variant thereof. The fluorescent protein can be a BFP variant comprising a histidine at amino acid position 66 (numbered relative to SEQ ID NO:1). Alternatively, the reporter protein may be a fusion protein of two fluorescent proteins linked via a linker including at least one stop codon and a PAM site.

The fourth nucleic acid sequence encoding a base editor can be a vector comprising a base editor operably linked to a heterologous promoter.

In another aspect, provided herein is a method for selecting a base edited cell. The method can comprise or consist essentially of introducing into a cell a first nucleic acid sequence encoding one or more reporter proteins, a second nucleic acid sequence encoding a first sgRNA adjacent to a protospacer adjacent motif (PAM), wherein the first sgRNA comprises a protospacer sequence and is complementary to a portion of the nucleic acid sequence encoding one or more reporter proteins; a third nucleic acid encoding a second sgRNA adjacent to a protospacer adjacent motif (PAM), wherein the second sgRNA comprises a protospacer adjacent sequence and is complementary to a portion of a gene of interest to be base edited; and a fourth nucleic acid sequence encoding a base editor, wherein the first nucleic acid includes a PAM site adjacent to a base that when edited causes a change in a function or characteristic of the one or more reporter proteins and wherein the change in function or characteristic results in a detectable signal; culturing the cell for about 48 hours to about 72 hours under conditions sufficient for expression of proteins encoded by the first, second, third and fourth nucleic acid sequences; sorting cells based on the presence or absence of a detectable signal, wherein a change in the detectable signal indicates that the base editor caused a base-to-base conversion or other genetic modification in the first nucleic acid sequence; and selecting cells exhibiting the changed detectable signal from the sorted cells, thereby selecting base edited cells. The base editor can be selected from a cytidine deaminase base editor, an adenine base editor, Cas9-mediated adenosine base editor, and a prime editor. One or more of the first, second, and third nucleic acids can be provided in a vector. The vector can be an episomal vector. The reporter protein can be a fluorescent protein or a variant thereof, luciferase or a variant thereof, β-galactosidase (lacZ), chloramphenyl acetyltransferase (CAT), β-glucuronidase (GUS), secretory alkaline phosphatase (SEAP), a survival selection protein, or a reporter protein that directly or indirectly produces or catalyzes a colorimetric reaction. The fluorescent protein can be a green fluorescent protein (GFP), a blue fluorescent protein (BFP), red fluorescent protein (RFP), luciferase, mCherry, or a variant or combination thereof. The fluorescent protein can be a BFP variant comprising a histidine at amino acid position 66 (numbered relative to SEQ ID NO:1). The cell can be a human cell. The human cell can be a human pluripotent stem cell. The human pluripotent stem cell can be a human induced pluripotent stem cell obtained from a somatic cell of a human subject having a disease-associated single nucleotide polymorphism. Selecting can be performed using flow cytometry. Sorting can be performed using a fluorescence activated cell sorter (FACS).

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 9 presents pDT-sgRNA sequence.

FIG. 13B discloses SEQ ID NOS 322, 200, 323, 201, 324, 202, and 324, respectively, in order of appearance. (c) Representative fluorescence microscopy images of HEK293 cells transfected with pEF-XMAS-1×Stop (left panels) or pEF-XMAS-2×Stop (right panels), pCMV-ABEmax, and sg(NT) (top panels) or sg(XMAS) (bottom panels). (d) Flow cytometry and (e) fluorescence microscopy analysis of HEK293 cells at various time points after transfection with pEF-XMAS-1×Stop (left panels) or pEF-XMAS-2×Stop (right panels), pCMVABEmax, and sg(XMAS).

FIG. 20B discloses SEQ ID NOS 325 and 210, respectively, in order of appearance. (c) Representative flow cytometry plot of HEK293 cells in which TREE was applied targeting the APOE(R158) locus. (d) HEK293 cells were transfected with pEF-BFP, pCMV-BE4-Gam, and pDT-sgRNA. Comparison of transfection efficiency (percentage of BFP-positive cells) and editing efficiency (percentage of C-to-T conversion at target nucleotide) in unsorted cell populations at Site-1, Site-2, Site-3, and APOE (R158) locus. (e) Representative Sanger sequencing chromatographs of APOE(R158) locus in GFP-positive, GFP-negative, and unsorted cell populations isolated with TREE-based methods. FIG. 20E discloses SEQ ID NOS 325 and 211, respectively, in order of appearance.

Figure 22:
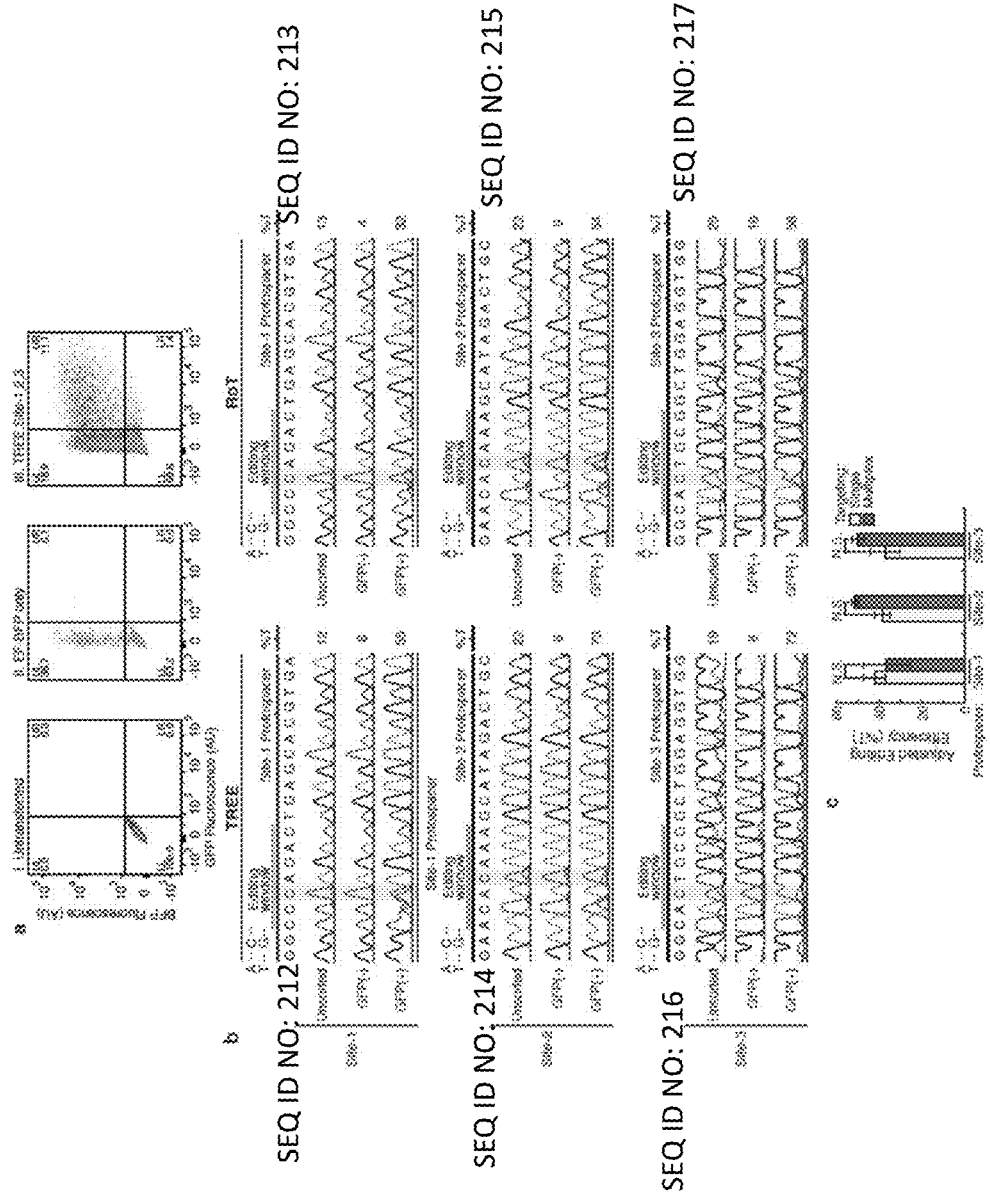

FIG. 22 shows an Analysis of multiplexed edited HEK293 cells using TREE- and RoT-based methods. (a) Representative flow cytometry plot of HEK293 cells in which multiplex TREE was applied simultaneously targeting Site-1, Site-2, and Site-3. (b) Representative Sanger sequencing chromatographs of the Site-1, Site-2, and Site-3 loci in GFP-positive, GFP-negative, and unsorted cell populations isolated with TREE multiplex-based methods. (c) Comparison of base editing efficiencies at Site-1, Site-2, and Site-3 in GFP-positive, GFP-negative, and unsorted cell populations using TREE-based methods to target these sites individually or in a multiplexed manner. n=3; N.S.=not significant.

Figure 23:
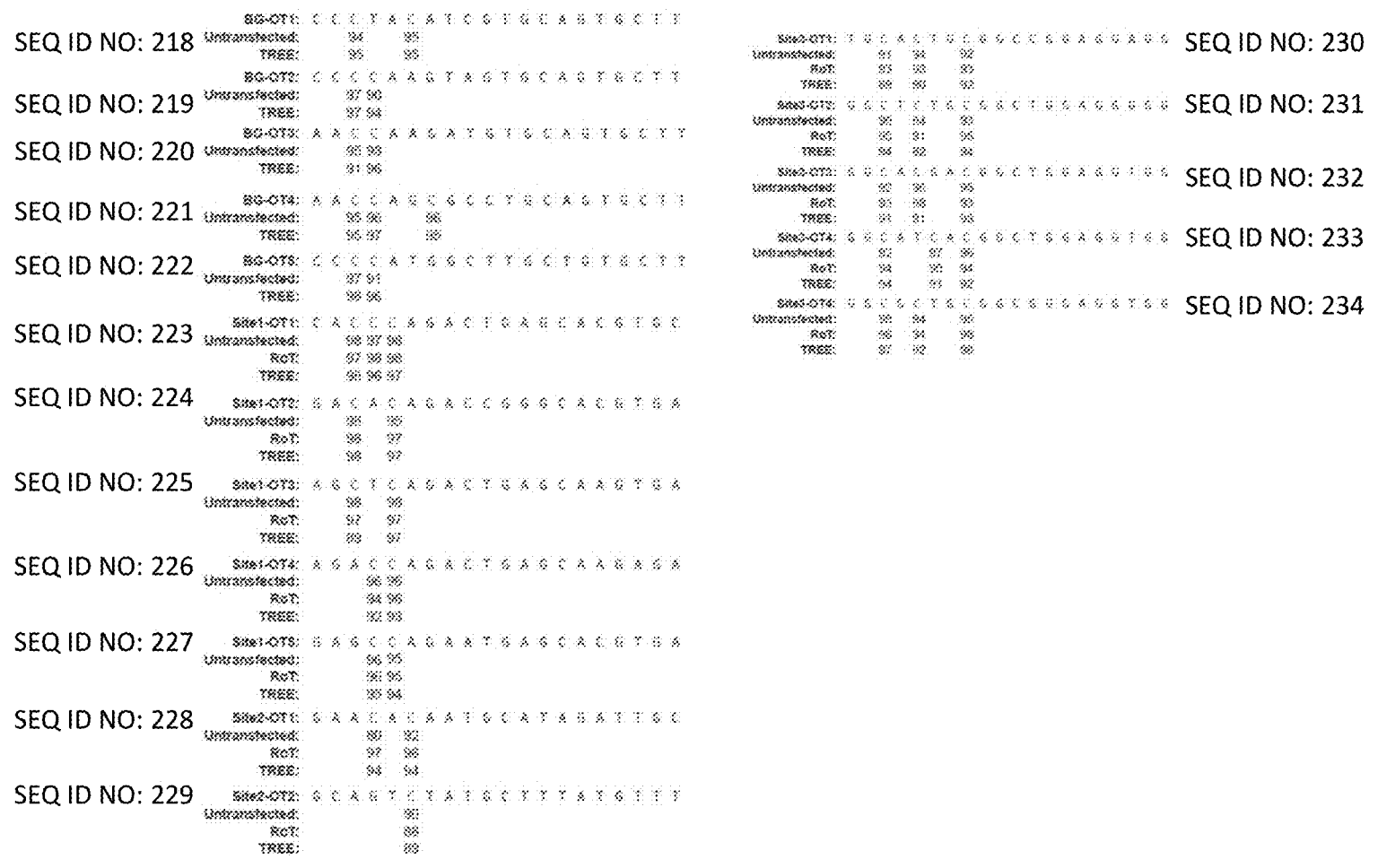

FIG. 23 shows an analysis of off-target sites in multiplexed edited HEK293 cells using TREE- and RoT-based methods. GFP-positive cell populations isolated from TREE and RoT approaches were PCR-amplified and subjected to Sanger sequencing on the top predicted off-target loci for the sgRNA sequences for sg(BG) and genomic Sites 1-3. The C nucleotides in red text are potential Cs that can undergo C-to-T conversion within the editing window in the protospacer. The numbers below each C are quantification of the percentage of Cs of the Sanger sequence chromatograms using EditR.

Figure 24:
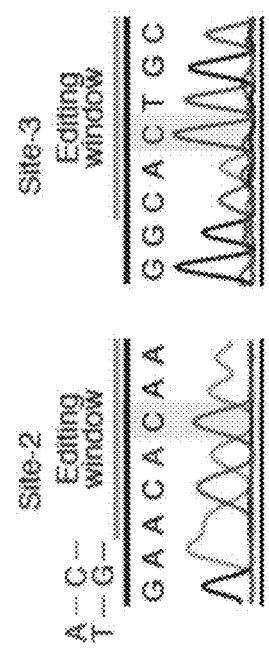

FIG. 24 depicts the identification of exclusive targeting events in clonal population in edited HEK293 cells using TREE. Representative Sanger sequencing chromatographs of clonal cell populations that contain edits exclusively at the target C and not any other Cs within the editing window.

Figure 25:
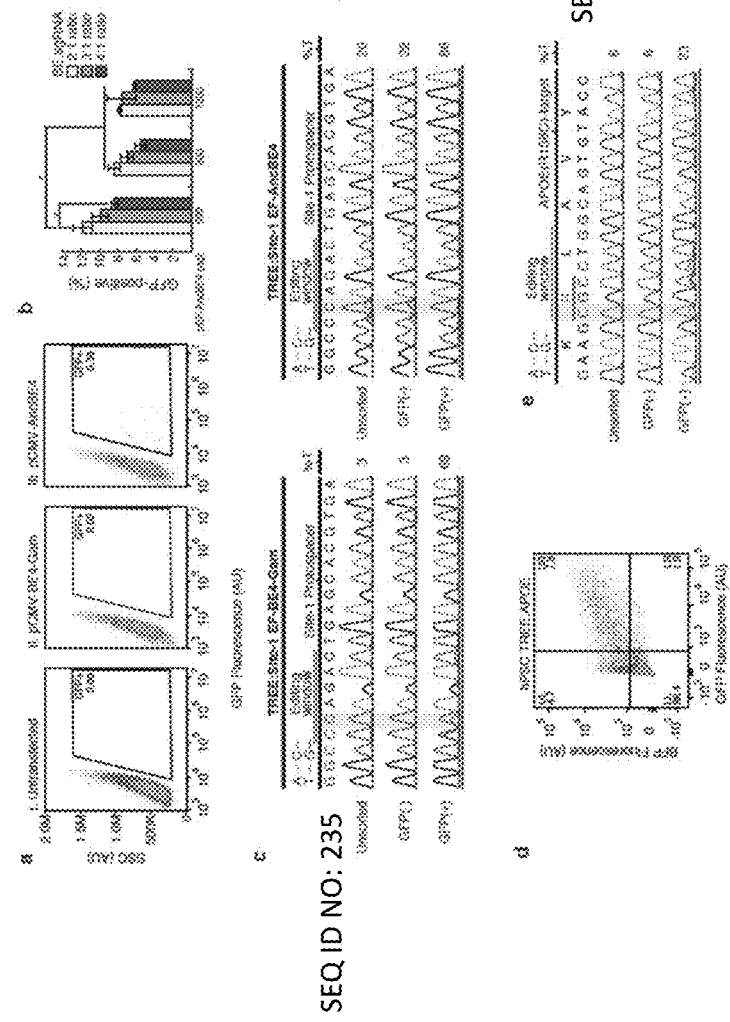

FIG. 25 demonstrates that TREE allows for base editing in hPSCs. (a) Representative flow cytometry plots in which TREE was employed in hPSCs utilizing (i) untransfected (ii) pCMV-BE4-Gam or (iii) pCMV-AncBE4. (b) Editing efficiency (percentage GFP-positive cells) of targeting in hPSCs line with various amounts of pEF-AncBE4 plasmid and ratios with the sg(BG) vector. n=3, *=p<0.05. (c) Representative Sanger sequencing chromatographs of Site-1 in GFP-positive, GFP-negative, and unsorted cell populations isolated with TREE- and RoT-based methods in which pEF-BE4-Gam or pEF-AncBE4 was utilized. (d) Representative flow cytometry plot of hPSCs in which TREE was applied targeting the APOE(R158) locus. (e) Representative Sanger sequencing chromatographs of APOE(R158) locus in GFP-positive, GFP-negative, and unsorted cell populations isolated with TREE-based methods.

Figure 26:
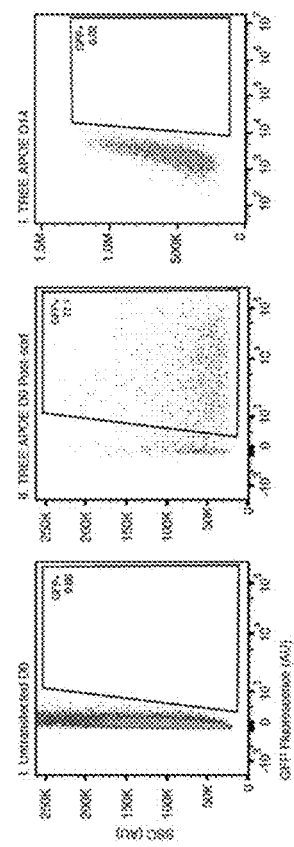

FIG. 26 shows that TREE fluorescent output in hPSCs is transient. Representative flow cytometry plots of (i) untransfected hPSCs, (ii) TREE-enriched GFP-positive hPSCs 0 days (iii) 14 days after sorting.

FIG. 27 demonstrates a Next generation sequencing (NGS) analysis of allelic outcomes at target sites in hPSCs. NGS analysis for the target site when TREE was applied to edit Site-1 or the APOE(R158) in hPSCs. The number to left of the allelic outcome indicates the position upstream (5') relative to the PAM. Abbreviation: WT=wild-type unedited locus.

Figure 28:
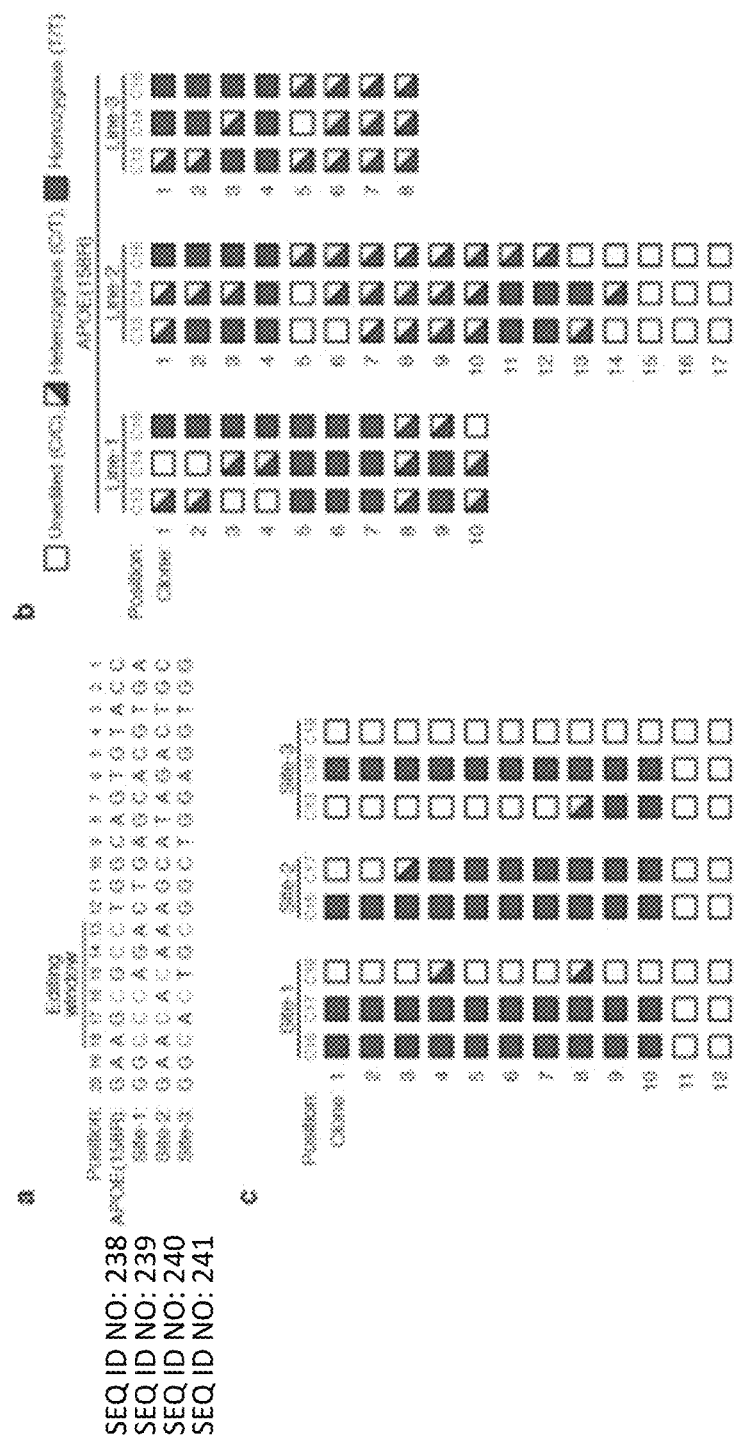

FIG. 28 depicts an Analysis of bystander editing in BIG-TREE edited hPSC clones. (a) Schematic of editing window and nucleotide position for target sites associated with FIG. 1 (APOE158R) and FIG. 2 (Genomic Sites 1-3). Red indicates target C within the editing window. Blue indicates bystander C within the editing window. (b) Distribution of bystander edits at the APOE(158R) locus in clonal hPSCs. (c) Distribution of bystander edits at genomic Sites1-3 in clonal hPSCs that were generated via multiplexed base editing.

Figure 29:
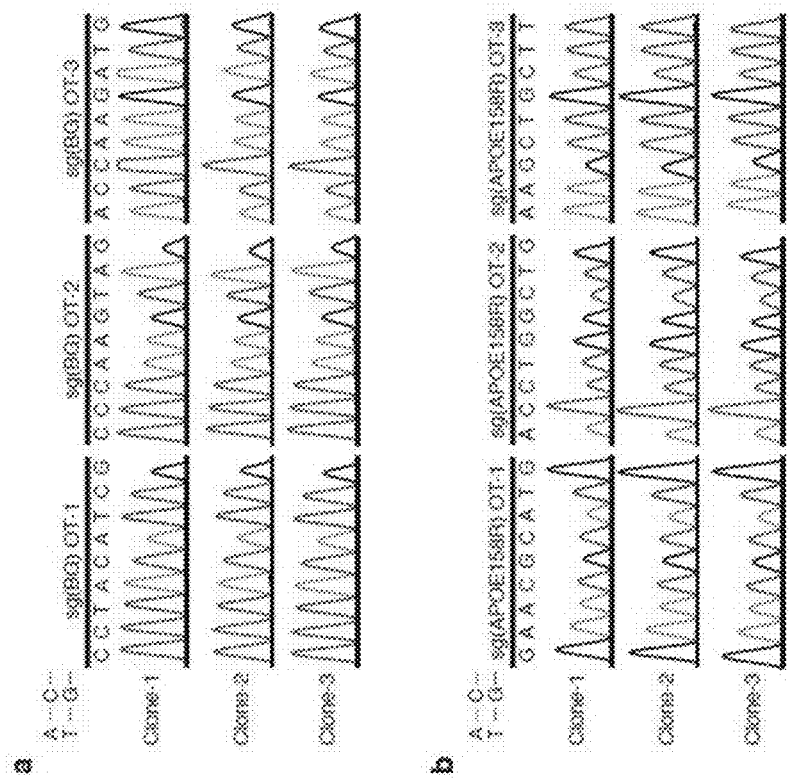

FIG. 29 shows Off-target analysis of hPSC clones generated via BIG-TREE. Representative clonal lines were subjected to Sanger sequencing on the top predicted off-target loci for the sgRNA sequences for (a) sg(BG) and (b) sg(APOE158R).

Figure 30:
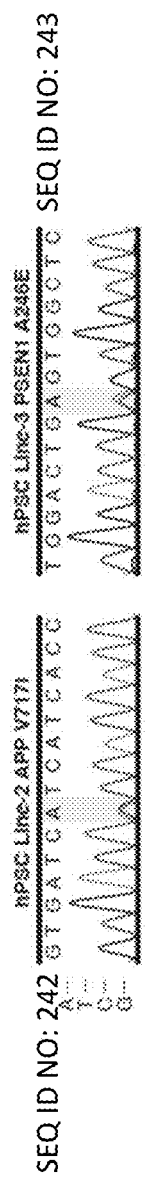

FIG. 30 shows an Analysis of FAD-related genotypes in clonal hPSC lines generated from hPSC lines 2 and 3. Representative clonal lines derived from hPSC lines 2 and 3 were subject to Sanger sequencing to confirm that they retained the APP V717I or PSEN1 A246E FAD-related mutations after editing at the APOE(158R) locus.

Figure 31:
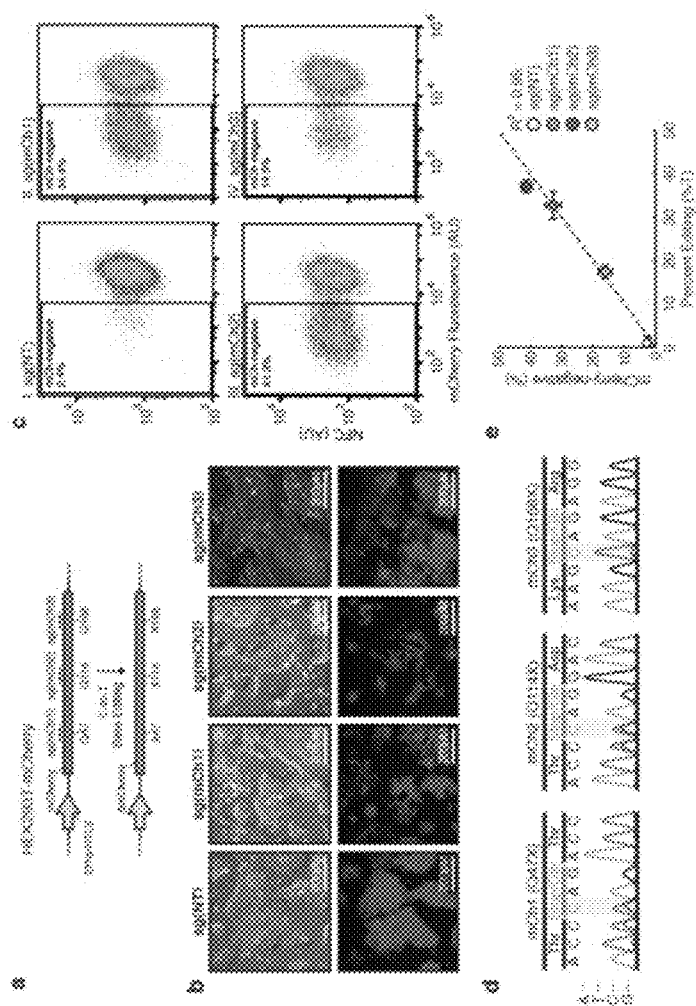

FIG. 31 shows Validation of BIG-TREE-based gene knock-out (KO) using a HEK293-mCherry line. (a) Schematic of using BIG-TREE to introduce stop codons into the genomically integrated mCherry cassette. Successful targeting with sg(mCh1), sg(mCh2), or sg(mCh3) will result in a C-to-T conversion causing a change in the amino acid at position 47, 114, or 168, respectively, from a glutamine (Q) to a premature stop codon (X). (b) Representative phase contrast (top panels) and fluorescent (bottom panels) images of HEK293-mCherry cells that had been targeted with a control non-targeting sgRNA [sg(NT)] or a sgRNA targeting mCherry [sg(mCh1), sg(mCh2), or sg(mCh3)]. (c) Representative flow cytometry plots of HEK293-mCherry cells that been targeted with a control non-targeting sgRNA [sg(NT)] or a sgRNA targeting mCherry [sg(mCh1), sg(mCh2), or sg(mCh3)]. (d) Sanger sequencing of sg(mCh1-3) protospacer sequences with codon translations indicated. Sequencing indicates conversion from target 'CAG' (Q) to 'TAG' (X). (e) Correlation between observed mCherry loss by flow cytometry and percent conversion of the target C to T within Sanger sequencing reads.

Figure 32:
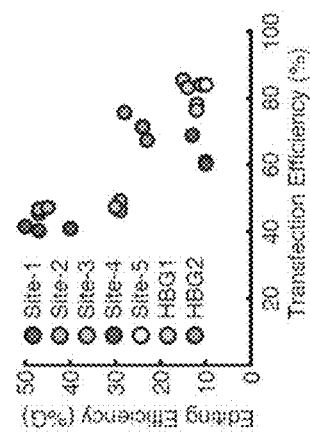

FIG. 32 shows that transfection efficiency is not predictive of editing efficiency. HEK293 cells were transfected with pEF-mCherry, pCMV-ABEmax, and sg(TS). Comparison of transfection efficiency (percentage of mCherry-positive cells) and editing efficiency (percentage of A-to-G conversion at target nucleotides) in unsorted cell populations targeted at various genomic loci.

Figure 33:
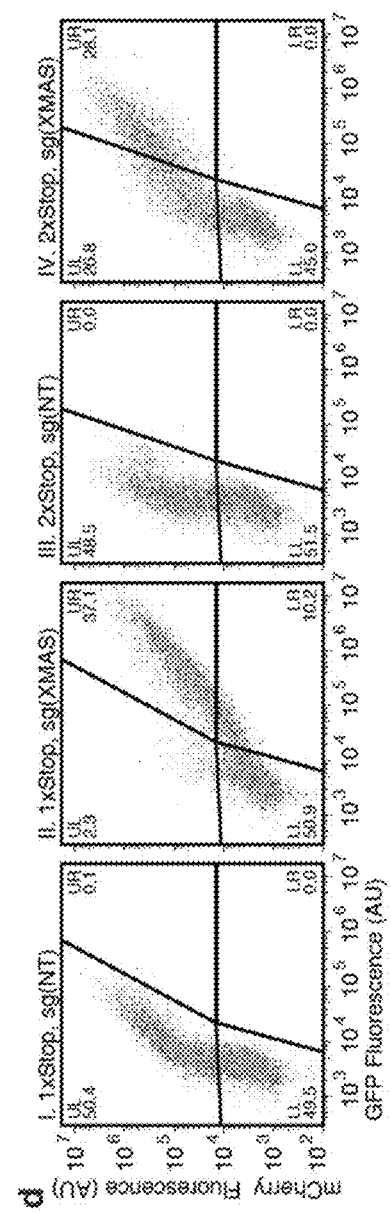

FIG. 33 shows flow cytometry-based characterization of XMAS-TREE reporter. Representative flow cytometry plots of HEK293 cells transfected with pEF-XMAS-1×Stop or pEF-XMAS-2×Stop, pCMV-ABEmax, and sg(NT) or sg(XMAS).

Figure 34:
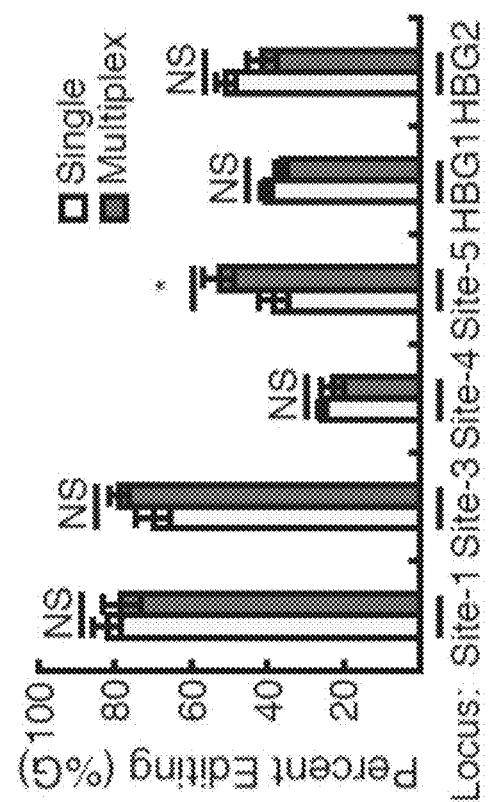

FIG. 34 demonstrates a comparison of XMAS-TREE editing efficiency in individual- or multiplexed-targeted genomic sites. Quantification of base editing efficiencies at targeted loci mCherry-positive/GFP-positive cell populations using XMAS-TREE-based targeting in a single or multiplexed manner. N.S.=not significant, *=p<0.05.

Figure 35:
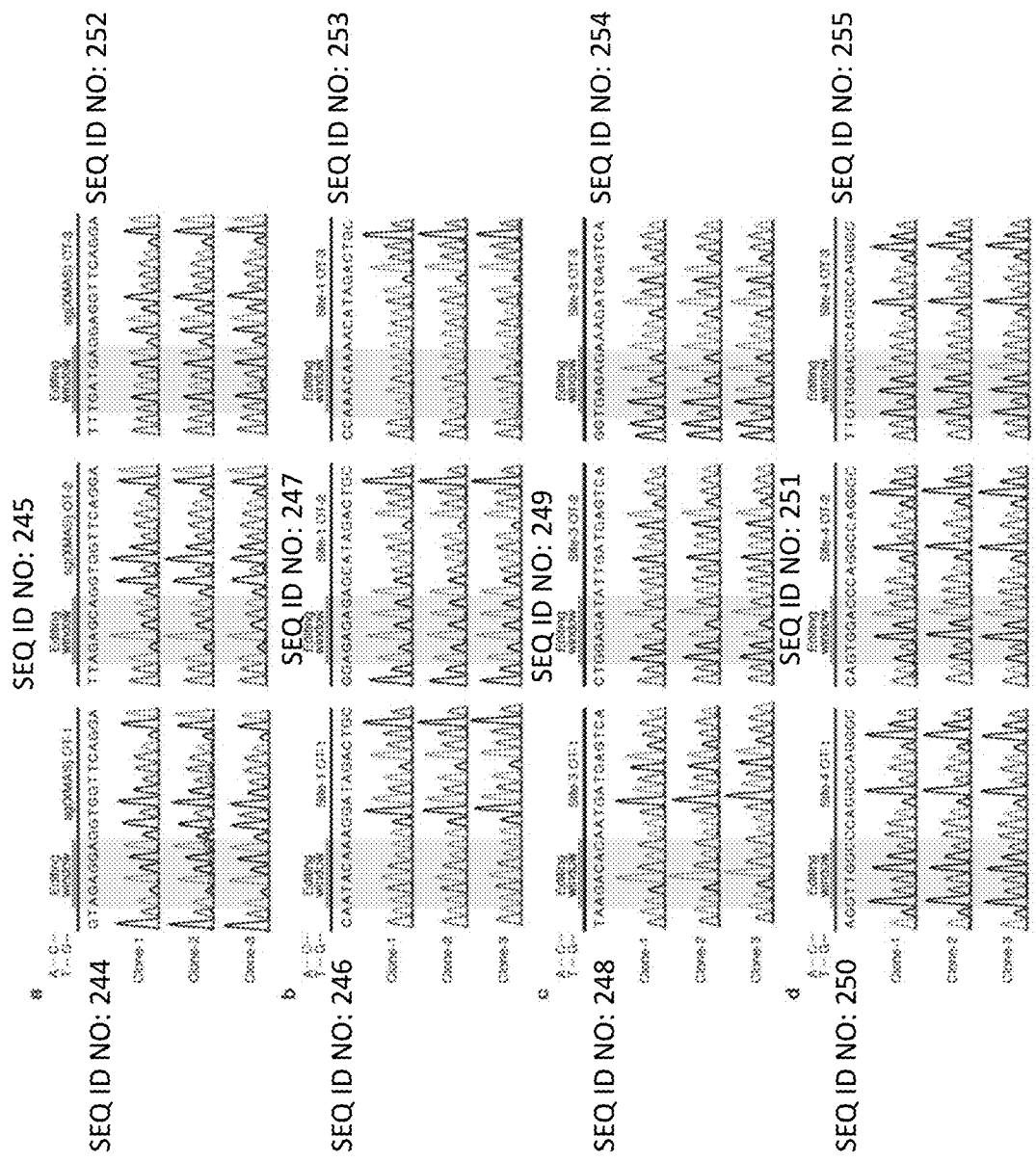

FIG. 35 shows off-target analysis of HEK293 clones generated using XMAS-TREE-based methods. Representative clonal lines were analyzed by Sanger sequencing at the top predicted off-target loci for the sgRNA sequences for (a) sg(XMAS), (b) sg(Site-1), (c) sg(Site-3), and (d) sg(Site-4).

Figure 36:
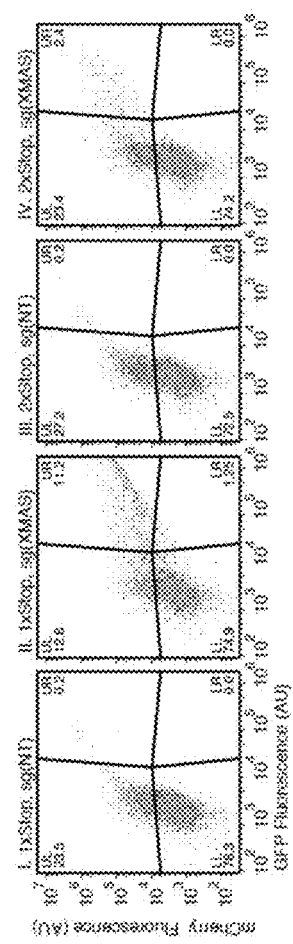

FIG. 36 shows the characterization of XMAS-TREE reporter in hPSCs. Representative flow cytometry of hPSCs transfected pEF-XMAS-1×Stop or pEF-XMAS-2×Stop, pEF-ABEmax, and sg(NT) or sg(XMAS).

Figure 37:
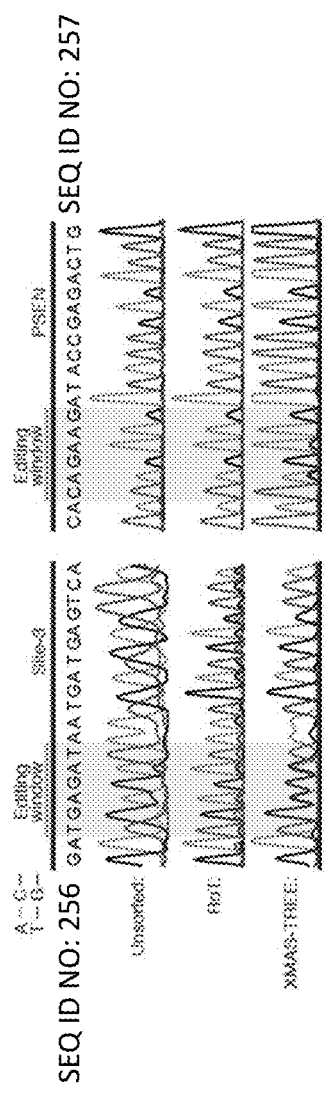

FIG. 37 demonstrates Representative Sanger sequencing chromatographs of edited hPSCs enriched using XMAS-TREE and RoT-based approaches. Sanger sequencing chromatographs of Site-3 and PSEN1 of unsorted hPSCs as well as mCherry-positive and mCherry-positive/GFP-positive cells isolated using RoT-based and XMAS-TREE strategies, respectively.

Figure 38:
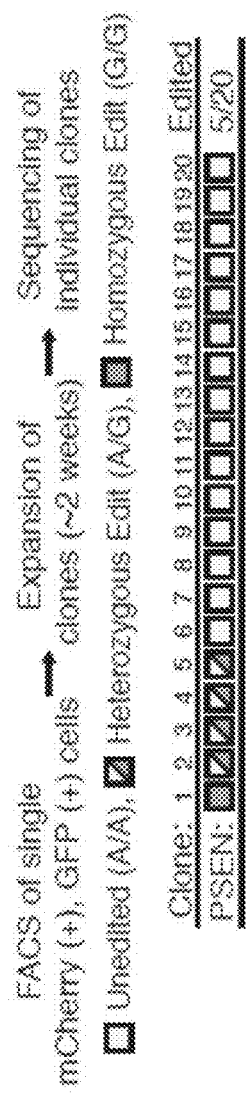

FIG. 38 shows the distribution of genotypes in clonal hPSCs generated using XMAS-TREE-based methods. Analysis of clonal editing efficiency in hPSCs that were targeted at the PSEN1 locus.

Figure 39:
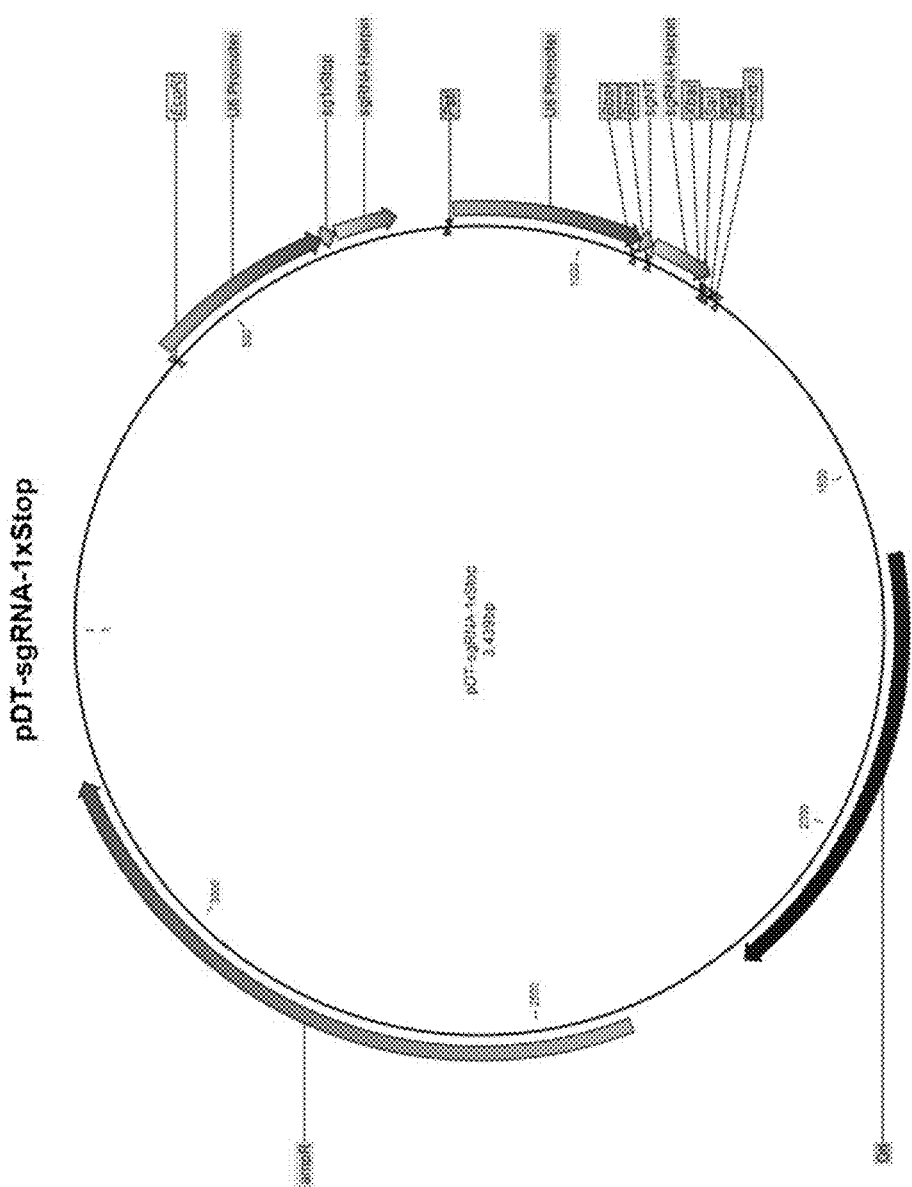

FIG. 39 shows a vector map and sequence for pDT-sgRNA-1×Stop.

Figure 40:
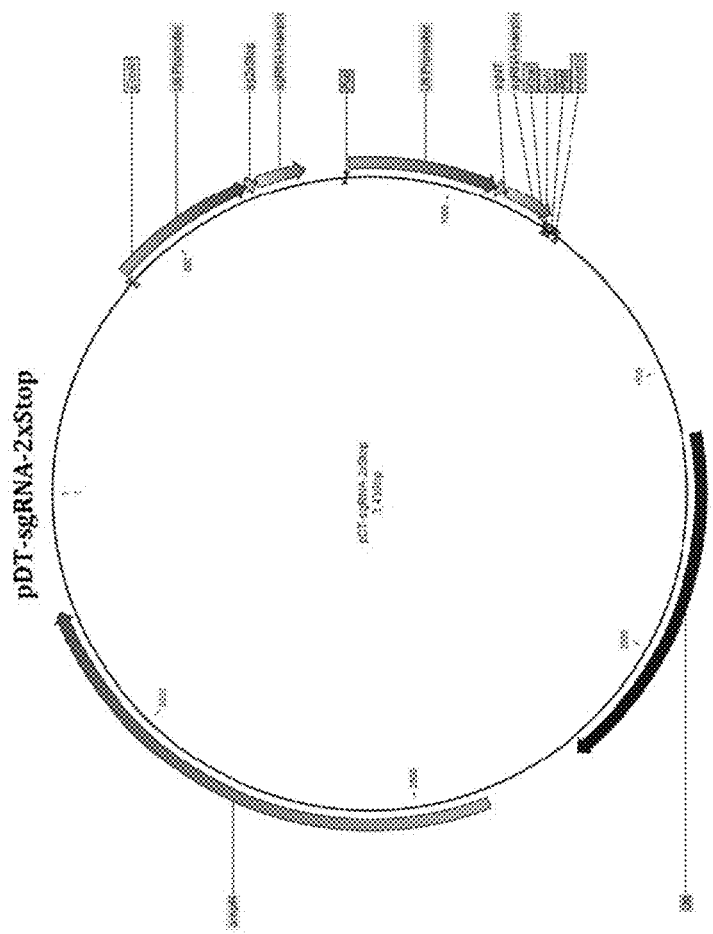

FIG. 40 shows a vector map and sequence for pDT-sgRNA-2×Stop.

Figure 41:
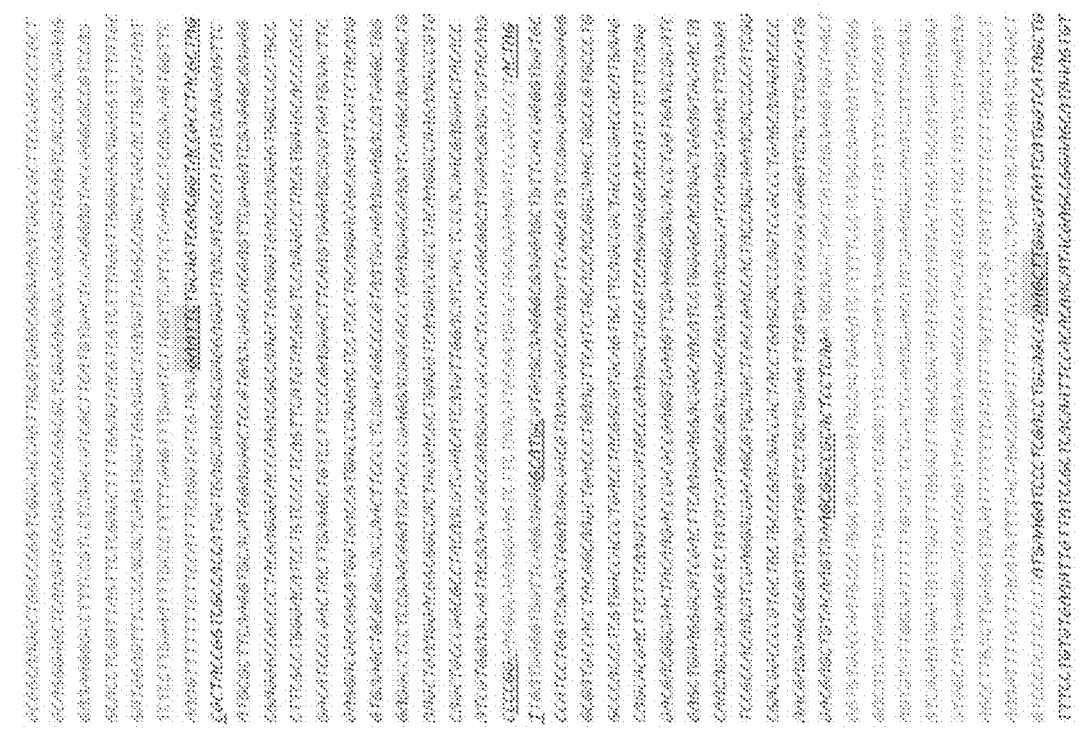
Figure 41:
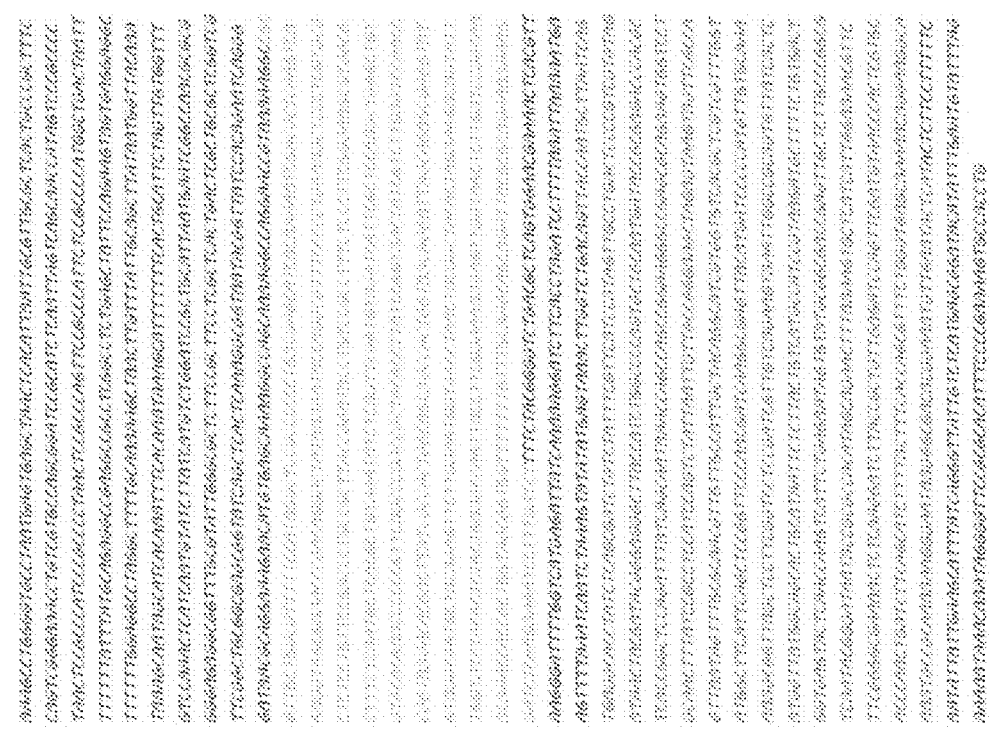

FIG. 41 shows a vector map and sequence for pEF-XMAS-1×Stop.

Figure 42:
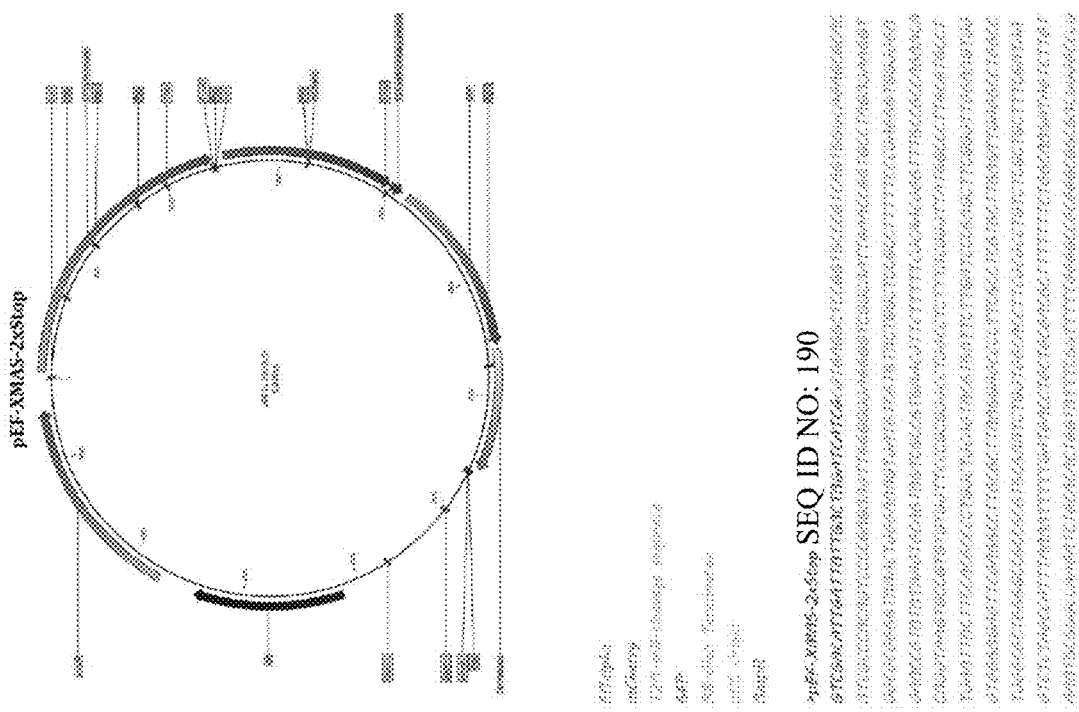
Figure 42:
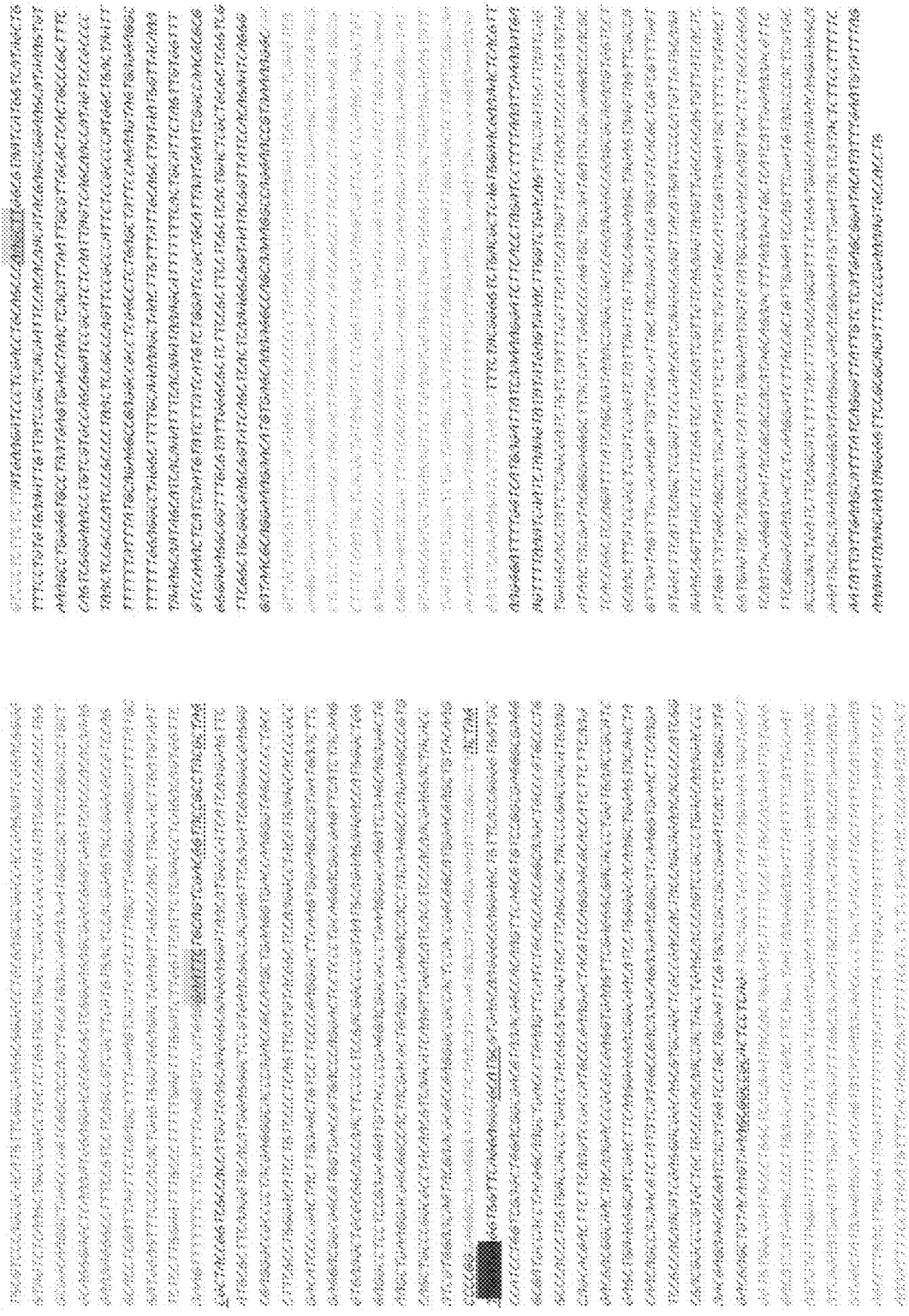

FIG. 42 shows a vector map and sequence for pEF-XMAS-2×Stop.

Figure 43:
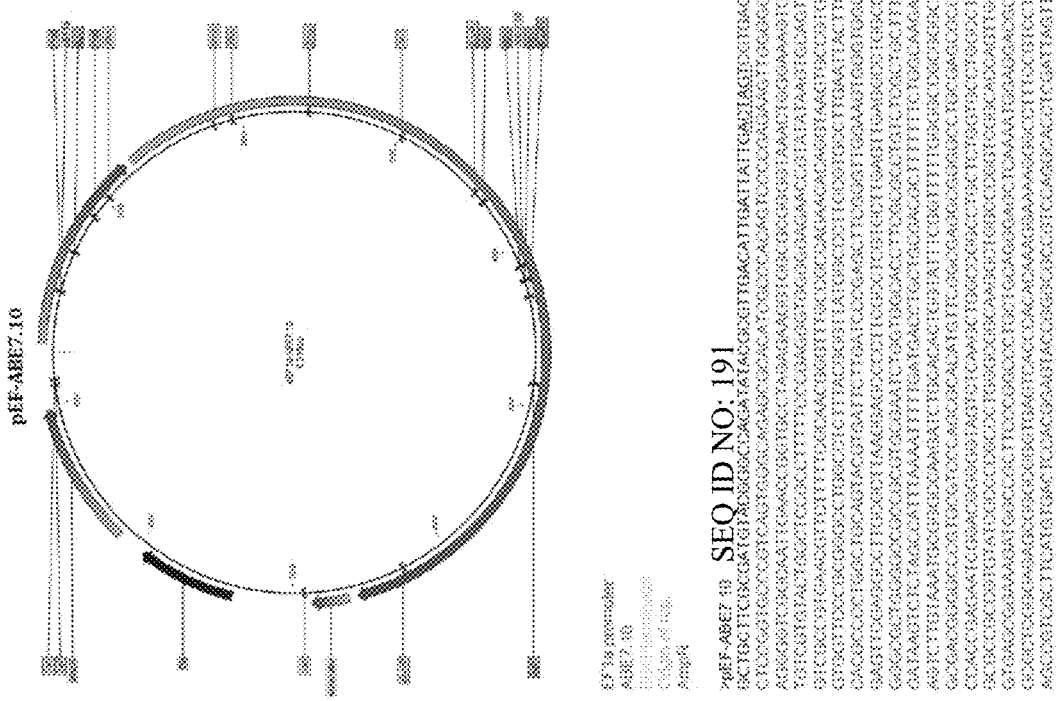
Figure 43:
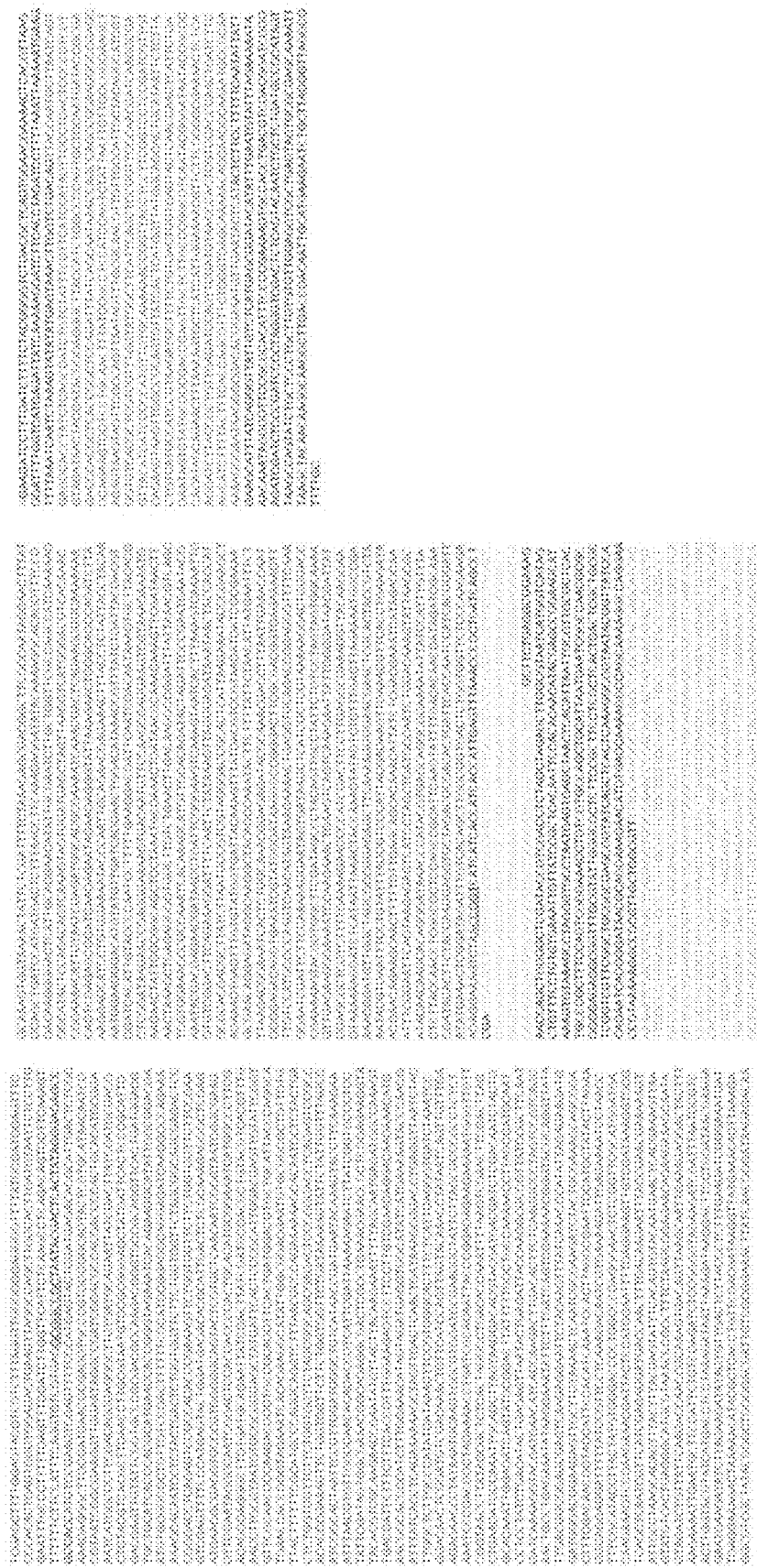

FIG. 43 shows a vector map and sequence for pEF-ABE7.10.

Figure 44:
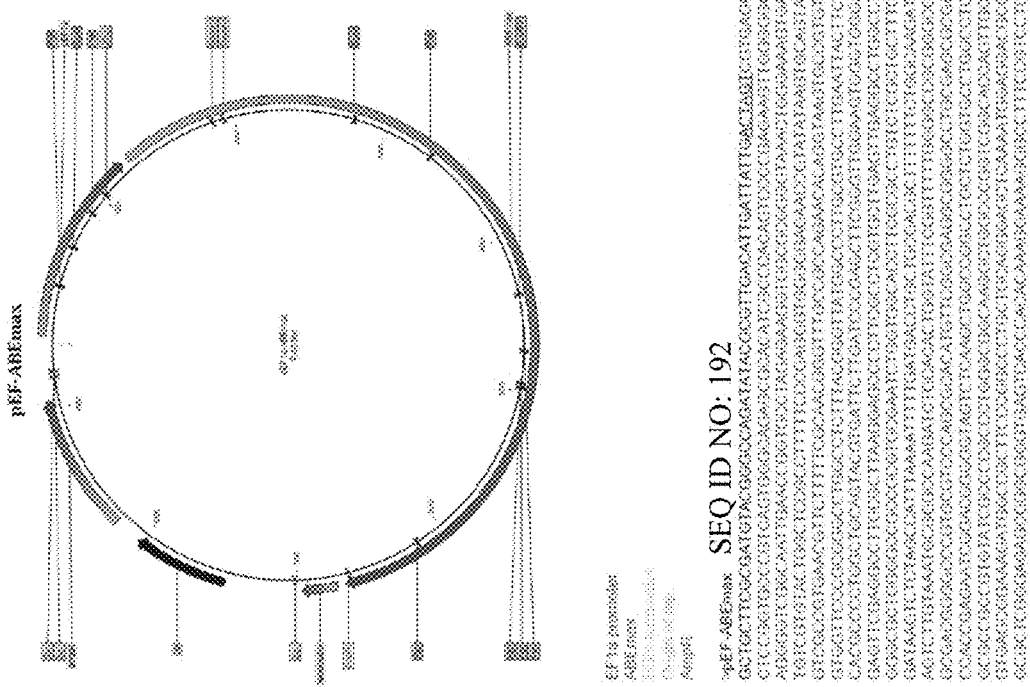
Figure 44:
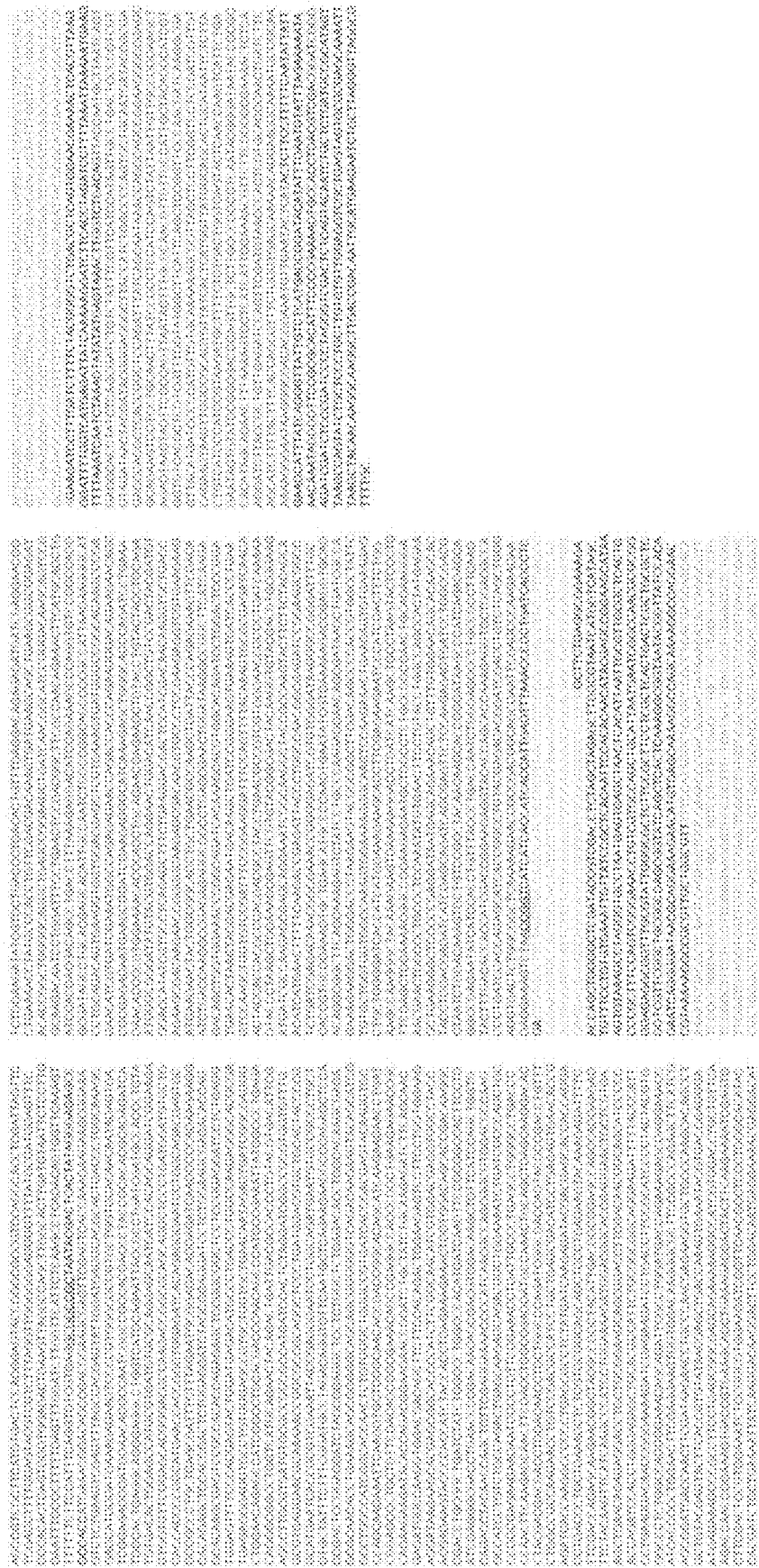

FIG. 44 shows a vector map and sequence for pEF-ABEmax.

FIG. 45 shows sequences for mCherry-1×Stop-GFP and mCherry-2×Stop-GFP and XMAS 1×Stop reporter sequences, XMAS 2×Stop reporter sequences. FIG. 45 discloses SEQ ID NOS 311, 320, 312 and 321, respectively, in order of appearance.

FIG. 46 shows sequences for GFP and mCherry and the sequences of the XMAS 1× stop and XMAS 2× stop prior to and after editing. FIG. 46 discloses SEQ ID NOS 313-316, 326, 317-318, 327, and 319, respectively, in order of appearance.

DETAILED DESCRIPTION

The compositions and methods provided herein are based at least in part on the Inventors' development of real-time, fluorescent-based methods for identification and isolation of base-edited cell populations. In particular, the disclosure provides a transient reporter for editing enrichment (TREE) to efficiently select and isolate base-edited cells from non-edited cells. As described herein, TREE takes advantage of a detectable change in a reporter protein signal as a direct reporter of base editing activity within a cell. Compared to conventional cell enrichment strategies that employ reporters of transfection (RoT), TREE significantly improved the editing efficiency at multiple independent loci, with efficiencies approaching 80%. Using these methods, it is possible to target multiple separate loci for gene editing and to identify and separate base edited cells from non-edited cells, all without homology directed repair (HDR). The combination of TREE with these base-editing methods yield isogenic genetically modified human pluripotent stem cell lines, with single-nucleotide editing efficiencies of >80% across multiple hPSC lines. Also described herein are methods that are particularly advantageous for efficient generation of loss-of-function and gain-of-function hPSC lines via introduction of premature stop codons or other genetic modifications, and for multiplex editing of hPSCs at several independent loci. These methods allow for the precise and efficient base editing of hPSCs for use in developmental biology, disease modeling, drug screening, and cell-based therapies.

Accordingly, in a first aspect, a polynucleotide encoding one or more reporter protein. The polynucleotide includes a PAM site adjacent to a base that when edited causes a change in a function or characteristic of the one or more reporter proteins. In one embodiment, the polynucleotide encodes a reporter protein with at least 90% sequence similarity to SEQ ID NO: 2, wherein the polynucleotide encodes histidine at amino acid at position number 66, relative to SEQ ID NO: 1 is provided, and encodes glycine at amino acid position number 72 relative to SEQ ID NO: 1. Alternatively, a reporter polypeptide may include two fluorescent proteins with at least 90% sequence identity to one of SEQ ID NO: 316 or 318. In another alternative, the polynucleotide comprises a polynucleotide selected from the group consisting of SEQ ID NO: 258, 259 and 260. The polypeptides may include a polypeptide having at least 80%, 85%, 90%, 95%, 96%, 97%, 98%, 99%, or 100% sequence identity to any one of the polypeptides provided herein. The polynucleotides encoding the polypeptides provided herein may include polynucleotides having at least 50%, 60%, 70%, 80%, 85%, 90%, 95%, 98%, 99% sequence identity to the polynucleotides provided herein. The polynucleotides encoding the polypeptides provided herein may be operably linked to a heterologous promoter. The polynucleotides may be included on constructs or in a vector, such as an expression vector, to allow for expression of the polypeptides in a cell.

The constructs and vectors provided herein may be prepared by methods available to those of skill in the art. Notably each of the constructs claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs provided herein may include a promoter operably linked to any one of the polynucleotides described herein. As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed polynucleotides are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may effect transcription of the polynucleotides. Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter.

Vectors including any of the constructs or polynucleotides described herein are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons, such as lentiviral vectors. Vectors may carry genetic elements, such as those that confer resistance to certain drugs or chemicals.

Cells including any of the polynucleotides, constructs, or vectors described herein are provided. Suitable "cells" that may be used in accordance with the present invention include eukaryotic or prokaryotic cells. Suitable eukaryotic cells include, without limitation, plant cells, fungal cells, and animal cells. Suitable prokaryotic cells include, without limitation, gram-negative and gram-positive bacterial species.

In a second aspect provided herein, is a kit comprising nucleic acid sequences that encode components having base editing activity when introduced into a cell as well as components that, when expressed in the cell, function as a transient reporter of successful base editing. As described herein, the transient reporter-containing compositions and methods of their use enable enrichment of base edited cells.

In some cases, the kit comprises a one or more vectors comprising nucleic acid sequences that encode elements that perform base editing and the transient reporter of base editing enrichment. In some cases, the composition comprises one or more vectors comprising a first nucleic acid encoding one or more reporter proteins, wherein the first nucleic acid includes a PAM site adjacent to a base that when edited causes a change in a function or characteristic of the one or more reporter proteins, a second nucleic acid sequence encoding a base editing targeting cassette (preferably comprising one or more sgRNAs and protospacer adjacent motifs (PAMs) directed to the nucleic acid sequence that encodes the reporter protein), a third nucleic acid sequence encoding a base editing targeting cassette (preferably comprising one or more sgRNAs and protospacer adjacent motifs (PAMs) directed to a nucleic acid sequence of interest), and a fourth nucleic acid sequence encoding a base editor, Any appropriate base editor capable of single nucleotide modifications without a need for double stranded DNA breaks can be used. In some cases, the base editor is a cytidine deaminase base editor (CBE) or adenine base editor (ABE). CBEs and ABEs install C•G-to-T•A and A•T-to-G•C transitions, respectively, and have been successfully used in many cell types including mammalian cells and plant cells. Cytidine deaminase base editors convert cytidine to uridine within a small editing window near the protospacer adjacent motif (PAM) site. Uridine is subsequently converted to thymidine through base excision repair, creating a C-to-T conversion (or G-to-A on the opposite strand). ABEs can convert adenine into inosine through deamination in any ABE protospacer (e.g. NGG, NG, and more) adjacent motif. The editing window will vary based on the type of base editor. For instance, the editing window for ABE is typically 12 to 17 nucleotides upstream of the ABE protospacer adjacent motif.

In some cases, the base editor is a prime editor. Prime editors are engineered Cas9 nickase-reverse transcriptase (RT) fusion proteins. When used in combination with prime editing guide RNAs (pegRNAs) that encode the desired edit, prime editors can edit bases in plant and animal cells without donor DNA or double-strand breaks. Unlike CBEs and ABE, prime editors are able to introduce point mutations, insertions, deletions, and all 12 possible base-to-base conversions. See Anzalone et al., i 576:149-157 (2019).

In some cases, the base editor is a Cas9-mediated adenosine base editor (referred to herein as "XMAS"). As described in Example 3, use of a Cas9-mediated adenosine base editor according to the methods of this disclosure introduces an A-to-G conversion. When a Cas9-mediated adenosine base editor used, for example, to target a TGA stop codon located between coding sequence for two different reporter proteins, the A-to-G conversion changes the TGA stop codon to TGG. Accordingly, expression of both reporter proteins allows for the real-time detection of adenosine base editing.

In some cases, the base editor is a dual adenine and cytosine base editor (e.g. CRISPR-Cas9-based synchronous programmable adenine and cytosine editor (SPACE), a codon-optimized fusion of cytosine deaminase PmCDA1, adenosine deaminase TadA, and a Cas9 nickase (Target-ACEmax), or a fusion of both adenine and cytosine deaminases with a Cas9 nickase (A&C-BEmax). When a dual editor is used, both C-T and A-G conversions happen simultaneously without the need for two base editor constructs.

In some cases, the base editor is any enzyme capable of modifying nucleobases is fused to a catalytically inactivated or impaired zinc finger nuclease (ZFN), or a transcription activator like effector (TALE). A ZF or TALE is designed to bind to a specific region of DNA, eliminating the potentially narrow editing window found with CRISPR systems.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

The reporter protein can be any detectable protein (e.g., detectable by fluorescence, color, bioluminescence indirect reporter system) for which a single base-to-base conversion or, in some cases, an insertion or deletion resulting in an observable change in the detectable protein. For example, the reporter protein can comprise a single nucleotide variation relative to the wild-type reporter protein. When a base-to-base conversion or other mutation is introduced into sequence encoding the reporter protein by base editing, the expressed reporter protein exhibits a detectable change (e.g., change in emitted fluorescent, change in color, change by way of indirect reporter) relative to the non-edited reporter protein. Examples of reporter proteins appropriate for this disclosure include, without limitation, fluorescent proteins (e.g., green fluorescent protein (GFP) and variants thereof, blue fluorescent protein (BFP) and variants thereof, red fluorescent protein (RFP) and variants thereof), luciferase and variants thereof, mCherry), β-galactosidase (lacZ), chloramphenyl acetyltransferase (CAT), β-glucuronidase (GUS), secretory alkaline phosphatase (SEAP), survival selection genes such as but not limited to antibiotic resistance, auxotrophies, flux redirection, toxin pumps, biosensors, reporter proteins that directly or indirectly produce or catalyze a colorimetric reaction, and those set forth in Table 1 below. In some cases, the reporter protein can be a blue fluorescent protein (BFP) variant that comprises a single nucleotide variation relative to the wild-type reporter protein. Referring to FIGS. 1A-1F, a blue fluorescent protein (BFP) variant can comprise a histidine at amino acid position 66 (numbered relative to SEQ ID NO:1) where the histidine is encoded by a C-A-C codon. In some cases, the reporter protein is a mutated, inactive form of luciferase. In such cases, it is advantageous to design a nucleic acid encoding the mutant luciferase such that a single base-to-base conversion or other genetic modification will introduce a corrective edit, resulting in expression of an active luciferase enzyme. In other embodiments the reporter protein is a fusion protein of two fluorescent proteins linked via a linker including at least one stop codon and a PAM site positioned to allow targeting and editing of the stop codon into a codon coding for an amino acid. Base editing allows for translation of the second reporter in the fusion protein and expression of the second reporter. The linker is positioned between the two reporter proteins such that expression of the reporter construct comprising the fusion protein in a cell results in expression of only the first reporter protein in the fusion protein. Once the polynucleotide encoding the fusion protein is edited, then both the first and second reporter will be detected. In this case the first reporter may be used as a measure of transfection efficiency and the second may be used to monitor and select for gene edited cells.

TABLE 1

Exemplary Reporter Proteins and Base Edits

| Gene Name: | Edit: | Function: | Notes: |
|---|---|---|---|
| Blue Fluorescent Protein (BFP) | C-to-T (CBE) H66Y | Change emission spectra from 448 nm to 508 nm | TREE |
| Green Fluorescent Protein (GFP) | A-to-G (ABE) Y66H | Change emission spectra from 508 nm to 448 nm | TREE reaction run in reverse |
| Activation of fluorescent Proteins | A-to-G (ABE) Stop-to-W | Removal of stop codon in coding sequence | XMAS-TREE |
| Introduction of premature stop codons | C-to-T (CBE) Q-to-Stop | Addition of premature stop codons | BIG-TREE |
| Activation of antibiotic resistance cassette | A-to-G (ABE) Stop-to-W | Removal of stop codon in coding sequence | |
| Activation of auxotrophic selection marker | A-to-G (ABE) Stop-to-W | Removal of stop codon in coding sequence | |
| Activation of gene function via editing splice junctions | CBE or ABE | Editing to restore functional splice junction in reporter | |

In some cases, the nucleic acid sequence that encodes a base editing cassette comprises a sgRNA adjacent to (e.g., located 5' to) a protospacer adjacent motif (PAM), where the sgRNA comprises a protospacer sequence and targets a portion of the nucleic acid sequence encoding the reporter protein for base editing. As used herein, the term "base editing cassette" refers to an expression cassette or framework comprising nucleic acid sequence encoding a RNA oligonucleotide containing, in some cases, 18-22 base pairs (the single guide RNA or "sgRNA") and PAM sequence. As used herein, a "single guide RNA" (sgRNA) is nucleotide sequence that is complementary to at least a portion of a target nucleic acid to be genetically modified by a base editor. Generally, a sgRNA comprises a nucleotide sequence that is partially or wholly complementary to a target sequence (such as a target genomic sequence or sequence in an expression vector) and comprises a target base pair. A gRNA target site also comprises a PAM located immediately downstream from the target site. In some cases, the PAM is a *S. pyogenes* Cas9 PAM 'NGG.' The PAM sequence may vary if other Cas9 variants are used. For some embodiments, the sgRNA preferably comprises a sequence of at least 10 contiguous nucleotides, and often a sequence of 18-22 contiguous nucleotides or more. In some embodiments, a sgRNA molecule can be from 20 to 300 or more bases in length, or more. In certain embodiments, a sgRNA molecule can be from 20 to 300 bases in length, or 20 to 120 bases, or 30 to 50 bases, or 39 to 46 bases. In some cases, no sgRNA is needed.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "target site" or "target sequence" refers to a genomic nucleic acid sequence that defines a portion of a nucleic acid to which biological molecules involved in base editing may specifically bind under conditions sufficient for binding to occur.

Preferably, nucleic acid sequences and vectors comprising sgRNAs are designed to allow for the facile cloning of new target sites via restriction enzyme digestion and ligation of oligonucleotides that target the desired genomic sequence. Depending on the PAM specificity and editing window configured in the base editing cassettes, the methods can be used in conjunction with any base editors or base editor variants. For instance, the PAM sequence and edit distance can be modified to match the editing specificity and window of the new base editor. Such modifications are straightforward to achieve with the BFP vector using TREE, or the stop codon between RFP and GFP using BIG-TREE.

Figures 1A, 1B, 1C, 1D, 1E, 1F:
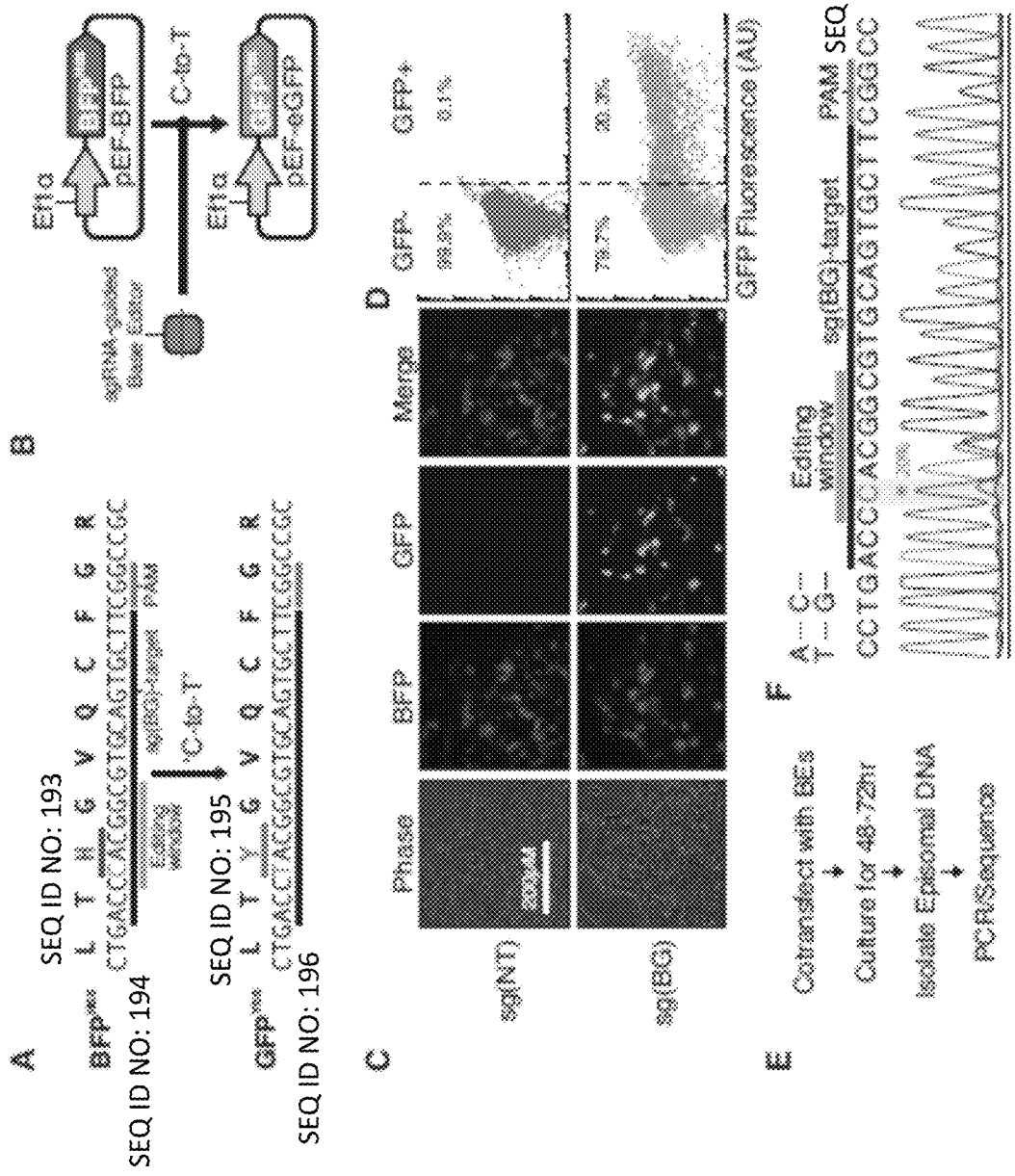
FIGS. 1A-1F demonstrate conversion of BFP to GFP enables detection of base-editing activity in cells. (A) A mutant BFP was designed to convert to GFP upon a C-to-T nucleotide conversion. The protospacer sequence (underlined black) for the sgRNA, sg (BG), targeting the 'CAC' codon (underlined blue) resulting in a C-to-T conversion to 'TAC' (underlined green) and the corresponding amino acid change of histidine (blue) to tyrosine (green) at the 66th amino acid position in BFP. A PAM (underlined red) was placed in the position to orient the base editing window (underlined orange) around the C nucleotide (red) to facilitate BFPH66 to GFPY66 conversion. All alternative C-to-T conversions in the editing window resulted in silent mutations of the coding sequence. (B) The BFP mutant was cloned into a vector, pEF-BFP, with a human EF1α promoter driving expression. Targeting pEF-BFP with a cytidine deaminase base editor results in a C-to-T conversion causing a shift in the fluorescent emission spectra from BFP to GFP. (C) Representative fluorescent microscopy images of HEK293 cells transfected with pEF-BFP, pCMV-BE4-Gam and sg(NT) (top row) or sg(BG) (bottom row). (D) Representative flow cytometry plots of HEK293 cells transfected with pEF-BFP, pCMV-BE4-Gam and sg(NT) (top) or sg(BG) (bottom). Y-axis is a non-fluorescent control channel. (E) Schematic for isolation and detection of editing of episomal DNA after transfection. (F) Representative Sanger sequencing chromatogram of amplicons of episomal DNA isolated from HEK293 cells transfected with pEF-BFP, pCMV-BE4-Gam and sg(BG). The presence of T-nucleotide (red trace) at the target nucleotide (red asterisk) demonstrates the C-to-T base conversion responsible for the amino acid change of histidine to tyrosine at the 66th amino acid position and subsequent shift of the BFP emission spectra of the resultant protein to a GFP variant.

By way of example, the sgRNA can be designed for editing of a nucleic acid sequence encoding a BFP variant as the reporter protein. As described in the Examples that follow, the sgRNA is designed to bring a cytidine deaminase base editor to the BFP variant-encoding nucleic acid sequence for base editing. Referring to FIG. 1A, the protospacer sequence (underlined black) for the sgRNA, sg(BG), targeting the 'CAC' codon (underlined blue) resulting in a C-to-T conversion to 'TAC' (underlined green) and the corresponding amino acid change of histidine (blue) to tyrosine (green) at the 66th amino acid position in BFP. A PAM (underlined red) was placed in the position to orient the base editing window (underlined orange) around the C nucleotide (red) to facilitate BFPH66 to GFPY66 conversion.

In some cases, the amino acid sequence for wild-type BFP is (SEQ ID NO: 1)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDEKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK.

In some cases, the amino acid sequence for variant BFP is (SEQ ID NO: 2)
MVSKGEELFTGVVPILVELDGDVNGHKFSVSGEGEGDATYGKLTLKFICT

TGKLPVPWPTLVTTLTHGVQCFGRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK*.

In SEQ ID NO:2, the histidine at residue position 66 is underlined. The S-to-G modification to introduce the PAM site is double underlined.

Preferably, nucleic acid sequence encoding the reporter protein is operably linked to a promoter that drives expression of the reporter protein upon introduction into a cell. A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb). The term "expression" as used herein is defined as the transcription and/or translation of a particular nucleotide sequence driven by its promoter. As used herein, the term "operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. As exemplified in FIG. 1B, the promoter can be human EF1a promoter, which is a strong constitutively active promoter, however other promoters can be used. In some cases the promoter is an inducible promoter or a cell-type specific promoter. Examples of base editing in different organisms and plus DOI citations for each example are set forth in Table 2.

TABLE 2

Examples of Base Editing in Different Organisms

|  | C-T | A-G |
|---|---|---|
| bacteria | | |
| E. coli | 10.1038/ncomms13330, 10.1038/s42003-018-0035-5 | |
| B. melitensis | 10.1038/s42003-018-0035-5 | |
| Streptomyces | 10.1073/pnas.1913493116 | |
| C. glutamicum | 10.1002/bit.27121 | |
| yeast | | |
| S. cerevesiae | 10.1126/science.aaf8729 | |
| plants | | |
| rice, wheat, maize | 10.1038/nbt.3811 | |
| rice and tomato | 10.1038/nbt.3833 | |
| rice and wheat | 10.1038/s41587-020-0455-x | |
| mammalian | | |
| mouse embryo | 10.1038/s41598-018-33533-5, | |
| mice | 10.1038/s41556-018-0202-4, | |
| | 10.1038/nbt.3816 | |
| | 10.1038/nbt.4194 | |
| | 10.1038/nature26155, | |
| | 10.1038/541587-019-0134-y, | |
| | 10.1016/j.molcel.2017.08.008, | |
| | 10.1038/nbt.4102, | |
| | 10.1038/s41467-019-11562-6, | 10.1038/s41587-019-0050-1, |
| | 10.1038/ncomms15790, | 10.1038/nbt.4172, |
| | 10.1038/nbt.3803, | 10.1038/nature24644, |
| | 10.1038/nature17946, | 10.1016/j.ymthe.2019.05.013, |
| human cells | 10.1038/nmeth.4027 | 10.1038/s41587-020-0491-6 |
| mouse embryo | | 10.1038/s41467-018-04768-7 |
| Pig | 10.1038/s41467-019-10421-8 | |
| mice, mouse zygote, mammalian | | 10.1016/j.ymthe.2019.11.022 |
| mice and mice embryo | | 10.1038/nbt.4148 |
| mice organs | 10.1038/s41551-019-0501-5 | 10.1038/s41551-019-0501-5 |
| dual base editing | 10.1038/s41587-020-0527-y, | |
| | 10.1038/s41587-020-0509-0, | |
| | 10.1038/s41587-020-0535-y | |

As used herein, the term "vector" is intended to mean a nucleic acid molecule capable of transporting another nucleic acid. By way of example, appropriate vectors for the compositions and methods of this disclosure include episomal vectors, viral vectors (e.g., retrovirus, adenovirus, baculovirus), plasmids, RNA vectors, or linear or circular DNA or RNA molecules which may comprise or consist of a chromosomal, non-chromosomal, semi-synthetic, or synthetic nucleic acid. Large numbers of suitable vectors are known to those of skill in the art and commercially available. Preferred vectors are episomal vectors, which are capable of autonomous replication due to the presence of an origin of replication. Preferably, vectors of the base editing compositions described herein are episomal vectors, meaning they are capable of autonomous replication due to the presence of an origin of replication. While the nucleic acid sequences can be provided on separate vectors, it will be understood that it is possible to configure a single or pair of expression vectors comprising the base editing elements described herein.

Methods

In another aspect, provided herein are methods for genome engineering (e.g., for altering or manipulating the expression of one or more genes or one or more gene products) in cells, in vitro, in vivo, or ex vivo. In particular, the methods provided herein are useful for targeted base editing or base correction in any cell.

In some cases, the methods comprise multiplex editing at multiple loci. In such cases, the methods described herein can be performed using a vector comprising dual-targeting sgRNAs. In such cases, a first nucleic acid sequence encodes a sgRNA for base editing in the reporter protein, and a second nucleic acid sequence encodes a sgRNA for a genomic target site. In some cases, methods described herein can be performed using a vector comprising a multiplex-targeting sgRNAs. In such cases, a first nucleic acid sequence encodes a sgRNA for base editing in the reporter protein, and a second, third, fourth, etc. nucleic acid sequence encodes a sgRNA for a genomic target site. When introduced into a cell with nucleic acid sequences encoding the base editor and reporter protein, it is possible to base edit two or more genomic target sites and also promote a base-to-base conversion or other genetic modification that yields a detectable change in fluorescent emission or color of the transient reporter protein. The Examples demonstrate successful base editing at two or more genomic target sites and plus introduction of a C-to-T conversion in nucleic acid sequence encoding a BFP variant, thus resulting in a shift in fluorescent emission spectra from BFP to GFP as described herein. In this manner, base-edited cells can be sorted and selected based on fluorescence emission spectra or other detectable signals. Accordingly, also provided herein are engineered cells that have been genetically modified according to these methods.

Although human pluripotent stem cells are exemplified herein, it will be understood by practitioners in the art that the base editing compositions and methods can be used with other cell types, including a variety of human cell types and cells of other types of animals. In some cases, the cell is a mammalian cell. Preferably, the mammalian cell is a human cell. Cells appropriate for use in the methods of this disclosure include, without limitation, pluripotent stem cells, multipotent cells, dissociated organs or organoids, terminally differentiated cells, immune cells, hematopoietic stem progenitor cells (HSPCs) (e.g., umbilical cord blood HSPCs), and fibroblasts. In addition to mammalian cells, it will be understood by practitioners in the art that the base editing compositions and methods can be used with other cell types such as bacteria cells, yeast cells, plant cells, and other single celled organisms.

As used herein, the term "pluripotent stem cell" (hPSC) means a cell capable of continued self-renewal and capable, under appropriate conditions, of differentiating into cells of all three germ layers. hPSCs exhibit a gene expression profile that includes $SOX2^+$ and $OCT4^+$. Examples of human PSCs (hPSCs) include human embryonic stem cells (hESCs) and human induced pluripotent stem cells (hiPSCs). As used herein, "iPS cells" or "iPSCs" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells. In some cases, the modified cells are human pluripotent stem cells such as human embryonic stem cells or induced pluripotent stem cells. In some cases, the modified cells are human embryonic stem cells isolated from human embryonic tissues. In other cases, the modified cells are cells isolated from human blastocysts and then modified. In some cases, the modified cells are human placental or umbilical cord stem cells.

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a method of this disclosure. For example, subject-specific cells can be expanded, differentiated, genetically modified, contacted to polypeptides, nucleic acids, or other factors, cryo-preserved, or otherwise modified prior to use according to the methods of this disclosure.

For the methods described herein, gene editing systems or components thereof (e.g., a vector encoding a base editor protein, a gRNA) are introduced into a cell (e.g., a human pluripotent stem cell). As used herein, the term "introducing" encompasses a variety of methods of introducing DNA into a cell, either in vitro or in vivo, such methods including transformation, transduction, transfection (e.g., electroporation), nucleofection (an electroporation-based transfection method which enables transfer of nucleic acids such as DNA and RNA into cells by applying a specific voltage and reagents) and infection. Where the introducing involves electroporation (e.g., nucleofection), a polynucleotide (e.g., a plasmid, a single stranded DNA, a minicircle DNA, RNA) is electroporated into a target cell. Vectors are useful for introducing DNA encoding molecules into cells. Any appropriate delivery vector can be used with the methods described herein. For example, delivery vectors include exosomes, viruses (viral vectors), and viral particles. Preferably, the delivery vector is a viral vector, such as a lenti- or baculo- or preferably adeno-viral/adeno-associated viral (AAV) vectors, but other non-viral means of delivery are known (such as yeast systems, microvesicles, gene guns/ means of attaching vectors to gold nanoparticles). Other methods of introducing a nucleic acid into a host cell are known in the art, and any known method can be used to introduce a nucleic acid (e.g., vector or expression construct) into a cell for the methods provided herein. Suitable methods include, without limitation, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv. Drug Deliv. Rev.), and the like. Delivery of components may also include use of ribonucleoproteins complexed with sgRNA alone, or in combination with nucleic acid delivery.

A cell is "genome edited" or "genetically modified" if the cell includes a modification to its genome compared to a non-genome edited cell of the same type. In some cases, a non-genome edited cell is a wild-type cell. As used herein, the terms "genetically modified" and "genetically engineered" are used interchangeably and refer to a prokaryotic or eukaryotic cell that includes an exogenous polynucleotide, regardless of the method used for insertion. In some cases, a cell has been modified to comprise a non-naturally occurring nucleic acid molecule that has been created or modified by the hand of man (e.g., using recombinant DNA technology) or is derived from such a molecule (e.g., by transcription, translation, etc.). A cell that contains an exogenous, recombinant, synthetic, and/or otherwise modified polynucleotide is considered to be an engineered or "genome edited" cell. Genetically editing or modifying a cell refers to modifying cellular nucleic acid within a cell, including genetic modifications to endogenous and/or exogenous nucleic acids within the cell. Genetic modifications can comprise deletions, insertions, integrations of exogenous DNA, gene correction and/or gene mutation.

The term "substantially pure cell composition of genetically modified cells" as used herein refers to a cell composition comprising at least 70%, more preferentially at least 90%, most preferentially at least 95% of genetically modified cells in the cell composition obtained by methods of this disclosure. The terms "purified" or "enriched" cell populations are used interchangeably herein, and refer to cell populations, in vitro or ex vivo, that contain a higher proportion of a specified cell type or cells having a specified characteristic than are found in vivo (e.g., in a tissue).

As used herein, the term "isogenic" refers to cells or organisms that are genetically related, or having the same or closely similar genotypes, such as cells of a cell line. For example, cells of a clonal population of cells are isogenic to each other. In some cases, a first population of human pluripotent stem cells can have a wild-type, genetically unmodified genome, and a second population of pluripotent stem cells can be isogenic to the first population except that they have been genetically modified (which term as used herein includes progeny of modified cells) to comprise a particular genetic modification. Individual cells of the second population may be isogenic to each other if obtained by clonal expansion of a single genetically modified cell.

In some cases, cells into which nucleic acid sequences encoding a base editor, reporter protein, and base editing cassette have been introduced and then cultured for about 48 to about 72 hours are sorted using any sorting technique capable of detecting expression of green fluorescent protein and, optionally, other cell markers. Methods and techniques for assessing the expression and/or levels of cell markers are known in the art. Antibodies and reagents for detection of such markers are well known in the art, and readily available. Assays and methods for detecting such markers include, but are not limited to, flow cytometry, including intracellular flow cytometry, ELISA, ELISPOT, cytometric bead array or other multiplex methods, Western Blot and other immunoaffinity-based methods. In preferred embodiments, cells genetically modified according to the methods of this disclosure are detected and sorted by fluorescence-based flow cytometry. As used herein, the term "flow cytometry" refers to a cell analysis technique that detects and measures physical and chemical characteristics of a population of cells or particles in a rapidly flowing fluid stream as they pass in front of a viewing aperture. The term "flow cytometry" encompasses fluorescence-based flow cytometry in which, generally, lasers are used to detect and count cells based on fluorescence emission of fluorophores associated with the cells. In some cases, flow cytometry is performed using a specialized flow cytometer known as a fluorescence activated cell sorter (FACS). Cell sorters like FACS use fluidics and fluorescence components similar to those in flow cytometers, but are able to divert a specific population from within a heterogeneous sample into a separate tube, typically based on specified fluorescence characteristics.

Any appropriate technique can be used to as an additional means to confirm that base editing has occurred. For example, Sanger sequencing or next generation sequencing (NGS) can be used to detect C-to-T conversions.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-C-A-G-T," is complementary to the sequence "5'-A-C-T-G." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules.

In another aspect, provided herein is a cell culture composition comprising the isogenic line of genetically modified human pluripotent stem cells produced according to the methods of this disclosure and a chemically defined culture medium. The term "chemically defined culture medium" or "chemically defined medium," as used herein, means that the molecular identity, chemical structure, and quantity of each medium ingredient is definitively known. The term "ingredient," as used herein, refers to a component the molecular identity and quantity of which is known. In some cases, a chemically defined medium is made xeno-free, and incorporates human proteins, which can be produced using recombinant technology or derived from placenta or other human tissues, in lieu of animal-derived proteins. In some embodiments, all proteins added to the medium are recombinant human proteins.

In some cases, the method is performed using human induced pluripotent stem cells obtained by reprogramming a somatic cell of a human subject, such as a human subject that has a genetic disorder caused by a single nucleotide polymorphism. In such cases, the resulting base-edited human cells are autologous to the human subject and, in some cases, can be administered back to the subject (e.g., cell therapy).

In another aspect, provided herein is an isogenic population of human cells genetically modified ex vivo to comprise a base-to-base conversion or other genetic modification. In some cases, the base-to-base conversion corrects or suppress a disease-associated single nucleotide polymorphism (SNP) or modifies an disease-associated isoform of a particular protein. As demonstrated in the Examples, the base editing-transient reporter enrichment methods of this disclosure were used to modify a nucleotide sequence encoding a APOE2 isoform of human APOE protein, such that the modified cell did not express any other isoform of the APOE protein. In this example, the human cells were induced pluripotent stem cells obtained from a somatic cell of a human subject having Familial Alzheimer's disease (FAD). Although correction of a SNP associated with FAD is exemplified herein, the methods of this disclosure can be used to correct introduce disease-correcting or disease-suppressing base edits in human cells provided that there is an appropriate PAM in the correct location downstream of the target SNP.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acids and/or other constructs (including cell populations) described in this disclosure may be isolated. As used herein, "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other compositions (e.g., cell population) described herein may be purified. As used herein, "purified" means separate from the majority of other compounds or entities, and encompasses partially purified or substantially purified. Purity may be denoted by a weight by weight measure and may be determined using a variety of analytical techniques such as but not limited to mass spectrometry, HPLC, etc.

Articles of Manufacture

In another aspect, provided herein is an article of manufacture such as a kit comprising a composition comprising expression vectors to perform base editing and editing enrichment using TREE as described herein. In certain embodiments, the kit comprises a plurality of vectors to achieve targeted base editing and for expression of the transient reporter (TREE). In some cases, the kit further comprises reagents and other materials useful for introducing vectors into cells and for culturing modified cells according to the methods. In some cases, the kit further comprises instructions for performing the methods of this disclosure.

In another aspect, provided herein is a kit for generating substantially pure populations of base-edited cells including, as a non-limiting example, base-edited human pluripotent stem cells. In exemplary embodiments, the kit comprises one or more of (i) a culture medium suitable for maintaining cells in vitro or ex vivo; (ii) base editing vectors as described herein; (iii) reagents for introduction of the base editing vectors into cells (e.g., transfection reagents, transduction reagents, electroporation reagents), and (iv) instructions describing a method for generating substantially pure populations of base-edited cells as described herein, the method employing one or more of the culture medium, the base editing vectors, and the reagents for introducing vectors into the cells. In some cases, the kit further comprises reagents and/or materials for flow cytometry and cell sorting using FACS.

All publications, including but not limited to patents and patent applications, cited in this specification are herein incorporated by reference as though set forth in their entirety in the present application.

In interpreting this disclosure, all terms should be interpreted in the broadest possible manner consistent with the context. It is understood that certain adaptations of the invention described in this disclosure are a matter of routine optimization for those skilled in the art, and can be implemented without departing from the spirit of the invention, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this invention belongs. As used herein and in the claims, the singular forms "a," "an," and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated All publications, including but not limited to patents and patent applications, cited in this specification are herein incorporated by reference as though set forth in their entirety in the present application.

EXAMPLES

Example 1—Transient Reporter for Editing Enrichment (TREE)

Current approaches to identify cell populations that have been modified with deaminase base editing technologies are inefficient and rely on downstream sequencing techniques. In this example, a blue fluorescent protein (BFP) that converts to green fluorescent protein (GFP) upon a C-to-T substitution was used as an assay to report directly on base editing activity within a cell. Using this assay, various base editing transfection parameters and delivery strategies were developed. Moreover, this assay was used in conjunction with flow cytometry to develop a transient reporter for editing enrichment (TREE) to efficiently purify base-edited cell populations. Compared to conventional cell enrichment strategies that employ reporters of transfection (RoT), TREE significantly improved the editing efficiency at multiple independent loci, with efficiencies approaching 80%. In addition, the BFP-to-GFP conversion assay was employed to develop base editor vector design for human pluripotent stem cells (hPSCs), a cell type that is resistant to genome editing and in which modification via base editors has not been previously reported. At last, using these optimized vectors in the context of TREE allowed for the highly efficient editing of hPSCs. It is envisioned that TREE is a readily adoptable method to facilitate base editing applications in synthetic biology, disease modeling, and regenerative medicine.

Materials and Methods

Plasmid construction: Unless otherwise noted, all molecular cloning polymerase chain reactions (PCR) were performed using Phusion® High-Fidelity DNA polymerase (New England Biolabs, Ipswich, MA, USA) using the using the manufacturer's recommended protocols. All restriction enzyme (New England Biolabs) digests were performed according to the manufacturer's instructions. Ligation reactions were performed with T4 DNA Ligase (New England Biolabs) according to the manufacturer's instructions. PCR primers and oligonucleotides were synthesized by Integrated DNA Technologies (Coralville, IA, USA). All PCR products and intermediate plasmid products were confirmed via Sanger sequencing (DNASU Sequencing Core Facility and Genewiz).

For construction of the pEF-BFP plasmid, we utilized PCR to add the H-66 and protospacer adjacent motif (PAM) site mutations into a GFP cassette (Addgene #11154). PCR products containing these mutations were digested with SapI/EcoRI and SapI/NotI and ligated into a EcoRI/NotI digested EF1α expression vector (Addgene #11154).

For construction of the pDT-sgRNA vector, sgRNAs were synthesized as pairs of oligonucleotides (Table 4). Subsequently, 5' phosphates were added to each oligonucleotide pair by incubating 1 μg oligonucleotide in 50 μl reactions containing 1× T4 DNA Ligase Buffer (New England Biolabs) and 10 units of T4 Polynucleotide Kinase at 37° C. overnight. Oligonucleotides were then duplexed by heating the kinase reactions to 90° C. on an aluminum heating block for 5 minutes followed by slowly returning the reaction to room temperature over 1 hour. Following duplexing, guides were cloned into a modified pSB1C3 vector containing a U6 promoter, inverted BbsI restriction enzyme digestion sites, and a *Streptococcus pyogenes* recognized sgRNA hairpin. For construction of pMT-sgRNA, pairs of sgRNAs (Table 4) were PCR amplified with primers adding EcoRI/SapI restriction enzyme digestion sites or SapI/XbaI restriction enzyme digestion sites. Purified PCR products were then digested with the respective restriction enzymes and ligated into EcoRI/XbaI digested pUC19 vector (Addgene #50005). The resultant vector contained pairs of sgRNA expression cassettes. To add additional sgRNA expression cassettes, pairs of sgRNAs were PCR amplified with primers that add HindIII/SapI or SapI/HindIII restriction enzyme digestion sites. These products were then digested with HindIII/SapI and ligated into HindIII digested and dephosphorylated pDT-sgRNA vector.

For insertion of the EF1α promoter into the pCMV-BE4-Gam (Addgene #100806) and pCMV-AncBE4max (Addgene #112094), EF1α was PCR amplified from an EF1α expression vector (Addgene #11154) adding SpeI/NotI restriction enzyme digestion sites. After purification and digestion, these PCR products were ligated into SpeI/NotI digested and dephosphorylated pCMV-BE4-Gam or pCMVAncBE4max vectors.

Cell Culture: All media component were purchased from ThermoFisher Scientific (Waltham, MA, USA) unless indicated otherwise. HEK293 cells were cultured on poly-L-ornithine (4 μg/ml; Sigma Aldrich, St Louis MO, USA) coated plates in the following media: 1× high glucose Dulbecco's modified Eagle's medium (DMEM), 10% (v/v) fetal bovine serum, 1% (v/v) L-glutamine penicillin/streptomycin. Culture medium changed was every other day and cells were passaged with Accutase (ThermoFisher) every 5 days. HPSCs were cultured on 12-well tissue culture plates coated with Matrigel™ (BD Biosciences, San Jose, CA, USA) in Essential 8™ Medium (E8) (ThermoFisher). HPSCs were cultured in mTESR1 medium (STEM CELL Technologies). Culture medium was changed every day and cells were passaged with Accutase every 4-5 days. After passaging, the medium was supplemented with 5 μM Rho kinase inhibitor (ROCKi; Y-27632 [BioGems, Westlake Village, CA, USA]) for 24 hours to aid in single cell survival.

Isolation of Episomal DNA: After 48 hours following transfection, HEK293 cells were dissociated from the tissue plates with Accutase, washed twice with phosphate-buffered saline and resuspended in RNAse-A containing solution. Cells were then lysed with alkaline lysis and the resultant debris was precipitated via centrifugation at $1.2 \times 10^4 \times$ g for 10 min. Supernatant DNA was isolated by column DNA purification using the manufacture recommended protocol (Sigma-Aldrich: NA0160).

Generation of HEK293-BFP line: The HEK293T-BFP cell line was generated via homology independent targeted integration (HITI). Briefly, the BFP coding sequence was PCR amplified with primers adding EcoRI restriction enzyme digestion sites. The resultant PCR product was EcoRI digested, phosphorylated and ligated into an EcoRI/SmaI digested vector containing an EF1α promoter, puromycin resistance cassette and HITI protospacer sequence (pEF-BFP-PuroR). The pEFBFP-PuroR vector was co-transfected in HEK293s with pX330 (Addgene #42230) and a custom sgRNA vector (pHSG(C1ORF228)-1C3) targeting the C1ORF228 locus. Transfections were conducted in a 24-well plate with 300 ng pX330, 400 ng pEF-BFP-PuroR, 50 ng sgRNA vector, 1.5 μl Lipofectamine 3000 (ThermoFisher Scientific) and 1 μl P3000 transfection reagent. Cells were passaged at 72 hours post-transfection into a single well of a 6-well plate and selected with 0.5 μg/ml puromycin for 2 weeks.

Results

BFP-to-GFP Conversion Allows for Detection of Base-Editing Activity

To establish that BFP to GFP conversion could be used as the basis for an assay to detect genomic base editing, we utilized a BFP mutant that converts to a GFP upon a C-to-T nucleotide conversion (FIG. 1A). Briefly, this BFP mutant ($BFP^{H66}$) contains a histidine at the 66th amino acid position encoded by a 'CAC' codon. The C-to-T conversion of that codon to 'TAC' or 'TAT' will result in an amino acid change from a histidine to a tyrosine. In turn, this amino acid change will cause a shift of the emission spectra of the resultant protein generating a GFP variant ($GFP^{Y66}$). Because the optimal nucleotide base editing window is typically 12-18 nt upstream from the PAM, we also placed a *S. pyogenes* Cas9 PAM 'NGG' in a position that would enable base editing to occur at the target 'CAC' codon. To verify the utility of this fluorescent protein to report on base editing activity, we cloned the BFP coding sequence into a vector with a human EF1a promoter to drive expression (pEF-BFP; FIG. 1B). In addition, we designed a sgRNA vector [sg(BG)] that would direct the base editing machinery to the target 'CAC' codon resulting in a C-to-T conversion and the subsequent amino acid change of histidine to tyrosine at the 66th amino acid position (FIG. 1A). HEK293 cells were co-transfected with pEF-BFP, a base editing vector (pCMV-BE4-Gam) and sg(BG) or a control non-targeting sgRNA [sg(NT)]. Fluorescent microscopy (FIG. 1C) and flow cytometry (FIG. 1D) revealed that targeting pEF-BFP with sg(BG) resulted in the generation of BFP/GFP double positive cells. However, targeting pEF-BFP with sg(NT) did not result in the generation of any BFP/GFP positive cells. To confirm GFP expression was a consequence of direct editing of the target codon in pEF-BFP, we implemented a strategy to isolate and detect editing of episomal DNA after transfection (v 1E). Sanger sequencing of isolated pEF-BFP DNA established that editing had occurred at the target 'CAC' codon in pEF-BFP resulting in a change to 'TAC' or 'TAT' reflected in the GFP emission (FIG. 1F). Overall, these results confirm that the GFP-to-BFP conversion corresponds to C-to-T conversion at targeted base editing sites.

Figures 2A, 2B, 2C, 2D, 2E, 2F:
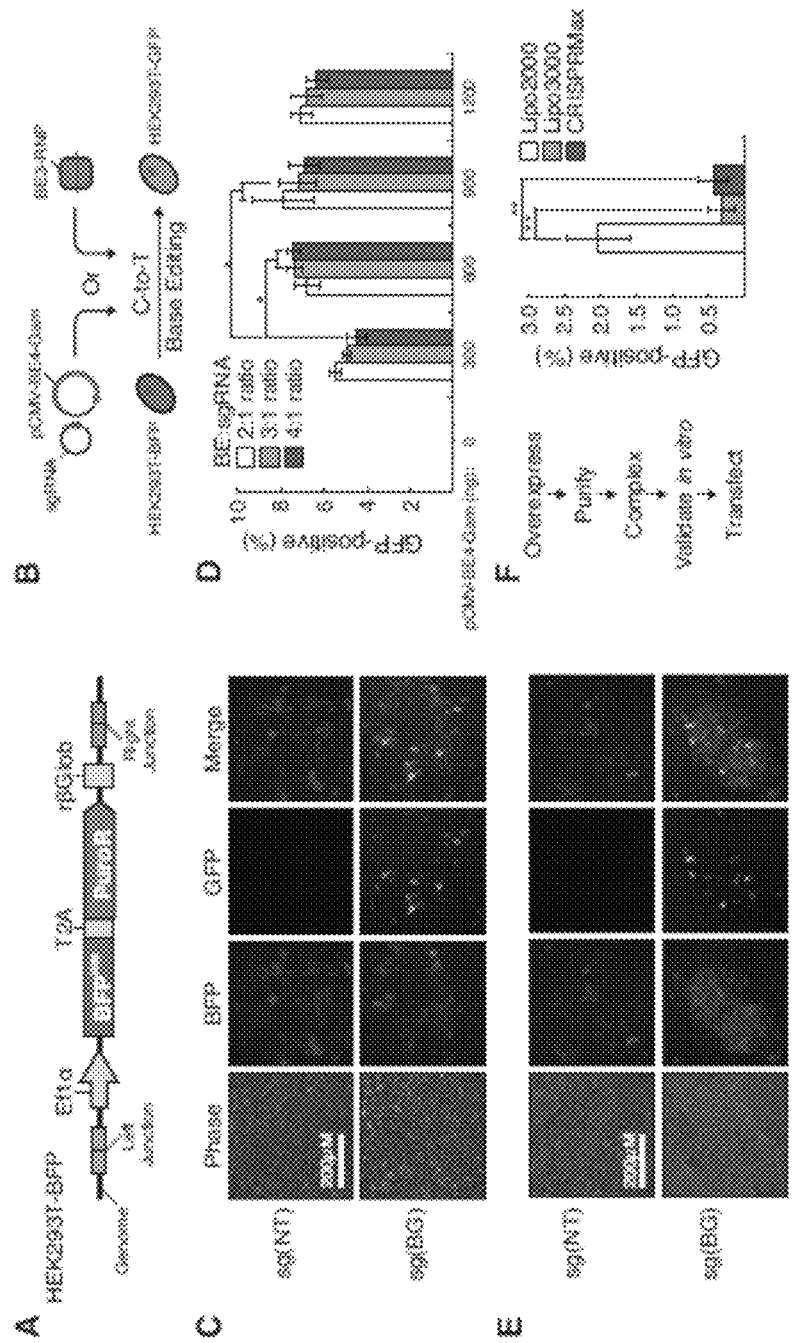
FIGS. 2A-2F demonstrate BFP-to-GFP conversion reports on base-editing at a chromosomal locus. (A) A pEF-BFP-PuroR vector was integrated into the C1ORF228 locus using homology-independent targeted integration to generate the HEK293-BFP cell line. (B) Schematic for plasmid or RNP base editing optimization using the HEK293-BFP line. (C) Representative fluorescent microscopy images of HEK293-BFP cells transfected with 600 ng pCMV-BE4-Gam and 200 ng sg(NT) (top row) or sg(BG) (bottom row). Scale bar=200 μm. (D) Editing efficiencies (GFP-positive cells) of HEK293-BFP cells transfected with various amounts of pCMV-BE4-Gam and ratios with the sg(BG) vector. n=3, *=P<0.05. (E) Representative fluorescent microscopy images of HEK293-BFP cells transfected with BE3-sg(BG) or -sg(NT) RNP complexes. (F) Schematic for RNP complex generation and transfection. BE3 was overexpressed, purified, complexed and validated in vitro, and transfected. Editing efficiencies (GFP-positive cells) of HEK293-BFP cells transfected with RNP complexes using various delivery reagents. n=3, *=P<0.05, **=P<0.01.

Next, we wanted to establish that the BFP-to-GFP conversion would correlate with base-editing efficiency at a chromosomal locus. To that end, we employed a HEK293 cell line (herein referred to as HEK293-BFP) in which BFP$^{H66}$ was stably integrated into a known genomic location (C1ORF228; FIG. 2A). We then used this line to enable the analysis of the efficiency of base editing genomic loci (FIG. 2B). To first assess plasmid-based base editing, we co-transfected pCMV-BE4-Gam and sg(BG) plasmid DNA in HEK293-BFP cells. Targeting with sg(BG), but not sg(NT), resulted in generation of detectable GFP+ cells, indicating successful base editing at the targeted genomic loci (FIG. 2C). Moreover, we were able to use this assay to systematically evaluate genomic base editing efficiencies using a range of pCMV-BE4-Gam plasmid amounts at varying ratios with the sg(BG) vector (FIG. 2D). This analysis revealed that base editing plasmid concentration and base editor to sgRNA ratios could enhance genomic base editing efficiencies approximately 2-fold. Because ribonucleoprotein (RNP) complex-based strategies have been previously shown as an attractive alternative to plasmid-based Cas9 genome engineering, we also utilized BFP-to-GFP conversion as an assay to optimize RNP-driven base editing. As such, we generated RNPs through the in vitro complexing of purified base editing protein with sg(BG) or sg(NT) (FIG. 2E). Our initial analysis revealed that RNP delivery using the same transfection reagent that was used for plasmid delivery of the base editor (i.e., Lipofectamine™ 3000) did not result in substantial BFP-to-GFP conversion (FIG. 2F). In turn, we utilized BFP-to-GFP to evaluate various commercially available transfection reagents to optimize RNP delivery for base editing applications. From this analysis, we were able to determine that Lipofectamine™ 2000 allowed for a >4-fold increase in genomic base editing efficiency compared to other commercially available reagents such as Lipofectamine™ and CRISPRMAX (FIG. 2F). Despite this, RNP-driven delivery was about 4-fold less efficient in genomic base editing compared to plasmid delivery. Thus, for the remainder of this example we proceeded with plasmid delivery of base editors. Nonetheless, this collective data demonstrates that BFP-to-GFP conversion correlates to base editing efficiency at genomic loci. Moreover, this approach allows for the facile and systematic optimization of base editing in human cells using plasmid- and RNP-based approaches.

Figures 3A, 3B, 3C, 3D, 3E:
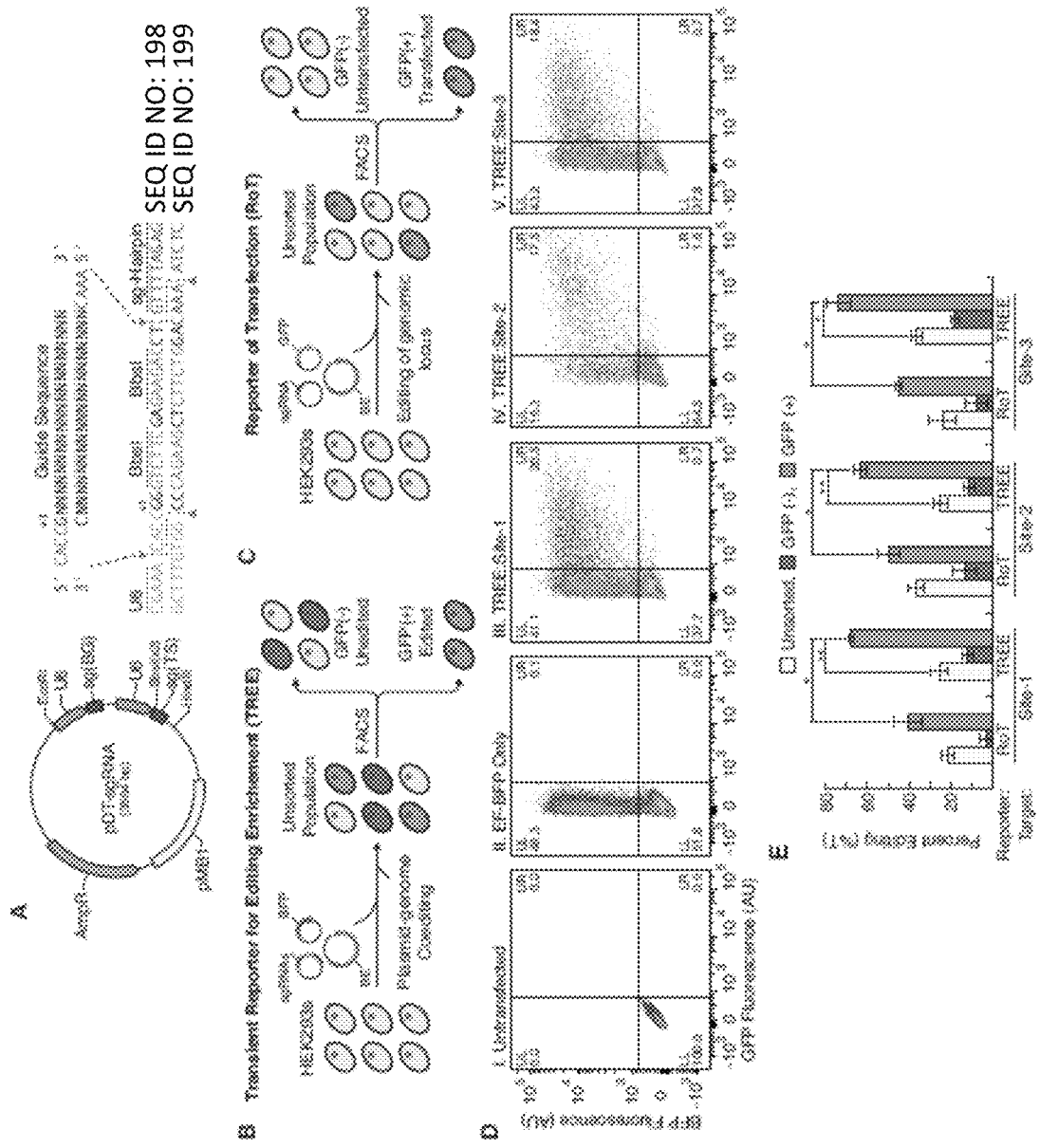
FIGS. 3A-3E demonstrate enrichment of base-edited cell populations using TREE. (A) Plasmid map of pDT-sgRNA vector that contains sg(BG) and sg(TS). Expression for both sgRNA cassettes is driven by separate U6 promoters (orange arrows). The BbsI restriction sites allow for direct restriction enzyme-based cloning of new target sites. (B) Schematic for enrichment of edited cells using TREE. HEK293 cells are co-transfected with pEF-BFP, pCMV-BE4-Gam and pDT-sgRNA vectors. After 48 h post-transfection, flow cytometry is used to sort cell populations into GFP-positive and -negative fractions. (C) Schematic for enrichment of edited cells using reporter of transfection (RoT). HEK293 cells are co-transfected with pEF-GFP, pCMV-BE4-Gam and sg(TS) vectors. After 48 h post-transfection, flow cytometry is used to sort cell populations into GFP-positive and -negative fractions. (D) Representative flow cytometry plots of (i) untransfected HEK293 cells and (ii) HEK293 cells transfected with pEF-BFP only as well as HEK293 cells in which TREE was applied targeting (iii) Site-1, (iv) Site-2 and (v) Site-3. (E) Quantification of base editing efficiency at Site-1, Site-2 and Site-3 in GFP-positive, GFP-negative and unsorted cell populations isolated using TREE- or RoT-based enrichment strategies. n=3; *=P<0.05, **=P<0.01.
Figure 19:
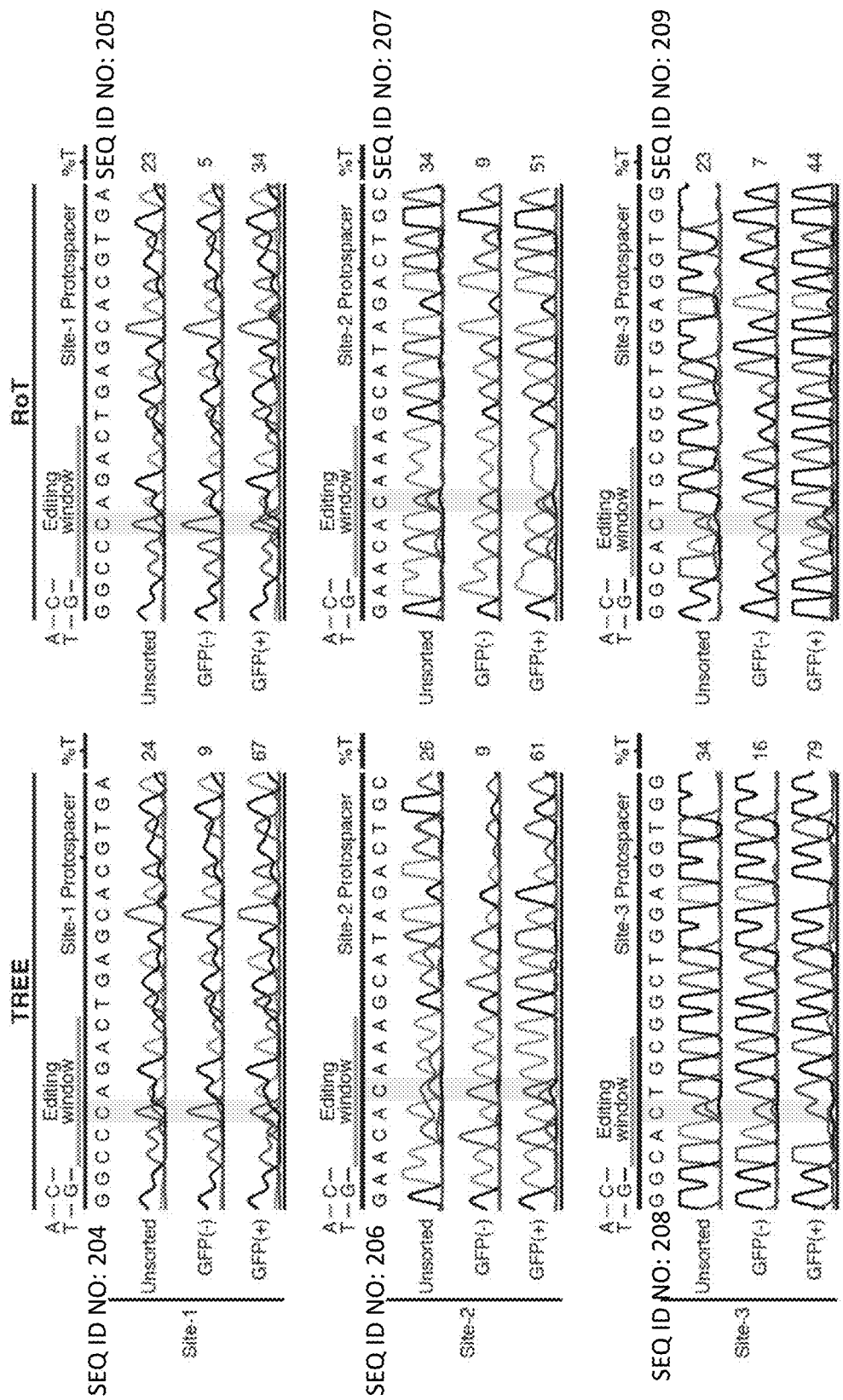
FIG. 19 shows Sanger sequencing chromatographs of Site-1, Site-2, and Site-3 of GFP-positive, GFP-negative, and unsorted cell populations isolated with TREE- and RoT-based approaches.

Development of Transient Reporter for Editing Enrichment (TREE) to Identify and Efficiently Isolate Base-Edited Cell Populations Conventional base editing approaches that use reporters of transfection (herein abbreviated as RoT) only report on the efficiency of plasmid delivery to a cell but not directly on the efficiency of base editing within these cells. As such, it was hypothesized that we BFP-to-GFP conversion, which directly correlates to base editing activity within a cell, could be employed as a TREE to allow for the identification and enrichment of cells in which targeted genomic base editing had occurred. To facilitate this, we engineered a dual-targeting sgRNA (pDT-sgRNA) vector that contains both sg(BG) and a sgRNA for a genomic target site [sg(TS)](FIG. 3A). Moreover, the pDT-sgRNA vector was designed to allow for the facile cloning of new target sites via BbsI restriction enzyme digestion and ligation of sg(TS) oligonucleotides (FIG. 3A). Accordingly, we designed pDT-sgRNA vectors with sequences targeting three genomic locations (Sites 1-3). To utilize TREE for enrichment of cells that have been edited at specific loci, we co-transfected these pDT-sgRNA vectors with pEF-BFP and pCMV-BE4-Gam into HEK293 cells using the optimized base editing parameters identified using the BFP-to-GFP conversion assay (FIG. 3B). Flow cytometry was then used to isolate GFP-positive and GFP-negative cells. For comparison, we used a conventional RoT as a strategy to enrich for edited cell populations (FIG. 3C). Specifically, after co-transfecting HEK293 cells with pEF-GFP and sg(TS) plasmids, we used flow cytometry to sort for GFP-positive and -negative cell populations. Flow cytometry analysis of cells in which TREE was applied confirmed the presence of BFP and GFP-positive cell populations indicative of active base editing (FIG. 3D). Importantly, in these cell populations there was also a significant percentage of cells that were BFP-positive but GFP-negative, suggesting that isolating cell populations exclusively based upon a reporter of transfection would significantly limit the enrichment of edited cells. To confirm this, we performed Sanger sequencing of the targeted genomic sites in GFP-positive, GFP-negative and unsorted cell populations isolated from TREE and RoT approaches (FIG. 3E and FIG. 19). As expected, GFP-positive cells isolated using both TREE- and RoT-based strategies were enriched for edited cells when com-pared to GFP-negative and unsorted cell populations. We found that base editing efficiency at these three target loci in HEK293 cells using RoT-based approaches was similar to those reported previously (Table 11). Importantly, this analysis also revealed across all three targeted sites that GFP-positive cells isolated via TREE had a statistically significant higher frequency of base editing than GFP-positive cells isolated using traditional RoT approaches.

Figure 20:
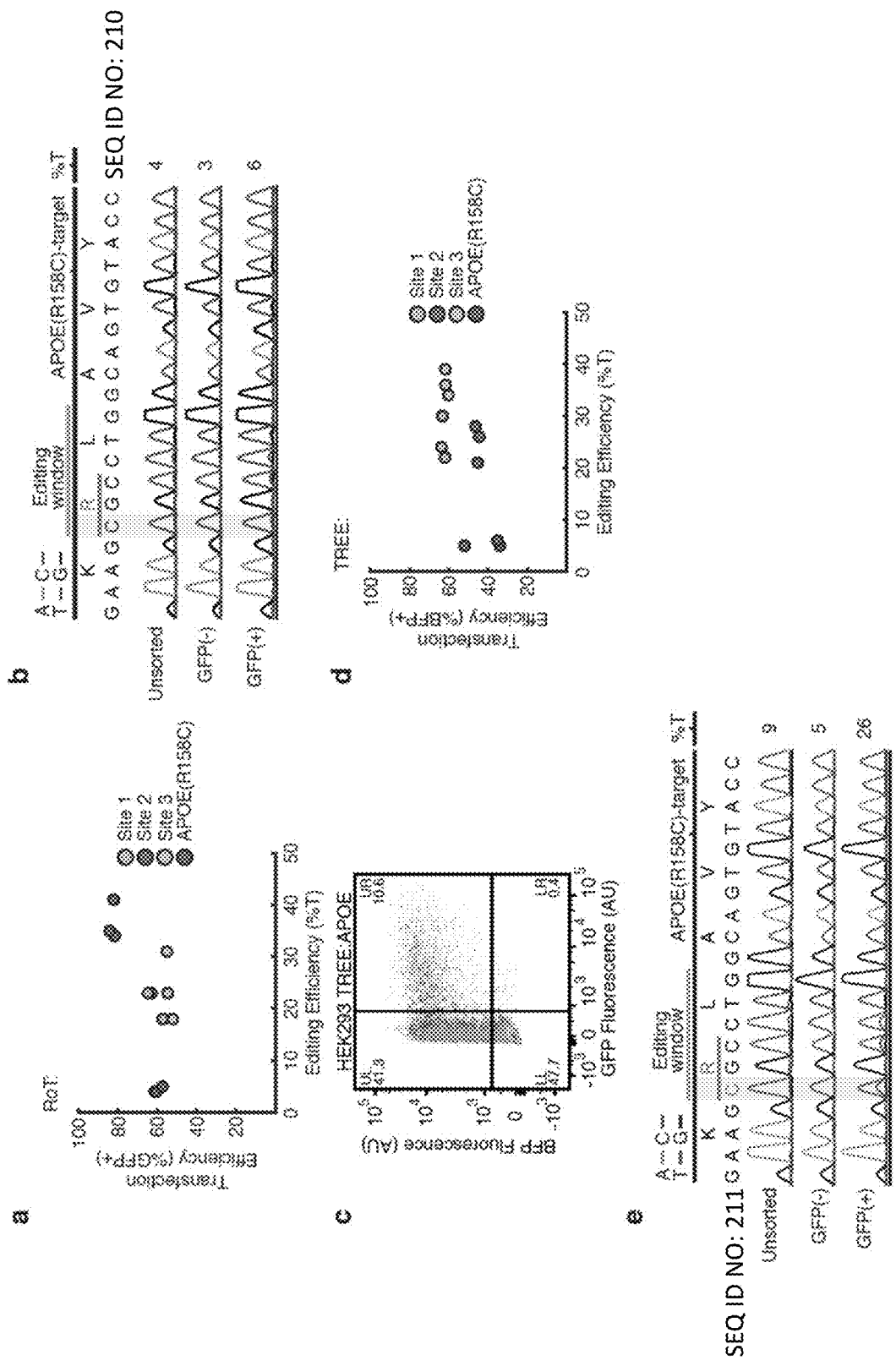
FIG. 20 demonstrates that TREE allows for base editing of refractory APOE(R158) locus in HEK293 cells. (a) HEK293 cells were transfected with pEF-GFP, pCMV-BE4-Gam, and sg(TS). Comparison of trans-fection efficiency (percentage of GFP-positive cells) and editing efficiency (percentage of C-to-T conversion at target nucleotide) in unsorted cell populations at Site-1, Site-2, Site-2, and APOE (R158) locus. (b) Representative Sanger sequencing chromatographs of APOE(R158) locus in GFP-positive, GFP-negative, and unsorted cell populations isolated with RoT-based methods.

Because of the success of targeting these loci, it was investigated if TREE could be utilized to target additional genomic sites that display very low editing efficiency when traditional RoT approaches are applied. One such example is the APOE locus, a well-established risk factor associated with altered probability of sporadic Alzheimer's disease onset. Human APOE has three major isoforms, ApoE2, ApoE3 and ApoE4, which differ by two amino acid substitutions at positions 112 and 158 in exon 4-ApoE2 (Cys112, Cys158), ApoE3 (Cys112, Arg158), ApoE4 (Arg112, Arg158). Attempts to use base editing to convert ApoE3 to ApoE2 by targeting the APOE(R158) locus revealed undetectable levels of editing in unsorted cell populations despite similar transfection efficiencies when other genomic sites (Sites 1-3) were targeted (FIG. 20). In addition, our attempts to use RoT-based methods in HEK293 cells to convert ApoE3 to ApoE2 by targeting the APOE(R158) locus revealed very low levels of editing in GFP+ isolated cells (FIG. 20B), further establishing the APOE(R158) locus as recalcitrant to genomic editing. Then, TREE-based methods were used to edit this same loci in HEK293 cells by co-transfecting pEF-BFP, pCMV-BE4-Gam and pDT-sgRNA with a sg(TS) targeting the APOE(R158) locus. As expected, flow cytometry analysis demonstrated that the transfection efficiency when TREE was used to target the APOE(R158) locus was similar to when TREE was used to target other genomic sites (FIG. 20C). In addition, despite these similarities in transfection efficiencies, there was no detectable editing in the unsorted cell populations using TREE to target the APOE(R158) locus, thereby confirming the difficulty in editing this genomic location (FIG. 20D). However, unlike in GFP-positive isolated using RoT methods, GFP-positive cells purified using TREE methods displayed a high level of base editing at the APOE(R158) locus (FIG. 20E). Together, these results demonstrate that TREE can not only provide for a higher level of enrichment of base-edited cell populations compared to conventional RoT strategies but also can allow for isolation of base-edited cells at genomic loci that were not previously achievable with traditional RoT approaches.

Figure 21:
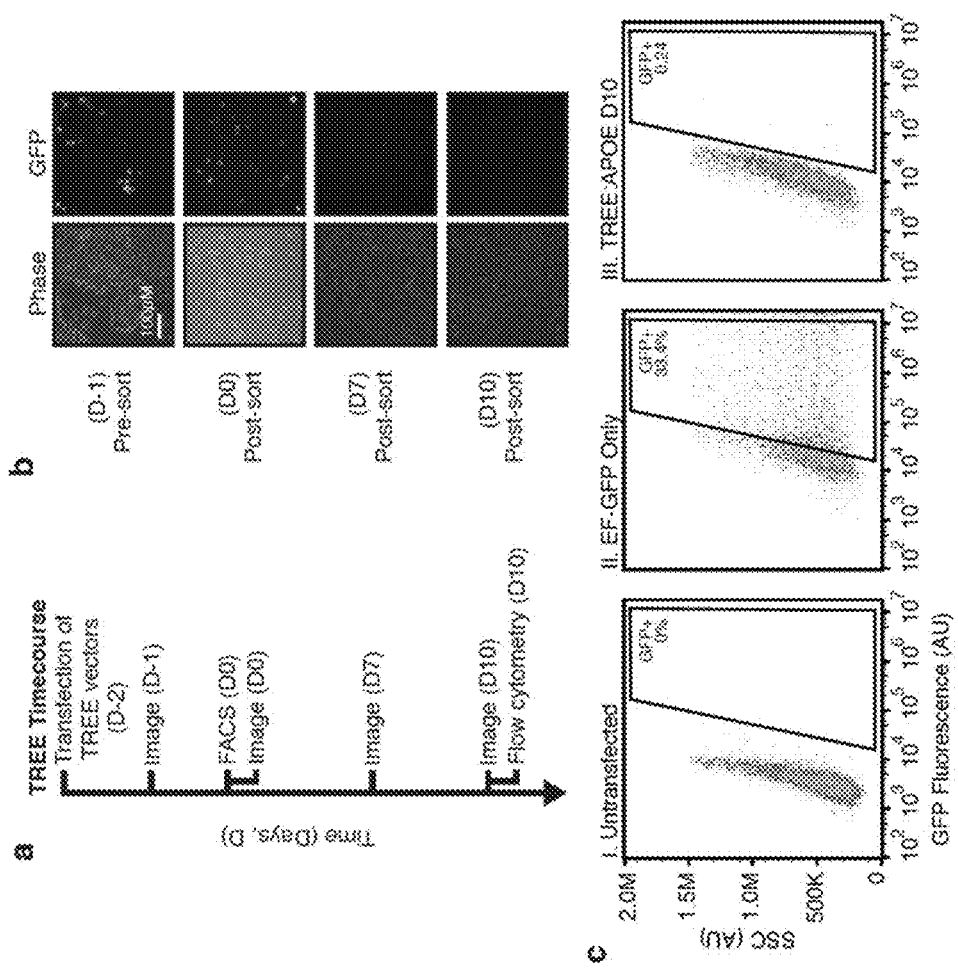
FIG. 21 demonstrates that TREE fluorescent output in HEK293 cells is transient. (a) HEK293 cells were transfected with pEF-BFP, pCMV-BE4-Gam, and pDT-sgRNA and GFP-positive cells were isolated by flow cytometry. Replated GFP-positive cells were analyzed by fluorescent microscopy and flow cytometry at various time points post-sorting. (b) Representative fluorescent microscopy images of cells prior to cell sorting (D-1, Pre-sort) and various time points (D0, D7, D10) after sorting. (c) Representative flow cytometry plots of (i) untransfected HEK293 cells, (ii) pEF-GFP transfected HEK293 cells, and (iii) TREE-enriched GFP-positive HEK293 cells 10 days after sorting.

At last, we wanted to confirm that the fluorescent signal associated with cells isolated by TREE was transient. To that end, we measured the long-term fluorescence of GFP-positive cells purified after TREE-based editing (FIG. 21A). Notably, analysis of these cells by fluorescent microscopy (FIG. 21B) and flow cytometry (FIG. 21C) revealed no long-term detectable GFP signal, verifying that the TREE fluorescent output is indeed transient in nature.

Multiplex Base-Editing Using TREE

Figures 4A, 4B, 4C:
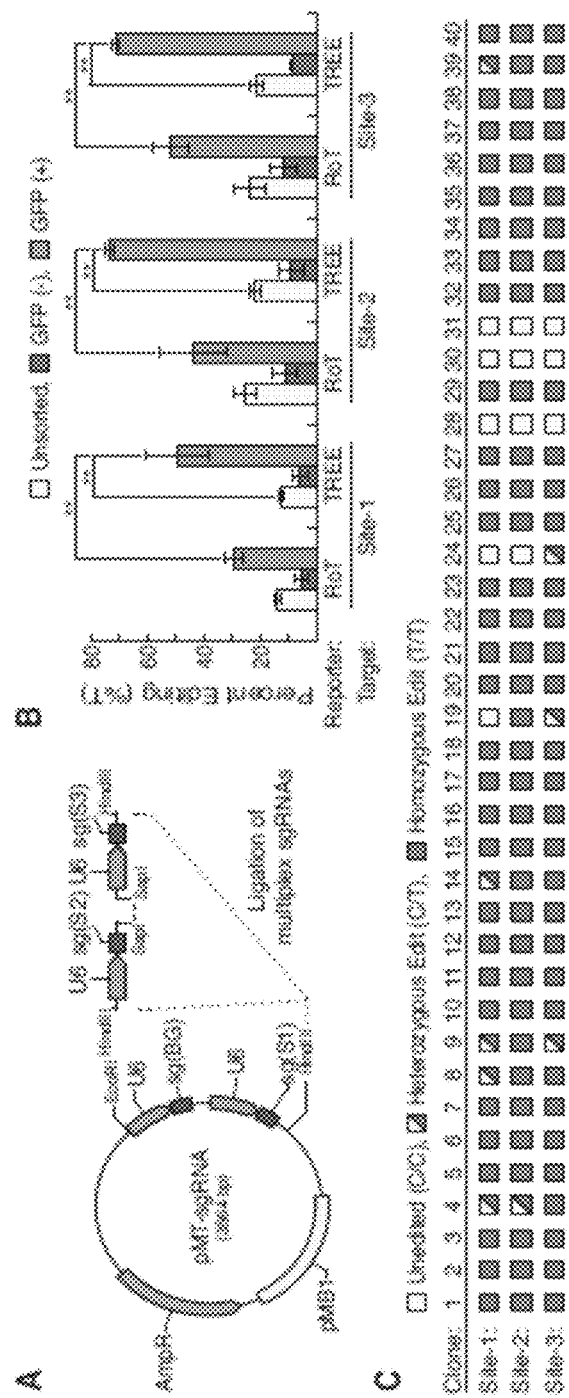
FIGS. 4A-4C demonstrate TREE enables efficient multiplex base editing. (A) Plasmid map of pMT-sgRNA vector that contains sg(BG) in addition to sgRNA for multiple target sites. Expression for all sgRNA cassettes is driven by separate U6 promoters (orange arrows). The HindIII restriction site allows for additional sgRNAs for target sites to be cloned in through restriction enzyme-based cloning. (B) Quantification of multiplex base editing efficiency at Site-1, Site-2 and Site-3 in GFP-positive, GFP-negative and unsorted cell populations using TREE- or RoT-based enrichment strategies. n=3; *=P<0.05, **=P<0.01. (C) Clonal analysis of editing at multiple genomic loci using TREE. 40 GFP-positive clones were isolated via single-cell sorting. Editing was detected via PCR and Sanger sequencing. Blank icon indicates no editing observed, half-red icon indicates heterozygous C and T at the target site, and solid red icon indicates homozygous T edits at the genomic site.

It was further investigated whether TREE could be utilized in con-junction with multiplexed genome engineering strategies. To accomplish this, we generated a multi-targeted vector (pMT-sgRNA) that contains sg(BG) as well as sgRNA for genomic targets Sites 1-3 (FIG. 4A). In a similar manner to when TREE was employed to target a single locus, we utilized TREE to simultaneously target multiple genomic sites by co-transfecting HEK293 cells with pMT-sgRNA, pEF-BFP and pCMV-BE4-Gam. In parallel, we used a RoT-based approach by co-transfecting HEK293 cells with pMT-sgRNA, pEF-GFP and pCMV-BE4-Gam. After 48 h, GFP-negative and GFP-positive cells were isolated using flow cytometry (FIG. 22A). Along similar lines to single locus targeting, Sanger sequencing of the multiplex targeted genomic sites in GFP-positive cell populations isolated from TREE and RoT approaches revealed that TREE allowed for statistically significant higher frequency of base editing than RoT approaches (FIG. 4B and FIG. 22B). Importantly, this analysis revealed that there was no statistically significant difference in editing efficiency when TREE was used to target these sites individually or a multiplexed manner (FIG. 22C). Finally, we wanted to determine if TREE increased the likelihood of C-to-T conversions at off-target loci. Therefore, in GFP-positive cell populations isolated from TREE and RoT approaches we PCR-amplified and Sanger sequenced the top predicted off-target loci for the sgRNA sequences used for multiplexed editing. Overall, quantification of the Sanger chromatographs by EditR revealed no observable C-to-T conversions at these off-target loci in either GFP-positive cells isolated with TREE- or RoT-based strategies when compared to that of untransfected cells (FIG. 23).

Sanger sequencing that was performed on bulk sorted GFP-positive cells suggested that multiplex editing in con-junction with TREE could result in multiplexed editing in the same cell. To confirm that this indeed occurred, we again used our multi-targeting vector (pMT-sgRNA) in conjunction with TREE to simultaneously target genomic Sites 1-3 in HEK293 cells. We then sorted single GFP-positive cells into a 96-well plate. After expansion, Sanger sequencing of the multiplexed genomic sites was performed on a total of 40 clones. This analysis revealed that 36 out of the 40 clones had base editing at more than one genomic site (FIG. 4C). Remarkably, this analysis revealed that almost 80% of the isolated clones (31 out of 40) had biallelic conversions at all three genomic loci.

One of the caveats of all base-editing approaches, regardless if RoT- or TREE-based enrichment strategies are employed, is that base editors can potentially edit non-target Cs that are located in an 6 nt window (termed the editing window) within the protospacer. As a consequence, this could potentially limit the application of base editing approaches in which conversion of non-target Cs result in a non-silent mutation or other phenotypic changes. To that end, we wanted to determine if any of our clones contained edits exclusively at the target C and not any other Cs within the editing window. Indeed, we identified a number of clones in which at genomic Site 2 and Site 3 modification only occurred at the target C (FIG. 24). Interestingly, we did not identify any clones in which at genomic Site 1 such exclusive modification of the target C occurred. We speculate that because another C occurs immediately adjacent to this target C, that such exclusive modification will require the use of recently published site-specific editors that allow for single nucleotide changes free from off-targeting conversions within the editing window.

TREE Allows for Highly Efficient Editing in Human Pluripotent Stem Cells (hPSCs)

Figures 5A, 5B, 5C, 5D:
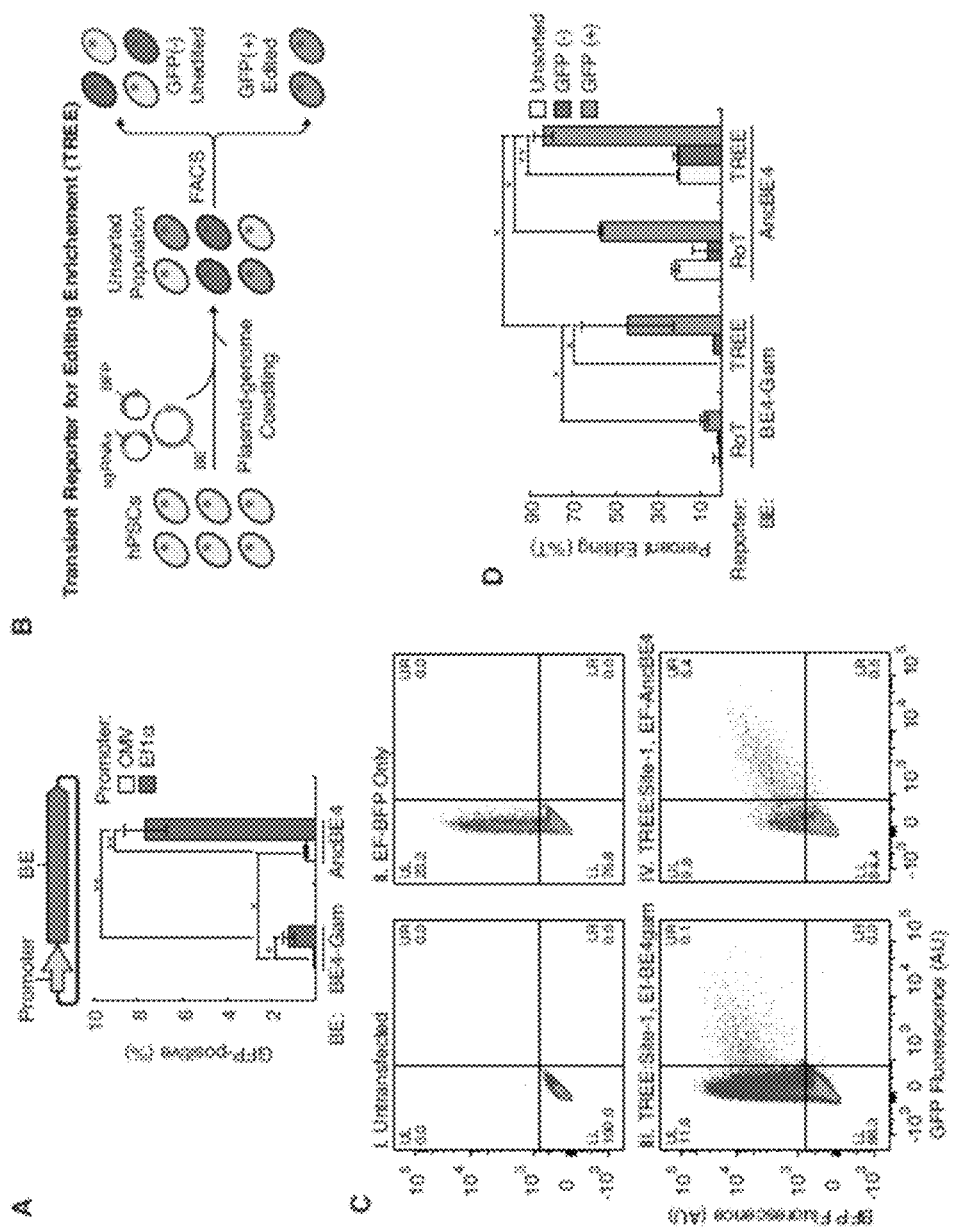
FIGS. 5A-5D demonstrate highly efficient editing in human pluripotent stem cells (hPSCs) using TREE (A) Quantification of base editing efficiency (percentage GFP-positive cells) when hPSCs were co-transfected with pEF-BFP, sg(BG) and various base editing vectors. n=3; *=P<0.05, **=P<0.01. (B) Schematic for enrichment of edited hPSC using TREE. HPSCs were co-transfected with pEF-BFP, pEF-BE4-Gam/pEF-AncBE4 and pDT-sgRNA vectors. 48 h post-transfection, flow cytometry was used to sort cell populations into GFP-positive and -negative fractions. (C) Representative flow cytometry plots of (i) untransfected hPSCs cells and (ii) hPSCs transfected with pEF-BFP only as well as hPSCs cells in which TREE was applied targeting Site-1 utilizing (iii) pEF-BE4-Gam or (iv) pEF-AncBE4. (D) Quantification of base editing efficiency at Site-1 in GFP-positive, GFP-negative and unsorted cell populations isolated using TREE- or RoT-based enrichment strategies in which pEF-BE4-Gam or pEF-AncBE4 was employed. n=3; *=P<0.05, **=P<0.01.
Figures 7A, 7B, 7C, 7D:
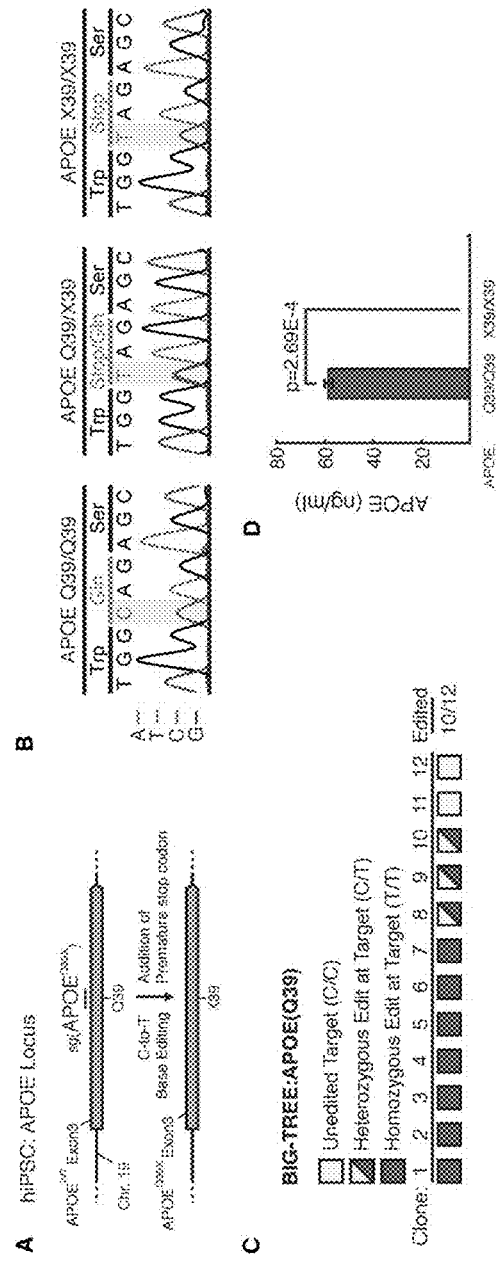
FIGS. 7A-7D demonstrate BIG-TREE-Based Gene Knockout of APOE in hPSCs. (A) Schematic of the APOE (39Q) locus in exon 3 of the APOE gene. Successful base editing of the APOE(39Q) locus would result in a C-to-T conversion causing a change in the amino acid at position 39 from a glutamine to a premature stop codon. (B) Representative Sanger sequencing of the APOE(39Q) locus in unedited wild-type cells (Q39/Q39; left panel) as well as hPSC clones in which a heterozygous (Q39/X39; middle panel) or homozygous (X39/X39; right panel) stop codon has been introduced. (C) Distribution of genotypes in clonal hPSCs that were generated via BIG-TREE targeting the APOE(39Q) locus. (D) Measurement of ApoE secretion in the condition medium of wild-type (Q39/Q39) and homozygous edited (X39/X39) hPSCs (n=3 independent experiments, p<0.05, two-tailed Student's t test).

Single base pair modification in hPSCs via CRISPR/Cas9-induced DSB followed by HDR suffers from low efficiencies. In addition, genomic modification of hPSCs using deaminase-based DNA base editor has yet to be reported. Therefore, we wanted to investigate if TREE could be utilized to efficiently edit specific loci in hPSCs. Hence, we co-transfected pEF-BFP and pCMV-BE4-Gam into hPSCs using a transfection reagent (Lipofectamine™ Stem) that had been previously used by others for the efficient delivery of Cas9-related plasmids to hPSCs. Surprisingly, we did not observe many GFP-positive cells in these cell populations (FIG. 5A and FIG. 25A). As such, we performed similar experiments in which we employed a more recently published, higher efficiency base editor, AncBE4max (herein referred to AncBE4). Briefly, AncBE4 is an improved version of BE4 that has been codon optimized for expression and contains an ancestral reconstructed deaminase to increase base editing efficiency at tar-get loci. Nonetheless, similar to when BE4-Gam was utilized, we observed very few GFP-positive cells when An-cBE4 was used (FIG. 25A). Because previous reports have suggested that the CMV promoter is inefficient for transgene expression in pluripotent stem cells, we replaced the promoter driving base editor expression with EF1a. When hPSCs were co-transfected with pEF-BE4-Gam or pEF-AncBE4 as well as pEF-BFP and sg(BG), a significant number of GFP-positive cells were observed (FIG. 5A). Using the pEF-AncBE4 vector, we also developed editing efficiency in hPSCs by using a range of base editor amount at varying ratio with sg(BG) (FIG. 25B). Similar to our experiments with HEK293 cells, this analysis revealed that base editing efficiencies were significantly affected by these parameters. Interestingly, the most optimal parameters in hPSCs differed from those identified in HEK293 cells (FIG. 2D) highlighting the utility of this assay to evaluate these variables. Using these base editing vector designs, we applied TREE to target a genomic loci in hPSCs by co-transfecting pEF-BE4-Gam/pEF-AncBE4, pEF-BFP and pDT-sgRNA (with a sg(TS) targeting site 1) (FIG. 5B). In turn, flow cytometry was used to isolate GFP-positive and -negative cell populations (FIG. 5C). Subsequently, Sanger sequencing was performed on the targeted genomic site in GFP-positive, GFP-negative and unsorted cell populations isolated from TREE and RoT approaches in which pEF-BE4-Gam and pEF-AncBE4 was used (FIG. 25C). This analysis demonstrated that GFP-positive hPSCs isolated via TREE had a statistically significant higher frequency of base editing than GFP-positive hPSCs isolated using traditional RoT approaches (FIG. 5D). In addition, TREE employed with the pEF-AncBE4 vector allowed for the efficient modification of the difficult to edit APOE(R158) locus (FIG. 7D-S7E).

Similar to our work with HEK293 cells, we wanted to confirm that the fluorescent output of TREE was transient in nature. In that regard, we measured the fluorescence of GFP-positive hPSCs isolated after TREE-based editing. Flow cytometry analysis revealed that after 2 weeks of culture there was no detectable GFP signal (FIG. 26), demonstrating that the fluorescent signal associated with hPSCs purified by TREE was transient.

Collectively, although this data demonstrates that TREE can be utilized for the efficient base editing of hPSCs, one of the caveats of all base editing approaches is the C-to-T conversion of non-target Cs within the editing window. Indeed, the Sanger sequencing analysis of GFP-positive populations isolated from TREE revealed editing of such non-target Cs when either Site 1 (FIG. 25C) or the APOE (R158)(FIG. 25E) locus was targeted in hPSCs. As such, to determine whether TREE allowed allelic outcomes in which targeting only occurred at the desired C, we performed NGS of PCR amplicons of Site 1 and APOE(R158) in GFP-positive cells purified using TREE. This analysis revealed at both these loci a very modest number of allelic outcomes in which base editing occurred exclusively at the target C, free from con-founding C-to-T conversions at other sites within the targeting window (FIG. 27). Instead, the most common editing outcome was one in which the majority of the Cs in the editing window were converted to Ts (FIG. 27). This suggests that for future applications which require a higher percentage of allelic outcomes where editing occurs only at the target C the use of recently published base editors that have a narrower editing window will be required. Nonetheless, this collective data demonstrates the broad utility of TREE to allow for the efficient editing in hPSCs.

Discussion

Since the first deaminase base editor was developed by Komor et al., multiple additional base-editing technologies have been rapidly developed with various endonucleases, deaminases, targeting windows and PAM specificities. Application of these emerging base editors to new cell types requires a slow, iterative process in which various base editing parameters are tested and editing efficiency is assessed through downstream sequencing methods. Additionally, as demonstrated herein, transfection efficiency does not precisely correlate with editing efficiency, so reporters of transfection do not provide accurate information about the efficacy of various base editing strategies. Here, it is described how BFP-to-GFP conversion and TREE can be utilized to rapidly optimize various factors that influence base editing efficiency, including base editor plasmid concentration and design as well as base editor to sgRNA ratios. In fact, these data show that these parameters are cell line-specific, demonstrating the advantage of TREE to allow for the high-throughput evaluation of base editing approaches. In the future, TREE may be used in the context of high-throughput screening to identify small molecules to further enhance base editing efficiency in a manner similar to that which has been previously achieved with CRISPR-mediated HDR approaches.

It has been shown that CRISPR/Cas9 genome engineering is compatible with a variety of delivery methods (e.g., lipid-mediated transfection, electroporation) and expression systems (e.g., plasmid DNA, Cas9-gRNA ribonucleo-protein complexes [RNP]), each with advantages and disadvantages that have been reviewed extensively elsewhere. In this example, we employed lipid-based delivery reagents that have been previously employed by others for the CRISPR/Cas9-based editing of HEK293 cells (Lipofectamine 3000) and hPSCs (Lipofectamine Stem). Given TREE's ease of use and readily detectable fluorescent output we anticipate that TREE can be employed with whatever transfection method that is preferred by the end user. For instance, the data presented here demonstrated that the TREE base editing assay was compatible with both plasmid and RNP approaches. Although we observed that the overall genomic base editing efficiency of RNP-based expression was lower than that of lipid-based expression, we provide proof-of-principle that TREE can be employed in future applications where the advantages of RNPs are desirable.

One potential limitation of the use of the plasmid DNA expression systems in the context of TREE approaches is random integration of all or part of the plasmid DNA into the genome of targeted cells. It should be noted that it has been reported by others that the stable integration of circular plasmid DNA into the host genome is infrequent, especially for cells such as hPSCs where it has been reported on the order of 1 per $1 \times 10^5$ cells. Indeed, as it relates to potential integration of the pEF-BFP plasmid, we demonstrate that the fluorescent output of TREE is transient in both HEK293 cells and hPSCs, suggesting that this plasmid does not integrate into the genome. As it relates to the integration of the base editing and sgRNA plasmids, it has been shown by others in CRISPR/Cas9 genome engineering that the Cas9 and sgRNA plasmids can be integrated at on- and off-target sites. However, we speculate that because base editors do not introduce DSBs the integration of these plasmids into the genome would be infrequent. In fact, we did not observe any integration of these plasmids when Sanger sequencing or NGS was performed at the on- or off-target sites. Moving forward, undesirable insertions of plasmid DNA sequences at target sites can be detected using PCR-based methods followed by Sanger sequencing or NGS of the resultant amplicons. On the other hand, similar insertions at off-target or random genomic sites are difficult to detect and will require the use of more comprehensive techniques such as whole genome sequencing.

Human cell models are critical for elucidating the mechanisms of disease progression as well as identifying and testing potential therapeutic interventions. Because a high percentage of human diseases are due to single nucleotide poly-morphisms (SNPs), base editors can allow for the precise engineering of in vitro models of human disease. Here we provide proof-of-principle that TREE can be employed to edit disease-relevant loci. Specifically, we demonstrate that TREE enables for the enrichment of cells that had been edited at the APOE(R158) locus, a gene associated with altered risk of Alzheimer's disease onset. Notably, conventional RoT-based methods did not allow for significant enrichment of edited cells at this same refractory locus. In addition, because many human diseases are multigenetic disorders that are a result of complex gene interactions, we also investigated the ability of TREE to be utilized in multiplexed genome engineering applications. By using a multi-targeted vector, we demonstrated that compared to RoT-based methods TREE resulted in a significantly higher level of cells enriched for simultaneous editing at multiple independent loci. In fact, we demonstrated that through analysis of single cell clones that 90% of the clones had simultaneous base editing at more than one genomic site and almost 80% of the clones had biallelic conversions at all three targeted loci. In this vein, TREE provides a highly efficient method for generating cell-based models of multigenic diseases.

Many immortalized cell lines, such as HEK293s, are aneuploid with unknown mutations and dosage at key disease-relevant genes. Alternatively, hPSCs, which have a normal euploid karyotype and the potential to differentiate into all cell types of the mature adult body, represent an attractive alternative to immortalized cell lines for disease modeling and drug screening applications. In particular, the ability to use gene editing technologies to generate isogenic hPSC lines that differ only with respect to disease mutations has great potential as it relates to precisely defining genotype to phenotype relationships. The RNA-guided CRISPR-Cas9 system has the potential to allow for precise genetic modifications in hPSCs through the introduction of site-specific DSBs. Although previous reports demonstrate that introduction of DSB via CRISPR/Cas9 significantly improves the ability to obtain knock out cell lines from hPSCs by the NHEJ pathway, single base modification using CRISPR/Cas9-induced DSB followed by HDR is extremely inefficient (1-2% of sequenced colonies in which one allele is targeted and <1% where both alleles are targeted. Recently, it has been reported that co-delivery of Cas9, sgRNA, and a puromycin selection cassette followed by transient puromycin selection can increase the HDR-mediated genome engineering in hPSCs However, these strategies rely on the introduction of DSBs, which in pluripotent stem cells can lead to large deletions and complex chromosomal rearrangements, significant cytotoxicity and increased acquisition of p53 mutations. In addition, it has been shown that the use of antibiotic selection, even in a transient manner, may lead to the se-lection of hPSCs, with chromosomal abnormalities. Yet, to our knowledge, base editors, which do not have these same limitations as CRISPR/Cas9-induced DSB followed by HDR, have not previously been used with hPSCs. In fact, our initial attempts to apply base editors in the context of both RoT- and TREE-based approaches with hPSCs did not allow for observable modification of target loci. Instead, by replacing the standard CMV promoter in the base editing plasmids with an EF1a promoter, we were able to achieve modification of genomic sites using both RoT- and TREE-centered methods. However, TREE allowed for significantly higher enrichment of edited hPSCs when com-pared to RoT isolation strategies. We contend that the use of TREE with hPSCs will significantly advance the use of these cells in disease modeling, drug screening, and cell-based therapies.

Despite their tremendous potential in a variety of downstream applications, base editing approaches have a few of caveats that should be noted, regardless of whether RoT- or TREE-based enrichment strategies are employed. First, as is the case with all Cas9-directed genome editing approaches, is the potential for genome modification at off-target loci. In this work, GFP-positive cells isolated via TREE did not display untargeted C-to-T conversions at the off-target genomic loci examined. Recently, it has been reported that base editors can induce site-specific inosine formation on RNA. Accordingly, in the future, the effect of TREE-based approaches on unwanted RNA modifications should be examined. Another limitation of base editing methods is modification of additional C nucleotides that are in close proximity to the target C. In fact, some base editors can cause C-to-T conversions at any Cs in up to a 9-nt window within the protospacer. Such C-to-T modifications could be especially problematic if they result in amino acid alterations during translation, induce epigenetic changes or cause other phenotypic changes in targeted cells. To that end, through clonal isolation and next generation sequencing (NGS) analysis we identified that such exclusive modifications of the target C were achieved in both edited HEK293 cells or hPSCs that were enriched using TREE-based methods. It should be noted, though, that at genomic Site-1, where a C lies adjacent to the target C, allelic outcomes in which modification only occurred at the target C were rare events. Moving forward, modified base editors that have a narrow editing window could be easily employed with TREE to target such genomic loci that contain multiple Cs in close proximity to the target C.

In summary, these data demonstrate that TREE allows not only for the optimization of base editing strategies in the context of a variety of cell types and genomic locations but also the enrichment of cell populations to be utilized in variety of downstream applications. In particular, with the rate at which the genome editing field has been progressing over the past few years, TREE is a readily adoptable method that will expedite and improve tractability of single-nucleotide genome engineering methods.

Example 2—Producing Base-Edited Isogenic Cell Lines Using a Transient Reporter for Editing Enrichment (BIG-TREE)

Current CRISPR-targeted single-nucleotide modifications and subsequent isogenic cell line generation in human pluripotent stem cells (hPSCs) require the introduction of deleterious double-stranded DNA breaks followed by inefficient homology-directed repair (HDR). This section describes the development of Cas9 deaminase base-editing technologies to co-target genomic loci and an episomal reporter to enable single-nucleotide genomic changes in hPSCs without HDR. Using this method, a base-edited isogenic hPSC line was generated using a transient reporter for editing enrichment (BIG-TREE) which allows for single-nucleotide editing efficiencies of >80% across multiple hPSC lines. Also described herein is use of BIG-TREE for efficient generation of loss-of-function hPSC lines via introduction of premature stop codons. Finally, BIG-TREE achieves efficient multiplex editing of hPSCs at several independent loci. These methods allow for the precise and efficient base editing of hPSCs for use in developmental biology, disease modeling, drug screening, and cell-based therapies.

Materials and Methods

Cells and Culture Conditions: Cell lines, media compositions, and conditions for culture of hPSC and HEK293 are listed in the Supplemental Experimental Procedures (End of Example 2).

Plasmid Construction: All plasmids were constructed using conventional restriction enzyme-based molecular cloning techniques. For construction of the sgRNA plasmids, the sgRNA sequences listed in Table 12 were used. Additional details for molecular cloning and plasmid construction are provided in the Supplemental Experimental Procedures (End of Example 2).

```
sgRNA Sequences in TREE: Guide and Cas9 Handle
>sg(BG)
                                      (SEQ ID NO: 3)
GACCCACGGCGTGCAGTGCTTGTTTTAGAGCTAGAAATAGCAAGTTAAAA

TAAGGCTAGTCCGTTATCAACTTGAAAAAGTGGCACCGAGTCGGTGCTTT

TTTGTTTT
```

-continued

```
>sg(NT)
                                         (SEQ ID NO: 4)
GGGTCTTCGAGAAGACCTGTTTTAGAGCTAGAAATAGCAAGTTAAAATAA

GGCTAGTCCGTTATCAACTTGAAAAAGTGGCACCGAGTCGGTGCTTTTTT

GTTTT

>sg(Site-1)
                                         (SEQ ID NO: 5)
GGCCCAGACTGAGCACGTGAGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(Site-2)
                                         (SEQ ID NO: 6)
GAACACAAAGCATAGACTGCGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(Site-3)
                                         (SEQ ID NO: 7)
GGCACTGCGGCTGGAGGTGGGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(APOE R158)
                                         (SEQ ID NO: 8)
GAAGCGCCTGGCAGTGTACCGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(C1ORF228)
                                         (SEQ ID NO: 9)
GTGCTGTTAGCACCCTGGAAAGTTTTAGAGCTAGAAATAGCAAGTTAAAA

TAAGGCTAGTCCGTTATCAACTTGAAAAAGTGGCACCGAGTCGGTGCTTT

TTTGTTTT

>sg(APOE Q39X)
                                         (SEQ ID NO: 10)
GTGGCAGAGCGGCCAGCGCTGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(mCh1)
                                         (SEQ ID NO: 11)
GCACCCAGACCGCCAAGCTGAGTTTTAGAGCTAGAAATAGCAAGTTAAAA

TAAGGCTAGTCCGTTATCAACTTGAAAAAGTGGCACCGAGTCGGTGCTTT

TTTGTTTT

>sg(mCh2)
                                         (SEQ ID NO: 12)
GACCCAGGACTCCTCCCTGCGTTTTAGAGCTAGAAATAGCAAGTTAAAAT

AAGGCTAGTCCGTTATCAACTTGAAAAAGTGGCACCGAGTCGGTGCTTTT

TTGTTTT

>sg(mCh3)
                                         (SEQ ID NO: 13)
GCAAGCAGAGGCTGAAGCTGAGTTTTAGAGCTAGAAATAGCAAGTTAAAA

TAAGGCTAGTCCGTTATCAACTTGAAAAAGTGGCACCGAGTCGGTGCTTT

TTTGTTTT
``` hPSC Base Editing, Clonal Isolation, and Characterization: Methods for transfection of hPSCs, clonal isolation, and characterization via tri-lineage differentiation are described in the Supplemental Experimental Procedures (End of Example 2).

Genotyping and Sequence Analysis at Off- and On-Target Analysis: Genomic DNA was prepared from expanded clones using the DNeasy kit (QIAGEN). PCR was performed with the primers listed in Table 5 using the methods described in the Supplemental Experimental Procedures (End of Example 2).

Karyotype Analysis: For each cell line, cytogenetic analysis was performed (Cell Line Genetics) on 20 metaphase cells using standard protocols for G-banding.

Immunofluorescence: Detailed protocols for immunofluorescence and antibodies used are provided in the Supplemental Experimental Procedures (End of Example 2).

HEK293 Transfections: Methods for transfection of HEK293s and Sanger sequencing of resultant populations are described in the Supplemental Experimental Procedures (End of Example 2).

Fluorescence Microscopy: Fluorescent imaging was performed on a Nikon Ti-Eclipse inverted microscope using the filters and acquisition settings described in the Supplemental Experimental Procedures (End of Example 2).

Flow Cytometry: Cells were dissociated with Accutase for 10 minutes at 37° C., triturated, and passed through a 40 mm cell strainer. Cells were then washed twice with flow cytometry buffer (BD Biosciences) and resuspended at a maximum concentration of $5 \times 10^6$ cells per 100 mL. Flow cytometry analysis was performed on an Attune NxT (Thermo Fisher Scientific). Flow cytometry files were analyzed using FlowJo (FlowJo LLC, Ashland, OR, USA).

Apolipoprotein E ELISA: Cells were seeded in a 6-well plate at a density of $3 \times 10^5$ cells per well. Medium was changed every 24 hours (h). On day 3, 24-h conditioned medium was collected, and ApoE levels in the medium were measured with the Human APOE (AD2) ELISA Kit (Thermo Scientific).

Statistical Analysis: Unless otherwise noted, all data are displayed as means±SD.

Results

Highly Efficient Generation of Clonal Isogenic hPSC Lines Using BIG-TREE

It was previously demonstrated that the efficiency at which a base editor is delivered to a cell does not precisely correlate with editing efficiency at a genomic locus. To overcome this limitation, an assay was developed, termed transient reporter for editing enrichment (TREE) (Standage-Beier et al., 2019). TREE utilizes a BFP variant that converts to a GFP upon a C-to-T nucleotide change (Standage-Beier et al., 2019). More specifically, this BFP mutant contains a histidine at the 66th amino acid position encoded by a "CAC" codon. The C-to-T conversion of that codon to a "TAC" or "TAT" will cause an amino acid change from a histidine to a tyrosine as well as a shift in the emission spectra of the modified protein resulting in a GFP variant. Thus, co-transfection of cells with this BFP construct (pEF-BFP), a base editor (pEF-AncBE4max), and a single guide RNA (sgRNA) targeting the "CAC" codon, sg(BG), will result in a BFP-to-GFP conversion in which the base editor machinery is present and actively functioning. In addition, we found that this BFP-to-GFP conversion was highly predictive of the likelihood of base editing at genomic loci within the same cell that had been transfected with a sgRNA for a genomic target site, sg(TS).

Figures 6A, 6B, 6C, 6D, 6E, 6F, 6G, 6H, 6I:
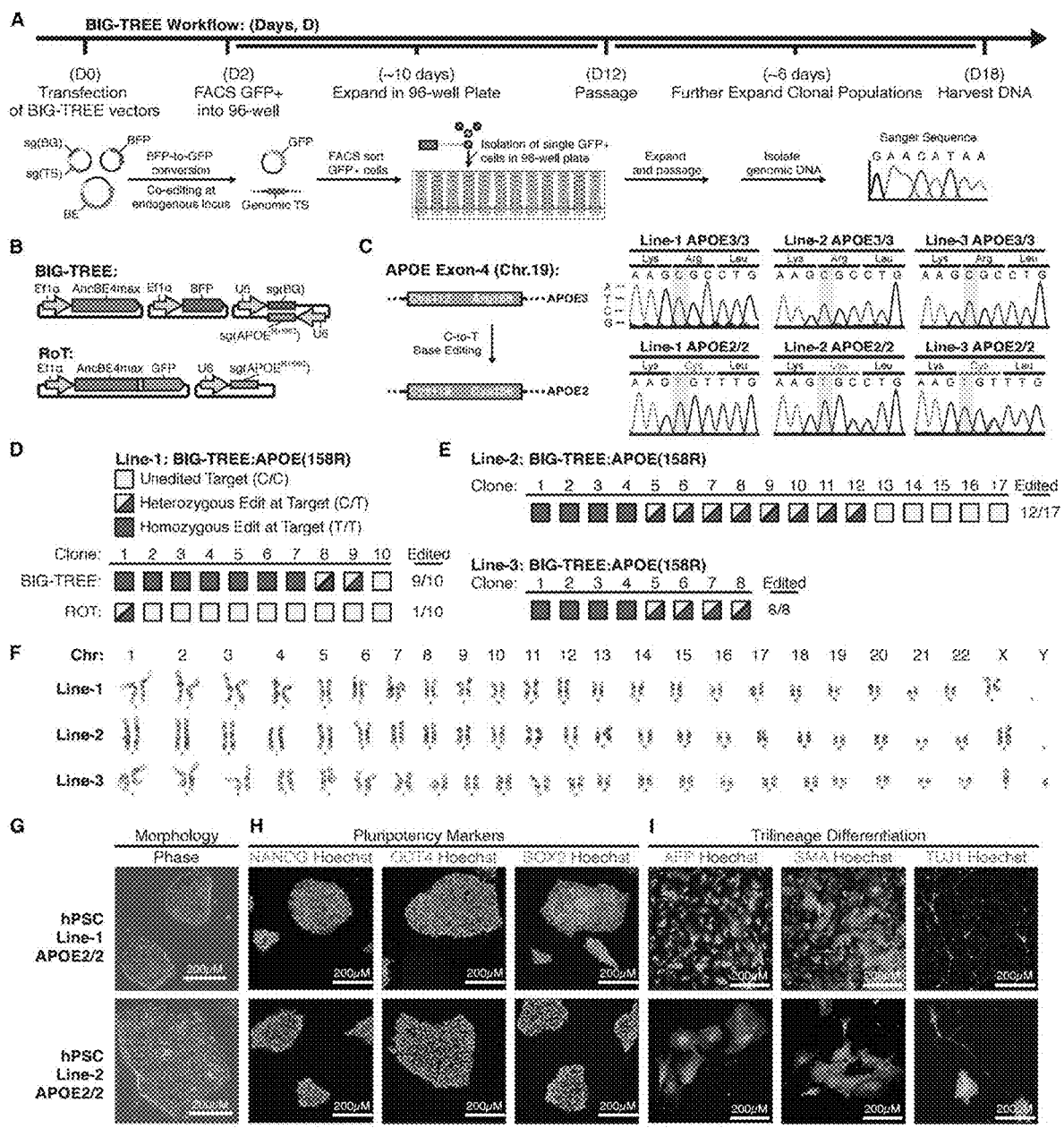
FIGS. 6A-6I demonstrate efficient generation of isogenic hPSC lines using BIG-TREE. (A) Schematic for generation of clonal isogenic hPSC lines using BIG-TREE. HPSCs are co-transfected with pEF-BFP, pEF-AncBE4max, and pDT-sgRNA plasmid vectors. Forty-eight hours post transfection, FACS is used to isolate single GFP-positive cells into 96-well plates. Cells are subsequently expanded, and target clones are identified by Sanger sequencing of the target loci. (B) Schematic of vectors used for BIG-TREE- and RoT-based generation of clonal hPSC lines in which the APOE (158R) locus has been targeted. (C) Schematic of the APOE (158R) target locus in exon 4 of the APOE gene. Successful base editing of the APOE(158R) locus would result in a C-to-T conversion causing a change in the amino acid position at 158 from an arginine (APOE3) to a cysteine (APOE2). Representative Sanger sequences of the APOE (158R) locus of unedited parental hPSC lines as well as clonal hPSC lines that have been edited at the APOE(158R) are shown. Each line shown is representative of clones obtained from three independent parental hPSC populations (hPSC lines 1-3) with different genetic backgrounds. (D) Distribution of genotypes in clonal hPSCs derived from hPSC line 1 that was targeted at the APOE(158R) locus using BIG-TREE- or RoT-based methods. (E) Distribution of genotypes in clonal hPSCs derived from hPSC lines 2 and 3 that were generated via BIG-TREE-based targeting at the APOE(158R) locus. (F) Karyotype analysis of representative clones edited at the APOE(158R) locus. (G) Phase contrast images of representative clones edited at the APOE (158R) locus. (H) Immunofluorescence staining of representative clones edited at the APOE(158R) locus for pluripotency markers NANOG, OCT4, and SOX2. (I) Alpha fetaprotein (AFP), smooth muscle actin (SMA), and beta-III tubulin (TUJ1) immunofluorescence staining of representative clones edited at the APOE(158R) locus that had been subject to tri-lineage differentiation.

This section describes efforts to extend this work to develop a rapid and efficient resource that uses TREE as the basis for the generation of clonal isogenic hPSC lines, termed base-edited isogenic hPSC line generation using a transient reporter for editing enrichment (BIG-TREE) (FIG. 6A). As proof-of-principle, we aimed to edit the APOE locus, a risk factor associated with altered probability of sporadic Alzheimer disease (AD) onset (Hauser and Ryan, 2013). Human APOE has three common isoforms that differ from each other by two amino acids at position 112 and 158 (APOE2=Cys112, Cys158; APOE3=Cys112, Arg158; APOE4=Arg112, Arg158). To this end, we transfected a non-demented control hPSC line (herein referred to as hPSC line 1) that has an APOE3/E3 genotype with pEF-BFP, pEF-AncBE4max, and a dual-targeting sgRNA (pDT-sgRNA) vector that contains both sg(BG) and a sgRNA for the APOE(R158) locus (FIG. 6B, top). Consequently, successful targeting of the APOE(R158) locus would result in C-to-T conversion that would cause a change from an APOE3 genotype (R158) to an APO E2 genotype (C158) (FIG. 6C). At 48 hours post transfection, fluorescent activated cell sorting (FACS) was used to sort single GFP-positive cells into 96-well plates. Clonal lines were then passaged and expanded over the course of 18 days prior to detailed analysis. First, genomic DNA was isolated from ten clones and the target region of the APOE locus, APOE (R158), was subject to Sanger sequencing after PCR amplification (FIG. 6C). Remarkably, this analysis revealed that 90% of the clones isolated had been edited, with seven of the clones having a homozygous and two of the clones having a heterozygous edit at the APOE(R158) locus (FIG. 6D). For comparison, we used a more conventional reporter of transfection (RoT) approach in which this same hPSC line was transfected with a plasmid in which a GFP and the AncBE4max base editor are driven by the same promoter, connected by a P2A post-translational self-cleavage peptide tag (pEFAncBE4max-P2A-GFP), as well as the same sgRNA for the APOE locus (FIG. 6B, bottom). In a manner analogous to that described for the BIG-TREE-based approach, single GFP-positive cells were then sorted into 96-well plates, expanded, and subject to Sanger sequencing. Analysis of ten clonal lines revealed this traditional RoT-based approach was significantly less efficient with only a single clone displaying a heterozygous edit at the target APOE(R158) locus (FIG. 6D). Given the large variability that exists between individual hPSC lines (Ortmann and Vallier, 2017), we wanted to determine the robustness of BIG-TREE to efficiently generate isogenic pairs in other independent hPSC lines. In this vein, we employed BIG-TREE to target the APOE (R158 locus) in two hPSC lines derived from patients with familial AD (FAD) (herein referred to hPSC line 2 and hPSC line 3). Analysis of single cell clones by Sanger sequencing (FIG. 6C) revealed that across all three hPSC lines tested, over 80% (33/41 clones examined) had an edit at the APOE(R158) locus, and greater than 50% of those edits were homozygous in nature (FIG. 6E). Importantly, we did not observe the presence of indels at the target site in any of clones examined. Finally, one of the limitations of base editor techniques, regardless if BIG-TREE strategies are employed, is that base editors can induce changes in the protospacer at a C other than the target C within the editing window-termed bystander editing (FIG. 21A). Indeed, with respect to generating isogenic lines at the APOE(R158) locus, editing at these bystander Cs was a common occurrence (FIG. 21B). In fact, only one of the clones analyzed (line 2, clone 5) had a heterozygous edit exclusively at the target C and no other Cs within the editing window. However, it should be noted that these bystander edits did not alter the amino acid sequence.

We performed detailed phenotypic analysis on representative biallelic edited clones from each hPSC line. Overall, these clones had a normal euploid karyotype (FIG. 6F), characteristic hPSC morphology (FIG. 1G), high expression of key pluripotency markers (FIG. 1H), and demonstrated tri-lineage differentiation potential (FIG. 6I). In addition, off-target analysis was performed at the top predicted sites for sg(BG) as well as the sgRNA used to target the APOE (R158) locus. At all of the off-target sites analyzed, we did not observe any C-to-T conversions at these off-target loci (FIG. 29). Furthermore, indels were not identified at any of the off-target sites in clones analyzed. Finally, Sanger sequencing revealed that the AD-related mutations in the hPSC clones derived from the FAD lines were retained in the edited clones (FIG. 30). Taken together, this analysis reveals that TREE can be employed for the highly efficient generation of isogenic hPSCs across multiple independent cell lines.

BIG-TREE can be Utilized for the Engineering of Gene Knockout hPSC Lines

To date, engineering of hPSC loss-of-function lines using CRISPR-based approaches has involved the generation of Cas9-mediated DSBs followed by non-homologous end joining (NHEJ), which typically results in a frameshift mutation and introduction of a downstream premature stop codon. Because of the aforementioned caveats associated with such DSB-driven approaches, we wanted to determine if BIG-TREE could be utilized to generate gene knockout hPSC lines without the introduction of DSBs. Because base editors have not been utilized previously to generate loss-of-function in hPSCs, we first wanted to establish this proof-of-principle in HEK293 cells. First, to validate base editor targeted introduction of premature stop codons, we designed a series of sgRNAs targeting an mCherry cassette in an HEK293T line, which would lead to conversion of a "CAG" codon encoding for glutamine to a "TAG" stop codon (FIG. 31A). We observed loss of mCherry expression via fluorescent microscopy and flow cytometry when targeting with sgRNAs (FIGS. 31B and 31C). In addition, we confirmed the targeted addition of stop codons by Sanger sequencing (FIG. 31D). Finally, this analysis revealed that loss of mCherry fluorescent signal was a direct consequence of introduction of a premature stop codon introduced into the genomically integrated mCherry cassette (FIG. 31E). Next, we sought to employ BIG-TREE to introduce premature stop codons in hPSCs at a disease relevant locus. To this end, we transfected hPSC line 1 with pEF-BFP, pEF-AncBE4max, and a dual-targeting sgRNA (pDT-sgRNA) vector that contained both sg(BG) and a sgRNA for the glutamine residue at amino acid position 39 in exon 3 of the APOE locus. Successful targeting would result in conversion of the glutamine encoding "CAA" codon to a premature "TAA" stop codon (FIG. 7A). Similar to as previously described, we isolated clonal cell lines established from single GFP-positive sorted cells. Analysis of these clones by Sanger sequencing (FIG. 7B) revealed that more than 80% of the clones had a stop codon introduced at the target site with greater than 50% of the edited clones displaying a biallelic modification (FIG. 7C). Importantly, none of the clones analyzed had indels at the same target site. Lastly, to demonstrate that introduction of a premature stop codon in exon 3 results in functional loss of APOE, we measured the amount of APOE in the conditioned media secreted by unedited and edited cells using ELISA. Compared with the unedited wild-type (Q39/Q39) cells that secreted robust amounts of APOE, cells in which a premature stop codon had been introduced into both alleles (X39/X39) did not secrete any detectable levels of APOE (FIG. 7D). Collectively, these data show that BIG-TREE enables efficient generation of loss-of-function hPSC lines through the introduction of premature stop codons.

BIG-TREE Enables High-Frequency, Multiplex Base Editing in hPSCs

Figures 8A, 8B, 8C:
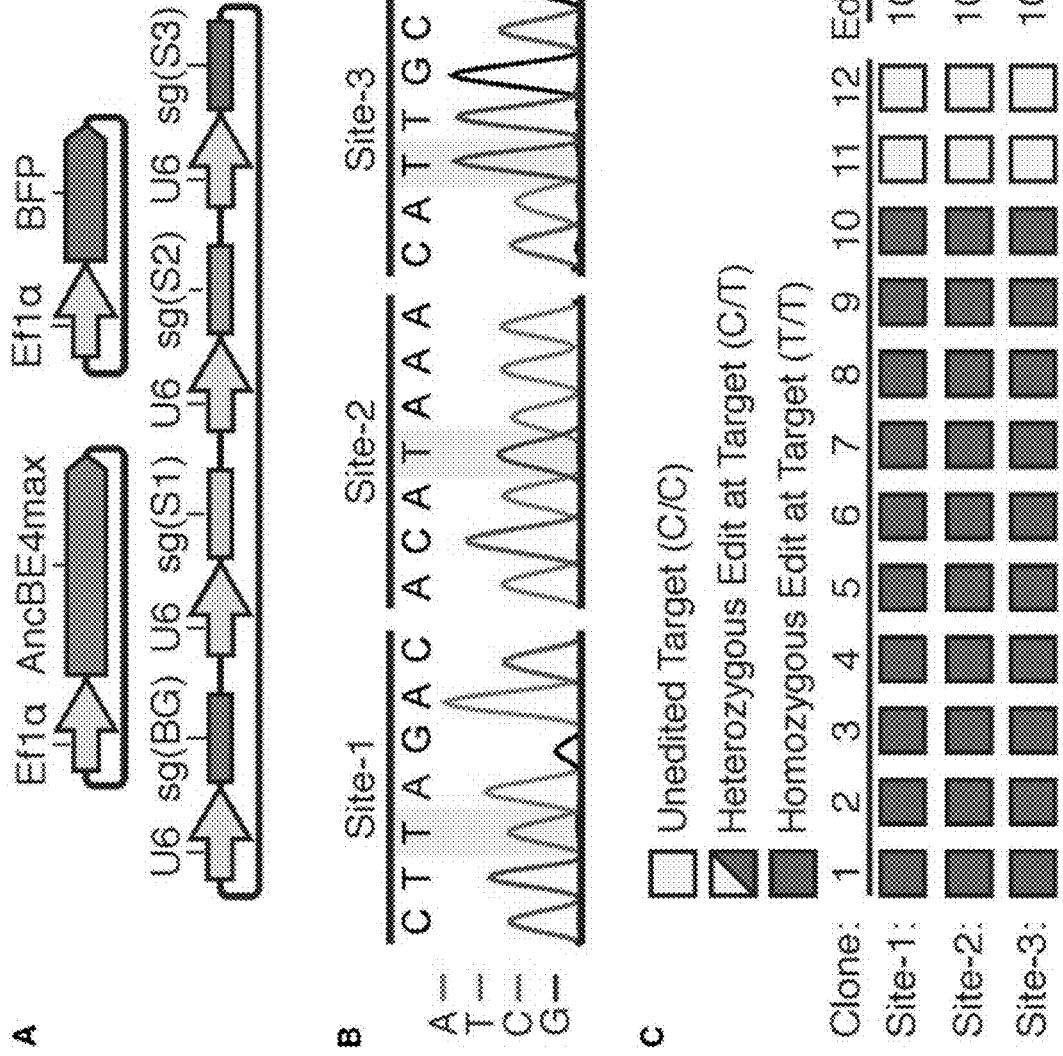
FIGS. 8A-8C demonstrate simultaneous base editing of multiple loci in hPSCs using BIG-TREE. (A) Schematic of plasmid vectors used for BIG-TREE-based generation of clonal hPSC lines in which multiple loci have been simultaneously targeted. The pMT-sgRNA vector contains sg(BG) in addition to sgRNA for multiple target sites (S1, genomic site 1; S2, genomic site 2; S3, genomic site 3). (B) Representative Sanger sequencing chromatographs of the site 1, site 2, and site 3 loci in clonal hPSCs that have been generated via BIG-TREE multiplexed base editing. (C) Distribution of genotypes in clonal hPSCs that were generated via BIG-TREE multiplexed base editing.
Figure 10:
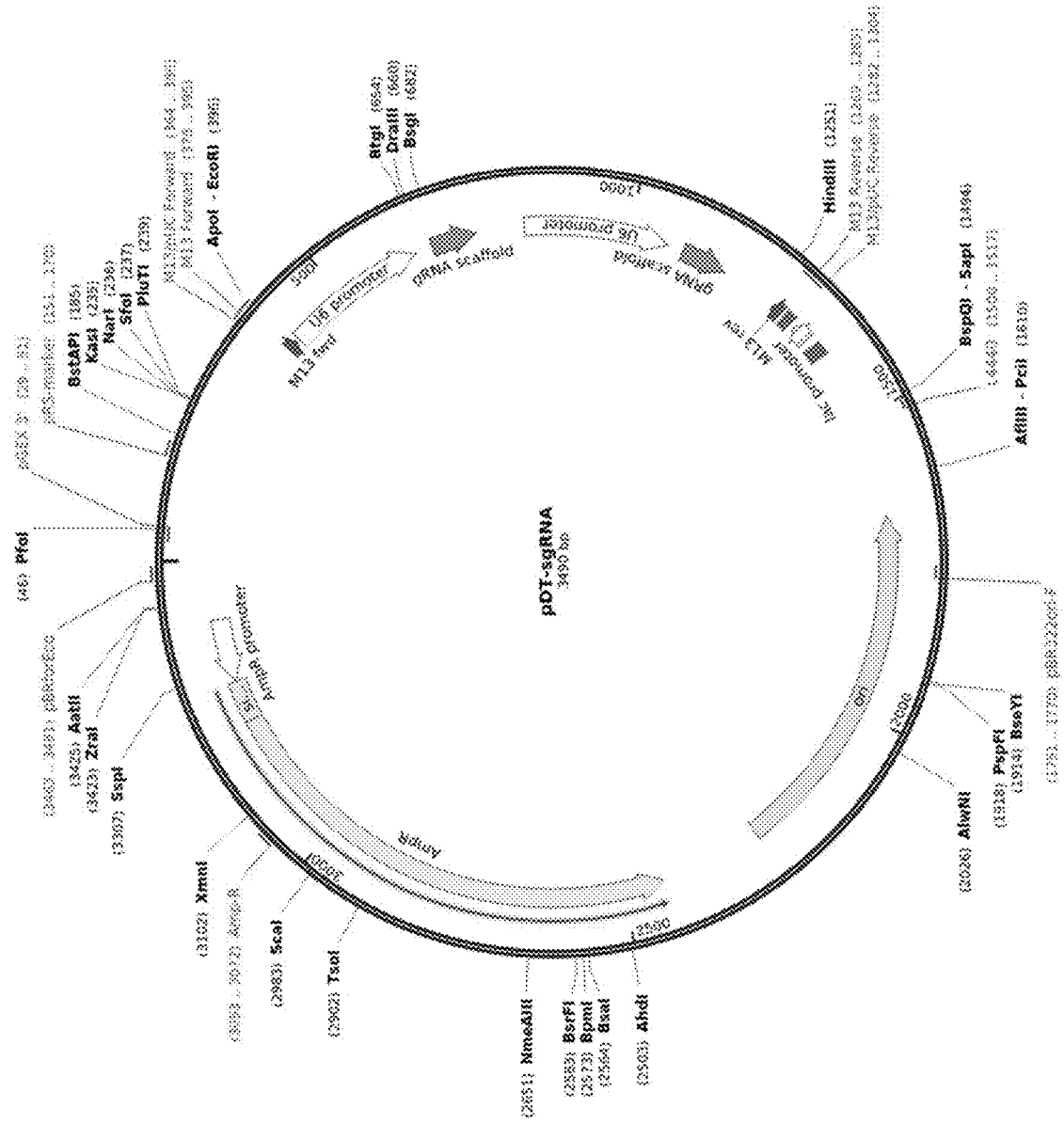
FIG. 10 is a schematic illustration of vector pDT-sgRNA.
Figure 11:
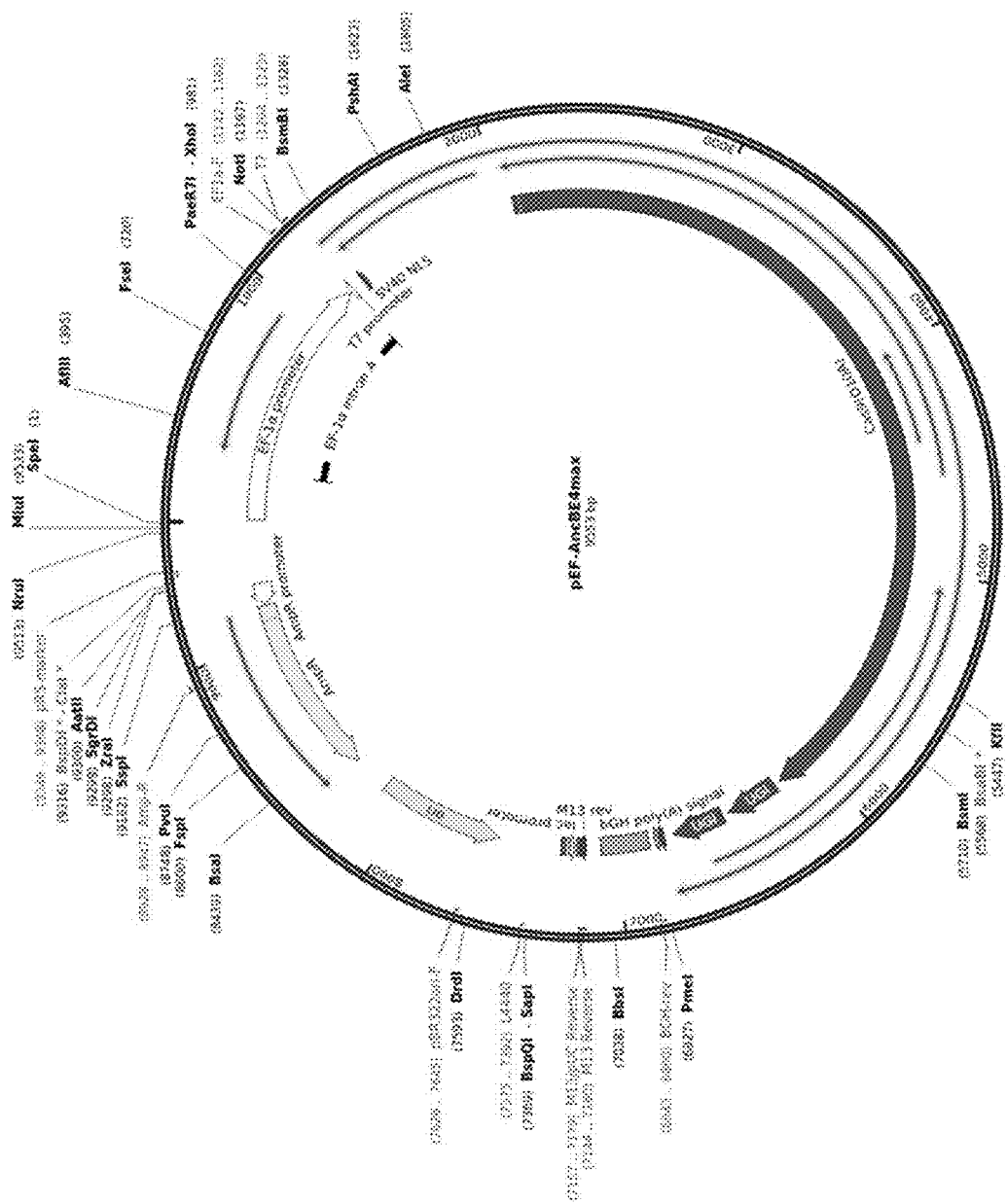
FIG. 11 is a schematic illustration of vector pEF-AncBE4max.
Figure 12:
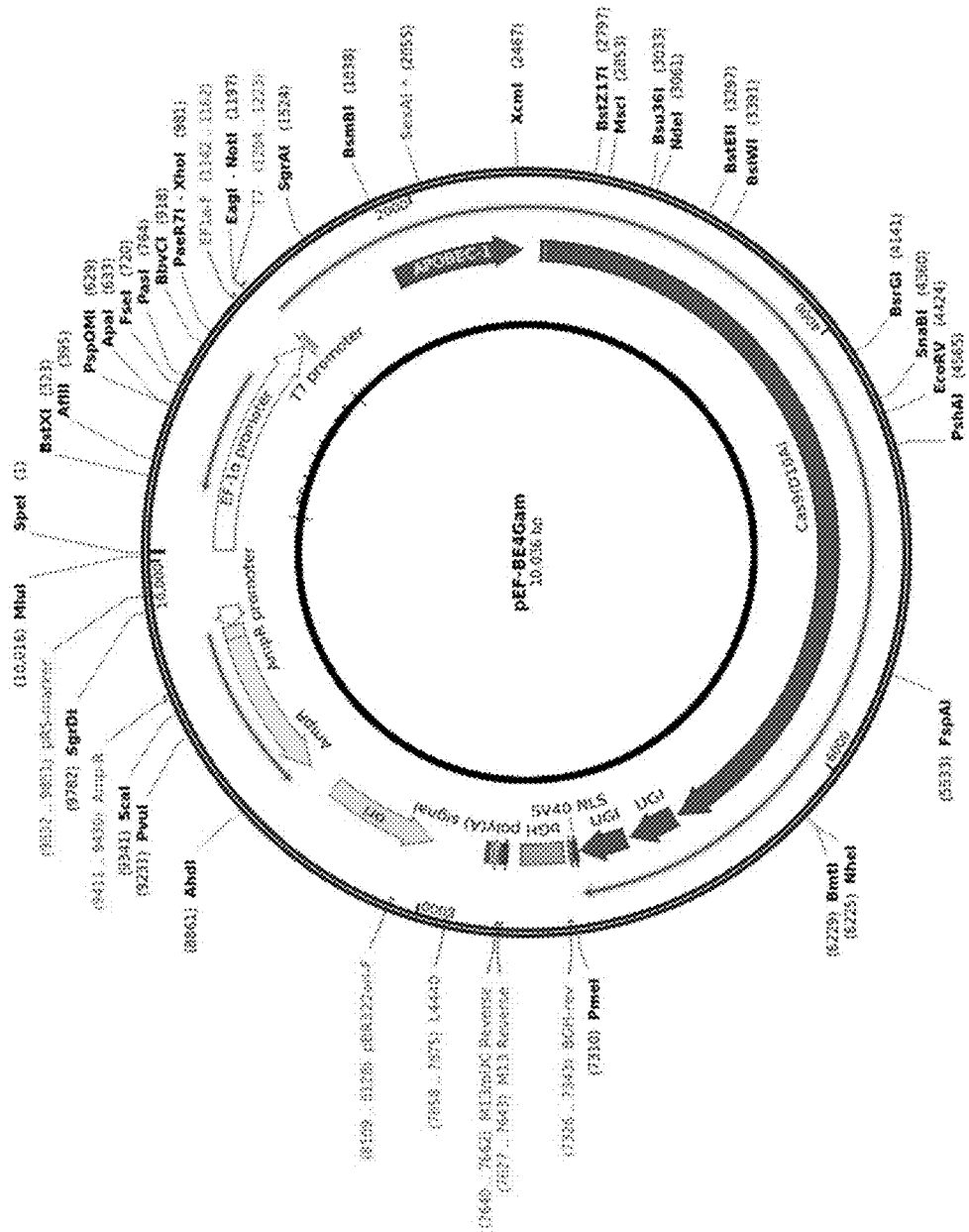
FIG. 12 is a schematic illustration of vector pEF-BE4Gam. Additional vector map illustrations are provided in FIGS. 39-44.

Finally, we wanted to determine if BIG-TREE could be utilized with multiplexed genome modification methods to establish hPSC lines that had been simultaneously edited at multiple genomic locations. Accordingly, a multi-targeting vector (pMT-sgRNA) that contains sg(BG) as well as sgRNAs for three independent genomic target sites (FIG. 8A) was used. Analogous to when BIG-TREE was used to target a single genomic location, TREE was employed to simultaneously target multiple loci by co-transfecting hPSC line 1 with pMT-sgRNA, pEF-BFP, and pEF-AncBE4-max. Sanger sequencing was then performed on the multiplex targeted genomic sites in clonal hPSC lines derived from single GFP-positive cells (FIG. 8B). Along similar lines to when BIG-TREE was used to target a single genomic locus, Sanger sequencing revealed that more than 80% of clones had been targeted at all three sites with all clones displaying biallelic edits (FIG. 8C). Moreover, indels were not identified in any of the clones across all three target sites. Lastly, examination of potential bystander edits within the editing window (FIG. 28A) revealed a number of clones in which at genomic site 2 and site 3 modification only occurred at the target C and not any other Cs within the editing window (FIG. 28C). Specifically, of the ten clones that had homozygous edits at the target C at all three sites, two clones were free from bystander edits at both sites 2 and 3 (clones 1 and 2) and five clones were free from bystander edits at site 3 only (clones 3-7). However, it should be noted that we did not identify any clones in which at genomic site 1 such exclusive modification of the target C occurred. We speculate that because another C occurs immediately adjacent to this target C, that such exclusive modification is likely a rare event that will require site-specific base editors that allow for single-nucleotide changes free from bystander editing at adjacent nucleotides.

Discussion

In summary, we establish that BIG-TREE is a fast and efficient protocol for the generation of clonal isogenic hPSC lines with homozygous and heterozygous single base pair edits. Because the number of diseases that are a consequence of single point mutations, as well as the growing number of genomic variants of uncertain significance that have been identified through large-scale sequencing efforts, the ability to rapidly engineer isogenic hPSC lines will have a significant impact on the establishment of in vitro models to assess pathogenic risk and dissect disease-causing mechanisms. In addition, in this example, we demonstrate that BIG-TREE can be employed to generate effective loss-of-function cell lines through the introduction of premature stop codons. Currently, most CRISPR/Cas9-based approaches to generate gene knockouts involve the introduction of deleterious DSBs followed by NHEJ-mediated repair that results in frameshift and loss of gene function. As we describe in this example, the ability to rapidly generate gene knockouts without the need for DSBs will have important implications for the use of hPSCs to elucidate the function of specific genes in development and disease. Lastly, we establish that BIG-TREE can allow for the generation of clonal hPSC lines that have been simultaneously edited at multiple independent loci, an important consideration given that many diseases are polygenetic in nature. By comparison, conventional CRISPR/Cas9-based approaches are too inefficient in hPSCs to employ multiplexing editing strategies.

Since the first base editors were engineered, numerous additional base editors with targeting windows, editing efficiencies, PAM specificities, and deaminases have been generated. In the context of BIG-TREE, we employed AncBE4max, which displays a relatively high editing efficiency with low off-target activity. However, one of the limitations of AncBE4max is that it can induce C-to-T conversions at bystander Cs within the editing window. Although bystander editing was a common occurrence in our clonal populations, we did observe clones with exclusive modifications of the target C. More specifically, when generating isogenic lines edited at the APOE(R158) locus, we only isolated one clone that had a monoallelic edit exclusively at the target C. Nonetheless, all of the bystander edits that we observed at the APOE(R158) locus did not impact the amino acid sequence, mitigating the impact on the downstream application of these hPSC lines. With regard to the multiplex editing, we did observe several clones that were free from bystander edits at genomic sites 2 and 3. However, at genomic site 1, where a C is present in the base pair position directly next to the target C, we did not isolate any clones where modification only occurred at the target C. In the future, given the ease of use, we anticipate that utilizing BIG-TREE with these other base editor variants with a narrow editing window will be easily achieved. In this regard, the end-user can select to employ such base editors with a more stringent editing window if editing at a bystander C is not tolerable (e.g., results in changes in the amino acid coding sequence).

In general, there are several enabling aspects to the methods presented in the example that will allow for the facile adoption by a broad set of researchers. First, the high editing frequencies do not require the screening of large numbers of clones to identify those with the desired modification. Moreover, we demonstrate that BIG-TREE is robust, as it allows for the efficient editing of multiple loci and across several independent hPSC lines. Because of these efficiencies, clonal lines can be identified, expanded, and characterized in the course of a few weeks. Along similar lines, the high efficiency of BIG-TREE allows for the biallelic or multiplexed targeting without the need for sequential re-targeting. In addition, BIG-TREE is compatible with off-the-shelf chemical transfection reagents and does not require the cloning of complex viral constructs or the use of specialized cell transfection systems. In fact, all sgRNA vectors were designed to allow for the facile cloning of new target sites via BbsI restriction enzyme digestion and ligation of oligonucleotides that target the desired genomic sequence. Lastly, BIG-TREE offers the flexibility to be used in conjunction with other base editor variants that have altered PAM specificities and editing windows. For instance, the PAM sequence and edit distance can be modified to match the editing specificity and window of the new base editor. Such modifications are straightforward to achieve with the BFP vector using TREE, or the stop codon between RFP and GFP using BIG-TREE. In this manner, BIG-TREE is a readily adoptable method that will enhance and accelerate the use of base-editing approaches in hPSCs.

Supplemental Experimental Procedures

Human iPSC and HEK293 culture. HPSCs were maintained in mTeSR1 medium (Stemcell Technologies) on feeder-free Matrigel (Corning)-coated plates. Subculture was performed every 3 days using Accutase (Life Technologies) in mTeSR1 medium supplemented with 5 µM Y-27632 (Tocris). Control and AD-patient hPSCs were generated from dermal fibroblasts as previously described (Park et al., 2008).

TABLE 3

HPSC lines described in the example

| Cell Line | Disease Status | MMSE | Mutation |
| --- | --- | --- | --- |
| hPSC Line 1 | Non-demented control | 30 | n/a |
| hPSC Line 2 | Familial AD | n/a | APP V7171 |
| hPSC Line 3 | Familial AD | n/a | PSEN1 A246E | mCherry expressing HEK293 line was generated using lentiviral integration of a constitutively expressing mCherry transgene as previously described (Standage-Beier et al., 2019). HEK293 cells were cultured on poly-L-ornithine (4 µg/mL; Sigma Aldrich, St. Louis MO, USA) coated plates in the following media: 1× high glucose DMEM, 10% (v/v) fetal bovine serum, 1% (v/v) L-glutamine penicillin/streptomycin. Culture medium was changed every other day and cells were passaged with Accutase every 5 days.

Plasmid construction. Unless otherwise noted, for all molecular cloning PCRs were performed using Phusion High-Fidelity DNA polymerase (New England Biolabs, Ipswich, MA, USA) using the manufacturer's recommended protocols. All restriction enzyme (New England Biolabs) digests were performed according to the manufacturer's instructions. Ligation reactions were performed with T4 DNA ligase (New England Biolabs) according to the manufacturer's instructions. PCR primers and oligonucleotides were synthesized by Integrated DNA Technologies (Coralville, IA, USA). All PCR products and intermediate plasmid products were confirmed via Sanger sequencing (DNASU Sequencing Core Facility). Complete plasmid sequences will be made available upon request.

For construction of the pEF-BFP plasmid, we utilized PCR to add the H-66 and PAM site mutations into a GFP cassette (Addgene #11154). PCR products containing these mutations were digested with SapI/EcoRI and SapI/NotI and ligated into an EcoRI/NotI digested EF1α expression vector (Addgene #11154).

For construction of the pDT-sgRNA vector, sgRNAs were synthesized as pairs of oligonucleotides (Table 12). Subsequently, 5' phosphates were added to each oligonucleotide pair by incubating 1 µg oligo nucleotide in 50 µL reactions containing 1× T4 DNA Ligase Buffer (New England Biolabs) and 10 units of T4 Polynucleotide Kinase at 37° C. overnight. Oligonucleotides were then duplexed by heating the kinase reactions to 90° C. on an aluminum heating block for 5 minutes followed by slowly returning the reaction to room temperature over 1 hour. Following duplexing, guides were cloned into a modified pSB1C3 vector containing a U6 promoter, inverted BbsI restriction enzyme digestion sites, and an S. pyogenes sgRNA hairpin. For construction of pMT-sgRNA, pairs of sgRNAs (Table 12) were PCR amplified with primers adding EcoRI/SapI restriction enzyme digestion sites or SapI/XbaI restriction enzyme digestion sites. Purified PCR products were then digested with the respective restriction enzymes and ligated into EcoRI/XbaI digested pUC19 vector (Addgene #50005). The resultant vector contained pairs of sgRNA expression cassettes. To add additional sgRNA expression cassettes, pairs of sgRNAs were PCR amplified with primers that add HindIII/SapI or SapI/HindIII restriction enzyme digestion sites. These products were then digested with HindIII/SapI and ligated into HindIII digested and dephosphorylated pDT-sgRNA vector.

For insertion of the EF1α promoter into pCMV-AncBE4max (Addgene #112094), EF1α was PCR amplified from an EF1α expression vector (Addgene #11154) adding SpeI/NotI restriction enzyme digestion sites. After purification and digestion, these PCR products were ligated into SpeI/NotI digested and dephosphorylated pCMV-AncBE4max vector.

hPSC base editing and clonal isolation. hPSCs were passaged onto Matrigel-coated 12-well plates with 5 µM Y-27632. Media was changed, and transfection were performed 24 hours after passage. 900 ng base editor (pEF1α-AncBE4max), 300 ng sgRNA, and 300 ng pEF1α-BFP was transfected per well using 4 µL Lipofectamine Stem transfection reagent (Life Technologies). Media was changed 24 hours post-transfection. Cells were dissociated using Accutase 48 hours post-transfection and passed through a 0.45 µm filter. Single GFP-positive hPSCs were FACS sorted into 96-well Matrigel coated plates in mTeSR1 supplemented with CloneR (Stemcell Technologies), plates were immediately centrifuged at 100*g for 1 minute and incubated at 37° C. Media was changed 48 hours post-sort with fresh mTeSR1 supplemented with CloneR. 96 hours post-sort, media was changed to mTeSR1 without supplement and clonal hPSC colonies were expanded with fresh media changes daily until ready for subculture.

Genotyping and Sequence Analysis.

Clones were amplified with the primers listed in Table 13 to determine genotype following base editing. Genomic DNA was prepared from expanded clones using the DNeasy kit (Qiagen) and PCR products were generated with Phusion High-Fidelity Polymerase (New England Biolabs). Amplicons were purified using the QIAquick PCR purification kit (Qiagen) according to manufacturer's instructions prior to Sanger sequencing (Genewiz). For multiplex clones, hPSCs were directly added to a 50 µL master mix consisting of 1× Phire Hot Start II DNA Polymerase (ThermoFisher), 1 µM forward primer, and 1 µM reverse primer. PCR was performed using the following conditions: 98° C. for 5 minutes, followed by 40 cycles at 99° C. for 5 seconds, 56° C. for 5 seconds, and 72° C. for 20 seconds, followed by a final 5 min 72° C. extension. All products sizes were confirmed on a 1% agarose gel prior to Sanger sequencing.

HEK293 transfections. HEK293 cells stably expressing mCherry were transfected in 24 well tissue culture plates at 40% confluence with the following reagents per well: 300 ng pEF1α-AncBE4max, 100 ng sgRNA vector or sg(NT), 0.75 uL Lipofectamine 3000 Transfection Reagent (ThermoFisher), and 1 uL P3000 reagent (Thermo Fisher). Flow cytometry was performed at 7 days post-transfection to evaluate loss of mCherry expression. Genomic DNA was isolated and mCherry was PCR amplified before Sanger sequencing to determine editing efficiency.

Immunofluorescence. Cultures were gently washed twice with PBS prior to fixation. Cultures were then fixed for 15 min at room temperature (RT) with BD Cytofix Fixation Buffer (BD Biosciences). The cultures were then washed twice with PBS and permeabilized with BD Phosflow Perm Buffer III (BD Biosciences) for 30 min at 40 C. Cultures were then washed twice with PBS. Primary antibodies were incubated overnight at 40 C and then washed twice with PBS at room temperature. Secondary antibodies were incubated at RT for 1 hr. Nucleic acids were stained for DNA with Hoechst 33342 (2 µg/mL; Life Technologies) for 10 min at RT and then washed twice with PBS. Antibodies used are as follows at the following concentrations: NANOG (ThermoFisher Scientific; Cat #PA1-097, RRID:AB_2539867; 1:500), OCT4 (ThermoFisher Scientific; Cat #PA5-27438, RRID:AB_2544914; 1:500), SOX2 (ThermoFisher Scientific; Cat #PA1-094, RRID: AB_2539862; 1:500), AFP (Santa Cruz Biotechnology; Cat #sc-15375, RRID:AB_2223935; 1:50), SMA (Santa Cruz Biotechnology; Cat #sc-53015, RRID:AB_628683; 1:50), TUJ1 (Fitzgerald; Cat #10R-T136A, RRID:AB_1289248; 1:1000), Alexa 488 donkey anti-mouse (ThermoFisher Scientific; Cat #A-21206, RRID:AB_2535792; 1:500), and Alexa 488 donkey anti-rabbit (ThermoFisher Scientific; Cat #A-21202, RRID:AB_141607; 1:500).

Tri-lineage differentiation of edited hPSCs. HPSCs were harvested using Accutase and plated on ultra-low attachment plates in mTeSR1 medium. The following day, media was changed to differentiation medium (DM; DMEM/F12, 20% FBS, 1% Pen/Strep). After 5 days, embryoid bodies were plated on Matrigel-coated plates and cultured with DM. After 21 days in DM, cells were fixed, permeabilized, and stained for germ layer markers.

Fluorescence microscopy. All imaging was performed on a Nikon Ti-Eclipse inverted microscope with an LED-based Lumencor SOLA SE Light Engine using a Semrock band pass filter. GFP was visualized with an excitation at 472 nm and emission at 520 nm. BFP was visualized with the DAPI fluorescence channel with excitation at 395 nm and emission at 460 nm. mCherry was visualized with an excitation of 562 nm and emission at 641/75 nm.

Flow cytometry. Cells were dissociated with Accutase for 10 min at 37° C., triturated, and passed through a 40 µm cell strainer. Cells were then washed twice with flow cytometry buffer (BD Biosciences) and resuspended at a maximum concentration of 5×106 cells per 100 µL. Flow cytometry analysis was performed on an Attune N×T (Thermo Fisher Scientific). Flow cytometry files were analyzed using with FlowJo (FlowJo LLC, Ashland, OR, USA).

Off-target analysis. For the data presented in FIG. 28, analysis was performed for the top three off-target loci for sg(BG) and sg(APOE-R158) predicted in silico via CCTop using default parameters for *S. pyogenes* Cas9 against human genome reference sequence hg38 (Stemmer et al., 2015). Determination of base editing at these off-target sites was performed in a similar manner to that at on-target sites. The PCR primers used to analyze these off-target sites are presented in Table 13.

Quantification of editing in mCherry expressing HEK293 cells. Sanger sequencing of PCRs from genomic DNA from mCherry HEK cells treated with or without base editor and sgRNA were analyzed using EditR (Kluesner et al., 2018). For forward sequencing reactions, the "sgRNA Sequence" was the same as the protospacer. For reverse sequencing reads, the "sgRNA Sequence" was the reverse complement of the protospacer. The 5' and 3' start are the corresponding nucleotide number (starting at 1 for the first nucleotide of the sequencing read) 100 bp upstream and downstream of the protospacer, respectively.

Apolipoprotein E (APOE) ELISA. Cells were seeded in a 6 well plate at a density of 3×105 cells per well. Media was changed every 24 hours. On day 3, 24-hour conditioned media was collected and ApoE levels in the medium were measured with the Human APOE (AD2) ELISA Kit (Thermo Scientific).

Statistical analysis. Unless otherwise noted, all data are displayed as mean f standard deviation (S.D).

SUPPLEMENTAL REFERENCES

Kluesner, M. G., Nedveck, D. A., Lahr, W. S., Garbe, J. R., Abrahante, J. E., Webber, B. R., and Moriarity, B. S. (2018). EditR: A Method to Quantify Base Editing from Sanger Sequencing. CRISPR J. 1, 239-250.

Park, I.-H., Arora, N., Huo, H., Maherali, N., Ahfeldt, T., Shimamura, A., Lensch, M. W., Cowan, C., Hochedlinger, K., and Daley, G. Q. (2008). Disease-specific induced pluripotent stem cells. Cell 134, 877-886.

Stemmer, M., Thumberger, T., Del Sol Keyer, M., Wittbrodt, J., and Mateo, J. L. (2015). CCTop: An Intuitive, Flexible and Reliable CRISPR/Cas9 Target Prediction Tool. PloS One 10, e0124633.

Example 3—CasMAs (XMAS)-TREE: A Cas9-Mediated Adenosine Transient Reporter for Editing Enrichment Adenine base editors (ABE) enable single nucleotide modifications without the need for harmful double stranded DNA breaks (DSBs) induced by conventional CRIPSR/Cas9-based approaches. However, most approaches that employ ABEs require inefficient downstream technologies to identify targeted cell populations. This example demonstrates development and characterization of a fluorescence-based method, entitled Cas9-mediated adenosine transient reporter for editing enrichment (CasMAs-TREE; herein abbreviated XMAS-TREE), to facilitate the real-time identification of base-edited cell populations. In particular, this section demonstrates use of XMAS-TREE to detect ABE activity. These studies also demonstrate that, at several independent loci, XMAS-TREE can be used to rapidly identify and purify modified cell populations. In addition, this section demonstrates that XMAS-TREE can be used in concert with multiplex editing schemes to efficiently edit several independent loci. In addition, XMAS-TREE can be used to edit human pluripotent stem cells (hPSCs), a cell type refractory to traditional gene editing approaches. In particular, XMAS-TREE allows for the efficient generation of clonal isogenic hPSCs at loci not editable using typical reporter of transfection (RoT)-based enrichment techniques. Collectively, XMAS-TREE is an easily implemented method that will greatly facilitate the use of ABEs in downstream basic biomedical science and translational applications.

Results

Development of a Fluorescent Reporter for Cas9-Mediated Adenosine Base Editing

Figures 13A, 13B, 13C, 13D, 13E:
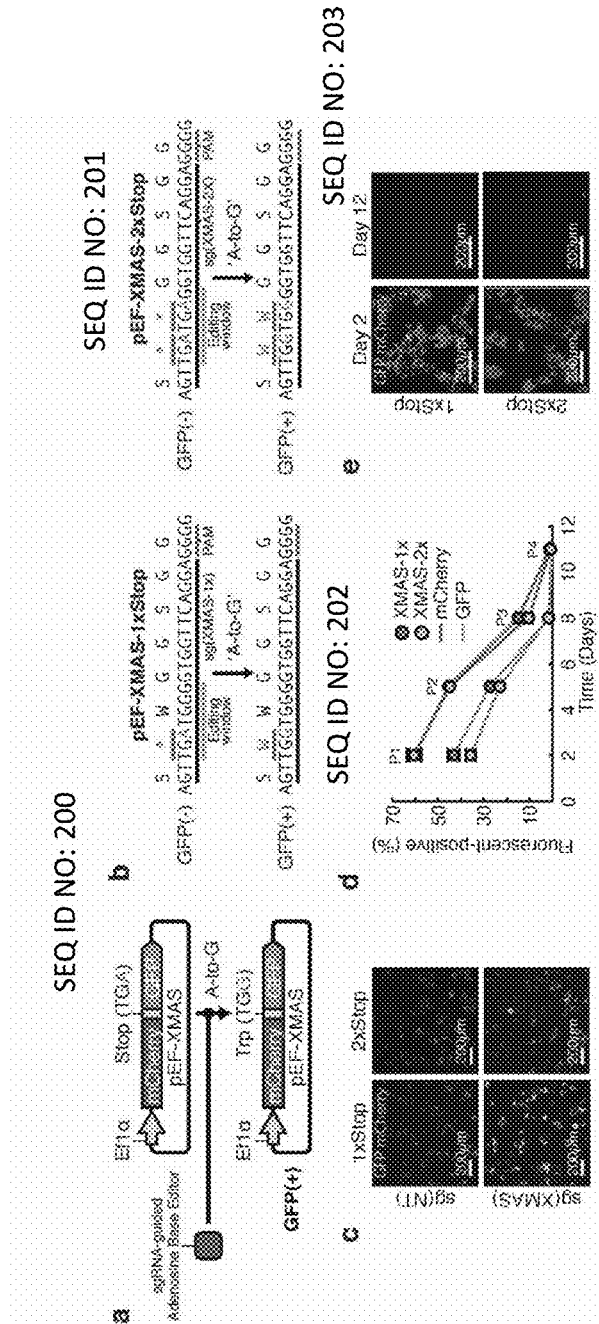
FIGS. 13A-13E illustrate a fluorescent reporter system for real-time measurement of adenosine base editing activity. (a) The XMAS-TREE reporter vector consists of a human EF1α promoter driving expression of an mCherry cassette followed by a stop codon (TGA) then a GFP cassette. Targeting pEF-XMAS with an adenine base editor and sg(XMAS) will result in an A-to-G conversion, enabling expression of the downstream GFP reporter. (b) Two versions of pEF-XMAS-TREE plasmid were designed, one with a single stop codon (XMAS-1×Stop) and another with two stop codons (XMAS-2×Stop), preceding the coding sequence for GFP. The protospacer sequence (underlined black) for the sgRNA, sg(XMAS), targeting the TGA codon (underlined red) resulting in an A-to-G conversion to TGG and the corresponding amino acid change to tryptophan. The PAM sequence (underlined red) was placed to position the base editing window (underlined orange) around the target nucleotides.

As we have previously shown with cytosine base editors (CBEs), conventional approaches that use reporters of transfection, such as co-transfection or co-expression with a fluorescent protein (herein abbreviated as RoT) only report on the efficiency of plasmid delivery to a cell but not directly on the efficiency of base editing within these cells. To determine if the same was true with adenosine base editing approaches, HEK293 cells were transfected with a reporter plasmid (mCherry), an adenine base editor (ABEmax; pCMV-ABEmax), and a sgRNA for a genomic target site [sg(TS)]. This analysis revealed no correlation between transfection efficiency (percentage of mCherry-positive cells) and editing efficiency (percentage of A-to-G conversion at target nucleotide) (FIG. 32). To that end, we sought to leverage our experience developing fluorescent reporters of editing activity to enable XMAS-TREE. To establish a fluorescent assay to detect ABE activity within a cell, we engineered a construct encoding a mCherry fluorescent protein followed by a stop codon (TGA) immediately preceding the coding sequence for a green fluorescent protein (GFP). Consequently, the A-to-G conversion of that codon to 'TGG' (encoding tryptophan) will enable translational read-through and expression of GFP. To determine the utility of this fluorescent-based construct to report on ABE activity, a vector was assembled with a human EF1α promoter to drive expression of the fluorescent reporters (pEF-XMAS; FIG. 13A). In addition, we engineered two versions of this vector, one with a single stop codon (pEF-XMAS-1×Stop) and another with two stop codons (pEF-XMAS-2×Stop; FIG. 13B). It was speculated that A-to-G conversion of two stop codons within the editing window would provide a higher degree of stringency with respect to reporting on base editing activity within a cell. In addition, we designed a sgRNA vector [sg(XMAS)] that would direct the ABE to the target 'TGA' resulting in an A-to-G conversion and allow for subsequent translation of the downstream GFP cassette. Next, HEK293 cells were co-transfected with pEF-XMAS, pCMV-ABEmax, and sg(XMAS) or a control non-targeting sgRNA [sg(NT)]. Fluorescence microscopy (FIG. 13C) and flow cytometry (FIG. 13D) revealed that targeting pEF-XMAS with sg(XMAS) resulted in the generation of mCherry/GFP double positive cells, suggesting A-to-G base editing in the target codons allowing for GFP expression. Conversely, targeting pEF-XMAS-1×Stop or pEF-XMAS-2×Stop with sg(NT) did not result in the generation of any GFP positive cells (FIG. 33). Despite similarities in transfection efficiency between pEF-XMAS-1×Stop and pEFX-MAS-2×Stop (as measured by percentage of mCherry-positive cells), the percentage of GFP-positive cells was significantly lower in sg(XMAS) targeted cells transfected with pEF-XMAS-2×Stop, suggesting that a higher level of base editing activity was necessary for the activation of GFP expression with the 2×Stop plasmid. Interestingly, a significant percentage of cells that were mCherry-positive were not GFP-positive, verifying that the reporter of transfection (mCherry) does not report on base editing activity within a cell (FIG. 13D). Finally, we wanted to demonstrate that the fluorescent output associated with the XMAS-TREE reporter was transient. As such, the long-term fluorescence of cells transfected with pEF-XMAS and targeted with sg(XMAS) was measured. Indeed, analysis of these cells by flow cytometry (FIG. 13D) and fluorescence microscopy (FIG. 13E) revealed no long-term detectable fluorescent signal, confirming that the XMAS-TREE fluorescent output was transient. Collectively, this data establishes that editing of the XMAS-TREE plasmid provides a transient fluorescent reporter for base editing activity within a cell.

Figures 14A, 14B:
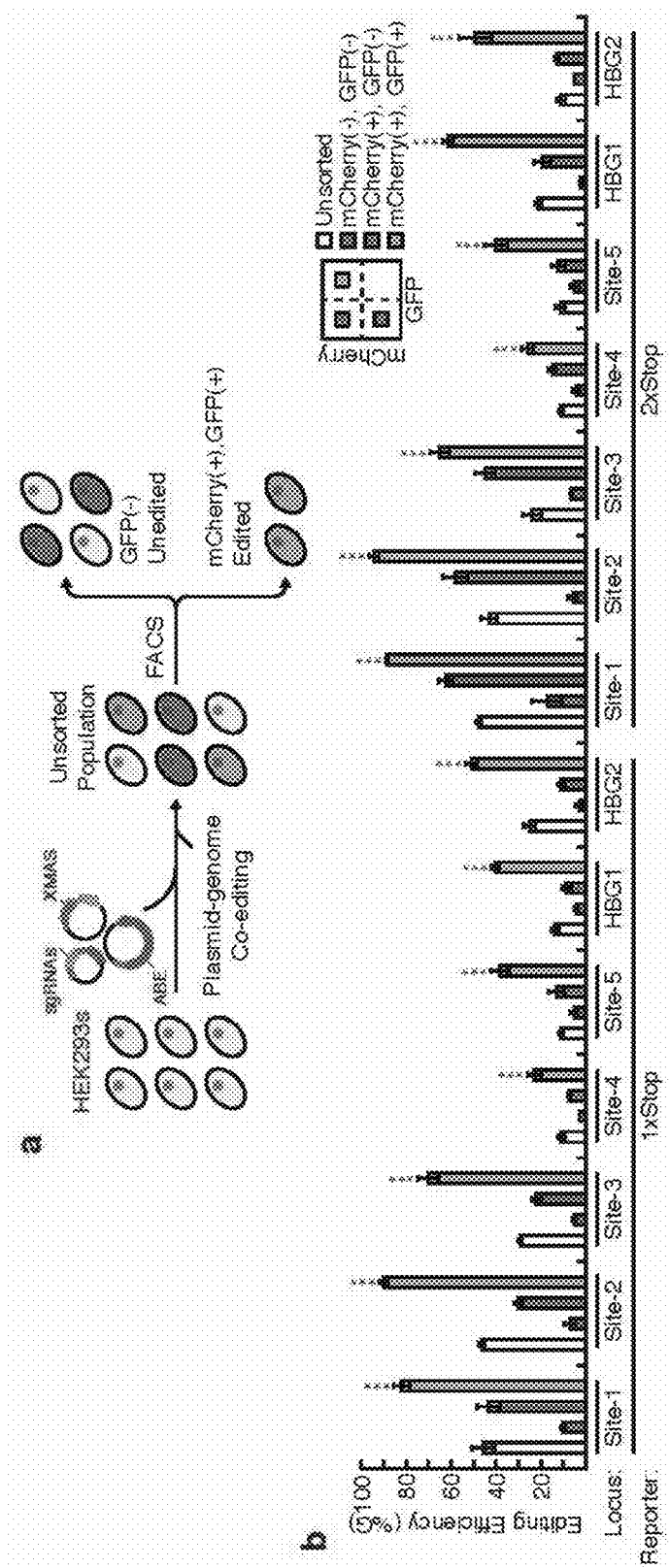
FIGS. 14A-14B demonstrate identification and enrichment of base-edited cell populations using XMAS-TREE. (a) Schematic for identification and enrichment of adenosine base edited cells using XMAS-TREE. Cells are transfected with pEF-XMAS, pCMV-ABEmax, and pST-sgRNA vectors. Posttransfection, flow cytometry is used to sort cell populations into reporter-positive and -negative populations based upon mCherry and GFP expression levels. (b) Quantification of base editing efficiency at various genomic loci in unsorted (white bar), mCherry-negative/GFP-negative (grey bar), mCherry-positive/GFP-negative (red bar), and mCherry-positive/GFP-positive (orange bar) isolated cells using XMAS-TREE-based methods. Statistical comparisons were made between cells positive for the transfection reporter but not the editing reporter (i.e. mCherry-positive/GFP-negative) and cells positive for both (i.e. mCherry-positive/GFP-positive); *=$p<0.05$, =$p<0.01$, *=$p<0.001$.

XMAS-TREE Allows for the Identification and Isolation of Base-Edited Cell Populations Next, we wanted to demonstrate the utility of XMAS-TREE for the identification and isolation of cells in which targeted genomic adenosine base editing had occurred. To facilitate this, a dual-targeting sgRNA (pDT-sgRNA) vector that contains both sg(XMAS) and a guide matching an endogenous target site, sg(TS) was designed. Additionally, the pDT-sgRNA vector was designed to allow for the straightforward cloning of new target sites via BbsI restriction enzyme digestion and ligation of sg(TS) oligonucleotides. We designed pDT-sgRNA vectors with sequences targeting five genomic loci (Sites 1-5) as well as the promoter of the γ-globin genes HBG1 and HBG2. To utilize XMAS-TREE for enrichment of cells that have been edited at a specific genomic location, we co-transfected these pDT-sgRNA vectors with pEF-XMAS-1×Stop or 2×Stop and pCMV-ABE into HEK293 cells (FIG. 14A). Flow cytometry was then used to isolate reporter positive cell populations and Sanger sequencing was performed on the targeted genomic sites in isolated populations (FIG. 14A). As expected, mCherry-positive/GFP-positive cells were enriched for edited cells when compared to double-negative cell populations (FIG. 14B). Importantly the transfection marker mCherry-positive population had significantly reduced editing compared to the editing reporter positive GFP-positive population. This demonstrates the benefit of utilizing a real-time reporter of base editing. (FIG. 14B). Finally, comparison of mCherry-positive/GFP-positive cells isolated using the 2×Stop versus the 1×Stop vector revealed that use of the 2×Stop vector led to increased editing efficiencies, especially at loci (i.e., HBG1, HBG2) that were more resistant to editing. This suggests that at more difficult to edit loci, the 2×Stop plasmid might provide a higher level of stringency necessary to enrich for edited cell populations. Overall, these results confirm that XMAS-TREE could be used to identify and enrich for adenosine base edited cell populations at a variety of genomic target sites.

XMAS-TREE Enables Efficient Multiplex Base Editing at Genomic Loci

Figures 15A, 15B, 15C:
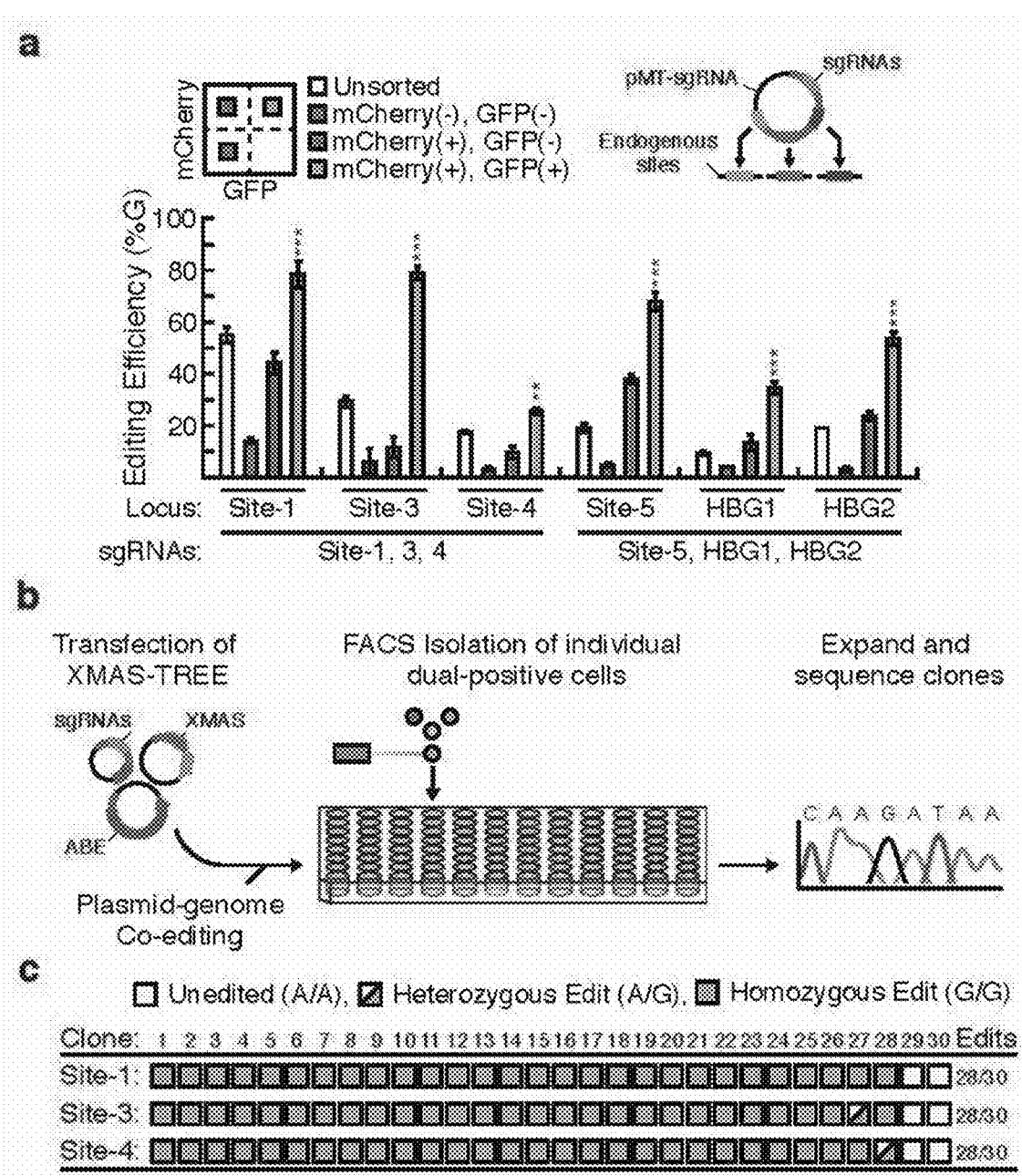
FIGS. 15A-15C demonstrate that XMAS-TREE enables highly efficient multiplex adenosine base editing. (a) Cells were transfected with pEF-XMAS, pCMV-ABEmax, and a pMT-sgRNA that simultaneously targeted Site-1/Site-3/Site-4 or Site-5/HBG1/HBG2. Base editing was quantified in unsorted as well as reporter-positive and -negative cell populations. Statistical comparisons were made between cells positive for the transfection reporter but not the editing reporter (i.e. mCherry-positive/GFP-negative) and cells positive for both (i.e., mCherry-positive/GFP-positive); *=$p<0.05$, =$p<0.01$, *=$p<0.001$. (b) Schematic for employing XMAS-TREE for generation of clonal lines that have been simultaneously edited at multiple loci. HEK293 cells are co-transfected with pEF-XMAS, pCMV-ABEmax, and pMT-sgRNA. At 48 hours post-transfection, single mCherry-positive/GFP-positive cells are sorted into 96-well plates. After expansion, target sites are identified by Sanger sequencing at the target sites. (c) Analysis of clonal editing efficiency at multiple independent genomic sites using XMAS-TREE. A total of 30 clones were examined at each locus. White box indicates no editing observed a specified locus, half-filled box indicates mono-allelic targeting at the genomic site, and full box indicates bi-allelic editing at the target locus.

XMAS-TREE was further evaluated to determine if it could be used for multiplexed genome editing. To that end, we generated a multi-targeting vector (pMT-sgRNA) that contains sg(TREE) as well as sgRNAs for multiple genomic targets. More specifically, we generated two pMT-sgRNA vectors—one that would target Site-1/Site-3/Site-4 and another that would simultaneously edit Site-5/HBG1/HBG2. We employed XMAS-TREE to simultaneously target multiple genomic sites by co-transfecting HEK293 cells with pMT-sgRNA, pEF-XMAS, and pCMV-ABEmax. Reporter-positive and -negative cells were isolated by flow cytometry and analyzed by Sanger sequencing at the targeted loci. Consistent with single locus targeting, mCherry-positive/GFP-positive cells displayed a significantly higher frequency of base editing at the target sites than editing levels that were observed in unsorted, mCherry-negative/GFP-negative, and mCherry-positive/GFP-negative cell populations (FIG. 15A). Importantly, there was no significant reduction in editing efficiency when XMAS-TREE was used to target these sites individually or a multiplexed fashion (FIG. 34).

Initial analysis of bulk sorted mCherry-positive/GFP-positive cells suggested that multiplexed editing with XMAS-TREE resulted in a large percentage of cells that had been simultaneously edited at multiple loci. To verify this observation, XMAS-TREE was used for the clonal isolation of base edited populations (FIG. 15B). Briefly, we co-transfected HEK293 cells with pEF-XMAS, pCMV-ABEmax, and a pMT-sgRNA designed to simultaneously target genomic Site-1/Site-3/Site-4. Single GFP-positive cells were sorted into a 96-well plate and expanded prior to analysis. Genomic DNA was isolated from clonal populations and the multiplexed genomic sites were subject to Sanger sequencing after PCR amplification. Remarkably, this analysis revealed that greater than 90% of the clones isolated had been edited, with 26 out of the 30 clones having biallelic conversions at all three genomic loci (FIG. 15C). In addition, we did not observe indels in any of the clones at these target sites. Lastly, we wanted to determine if XMAS-TREE increased A-to-G conversion at off-target loci. Therefore, in several clones that had biallelic edits at all three target sites, we performed off-target analysis at the top predicted sites for sg(XMAS) as well as the sgRNAs used to target Site-1/Site-3/Site-4. At all of the off-target sites analyzed, we did not observe substantial A-to-G edits at these off-target loci (FIG. 35). In addition, indels were not observed at any of the off-target sites in the clones analyzed. Collectively, these results demonstrate the broad utility of XMAS-TREE to allow for the highly efficient, simultaneous editing of multiple independent loci.

Highly Efficient Editing of Human Pluripotent Stem Cells (hPSCs) Using XMAS-TREE Traditional CRISPR-based approaches to modify single base pairs in hPSCs suffer from extremely low efficiencies. Therefore, we wanted to determine if XMAS-TREE could be utilized to efficiently mediate A-to-G conversions at specific loci in hPSCs. To confirm that the XMAS reporter was functioning in hPSCs, we transfected hPSCs with pEF-XMAS1×Stop/2×Stop, pEF-ABEmax, and sg(XMAS) or sg(NT). Similar to our experiments with HEK293 cells, fluorescence microscopy (FIG. 16A) and flow cytometry (FIG. 16B) with sg(XMAS), but not with sg(NT) (FIG. 36), resulted in the generation of mCherry-positive/GFP-positive cells, indicative of adenosine base editing of the pEF-XMAS reporter plasmid. Additionally, this analysis revealed that the proportion of cells that were positive for the base editing reporter (GFP) relative to the transfection reporter (mCherry) were markedly reduced in hPSCs, consistent with reports that hPSCs are recalcitrant to genomic modification. In this vein, these results suggest that purifying hPSC populations solely with a reporter of transfection (mCherry) would significantly dilute out cells with targeted genomic base edits. In addition, the level of base editing of the 2×Stop plasmid was significantly lower that than observed with the 1×Stop, suggesting that the 2×Stop plasmid provides a higher degree of stringency in identifying base edited populations in hPSCs. Finally, flow cytometry (FIG. 16B) and fluorescence analysis (FIG. 16C) demonstrated that there was no detectable mCherry or GFP signal after 2 weeks of culture, confirming that the fluorescent signal associated with the XMAS-TREE reporter was transient in hPSCs.

Figures 16A, 16B, 16C, 16D:
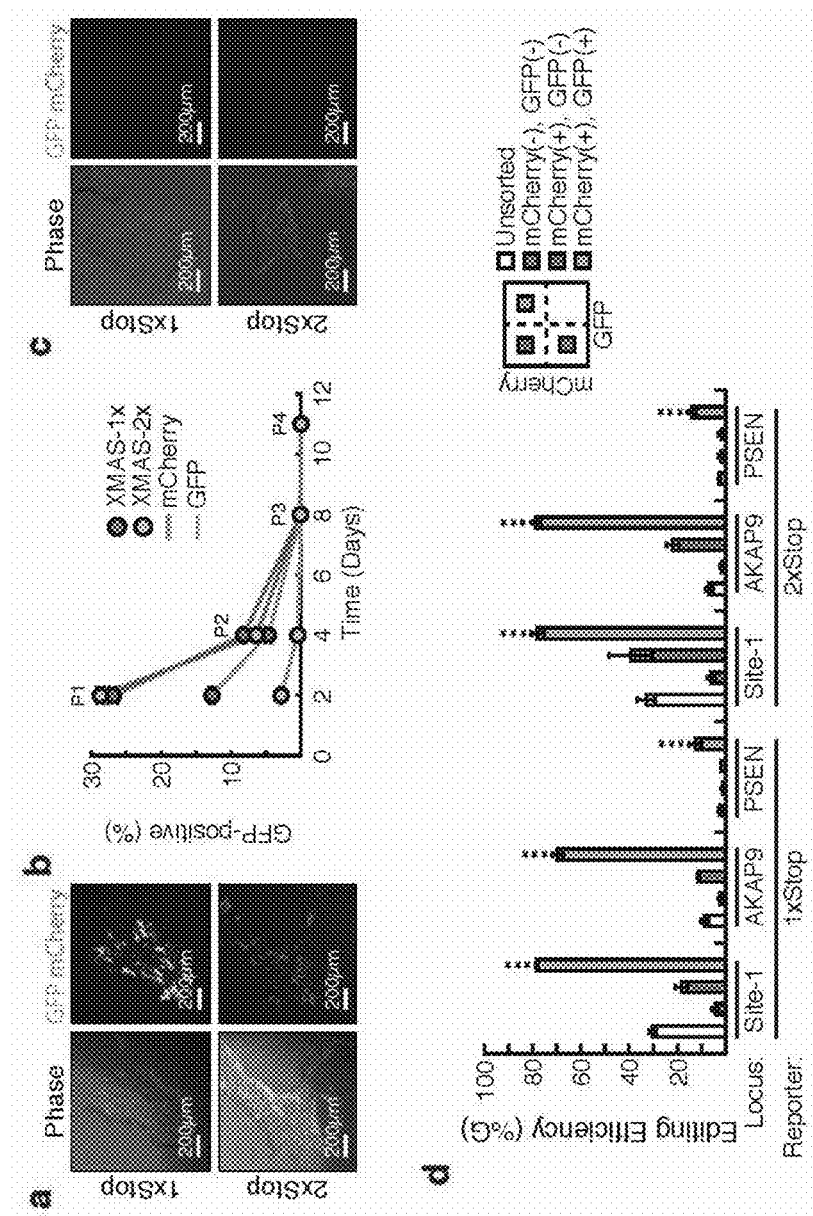
FIGS. 16A-16D demonstrate that XMAS-TREE can be employed for the highly efficient base editing of human pluripotent stem cells (hPSCs). (a) Representative fluorescence microscopy images of hPSCs transfected with pEF-XMAS-1×Stop (top panels) or pEF-XMAS-2×Stop (bottom panels), pEFABEmax, and sg(XMAS). (b) Flow cytometry and (c) fluorescence microscopy analysis of hPSCs at various time points after transfection with pEF-XMAS-1×Stop (top panels) or pEF-XMAS-2×Stop (bottom panels), pEF-ABEmax, and sg(XMAS). (d) Quantification of base editing efficiency at various genomic loci in unsorted (white bar), mCherry-negative/GFP-negative (grey bar), mCherry-positive/GFP-negative (red bar), and mCherry-positive/GFP-positive (orange bar) isolated hPSCs using XMAS-TREE-based methods. Statistical comparisons were made between hPSCs positive for the transfection reporter but not the editing reporter (i.e., mCherry-positive/GFP-negative) and cells positive for both (i.e. mCherry-positive/GFP-positive); *=$p<0.05$, =$p<0.01$, *=$p<0.001$.

Since we established pEF-XMAS reports on functional base editing in hPSCs, we wanted to determine if XMAS-TREE could be employed to enrich for cells with single-base pair edits at target loci in hPSCs. In this regard, we co-transfected hPSCs with pEF-XMAS1×Stop/2×Stop and pEF-ABEmax along with a pDT-sgRNA targeting genomic Site-1 or single base pair changes in AKAP9 and PSEN1 that have been previously associated with increased risks of developing Alzheimer's disease (AD). In turn, flow cytometry was used to purify reporter-positive and -negative cell populations and Sanger sequencing was performed on the targeted genomic locations in isolated populations. This analysis demonstrated that mCherry-positive/GFP-positive cells displayed a statistically significant increase in editing efficiency at the target loci when compared to other populations analyzed (FIG. 16D). In fact, in the more difficult to edit loci, AKAP9 and PSEN1, editing was virtually absent in populations not positive for our base editing reporter (GFP). Furthermore, mCherry-positive/GFP-positive cells isolated using the 2×Stop plasmid allowed for greater level of enrichment. Together, these results demonstrated that XMAS-TREE can been used for the isolation of base-edited hPSC populations.

XMAS-TREE Enables Highly Efficient Generation of Clonal Isogenic hPSC Lines

Figures 17A, 17B, 17C:
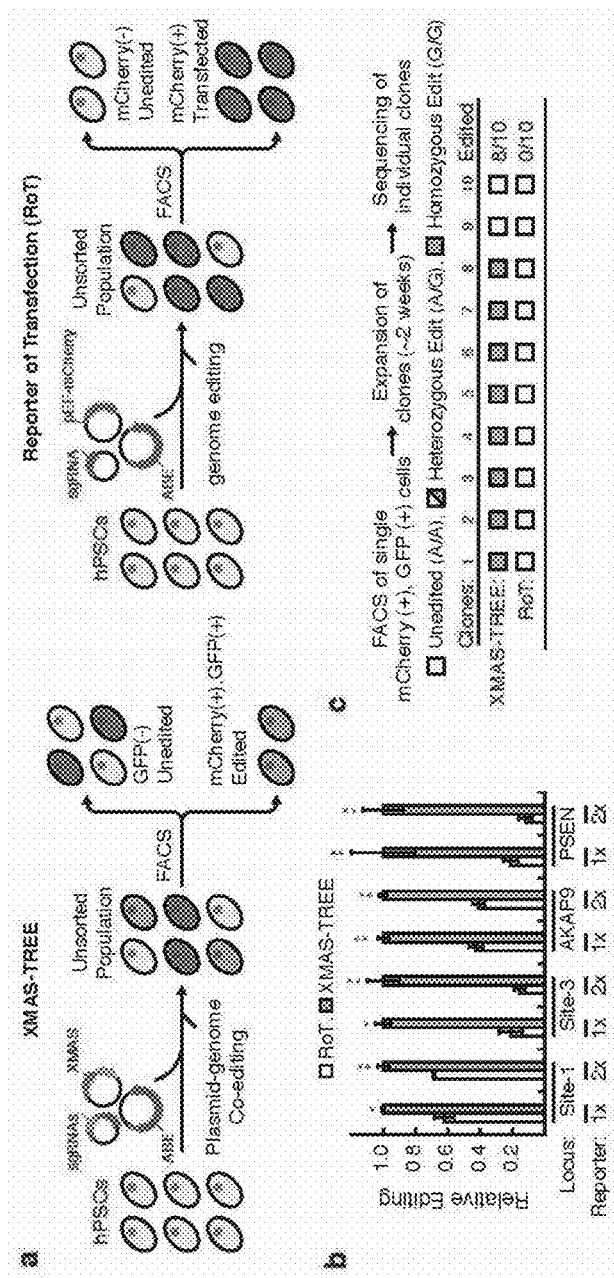
FIGS. 17A-17C demonstrate highly efficient generation of clonal isogenic hPSC lines using XMAS-TREE. (a) Schematic for enrichment of adenosine base-edited cells using XMAS-TREE and reporter of transfection (RoT) based approaches. (b) Quantification of relative base editing in mCherry-positive cells isolated using RoT and mCherry-positive/GFP-positive cells isolated using XMASTREE. *=$p<0.05$, =$p<0.01$, *=$p<0.001$ (c) Analysis of clonal editing efficiency in hPSCs that were targeted at the Site-3 locus using XMAS-TREE- or RoT-based methods.

We next wanted to compare the editing efficiency enabled by XMAS-TREE compared to conventional reporters of transfection (RoT). Accordingly, we co-transfected hPSCs with a reporter plasmid (pEF-mCherry), an adenine base editor (pEF-ABEmax), and a sgRNA for various genomic target sites [sg(TS)] (FIG. 17A). Flow cytometry was then used to sort mCherry-positive cell populations (RoT) and Sanger sequencing was performed on the targeted genomic sites. This analysis revealed that across all targeted sites that mCherry-positive/GFP-positive cells isolated using XMAS-TREE had a significantly higher frequency of base editing than mCherry-positive cells isolated using traditional RoT approaches (FIG. 17B). In fact, several targeted loci (i.e. Site-3, PSEN) displayed undetectable levels of editing when traditional RoT approaches were applied (FIG. 37). We then wanted to directly compare the efficiency by which XMAS-TREE and RoT-based methods could be utilized to generate clonal isogenic lines modified at these difficult to edit sites. To this end, we transfected hPSCs with pEF-XMAS, pEF-ABEmax, and pDT-sgRNA containing a sgRNA to target genomic Site-3. Single mCherry-positive/GFP-positive cells were sorted into 96-well plates, expanded, and subject to Sanger sequencing. Of the 10 clones analyzed, 80% had a homozygous A-to-G edit at the genomic Site-3 locus (FIG. 17C). Importantly, indels were not identified in any of the clones at the target site. For comparison to a more conventional RoT approach to generate isogenic lines, this same hPSC line was transfected with a plasmid in which the base-editor (ABEmax) was co-transfected with a pEFmCherry vector as well as the same sgRNA for the Site-3 locus. After 48 hours post-transfection, single GFP-positive cells were sorted into 96-well plates. Clonal lines were then passaged, expanded, and subjected to Sanger sequencing at the targeted locus. Notably, analysis of 10 clonal lines revealed that this RoT-based approach did not result in generation of a single isogenic clone at the target site (FIG. 17C). This ability of XMAS-TREE to generate isogenic clonal lines at sites that did not display significant editing in bulk RoT approaches was also confirmed at the PSEN locus (FIG. 38). In sum, these results demonstrate that XMAS-TREE can not only provide for a higher level of enrichment of base-edited cell populations compared to RoT approaches, but also can allow for the generation of isogenic lines at genomic loci that are not achievable with conventional RoT methods.

Multiplex Editing of hPSCs Using XMAS-TREE

Figures 18A, 18B:
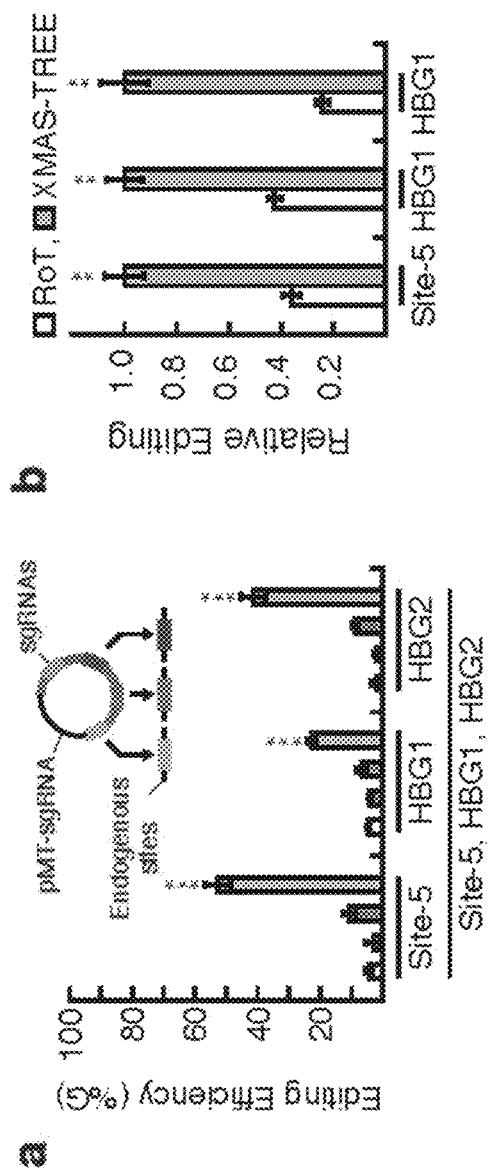
FIGS. 18A-18B demonstrate simultaneous adenosine base editing of multiple target sites in hPSCs using XMAS-TREE. (a) HPSCs were co-transfected with pEF-XMAS, pEF-ABEmax, and a pMT-sgRNA that simultaneously targeted Site-5/HBG1/HBG2. Flow cytometry was used to sort reporter-positive and -negative cell populations and base-editing was quantified at target loci. Statistical comparisons were made between cells positive for the transfection reporter but not the editing reporter (i.e., mCherry-positive/GFP-negative) and cells positive for both (i.e., mCherry-positive/GFP-positive); *=$p<0.05$, =$p<0.01$, *=$p<0.001$. (b) Quantification of relative base editing in mCherry-positive and mCherry-positive/GFP-positive cells isolated using RoT and XMAS-TREE, respectively.

Lastly, we wanted to establish that XMAS-TREE could allow for multiplexed genome modification in hPSCs. HPSCs were co-transfected with pEF-XMAS, pEF-ABEmax, and a pMT-sgRNA with sgRNAs targeting Site-5, HBG1, and HBG2. Similar to our results obtained with HEK293 cells, mCherry-positive/GFP-positive cells had a statistically significant higher level of base editing at all three target sites when compared to those in unsorted, mCherry-negative/GFP-negative, and mCherry-positive/GFP-negative cell populations (FIG. 18A). In addition, direct comparison of multiplex editing using XMAS-TREE and RoT approaches demonstrated that XMAS-TREE allowed for a statistically significant higher level of base editing than by RoT-based methods (FIG. 18B). Altogether, this data demonstrates that XMAS-TREE enables efficient simultaneous editing of multiple loci in hPSCs.

Discussion

Together, CBEs and ABEs have the potential ability to modify up to 60% of the disease-causing point mutations.

That said, BEs can be used in the context of cellular models of human disease models to establish genotype-to-phenotype relationship associated with genetic risk factors, investigate disease mechanisms, and test therapeutic strategies. In our previous work, we describe the development of a transient reporter for editing enrichment (TREE) as a fluorescence-based assay to report on cytosine base editing (CBE) activity within a single cell. In this work, we develop an analogous reporter system, Cas9-mediated adenosine transient reporter for editing enrichment (CasMAs-TREE; XMAS-TREE) that allows for the real-time detection of adenosine base editing for the identification and enrichment of base-edited cell populations. Notably, at several loci, XMAS-TREE allows for the targeted gene editing at efficiencies approaching 90%. As part of these efforts, we also utilized XMAS-TREE to enrich for cells that have been edited at several disease-relevant loci including those associated with sickle-cell anemia (i.e., HBG1, HBG2) and Alzheimer's disease (i.e., AKAP9, PSEN1). In addition, we demonstrate that XMAS-TREE can be used in the context of multiplex genome engineering strategies to facilitate simultaneous A-to-G (or T-to-C) conversions at several independent loci at the same efficiencies when single loci were targeted. Critically, the ability of XMAS-TREE to generate clonal lines that had been simultaneously edited at multiple loci will enable the facile generation of cell-based models of polygenetic diseases. Finally, we establish that the same XMAS-TREE-based methods can be applied in human pluripotent stem cells (hPSCs), a cell population in which gene editing technologies, including base editors and multiplex genome modification, have been challenging to implement. In particular, we show that XMAS-TREE can facilitate the establishment of isogenic hPSC lines at loci that were not able to be modified using well-accepted reporter of transfection (RoT) methods. In fact, we show that at certain target sites that XMAS-TREE can allow for derivation of isogenic clonal populations with biallelic modification with 80% efficiency. Notably, all targeted clones were free from indels at all on-target sites. The clonal targeting efficiencies that we observe with XMAS-TREE in hPSCs are significantly higher than those previously reported with other CRISPR/Cas9-based methods, which are often in the single digits at most loci. In addition, the inefficiencies associated with these well-established methods make it difficult to achieve homozygous or multiplexed editing in hPSCs.

We speculate that XMAS-TREE can be utilized in other applications not described in this example. For example, several groups have reported the generation of additional ABEs with non-NGG PAM specificities, narrower targeting windows, and reduced by-product formation 34-36. Accordingly, future application of XMAS-TREE with these next-generation ABE variants will be straightforward. In addition, we anticipate that XMAS-TREE can be applied to induce alterations in target gene expression. More specifically, we previously described how CBEs can be used with other TREE-based strategies to generate gene knockout lines without the introduction of DSBs through in-frame conversion of 'CAG' codon encoding for glutamine to a 'TAG' premature stop codon. However, these approaches do not allow targeting for all genes and can be limited by the propensity of CBEs to induce genome-wide Cas9-independent off-target mutations. As an alternative, Wang and colleagues recently described an ABE-mediated strategy to induce gene knockout through modification of the ATG start codon to ACG or GTG. Moving forward, XMAS-TREE can be utilized with such strategies to enrich for cell populations with targeted gene knockouts.

In summary, there are several features of XMAS-TREE based methods that will enable extensive use by the research community. First, XMAS-TREE only requires the use of common lipid-based reagents for cell transduction. We envision that XMAS-TREE is compatible with other DNA delivery systems (i.e., electroporation) or expression methods (i.e., ribonucleoprotein complexes [RNP]) that have been utilized in other CRISPR/Cas9- and BE-based genome engineering strategies. In the future, XMAS-TREE associated plasmids can also be easily cloned into nonintegrating viral vectors to facilitate the development of in vivo gene editing methods 2. Second, we have designed the sgRNA vectors to allow for the simple restriction enzyme-based cloning of new target sites. In this regard, we show that XMAS-TREE can allow for the highly efficient editing of a diverse set of loci across multiple cell lines. In the future, XMAS-TREE can be easily utilized in other animal, primary, or immortalized cell types. In addition, because of the high editing efficiencies associated with XMAS-TREE, establishment of clonal lines with the targeted base pair edit does not require the screening of hundreds of clones, which is typical of other methods. Finally, we demonstrate that the use of XMAS-1×Stop and -2×Stop plasmids allows the end-user to balance the need for cell yield versus editing stringency. Specifically, the XMAS-1×Stop plasmid provides for a higher degree of cell yield compared to the XMAS-2×Stop plasmid while allowing for enrichment of editing cells at levels higher than conventional approaches. Alternatively, the XMAS-2×Stop plasmid enables a higher degree enrichment at the target loci, especially at difficult to edit genomic locations. Collectively, these enabling features of XMAS-TREE will significantly enhance the use of ABE-based technologies in a variety of contexts and cell populations.

It should be noted that the above description, attached figures and their descriptions are intended to be illustrative and not limiting. Many themes and variations of this disclosure will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

TABLE 4

List of sgRNA sequences used in this example.

| Site | Sequence (5'→3') |
|---|---|
| Site-1 | GGCCCAGACTGAGCACGTGA (SEQ ID NO: 14) |
| Site-2 | GAACACAAAGCATAGACTGC (SEQ ID NO: 15) |

TABLE 4-continued

List of sgRNA sequences used in this example.

| Site | Sequence (5'→3') |
|---|---|
| Site-3 | GGCACTGCGGCTGGAGGTGG (SEQ ID NO: 16) |
| APOE(R158) | GAAGCGCCTGGCAGTGTACC (SEQ ID NO: 17) |
| BFP(H66Y) | GACCCACGGCGTGCAGTGCTT (SEQ ID NO: 18) |
| C1ORF228 | GTGCTGTTAGCACCCTGGAAA (SEQ ID NO: 19) |

TABLE 5

List of primers used in this example to amplify on-target sites.

| Primer | Forward Sequence (5'→3') | Reverse Sequence (5'→3') |
|---|---|---|
| Site-1 | ATGTGGGCTGCCTAGAAAGG (SEQ ID NO: 20) | CCCAGCCAAACTTGTCAACC (SEQ ID NO: 21) |
| Site-2 | CCAGCCCCATCTGTCAAACT (SEQ ID NO: 22) | TGAATGGATTCCTTGGAAACAATGA (SEQ ID NO: 23) |
| Site-3 | TGGTCTTCTTTCCCCTCCCCTGCCCTCC (SEQ ID NO: 24) | GGCCTGGAGGCGGGGGCTCAGAGA (SEQ ID NO: 25) |
| APOE(R158) | GGACGAGACCATGAAGGAGTTGAAGGC (SEQ ID NO: 26) | CCACCTGCTCCTTCACCTCGTCCAG (SEQ ID NO: 27) |

TABLE 6

Parameters for EditR analysis.

| Target Site | Sequencing Direction | Protospacer | 5' bound | 3' bound |
|---|---|---|---|---|
| Site 1 | Forward | GGCCCAGACTGAGCACGTGA (SEQ ID NO: 28) | GGCCTGGGTCAA (SEQ ID NO: 29) | TTCCTTTCCTCTG (SEQ ID NO: 30) |
| | Reverse | TCACGTGCTCAGTCTGGGCC (SEQ ID NO: 31) | GAGGAAAGGAAGCCCTGCT (SEQ ID NO: 32) | CAGGCCAGGGCTGGA (SEQ ID NO: 33) |
| Site-2 | Forward | GAACACAAAGCATAGACTGC (SEQ ID NO: 34) | CCCGCTGGCCCTGT (SEQ ID NO: 35) | TCAGGCTGGCCCGC (SEQ ID NO: 36) |
| | Reverse | GCAGTCTATGCTTTGTGTTC (SEQ ID NO: 37) | CCAGCCCGCTGGCCCTGTA (SEQ ID NO: 38) | AGCTATTCAGGCT (SEQ ID NO: 39) |
| Site 3 | Forward | GTGGCACTGCGGCTGGAGGT (SEQ ID NO: 40) | GATGACAGGCAGGGGCA (SEQ ID NO: 41) | CAGCACCAGA (SEQ ID NO: 42) |
| | Reverse | ACCTCCAGCCGCAGTGCC (SEQ ID NO: 43) | CCGCGGTGCCCCTGCCT (SEQ ID NO: 44) | AAGCGGAGACTCTGGTGC (SEQ ID NO: 45) |
| APOE(R158) | Forward | GAAGCGCCTGGCAGTGTACC (SEQ ID NO: 46) | CTGCGCAAGCTGCG (SEQ ID NO: 47) | TCGGCGCCCTCGCG (SEQ ID NO: 48) |
| | Reverse | GGTACACTGCCAGGCGCTTC (SEQ ID NO: 49) | GGATGGCGCTGA (SEQ ID NO: 50) | GCCTCGCCTCCCACC (SEQ ID NO: 51) |

TABLE 7

PCR conditions for each target site analyzed by Sanger sequencing.

| Target | Initial denature time and temperature | Denature time and temperature | Annealing time and temperature 40 cycles | Extension time and temperature | Final extension time and temperature |
|---|---|---|---|---|---|
| Site-1 | 98° C., 45 seconds | 98° C., 10 seconds | 54° C., 5 seconds | 72° C., 20 seconds | 72° C., 10 minutes |
| Site-2 | 98° C., 45 seconds | 98° C., 10 seconds | 56° C., 5 seconds | 72° C., 20 seconds | 72° C., 10 minutes |

TABLE 7-continued

PCR conditions for each target site analyzed by Sanger sequencing.

| Target | Initial denature time and temperature | Denature time and temperature | Annealing time and temperature 40 cycles | Extension time and temperature | Final extension time and temperature |
|---|---|---|---|---|---|
| Site-3 | 98° C., 45 seconds | 98° C., 10 seconds | 56° C., 5 seconds | 72° C., 20 seconds | 72° C., 10 minutes |
| APOE(R158) | 98° C., 45 seconds | 98° C., 10 seconds | 62° C., 5 seconds | 72° C., 20 seconds | 72° C., 10 minutes |

TABLE 8

List of primers used in this example to amplify off-target sites. Abbreviations: BG-OT = Off-targets associated with sg(BG), Site 1-OT = Off-targets associated with sg(Site-1), Site2-OT = Off-targets associated with sg(Site-2), Site3-OT = Off-targets associated with Sg(Site-3).

| Primer | Forward Sequence (5'→3') | Reverse Sequence (5'→3') |
|---|---|---|
| BG-OT1 | GATGCGCTTCCGGAAGACC (SEQ ID NO: 52) | GCTTCTTGAGCTTCTCAGCG (SEQ ID NO: 53) |
| BG-OT2 | GGTAGCATGTTCAGGCACCAG (SEQ ID NO: 54) | CATCCCTAGTACCGAATCCCATATAGC (SEQ ID NO: 55) |
| BG-OT3 | CATCCTCCCACCTAAGCCTTTCAA (SEQ ID NO: 56) | TTGAGTTAATAGCATTATAACAATTTCCACA (SEQ ID NO: 57) |
| BG-OT4 | ACTCCTTACAACCGGAAGGCAAAC (SEQ ID NO: 58) | TGGACGTGGTGAAGCCCGTGGTG (SEQ ID NO: 59) |
| BG-OT5 | TAGGTCTCTAGGGGGCCTCTG (SEQ ID NO: 60) | AGGCTGCCCAACAGCCCCACT (SEQ ID NO: 61) |
| Site1-OT1 | TCCCCTGTTGACCTGGAGAA (SEQ ID NO: 62) | CACTGTACTTGCCCTGACCA (SEQ ID NO: 63) |
| Site1-OT2 | TGAGATGTGGGCAGAAGGG (SEQ ID NO: 64) | TTGGTGTTGACAGGGAGCAA (SEQ ID NO: 65) |
| Site1-OT3 | GTCCAAAGGCCCAAGAACCT (SEQ ID NO: 66) | TGAGAGGGAACAGAAGGGCT (SEQ ID NO: 67) |
| Site1-OT4 | GCTCATCTTAATCTGCTCAGCC (SEQ ID NO: 68) | TCCTAGCACTTTGGAAGGTCG (SEQ ID NO: 69) |
| Site1-OT5 | AAAGGAGCAGCTCTTCCTGG (SEQ ID NO: 70) | GTCTGCACCATCTCCCACAA (SEQ ID NO: 71) |
| Site2-OT1 | GTGTGGAGAGTGAGTAAGCCA (SEQ ID NO: 72) | ACGGTAGGATGATTTCAGGCA (SEQ ID NO: 73) |
| Site2-OT2 | TTTTTTGGTACTCGAGTGTTATTCAG (SEQ ID NO: 74) | CACAAAGCAGTGTAGCTCAGG (SEQ ID NO: 75) |
| Site3-OT1 | GGCATGGCTTCTGAGACTCA (SEQ ID NO: 76) | CCCCTTGCACTCCCTGTCTTT (SEQ ID NO: 77) |
| Site3-OT2 | GAAGAGGCTGCCCATGAGAG (SEQ ID NO: 78) | TTTGGCAATGGAGGCATTGG (SEQ ID NO: 79) |
| Site3-OT3 | GGTCTGAGGCTCGAATCCTG (SEQ ID NO: 80) | CTGTGGCCTCCATATCCCTG (SEQ ID NO: 81) |
| Site3-OT4 | TTTCCACCAGAACTCAGCCC (SEQ ID NO: 82) | CCTCGGTTCCTCCACAACAC (SEQ ID NO: 83) |
| Site3-OT5 | GCAGGGGAGGGATAAAGCAG (SEQ ID NO: 84) | CACGGGAAGGACAGGAGAAG (SEQ ID NO: 85) |

TABLE 9

List of primers used in this example for NGS analysis.

| Primer | Forward Sequence (5'→3') | Reverse Sequence (5'→3') |
|---|---|---|
| Site-1 | ATGTGGGCTGCCTAGAAAGG (SEQ ID NO: 86) | CCCAGCCAAACTTGTCAACC (SEQ ID NO: 87) |
| APOE(R158) | GGACGAGACCATGAAGGAGTTGAAGGC (SEQ ID NO: 88) | CCACCTGCTCCTTCACCTCGTCCAG (SEQ ID NO: 89) |

TABLE 10

PCR conditions for each target site subjected to NGS analysis.

| Target | Initial denature time and temperature | Denature time and temperature | Annealing time and temperature 40 cycles | Extension time and temperature | Final extension time and temperature |
|---|---|---|---|---|---|
| Site-1 | 98° C., 45 seconds | 98° C., 10 seconds, | 54° C., 5 seconds | 72° C., 20 seconds | 72° C., 10 minutes |
| APOE(R158) | 98° C., 45 seconds | 98° C., 10 seconds, | 62° C., 5 seconds | 72° C., 20 seconds | 72° C., 10 minutes |

TABLE 11

Comparison of editing efficiency using RoT-based approaches at the same target loci in this example, Komar et al., and Koblan et al.

| | Figure 3E Standage-Beier et al. Reporter of Transfection | | | Figure 5C Komar et.al Sci Adv. 2017 Aug 30;3(8) No Reporter | | | Figure 1C Koblan et. al Nat Biotechnol. 2018 October;36(9):843-846 Reporter of Transfection | | |
|---|---|---|---|---|---|---|---|---|---|
| | Unsorted | Reporter− | Reporter+ | Unsorted | Reporter− | Reporter+ | Unsorted | Reporter− | Reporter+ |
| Site-1 (HEK 3) | 21.3 ± 2.9 | 3.3 ± 2.8 | 40.7 ± 7.0 | ~45 | N/A | N/A | ~38 | N/A | ~55 |
| Site-2 (HEK 2) | 36.6 ± 3.8 | 13.3 ± 5.9 | 49.7 ± 5.1 | ~35 | N/A | N/A | ~20 | N/A | ~38 |
| Site-3 (HEK 4) | 24.0 ± 6.6 | 7.6 ± 5.0 | 45.3 ± 1.5 | ~45 | N/A | N/A | ~25 | N/A | ~40 |

TABLE 12

List of sgRNA sequences used in this example.

| Site | Sequence (5'→3') |
|---|---|
| BFP(H66Y) | GACCCACGGCGTGCAGTGCT T (SEQ ID NO: 90) |
| Site-1 | GGCCCAGACTGAGCACGTGA (SEQ ID NO: 91) |
| Site-2 | GAACACAAAGCATAGACTGC (SEQ ID NO: 92) |
| Site-3 | GGCACTGCGGCTGGAGGTGG (SEQ ID NO: 93) |
| APOE(R158C) | GAAGCGCCTGGCAGTGTACC (SEQ ID NO: 94) |
| APOE(Q39X) | GTGGCAGAGCGGCCAGCGCT (SEQ ID NO: 95) |
| mCh1 | GCACCCAGACCGCCAAGCTG A (SEQ ID NO: 96) |
| mCh2 | GACCCAGGACTCCTCCCTGC (SEQ ID NO: 97) |
| mCh3 | GCAAGCAGAGGCTGAAGCTG A (SEQ ID NO: 98) |
| Non-target (NT) | GGGTCTTCGAGAAGACCT (SEQ ID NO: 99) |

TABLE 13

List of primer sequences used in this example for on- and off-target sites. Abbreviations: BG-OT = Off-targets associated with sg(BG), APOE(R158C) = Off-targets associated with sg(APOE$^{R158C}$)

| Primer | Forward Sequence (5'→3') | Reverse Sequence (5'→3') |
|---|---|---|
| Site-1 | ATGTGGGCTGCCTAGAAAGG (SEQ ID NO: 100) | CCCAGCCAAACTTGTCAACC (SEQ ID NO: 101) |

TABLE 13-continued

List of primer sequences used in this example for on- and off-target sites.
Abbreviations: BG-OT = Off-targets associated with sg(BG), APOE(R158C) = Off-targets associated with sg(APOE$^{R158C}$)

| Primer | Forward Sequence (5'→3') | Reverse Sequence (5'→3') |
| --- | --- | --- |
| Site-2 | CCAGCCCCATCTGTCAAACT (SEQ ID NO: 102) | TGAATGGATTCCTTGGAAACAATGA (SEQ ID NO: 103) |
| Site-3 | TGGTCTTCTTTCCCCTCCCCTGCCCTC C (SEQ ID NO: 104) | GGCCTGGAGGCGGGGGCTCAGAGA (SEQ ID NO: 105) |
| APOE(R158C) | GGACGAGACCATGAAGGAGTTGAAGG C (SEQ ID NO: 106) | CCACCTGCTCCTTCACCTCGTCCAG (SEQ ID NO: 107) |
| APOE(Q39X) | TCAGAAGGACCCTGACCCACCT (SEQ ID NO: 108) | ATGAAACCTGGACCTGGGGAGGTATA (SEQ ID NO: 109) |
| mCherry | AGCTGTGACCGGCGCCTACG (SEQ ID NO: 110) | GGGATTCTCCTCCACGTCAC (SEQ ID NO: 111) |
| BG-OT1 | GATGCGCTTCCGGAAGACC (SEQ ID NO: 112) | GCTTCTTGAGCTTCTCAGCG (SEQ ID NO: 113) |
| BG-OT2 | GGTAGCATGTTCAGGCACCAG (SEQ ID NO: 114) | CATCCCTAGTACCGAATCCCATATAGC (SEQ ID NO: 115) |
| BG-OT3 | CATCCTCCCACCTAAGCCTTTCAA (SEQ ID NO: 116) | TTGAGTTAATAGCATTATAACAATTTC CACA (SEQ ID NO: 117) |
| APOE(R158C)-OT1 | GATACACCATAAAGGGGTTTGACTG (SEQ ID NO: 118) | ACCATTTCCCCCCAATTCTACTC (SEQ ID NO: 119) |
| APOE(R158C)-OT2 | CATCTGCATTGGCTTGAAACATC (SEQ ID NO: 120) | TTACAAAAGTGCTAAATGATGCACAT (SEQ ID NO: 121) |
| APOE(R158C)-OT3 | ACTCAGTAAAGCTCCTCTTCAAC (SEQ ID NO: 122) | TTTTGCTTAGGTCCACTGGGC (SEQ ID NO: 123) |

TABLE 14

List of sgRNA sequences used in this example.

| Site | Sequence (5'→3') |
| --- | --- |
| XMAS-1xStop | GTTGATGGGGTGGTTCAGGA (SEQ ID NO: 124) |
| XMAS-2xStop | GTTGATGAGGTGGTTCAGGA (SEQ ID NO: 125) |
| Site-1 | GAACACAAAGCATAGACTGC (SEQ ID NO: 126) |
| Site-2 | GAGTATGAGGCATAGACTGC (SEQ ID NO: 127) |
| Site-3 | GATGAGATAATGATGAGTCA (SEQ ID NO: 128) |
| Site-4 | GGATTGACCCAGGCCAGGGC (SEQ ID NO: 129) |
| Site-5 | GTAGAAAAAGTATAGACTGC (SEQ ID NO: 130) |
| HBG1 | GCTTGACCAATAGCCTTGACA (SEQ ID NO: 131) |
| HBG2 | GATATTTGCATTGAGATAGTG (SEQ ID NO: 132) |
| AKAP9 | GAAAATAGTTGAAGAAAAAG (SEQ ID NO: 133) |
| PSEN | GCACAGAAGATACCGAGACTG (SEQ ID NO: 134) |
| Non-target (NT) | GGGTCTTCGAGAAGACCT (SEQ ID NO: 135) |

TABLE 15

List of primer sequences used in this example.

| Primer | Forward Sequence (5'→3') | Reverse Sequence (5'→3') |
| --- | --- | --- |
| Site-1 | TCCTTGGAAACAATGATAACAAGAC (SEQ ID NO: 136) | CCAGCCCCATCTGTCAAACT (SEQ ID NO: 137) |
| Site-2 | GCTTATATTCTAGGGAGACAGACAT (SEQ ID NO: 138) | ACCTGAGGTCAGAAGTTTGAGA (SEQ ID NO: 139) |

TABLE 15-continued

List of primer sequences used in this example.

| Primer | Forward Sequence (5'→3') | Reverse Sequence (5'→3') |
|---|---|---|
| Site-3 | GTCTGAGGTCACACAGTGGG (SEQ ID NO: 140) | AGAGCAGGGACCACATCTAC (SEQ ID NO: 141) |
| Site-4 | GCCAAACTTGTCAACCAGTA (SEQ ID NO: 142) | ATGTGGGCTGCCTAGAAAGG (SEQ ID NO: 143) |
| Site-5 | TCCATTTATATGAAATGTTCAGAAAAGGCAAAT (SEQ ID NO: 144) | GTAACTATATGCTCTCTGATTCTCCTATTAGC (SEQ ID NO: 145) |
| HBG1 | CCTACCTTCCCAGGGTTT (SEQ ID NO: 146) | AAGAAGTCCTGGTATCTTCTATG (SEQ ID NO: 147) |
| HBG2 | TCAGACGTTCCAGAAGCGAG (SEQ ID NO: 148) | GACAAGAAGGTGAAAAACGGCTG (SEQ ID NO: 149) |
| AKAP9 | GATTCAAAGCATACCAGAGAATAGT (SEQ ID NO: 150) | TCAAACTAGTATGCATTTCAACAAC (SEQ ID NO: 151) |
| PSEN1 | GAGTGTAGCTGTTTTTCTCAGGTT (SEQ ID NO: 152) | GAATACCCAACCATAAGAAGAACAG (SEQ ID NO: 153) |

TABLE 16

Phire PCR conditions for each target site analyzed by Sanger sequencing.

| Target | Initial denature time and temperature | Denature time and temperature | Annealing time and temperature 40 cycles | Extension time and temperature | Final extension time and temperature |
|---|---|---|---|---|---|
| Site-1 | 98 C. 5 min | 98 C. 5 sec | 58 C. 5 sec | 72 C. 30 sec | 72 C. 5 min |
| Site-2 | 98 C. 5 min | 98 C. 5 sec | 62 C. 5 sec | 72 C. 30 sec | 72 C. 5 min |
| Site-3 | 98 C. 5 min | 98 C. 5 sec | 56.8 C. 5 sec | 72 C. 30 sec | 72 C. 5 min |
| Site-4 | 98 C. 5 min | 98 C. 5 sec | 61.3 C. 5 sec | 72 C. 30 sec | 72 C. 5 min |
| Site-5 | 98 C. 5 min | 98 C. 5 sec | 65 C. 5 sec | 72 C. 30 sec | 72 C. 5 min |
| HBG1 | 98 C. 5 min | 98 C. 5 sec | 59.2 C. 5 sec | 72 C. 30 sec | 72 C. 5 min |
| HBG2 | 98 C. 5 min | 98 C. 5 sec | 59 C. 5 sec | 72 C. 30 sec | 72 C. 5 min |
| AKAP9 | 98 C. 5 min | 98 C. 5 sec | 64 C. 5 sec | 72 C. 30 sec | 72 C. 5 min |
| PSEN1 | 98 C. 5 min | 98 C. 5 sec | 63 C. 5 sec | 72 C. 30 sec | 72 C. 5 min |

TABLE 17

Parameters for EditR analysis.

| Target Site | Protospacer | 5' bound | 3' bound |
|---|---|---|---|
| Site-1 | GAACACAAAGCATAGACTGC (SEQ ID NO: 154) | 50 | 120 |
| Site-2 | GAGTATGAGGCATAGACTGC (SEQ ID NO: 155) | 140 | 200 |
| Site-3 | GATGAGATAATGATGAGTCA (SEQ ID NO: 156) | 100 | 180 |
| Site-4 | GGATTGACCCAGGCCAGGGC (SEQ ID NO: 157) | 80 | 160 |
| Site-5 | GCAGTCTATACTTTTTCTAC (SEQ ID NO: 158) | 40 | 120 |
| HBG1 | CTTGACCAATAGCCTTGACA (SEQ ID NO: 159) | 160 | 260 |
| HBG2 | ATATTTGCATTGAGATAGTG (SEQ ID NO: 160) | 120 | 220 |
| AKAP9 | GAAAATAGTTGAAGAAAAAG (SEQ ID NO: 161) | 200 | 300 |
| PSEN1 | CACAGAAGATACCGAGACTG (SEQ ID NO: 162) | 120 | 200 |

TABLE 18

List of primers used in this example to amplify off-target sites.

| Primer | Forward Sequence (5'→3') | Reverse Sequence (5'→3') |
|---|---|---|
| XMAS-OT1 | CAGCATTATCCATTTGCTGCCA (SEQ ID NO: 163) | TGGAGACAGCGAGTCTACAGC (SEQ ID NO: 164) |

TABLE 18-continued

List of primers used in this example to amplify off-target sites.

| Primer | Forward Sequence (5'→3') | Reverse Sequence (5'→3') |
| --- | --- | --- |
| XMAS-OT2 | TAACACCATTATAGCTGAAGTGGGG (SEQ ID NO: 165) | TGAGTTACACACAAGCCAGTTAAATTC (SEQ ID NO: 166) |
| XMAS-OT3 | AGGGAGTGGACATGAGGCGA (SEQ ID NO: 167) | CCCAAGAGGAAGTCCCAAGG (SEQ ID NO: 168) |
| Site-1-OT1 | CCTTGGGAAGAGAAGGGGTC (SEQ ID NO: 169) | GAGATACCGGAAGCTTTGATGTAAGA (SEQ ID NO: 170) |
| Site-1-OT2 | CTTGGGGAGAAAGGTCCAGG (SEQ ID NO: 171) | CAAGCTTTTCCTCCTGGGATGTAAAA (SEQ ID NO: 172) |
| Site-1-OT3 | CTGGCAAGCTGTTCTCACATG (SEQ ID NO: 173) | GAGGCTGAGGCAGGAGTATG (SEQ ID NO: 174) |
| Site-3-OT1 | GTTTTCAGTAGAAGAGTATATAATACATAAT (SEQ ID NO: 175) | ATATTCTCAGCCTAGGCCTG (SEQ ID NO: 176) |
| Site-3-OT2 | TGTTGGACATGGGTGCCTTATT (SEQ ID NO: 177) | TTCACCCTCTCTGGATGGCG (SEQ ID NO: 178) |
| Site-3-OT3 | GCAGGAGGAGGCAGTGAAAG (SEQ ID NO: 179) | CAGAGAAATAACACTCTGGCAGCTG (SEQ ID NO: 180) |
| Site-4-OT1 | CAGCATTTATCACGCAGTATTGTTATTG (SEQ ID NO: 181) | TCATTTCGTGTTGTGCTTTATCACTTAAAA (SEQ ID NO: 182) |
| Site-4-OT2 | GTGAGCAGTAAACTTAATTGTTGATACAATAAATC (SEQ ID NO: 183) | CTTTTAGAATGAAAGTGTGCATCTTAGTAAAGAAA (SEQ ID NO: 184) |
| Site-4-OT3 | GTTCCTCACTGATTCTCAGCAGG (SEQ ID NO: 185) | CACAAAAGGGATAAATGCTCTATCCATTT (SEQ ID NO: 186) |

We claim:

1. A polynucleotide encoding one or more reporter polypeptides, the polynucleotide including a PAM site adjacent to a base that when edited causes a change in a function or characteristic of the one or more reporter polypeptides, wherein the polynucleotide comprises a sequence selected from the group consisting of: SEQ ID NO: 258; SEQ ID NO:259; and SEQ ID NO: 260; and wherein the one or more reporter polypeptides are selected from:
- a reporter polypeptide comprising SEQ ID NO: 2, wherein the polypeptide comprises histidine at amino acid position number 67 and glycine at amino acid position number 73;
- a reporter polypeptide comprising SEQ ID NO: 316; and
- a reporter polypeptide comprising SEQ ID NO: 318.

* * * * *